US012618112B2

(12) United States Patent
Anton et al.

(10) Patent No.: US 12,618,112 B2
(45) Date of Patent: May 5, 2026

(54) EPIGENETIC MODERATORS OF NALTREXONE EFFICACY IN REDUCING HEAVY DRINKING IN INDIVIDUALS DIAGNOSED WITH ALCOHOL USE DISORDER

(71) Applicants: MUSC Foundation for Research Development, Charleston, SC (US); The Regents of the University of Colorado, a body corporate, Denver, CO (US)

(72) Inventors: Raymond F. Anton, Charleston, SC (US); Joseph P. Schacht, Denver, CO (US)

(73) Assignees: MUSC Foundation for Research Development, Charleston, SC (US); The Regents of the University of Colorado, Denver, CO (US)

( * ) Notice: Subject to any disclaimer, the term of this patent is extended or adjusted under 35 U.S.C. 154(b) by 712 days.

(21) Appl. No.: 17/824,784

(22) Filed: May 25, 2022

(65) Prior Publication Data

US 2022/0389509 A1    Dec. 8, 2022

Related U.S. Application Data

(60) Provisional application No. 63/192,952, filed on May 25, 2021.

(51) Int. Cl.
*C12Q 1/68* (2018.01)
*C12Q 1/6883* (2018.01)
*C12Q 1/6806* (2018.01)

(52) U.S. Cl.
CPC ......... *C12Q 1/6883* (2013.01); *C12Q 1/6806* (2013.01); *C12Q 2600/106* (2013.01); *C12Q 2600/154* (2013.01)

(58) Field of Classification Search
None
See application file for complete search history.

(56) References Cited

U.S. PATENT DOCUMENTS

| | | |
|---|---|---|
| 7,425,415 B2 | 9/2008 | Pfeifer et al. |
| 2009/0307181 A1 | 12/2009 | Brandon et al. |
| 2011/0065628 A1 | 3/2011 | Bankole et al. |
| 2015/0072881 A1 | 3/2015 | Kenneth |
| 2017/0191987 A1 | 7/2017 | Force et al. |
| 2017/0247760 A1 | 8/2017 | Andria et al. |
| 2018/0369238 A1 | 12/2018 | Anton et al. |
| 2018/0371542 A1 | 12/2018 | Anton |

FOREIGN PATENT DOCUMENTS

| | | |
|---|---|---|
| CA | 3219484 A1 | 12/2022 |
| EP | 4326904 A2 | 2/2024 |
| JP | 2024521754 A | 6/2024 |
| WO | WO-97/46705 A1 | 12/1997 |
| WO | WO-2022/251375 A2 | 12/2022 |

OTHER PUBLICATIONS

Akey, D.T., et al., Assaying DNA methylation based on high-throughput melting curve approaches, Genomics, vol. 80, Issue. 4, Oct. 2002, pp. 376-384.
Andria, M.L., et al., "Localization of Promoter Elements in the Human Mu-opioid Receptor Gene and Regulation by DNA Methylation," Brain Research. Molecular Brain Research, vol. 70, Issue. 1, Jun. 18, 1999, pp. 54-65.
Anton, R.F., et al., "Naltrexone Modification of Drinking Effects in a Subacute Treatment and Bar-lab Paradigm: Influence of OPRM1 and Dopamine Transporter (SLC6A3) Genes," Alcoholism: Clinical and Experimental Research, vol. 36, Issue. 11, Nov. 2012, pp. 2000-2007, 16 pages.
Anton, R.F., et al., "Opioid and Dopamine Genes Interact to Predict Naltrexone Response in a Randomized Alcohol Use Disorder Clinical Trial," Alcoholism: Clinical and Experimental Research, vol. 44, Issue. 10, Oct. 2020, pp. 2084-2096, 23 pages.
Assenov, Y., et al., "Comprehensive Analysis of DNA Methylation Data with RnBeads," Nature Methods, vol. 11, Issue. 11, Nov. 2014, pp. 1138-1140, 19 pages.
Auerkari, E.I., "Methylation of Tumor Suppressor Genes p16(INK4a), p27(Kip1) and E-Cadherin in Carcinogenesis," Oral Oncology, vol. 42, Issue. 1, Jan. 2006, pp. 5-13
Barrett, L.W., et al., "Regulation of Eukaryotic Gene Expression by the Untranslated Gene Regions and Other Non-Coding Elements," Cellular and Molecular Life Sciences, vol. 69, Issue. 21, Nov. 2012, pp. 3613-3634.
Benjamin, D., et al., "Naltrexone Reverses Ethanol-induced Dopamine Release in the Nucleus Accumbens in Awake, Freely Moving Rats," Brain Research, vol. 621, Issue. 1, Sep. 3, 1993, pp. 137-140.
Boileau, I., et al., "Alcohol Promotes Dopamine Release in the Human Nucleus Accumbens," Synapse, New York, NY, vol. 49, Issue. 4, Sep. 15, 2003, pp. 226-231. .

(Continued)

*Primary Examiner* — Stephanie K Mummert
(74) *Attorney, Agent, or Firm* — Jenkins, Taylor & Hunt, P.A.

(57) ABSTRACT

Disclosed are method for predicting naltrexone response in subjects with AUD. In some embodiments, the methods include performing or having performed one or more methylation assays on a genomic DNA sample isolated from the subject to determine the methylation status of one or more regions of the isolated genomic DNA, wherein the one or more regions are subsequences of a gene selected from a mu opioid receptor (OPRM1) gene, a catechol-O-methyltransferase (COMT) gene, and a dopamine transporter (SLC6A3) gene, wherein the methylation status of the one or more regions of the isolated genomic DNA determined is predictive of naltrexone response in the subject. Also provided are method for treating patients diagnosed with AUD with the medication naltrexone based on a methylation status of a combination of specific methylation sites located associated with an OPRM1 gene, a COMT gene, and/or an SLC6A3 gene in obtained from each AUD patient.

8 Claims, 7 Drawing Sheets

Specification includes a Sequence Listing.

(56) References Cited

OTHER PUBLICATIONS

Bond, C., et al., et al., "Single-nucleotide Polymorphism in the Human Mu Opioid Receptor Gene Alters Beta-endorphin Binding and Activity: Possible Implications for Opiate Addiction," Proceedings of the National Academy of Sciences of the United States of America, vol. 95, No. 16, Aug. 4, 1998, pp. 9608-9613.

Chen, J., et al., "Functional Analysis of Genetic Variation in Catechol-O-Methyltransferase (COMT): Effects on mRNA, Protein, and Enzyme Activity in Postmortem Human Brain," American Journal of Human Genetics, vol. 75, Issue. 5, Nov. 2004, pp. 807-821.

Ciliax., B.J., et al., "Immunocytochemical Localization of the Dopamine Transporter In Human Brain," The Journal of Comparative Neurology, vol. 409, Issue. 1, Jun. 21, 1999, pp. 38-56.

Communication of Publication corresponding to European Patent Application No. 22812081.2 dated Jan. 31, 2024, 1 page.

Cottrell, S.E., et al., "A Real-Time PCR Assay for DNA-Methylation Using Methylation-Specific Blockers," Nucleic Acids Research, vol. 32, Issue. 1, Jan. 13, 2004, e10, 8 pages.

Cross, S.H., et al., "Purification of CpG Islands Using a Methylated DNA Binding Column," Nature Genetics, vol. 6, No. 3, Mar. 1994, pp. 236-244.

Doucette-Stamm, L.A., et al., "Population Genetic Study of the Human Dopamine Transporter Gene (DAT1)," Genetic Epidemiology, vol. 12, No. 3, 1995, pp. 303-308.

Eads, C.A., et al. "MethyLight: a High-Throughput Assay To Measure DNA Methylation," Nucleic Acids Research, vol. 28, Issue. 8, Apr. 15, 2000, e32, 8 pages.

European Search Report corresponding to EP Patent Application No. 22812081.2 dated Feb. 21, 2025.

Fuke, S., et al., "The VNTR Polymorphism of the Human Dopamine Transporter (DAT1) Gene Affects Gene Expression," The Pharmacogenomics Journal, vol. 1, Issue. 2, 2001, pp. 152-156.

Furuichi, Y., et al., "Chemical Modification of tRNA-Tyr-Yeast Tyr with Bisulfite. A New Method to Modify Isopentenyladenosine Residue," Biochemical and Biophysical Research Communications, vol. 41, Issue. 5, Dec. 9, 1970, pp. 1185-1191.

Gonzales, R.A., et al., "Suppression of Ethanol-Reinforced Behavior by Naltrexone is Associated With Attenuation of the Ethanol-induced Increase in Dialysate Dopamine Levels in the Nucleus Accumbens," The Journal of Neuroscience, vol. 18, Issue. 24, Dec. 15, 1998, 10663-10671.

Hartwell, E.E., et al., "Systematic Review and Meta-Analysis of the Moderating Effect of rs1799971 in OPRM1, the Mu-Opioid Receptor Gene, on Response to Naltrexone Treatment of Alcohol Use Disorder," Addiction, vol. 115, Issue. 8, Aug. 2020, pp. 1426-1437.

Heinz, A., et al., "Genotype Influences in Vivo Dopamine Transporter Availability in Human Striatum," Neuropsychopharmacology, vol. 22, Issue. 2, Feb. 2000, pp. 133-139.

Herman, J.G., et al., "Methylation-Specific PCR: a Novel PCR Assay for Methylation Status of CpG Islands," Proceedings of the National Academy of Sciences of the United States of America, vol. 93, Issue. 18, Sep. 3, 1996, pp. 9821-9826.

Hillemacher, T., et al., "Promoter Specific Methylation of the Dopamine Transporter Gene is Altered in Alcohol Dependence and Associated with Craving," Journal of Psychiatric Research, vol. 43, No. 4, Jan. 2009, pp. 388-392.

Horvath, S., et al., "Aging Effects on DNA Methylation Modules in Human Brain and Blood Tissue," Genome Biology, vol. 13, Issue. 10, Oct. 3, 2012, R97, 18 pages.

Horvath, S., et al., "DNA Methylation Age of Human Tissues and Cell Types," Genome Biology, vol. 14, Issue. 10, 2013, R115, 20 pages.

Illingworth, R., et al., "A Novel CpG Island Set Identifies Tissue-specific Methylation at Developmental Gene Loci," PLOS Biology, vol. 6, Issue. 1, Jan. 2008, e22.

International Preliminary Report on Patentability for Application No. PCT/US2022/030946, mailed Nov. 21, 2023, 8 pages.

International Search Report and Written Opinion for Application No. PCT/US2022/030946, mailed Oct. 17, 2022, 13 pages.

Jasiewicz, A., et al., "DAT1 Methylation Changes in Alcohol-dependent Individuals vs. Controls," Journal of Psychiatric Research, vol. 64, May 2015, pp. 130-133.

Joehanes, R., et al., "Epigenetic Signatures of Cigarette Smoking," Circulation. Cardiovascular genetics, vol. 9, Issue. 5, Oct. 2016, pp. 436-447, 28 pages.

Jonas, D.E., et al., "Genetic Polymorphisms and Response to Medications for Alcohol Use Disorders: A Systematic Review and Meta-Analysis," Pharmacogenomics, vol. 15, Issue. 13, Sep. 2014, pp. 1687-1700.

Jonas, D.E., et al., "Pharmacotherapy for Adults With Alcohol Use Disorders in Outpatient Settings: a Systematic Review and Meta-Analysis," JAMA, vol. 311, Issue. 18, May 14, 2014, pp. 1889-1900.

Jones, P.A., "Functions of DNA Methylation: Islands, Start Sites, Gene Bodies and Beyond," Nature Reviews Genetics, vol. 13, Issue. 7, Published online May 29, 2012, Jul. 2012, pp. 484-492.

Jorgensen, H.F., et al., "Engineering a High-affinity Methyl-CpG-Binding Protein," Nucleic Acids Research, vol. 34, Issue. 13, Aug. 7, 2006, e96, 7 pages.

Lachman, H.M., et al., "Human Catechol-O-Methyltransferase Pharmacogenetics: Description of a Functional Polymorphism and Its Potential Application To Neuropsychiatric Disorders," Pharmacogenetics, vol. 6, Issue. 3, Jun. 1996, pp. 243-250.

Laird, P.W., "The Power and the Promise of DNA Methylation Markers," Nature Reviews Cancer, vol. 3, Issue. 4, Apr. 2003, pp. 253-266.

Lin, Y., et al., "An Analysis of the Effect of Mu-opioid Receptor Gene (OPRM1) Promoter Region DNA Methylation on the Response of Naltrexone Treatment of Alcohol Dependence," Pharmacogenomics Journal, vol. 20, Issue. 5, Oct. 2020, pp. 672-680, 19 pages.

Maisel, N.C., et al., "Meta-analysis of Naltrexone and Acamprosate for Treating Alcohol Use Disorders: When are these Medications Most Helpful?," Addiction, vol. 108, Issue. 2, Feb. 2013, pp. 275-293.

Matsumoto, M., et al., "Catechol O-Methyltransferase mRNA Expression In Human and Rat Brain: Evidence for a Role In Cortical Neuronal Function," Neuroscience, vol. 116, Issue. 1, 2003, pp. 127-137.

Maunakea, A.K., et al., "Conserved Role of Intragenic DNA Methylation In Regulating Alternative Promoters," Nature, vol. 466, No. 7303, Jul. 8, 2010, pp. 253-257, 19 pages.

Melnikov et al. (2005) MSRE-PCR for analysis of gene-specific DNA methylation. Nucleic Acids Research 33(10):e93.

Murphy, B.C., et al., "Site-Specific Cytosine Methylation in S-COMT Promoter in 31 Brain Regions With Implications for Studies Involving Schizophrenia," American Journal of Medical Genetics. Part B, Neuropsychiatric Genetics, vol. 133B, Issue. 1, Feb. 5, 2005, pp. 37-42.

Pidsley, R., et al., "A Data-driven Approach to Preprocessing Illumina 450k Methylation Array Data," BMC Genomics, vol. 14, May 1, 2013, 293, 10 pages.

Rand, K., et al., "Conversion-Specific Detection of DNA Methylation Using Real-Time Polymerase Chain Reaction (ConLight-MSP) to Avoid False Positives," Methods, vol. 27, Issue. 2, Jun. 2002.

Rein, T., et al., "Identifying 5-Methylcytosine and Related Modifications in DNA Genomes," Nucleic Acids Research, vol. 26, Issue. 10, May 15, 1998, pp. 2255-2264.

Sasaki, M., et al., "Bisulfite Conversion-Specific and Methylation-Specific PCR: a Sensitive Technique for Accurate Evaluation of CpG Methylation," Biochemical and Biophysical Research Communications, vol. 309, Issue. 2, Sep. 19, 2003, pp. 305-309.

Schacht, J.P., et al., "Interacting Effects of Naltrexone and OPRM1 and DAT1 Variation on the Neural Response to Alcohol Cues," Neuropsychopharmacology, vol. 38, Issue. 3, Feb. 2013, pp. 414-422.

Schacht, J.P., et al., "Predictors of Naltrexone Response in a Randomized Trial: Reward-Related Brain Activation, OPRM1 Genotype, and Smoking Status," Neuropsychopharmacology, vol. 42, Issue. 13, Dec. 2017, pp. 2640-2653.

(56)                    References Cited

OTHER PUBLICATIONS

Shiraishi, M., et al., "Isolation of DNA Fragments Associated With Methylated Cpg Islands in Human Adenocarcinomas of the Lung Using a Methylated DNA Binding Column and Denaturing Gradient Gel Electrophoresis," Proceedings of National Academy of Sciences, USA, vol. 96, Issue. 6, Mar. 16, 1999, pp. 2913-2918.

Sobell, L.C., et al., Timeline Follow-Back: A Technique For Assessing Self-Reported Alcohol Consumption. In: Allen JP, Litten RZ (eds) Measuring Alcohol Consumption: Psychosocial and Biochemical Methods, Humana Press: Totowa, NJ, 1992, pp. 41-72.

Stout, R.L., et al., "Ensuring Balanced Distribution of Prognostic Factors in Treatment Outcome Research," Journal of Studies on Alcohol. Supplement, vol. 12, Dec. 1994, pp. 70-75.

Swift-Scanlan, T., et al., "Comprehensive Interrogation of CpG Island Methylation in the Gene Encoding COMT, a Key Estrogen and Catecholamine Regulator," BMC Medical Genomics, vol. 7, Jan. 24, 2014, 5, 14 pages.

Tenhunen, J., et al., "Genomic Organization of the Human Catechol O-methyltransferase Gene and Its Expression From Two Distinct Promoters," European Journal of Biochemistry, vol. 223, Issue. 3, Aug. 1, 1994, pp. 1049-1059.

Ursini, G., et al., "Stress-Related Methylation of the Catechol-O-Methyltransferase Val 158 Allele Predicts Human Prefrontal Cognition and Activity," The Journal of Neuroscience, vol. 31, Issue, 18, May 4, 2011, pp. 6692-6698.

Weerts, E.M., et al., "Independent and Interactive Effects of OPRM1 and DAT1 Polymorphisms on Alcohol Consumption and Subjective Responses in Social Drinkers," Alcoholism: Clinical and Experimental Research, vol. 41, Issue. 6, Jun. 2017, pp. 1093-1104.

Weerts, E.M., et al., "Influence of OPRM1 Asn40Asp variant (A118G) on [11C]Carfentanil Binding Potential: Preliminary Findings in Human subjects," The International Journal of Neuropsychopharmacology, vol. 16, Issue. 1, Feb. 2013, pp. 47-53.

Wiers, C.E., et al., "Effects of Depressive Symptoms and Peripheral DAT Methylation on Neural Reactivity to Alcohol Cues in Alcoholism," Translational psychiatry, vol. 5, Issue. 9, Sep. 29, 2015, e648, 8 pages.

Wiers, C.E., et al., "Methylation of the Dopamine Transporter Gene in Blood is Associated with Striatal Dopamine Transporter Availability in ADHD: A Preliminary Study," European Journal of Neuroscience, vol. 48, Issue. 3, Aug. 2018, pp. 1884-1895, 21 pages.

Zeschnigk, M., et al., "A Novel Real-Time PCR Assay for Quantitative Analysis of Methylated Alleles (QAMA): Analysis of the Retinoblastoma Locus," Nucleic Acids Research, vol. 32, Issue. 16, Sep. 7, 2004, e125, 5 pages.

Zhang, H., et al., "Hypermethylation of OPRM1 Promoter Region in European Americans with Alcohol Dependence," Journal of Human Genetics, vol. 57, Issue. 10, Oct. 2012, pp. 670-675, 13 pages.

*OPRM1* promoter

5'-ttgcccagtgaagagacctactccttggatcg^1ctttgcg^2caaaatccacccctttttccct
cctccctccttccagcctccgaatcccgcatggcccacgctccctcctgcagcggtgcgggg
caggt▓▓▓GAGCCTCTGTGAACTACTAAGGTGGGAGGGGGCTATACG^3CAGAGGAGAATGTCAGA
TGCTCAGCTCGGTCCCCTCCG^4CCTGACG^5CTCCTCTCTGTCTCAGCCAGGACTGGTTTCTGTAA
GAAACAGCAGGAGCTGTGGCAGCG^6GCG^7AAAGGAAGCGGCTGAGGCGCTTGGAACCCGAAAAGT
CTCGGTGCTCCTGGCTACCTCGCACAGCGGTGCCCGCCCGGCCG^8TCAGTACCATGGACAGCAGC
GCTGCCCCCACGAACGCCAGCAATTGCACTGATGCCTTGGCG^9TACTCAAGTTGCTCCCCAGCAC
CCAGCCCCGGTTCCTGGGTCAACTTGTCCCACTTAGATGGCAACCTGTCCGACCCATGCGGTCC
GAACCGCACCGACCTGGGCGGGAGAGACAGCCTGTGCCCTCCGACCGGCAGTCCCTCCATGATC
ACGGCCATCACG^10ATCATGGCCCTCTACTCCATCGTGTGCGTGGTGGGGCTCTTCGGAAACTTC
CTGGTCATGTATGTGATTGTCAG-3'

*Fig. 4A*

| CpG site # | Illumina ID | Chromosomal position | Gene feature | Mean methylation (SD) |
|---|---|---|---|---|
| 1 | cg22370006 | 154360344 | TSS200 | 0.142 (0.049) |
| 2 | cg14262937 | 154360351 | TSS200 | 0.156 (0.049) |
| 3 | cg06649410 | 154360483 | 5' UTR | 0.222 (0.036) |
| 4 | cg23143142 | 154360521 | 5' UTR | 0.083 (0.015) |
| 5 | cg23706388 | 154360528 | 5' UTR | 0.067 (0.014) |
| 6 | cg05215925 | 154360587 | 5' UTR | 0.147 (0.021) |
| 7 | cg14348757 | 154360590 | 5' UTR | 0.157 (0.035) |
| 8 | cg12838303 | 154360670 | 5' UTR | 0.126 (0.027) |
| 9 | cg22719623 | 154360732 | 1^st exon | 0.488 (0.027) |
| 10 | cg15085086 | 154360894 | 1^st exon | 0.128 (0.069) |

*Fig. 4B*

SLC6A3 promoter

5'~ tgcctcccagtagctgggactacaggtgtgggccaccatgcctggctaattttttttttcaaagtcagggtttgccatgtggcccaggctggtctcaaactcctggcct
caagagatcctccttcctcggcctcccagagtgctgggattacaagcgtgagccctcactcctg
gcctgtgtatttttaatatacctgaacatccattctctctgtgtgtttttatttaacagcctccc
ttagtcacctgcaaagtcttttccttgggagactgtttcctcaaccctgctgctctggggccaa
gccctggctcactccttttttattgaaacctgtgccatggagataataggggtagagagatccct
tctgtggcagccactgacacactacagcttcgaggtggcacatcccctctcctgaagtcccct
cacctccctggcgatgaagtcccacccctgatgggaggtggtgtcaggaggccttcaggtggtc
aggccaggagggctccaccctgaggaatgggaccagtgccctcataaaacagacccggagagc
tctccccagccctagcg[1]tggggagatacaggagagaactgtctgcaaccccgaagcggccct
caccagacacagagtcggccaggccttggcctcgggacaccggaaccgttagaactgaaggctt
ctgtgtgagccccaggctgtggagttttttgtcatggcagccccaggggtcactaggctccc
acttgattccaactcagcgtgaagtcacagccctgagtgccttctgcctgggtgccagccccgg
agccggggagcggggagcggggggcggggaggggagtggtggtgtgcggggagtgcggggcgg
gcgcaggggtggggcaccgcgctgcggcgggtactgcggagtcaggcaccaaggtccctgc
ctccctcactgctgagcgcgggctgcaggctggaatggctggagagccccaggctcgcctgga
cgcccaggcaggtgctcacgggagcatcgagggtacacggggaggaacgccggggttcgggc
gacctaggggcgacgcacagagctgggcgcg[2]gccactcacctcggtgccttctaaggacctgg
acatcctgggccttggcggcctggggctccattcctccgcgcgctgaatggaagaaatcccgc
ccgggcatctcggaaggaaagcctcggagtccattcggccctggagccggataccaaccgccag
ggcttccaggcccgtcccgggaaatggttttcttaggcgagtgcgaggcgggcccctcggttc
cgatgcaggcg[3]cactagatgccggcaaggcggggactaggcctaggggacctcggtcgcctcga
ggtcgcggagaccccaaggccacggaaggacccgcgtctccgcagcccgcacgcgggaagcgt
gcagagtcctcggcggggtcccgagcccgctggtcagagcgtggagcggcggggtgggagggac
gtggtccccagagcgcggggccaccgtagggcccctgatggggaggaagggtcggccc
gacggggtcccagcagttccccgcgcgcagccgctcggctccctccccgtccagctgggagccg
ccagccctgggcgtccgaagatagcgggtgcccggggcagccccagggggtgcgggcgagggcg
cagggcggcccagacagttcccgcgtggaaggcgcccgtctagatccgcgacgtctcggacccc
caggcccccgcaccccgtgtccgaggctccgggacgcgcaggacagtggagccgtggccgccgc
ttgctccagccatctgcgtccgggaggcggggcggggcgcggcccggggaggtgaggagga
ggagccaggacgcgagggcgacccgtcggcgggaggcggggcggggcg[4]gacctgtctactg
gataagagcccg[5]aggccg[6]aggctGGACCG[7]CCCAGCCG[8]CTGCGGAGCGGGAGGGGAGGCTTCG
CGGAACGCTCTCGGCGCCAGGACTCGCGTGCAAAGCCCAGGCCCGGGCGGCCAGgtgaggccag
cgtcgctcgcggcatcggggcgccccgctccttccgcagaccccgaagtggggcgcaggggcgg
gggccggggaccgggcacagtctggggtccccgcg[9]tcccgcagaccgcgccgtctccaaagtcg
ccaacagtcgcgggtgccgagcgcccccgatagcgccacatggaccctgaggccgtccgagg
cgcgag~3'

*Fig. 5A*

SLC6A3 3' UTR

5'-
AGGAGCGTGTCCTATCCCCGGACGCATGCAGGGCCCCCACAGGAGCG[10]TGTCCTATCCCCGGAC
GCATGCAGGGCCCCCACAGGAGCATGTCCTATCCCTGGACGCATGCAGGGCCCCCACAGGAGCG
TGTACTACCCCAGAACGCATGCAGGGCCCCCACAGGAGCG[11]TGTACTACCCCAGGACGCATGCA
GGGCCCCCACTGGAGCGTGTACTACCCCAGGACGCATGCAGGGCCCCCACAGGAGCGTGTCCTA
TCCCCGGACCGGACGCATGCAGGGCCCCCACAGGAGCGTGTACTACCCCAGGACGCATGCAGGG
CCCCCACAGGAGCGTGTACTACCCCAGGATGCATGCAGGGCCCCCACAGGAGCGTGTACTACCC
CAGGACGCATGCAGGGCCCCCAT-3'

*Fig. 5B*

| CpG site # | Illumina ID | Chromosomal position | Gene feature | Mean methylation (SD) |
|---|---|---|---|---|
| Promoter | | | | |
| 1 | cg16180821 | 1446969 | TSS1500 | 0.651 (0.065) |
| 2 | cg13202751 | 1446443 | TSS1500 | 0.242 (0.038) |
| 3 | cg14502484 | 1446208 | TSS1500 | 0.086 (0.029) |
| 4 | cg05030481 | 1445593 | TSS200 | 0.05 (0.012) |
| 5 | cg27037018 | 1445567 | TSS200 | 0.03 (0.016) |
| 6 | cg04210284 | 1445561 | TSS200 | 0.034 (0.005) |
| 7 | cg12882697 | 1445549 | 5' UTR | 0.089 (0.016) |
| 8 | cg04598517 | 1445542 | 5' UTR | 0.14 (0.026) |
| 9 | cg27348223 | 1445354 | 5' UTR | 0.036 (0.013) |
| 3' UTR | | | | |
| 10 | cg15600751 | 1394054 | 3' UTR | 0.648 (0.039) |
| 11 | cg16392193 | 1393934 | 3' UTR | 0.591 (0.04) |

*Fig. 5C*

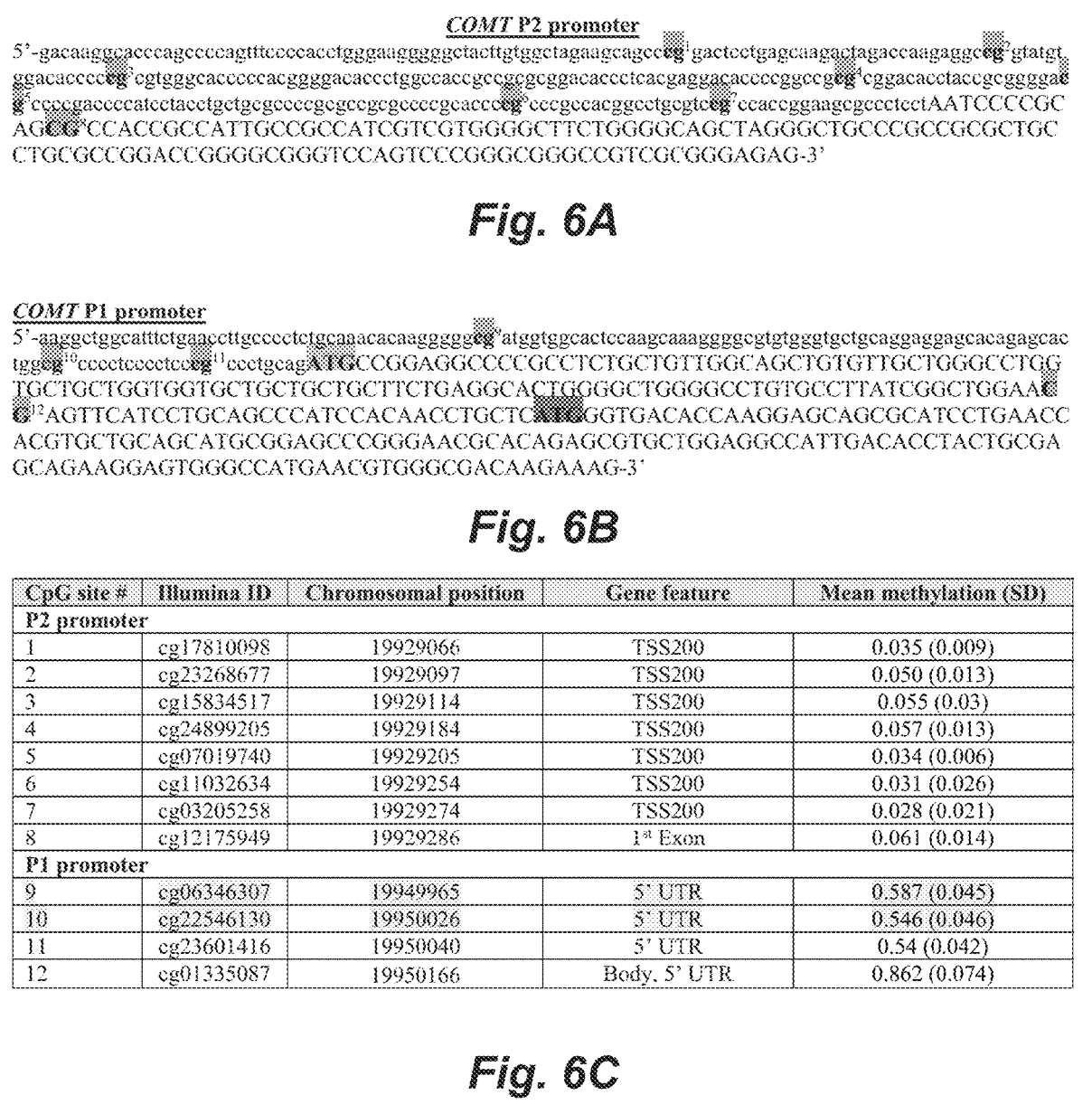

_COMT_ P2 promoter

5'-gacaaggcacccagcccagtttccccacctgggaaggggggctacttgtggctagaagcagccag⁶gactcctgagcaagactagaccaagaggcⁿg⁷gtatgt ggacaccccⁿg⁸cgtgggcaccccacggggacaccctggccaccgccgcgcggacacctcacgaggacaccccggccgⁿg⁴cggacacctaccgcggggaⁿ ⁵cⁿ cgccgaccccatcctacctgctgcgccccgcgccgcgccccgcacccⁿg⁵cccgccacggcctgcgtcⁿg⁶ccacgggaagcgccctcctAATCCCCGC AGⁿⁿⁿ⁷CCACCGCCATTGCCGCCATCGTCGTGGGGCTTCTGGGGCAGCTAGGGCTGCCCGCCGCGCTGC CTGCGCCGGACCGGGGCGGGTCCAGTCCCGGGCGGGCCGTCGCGGGAGAG-3'

Fig. 6A

_COMT_ P1 promoter

5'-aaggctggcatttctgaaccttgccctctgcaaacacaaggggⁿgⁿ⁹atggtggcactccaagcaaaggggcgtgtgggtgctgcaggaggagcacagagcac tggⁿⁿ¹⁰ccctcccctccⁿgⁿ¹¹ccctgcagATGCCGGAGGCCCCGCCTCTGCTGTTGGCAGCTGTGTTGCTGGGCCTGG TGCTGCTGGTGGTGCTGCTGCTGCTTCTGAGGCACTGGGGCTGGGGCCTGTGCCTTATCGGCTGGAAⁿ ⁿ¹²AGTTCATCCTGCAGCCCATCCACAACCTGCTCⁿⁿⁿGGTGACACCAAGGAGCAGCGCATCCTGAACC ACGTGCTGCAGCATGCGGAGCCCGGGAACGCACAGAGCGTGCTGGAGGCCATTGACACCTACTGCGA GCAGAAGGAGTGGGGCCATGAACGTGGGCGACAAGAAAG-3'

Fig. 6B

| CpG site # | Illumina ID | Chromosomal position | Gene feature | Mean methylation (SD) |
|---|---|---|---|---|
| P2 promoter | | | | |
| 1 | cg17810098 | 19929066 | TSS200 | 0.035 (0.009) |
| 2 | cg23268677 | 19929097 | TSS200 | 0.050 (0.013) |
| 3 | cg15834517 | 19929114 | TSS200 | 0.055 (0.03) |
| 4 | cg24899205 | 19929184 | TSS200 | 0.057 (0.013) |
| 5 | cg07019740 | 19929205 | TSS200 | 0.034 (0.006) |
| 6 | cg11032634 | 19929254 | TSS200 | 0.031 (0.026) |
| 7 | cg03205258 | 19929274 | TSS200 | 0.028 (0.021) |
| 8 | cg12175949 | 19929286 | 1ˢᵗ Exon | 0.061 (0.014) |
| P1 promoter | | | | |
| 9 | cg06346307 | 19949965 | 5' UTR | 0.587 (0.045) |
| 10 | cg22546130 | 19950026 | 5' UTR | 0.546 (0.046) |
| 11 | cg23601416 | 19950040 | 5' UTR | 0.54 (0.042) |
| 12 | cg01335087 | 19950166 | Body, 5' UTR | 0.862 (0.074) |

Fig. 6C

SEQUENCE LISTING

```
<160> NUMBER OF SEQ ID NOS: 48

<210> SEQ ID NO 1
<211> LENGTH: 656
<212> TYPE: DNA
<213> ORGANISM: Homo sapiens

<400> SEQUENCE: 1
ttgcccagtg aagagaccta ctccttggat cgctttgcgc aaaatccacc ccttttccct      60
cctccctccc ttccagcctc cgaatcccgc atggcccacg ctcccctcct gcagcggtgc     120
ggggcaggtg atgagcctct gtgaactact aaggtgggag ggggctatac gcagaggaga     180
atgtcagatg ctcagctcgg tcccctccgc ctgacgctcc tctctgtctc agccaggact     240
ggtttctgta agaaacagca ggagctgtgg cagcggcgaa aggaagcggc tgaggcgctt     300
ggaacccgaa aagtctcggt gctcctggct acctcgcaca gcggtgcccg cccggccgtc     360
agtaccatgg acagcagcgc tgcccccacg aacgccagca attgcactga tgccttggcg     420
```

-continued

```
tactcaagtt gctccccagc acccagcccc ggttcctggg tcaacttgtc ccacttagat      480
ggcaacctgt ccgacccatg cggtccgaac cgcaccgacc tgggcgggag agacagcctg      540
tgccctccga ccggcagtcc ctccatgatc acggccatca cgatcatggc cctctactcc      600
atcgtgtgcg tggtggggct cttcggaaac ttcctggtca tgtatgtgat tgtcag         656

<210> SEQ ID NO 2
<211> LENGTH: 50
<212> TYPE: DNA
<213> ORGANISM: Homo sapiens

<400> SEQUENCE: 2
atgtgtttgc acagaagagt gcccagtgaa gagacctact ccttggatcg                  50

<210> SEQ ID NO 3
<211> LENGTH: 50
<212> TYPE: DNA
<213> ORGANISM: Homo sapiens

<400> SEQUENCE: 3
tgcacagaag agtgcccagt gaagagacct actccttgga tcgctttgcg                  50

<210> SEQ ID NO 4
<211> LENGTH: 50
<212> TYPE: DNA
<213> ORGANISM: Homo sapiens

<400> SEQUENCE: 4
ctaaggtggg agggggctat acgcagagga gaatgtcaga tgctcagctc                  50

<210> SEQ ID NO 5
<211> LENGTH: 50
<212> TYPE: DNA
<213> ORGANISM: Homo sapiens

<400> SEQUENCE: 5
cgcagaggag aatgtcagat gctcagctcg gtccctccg cctgacgctc                   50

<210> SEQ ID NO 6
<211> LENGTH: 50
<212> TYPE: DNA
<213> ORGANISM: Homo sapiens

<400> SEQUENCE: 6
gtctcagcca ggactggttt ctgtaagaaa cagcaggagc tgtggcagcg                  50

<210> SEQ ID NO 7
<211> LENGTH: 49
<212> TYPE: DNA
<213> ORGANISM: Homo sapiens

<400> SEQUENCE: 7
aggactggtt tctgtaagaa acagcaggag ctgtggcagc ggcgaaagg                   49

<210> SEQ ID NO 8
<211> LENGTH: 50
<212> TYPE: DNA
<213> ORGANISM: Homo sapiens

<400> SEQUENCE: 8
cgtcagtacc atggacagca gcgctgcccc cacgaacgcc agcaattgca                  50
```

-continued

```
<210> SEQ ID NO 9
<211> LENGTH: 50
<212> TYPE: DNA
<213> ORGANISM: Homo sapiens

<400> SEQUENCE: 9
cgtactcaag ttgctcccca gcacccagcc ccggttcctg ggtcaacttg              50

<210> SEQ ID NO 10
<211> LENGTH: 50
<212> TYPE: DNA
<213> ORGANISM: Homo sapiens

<400> SEQUENCE: 10
cgatcatggc cctctactcc atcgtgtgcg tggtggggct cttcggaaac              50

<210> SEQ ID NO 11
<211> LENGTH: 2291
<212> TYPE: DNA
<213> ORGANISM: Homo sapiens

<400> SEQUENCE: 11
tgcctcccca gtagctggga ctacaggtgt gggccaccat gcctggctaa tttttttttt      60
caaagtcagg gttttgccat gtggcccagg ctggtctcaa actcctggcc tcaagagatc     120
ctccttcctc ggcctcccag agtgctggga ttacaagcgt gagccctcac tcctggcctg     180
tgtattttta atatacctga acatccattc tctctgtgtg ttttatttaa cagcctccct     240
tagtcacctg caaagtcttt tccttgggag actgtttcct caaccctgct gctctggggc     300
caagccctgg ctcactcctt tttattgaaa cctgtgccat ggagataata ggggtagaga     360
gatcccttct gtggcagcca ctgacacact acagcttcga ggtggcacat ccccctctcc     420
tgaagtcccc tcacctccct ggcgatgaag tcccacccct gatgggaggt ggtgtcagga     480
ggccttcagg tggtcaggcc aggagggctc caccctgagg aatgggacca gtgccctcat     540
aaaacagacc ccggagagct ctccccagcc cctagcgtgg ggagatacag ggagagaact     600
gtctgcaacc ccgaagcggc cctcaccaga cacagagtcg gccaggcctt ggcctcggga     660
caccggaacc gttagaactg aaggcttctg tgtgagcccc caggctgtgg agtttttgt      720 catggcagcc ccaggggggtc actaggctcc cacttgattc caactcagcg tgaagtcaca     780
gccctgagtg ccttctgcct gggtgccagc cccggagccg gggagcgggg gagcggggggg     840 cggggagggg agtggtggtg tgcggggagt gcggggcggg cgcaggggggt ggggcaccgc     900 gctgcgggcg ggtactgcgg agtcaggcac caagggtccc tgcctccctc actgctgagc     960
gcgggctgca ggctggaatg gctggagagc cccaggggctc gcctggacgc ccaggggcagg    1020 gtgctcacgg gagcatcgag ggtacacggg gaggaacgcc ggggttcggg cgaccctagg    1080
ggcgacgcac agagctgggc gcggccactc acctcggtgc cttctaagga cctggacatc    1140
ctgggccttg gcggcctggg ggctccattc ctccgcgcgc tgaatggaag aaatcccgcc    1200
cgggcatctc ggaaggaaag cctcggagtc cattcggccc tggagccgga taccaaccgc    1260
cagggctttc caggcccgtc ccgggaaatg gtttttcttag gcgagtgcga ggcgggcccc    1320
tcggttccga tgcaggcgca ctagatgccg gcaaggcggg gactaggcct aggggacctc    1380
ggtcgcctcg aggtcgcgga gaccccaagg ccacggaagg accgcgcgtct ccgcagcccg    1440 cacgccggga agcgtgcaga gtcctcggcg gggtcccgag cccgctggtc agagcgtgga    1500
gcggcggggt gggagggacg tggtccccag agcgcggggc caccgtaggg gcccctgatg    1560
```

-continued

```
gggaggggagg gaagggtcgg cccgacgggg tcccagcagt tccccgcgcg cagccgctcg      1620
gctccctccc cgtccagctg ggagccgcca gccctgggcg tccgaagata gcgggtgccc      1680
ggggcagccc ccaggggtgc gggcgagggc gcagggcggc ccagacagtt cccgcgtgga      1740
aggcgcccgt ctagatccgc gacgtctcgg acccccaggc ccccgcaccc cgtgtccgag      1800
gctccgggac gcgcaggaca gtggagccgt ggccgccgct tgctcccagc catctgcgtc      1860
cgggaggcgg gggcgggggc gcggcccggg gaggtgagga ggaggagcca ggacgcgagg      1920
gcgaccccgt cggcgggagg gcggggcggg gcggaccctg tctactggat aagagcccga      1980
ggccgaggct gagaccgccc agcgctgcgg agcgggaggg gaggcttcgc ggaacgctct      2040
cggcgccagg actcgcgtgc aaagcccagg cccgggcggc caggtgaggc cagcgtcgct      2100
cgcggcatcg gggcgccccg ctccttccgc agaccccgaa gtggggcgca ggggcggggg      2160
ccggggaccg ggcacagtct ggggtccccg cgtcccgcag accgcgccgt ctccaaagtc      2220
gccaacagtc gcgggtgccg agcgcccccc gatagcgcca catgggaccc tgaggccgtc      2280
cgaggcgcga g                                                           2291
```

<210> SEQ ID NO 12
<211> LENGTH: 50
<212> TYPE: DNA
<213> ORGANISM: Homo sapiens

<400> SEQUENCE: 12

```
cgtggggaga tacagggaga gaactgtctg caaccccgaa gcggccctca                  50
```

<210> SEQ ID NO 13
<211> LENGTH: 50
<212> TYPE: DNA
<213> ORGANISM: Homo sapiens

<400> SEQUENCE: 13

```
cggccactca cctcggtgcc ttctaaggac ctggacatcc tgggccttgg                  50
```

<210> SEQ ID NO 14
<211> LENGTH: 50
<212> TYPE: DNA
<213> ORGANISM: Homo sapiens

<400> SEQUENCE: 14

```
tggttttctt aggcgagtgc gaggcgggcc cctcggttcc gatgcaggcg                  50
```

<210> SEQ ID NO 15
<211> LENGTH: 50
<212> TYPE: DNA
<213> ORGANISM: Homo sapiens

<400> SEQUENCE: 15

```
cggaccctgt ctactggata agagcccgag gccgaggctg agaccgccca                  50
```

<210> SEQ ID NO 16
<211> LENGTH: 50
<212> TYPE: DNA
<213> ORGANISM: Homo sapiens

<400> SEQUENCE: 16

```
tcggcgggag ggcggggcgg ggcggaccct gtctactgga taagagcccg                  50
```

<210> SEQ ID NO 17

-continued

```
<211> LENGTH: 50
<212> TYPE: DNA
<213> ORGANISM: Homo sapiens

<400> SEQUENCE: 17
ggagggcggg gcggggcgga ccctgtctac tggataagag cccgaggccg              50

<210> SEQ ID NO 18
<211> LENGTH: 50
<212> TYPE: DNA
<213> ORGANISM: Homo sapiens

<400> SEQUENCE: 18
ggggcggacc ctgtctactg gataagagcc cgaggccgag gctgagaccg              50

<210> SEQ ID NO 19
<211> LENGTH: 48
<212> TYPE: DNA
<213> ORGANISM: Homo sapiens

<400> SEQUENCE: 19
cgaggccgag gctgagaccg cccagcgctg cggagcggga ggggaggc               48

<210> SEQ ID NO 20
<211> LENGTH: 50
<212> TYPE: DNA
<213> ORGANISM: Homo sapiens

<400> SEQUENCE: 20
ccgggcacag tctggggtcc ccgcgtcccg cagaccgcgc cgtctccaaa             50

<210> SEQ ID NO 21
<211> LENGTH: 405
<212> TYPE: DNA
<213> ORGANISM: Homo sapiens

<400> SEQUENCE: 21
aggagcgtgt cctatccccg gacgcatgca gggcccccac aggagcgtgt cctatccccg    60
gacgcatgca gggcccccac aggagcatgt cctatccctg gacgcatgca gggcccccac   120
aggagcgtgt actacccag aacgcatgca gggcccccac aggagcgtgt actaccccag    180
gacgcatgca gggcccccac tggagcgtgt actaccccag gacgcatgca gggcccccac   240
aggagcgtgt cctatccccg gaccggacgc atgcagggcc cccacaggag cgtgtactac   300
cccaggacgc atgcagggcc cccacaggag cgtgtactac cccaggatgc atgcagggcc   360
cccacaggag cgtgtactac cccaggacgc atgcagggcc cccat                  405

<210> SEQ ID NO 22
<211> LENGTH: 50
<212> TYPE: DNA
<213> ORGANISM: Homo sapiens

<400> SEQUENCE: 22
cctatccccg gacgcatgca gggcccccac aggagcgtgt cctatccccg             50

<210> SEQ ID NO 23
<211> LENGTH: 50
<212> TYPE: DNA
<213> ORGANISM: Homo sapiens

<400> SEQUENCE: 23
cgtgtcctat ccccggacgc atgcagggcc cccacaggag catgtcctat             50
```

-continued

```
<210> SEQ ID NO 24
<211> LENGTH: 49
<212> TYPE: DNA
<213> ORGANISM: Homo sapiens

<400> SEQUENCE: 24
gcatgcaggg cccccacagg agcgtgtact accccaggac gcatgcagg                49

<210> SEQ ID NO 25
<211> LENGTH: 50
<212> TYPE: DNA
<213> ORGANISM: Homo sapiens

<400> SEQUENCE: 25
cgcatgcagg gccccacag gagcgtgtcc tatccccgga ccggacgcat               50

<210> SEQ ID NO 26
<211> LENGTH: 418
<212> TYPE: DNA
<213> ORGANISM: Homo sapiens

<400> SEQUENCE: 26
gacaaggcac ccagccccag tttccccacc tgggaagggg gctacttgtg gctagaagca    60
gcccggactc ctgagcaaga ctagaccaag aggccggtat gtggacaccc ccgcgtgggc   120 accccacgg ggacaccctg gccaccgccg cgcggacacc ctcacgagga caccccggcc    180
gcgcggacac ctaccgcggg gacgccccga ccccatccta cctgctgcgc cccgcgccgc   240
gccccgcacc ccgcccgcca cggcctgcgt ccgccaccgg aagcgccctc ctaatccccg   300
cagcgccacc gccattgccg ccatcgtcgt ggggcttctg gggcagctag ggctgcccgc   360
cgcgctgcct gcgccggacc ggggcgggtc cagtcccggg cgggccgtcg cgggagag     418

<210> SEQ ID NO 27
<211> LENGTH: 419
<212> TYPE: DNA
<213> ORGANISM: Homo sapiens

<400> SEQUENCE: 27
aaggctggca tttctgaacc ttgcccctct gcaaacacaa gggggcgatg gtggcactcc    60
aagcaaaggg gcgtgtgggt gctgcaggag gagcacagag cactggcgcc cctcccctcc   120
cgccctgcag atgccggagg ccccgcctct gctgttggca gctgtgttgc tgggcctggt   180
gctgctggtg gtgctgctgc tgcttctgag gcactgggc tggggcctgt gccttatcgg    240
ctggaacgag ttcatcctgc agcccatcca caacctgctc atgggtgaca ccaaggagca   300
gcgcatcctg aaccacgtgc tgcagcatgc ggagcccggg aacgcacaga gcgtgctgga   360
ggccattgac acctactgcg agcagaagga gtgggccatg aacgtgggcg acaagaaag    419

<210> SEQ ID NO 28
<211> LENGTH: 50
<212> TYPE: DNA
<213> ORGANISM: Homo sapiens

<400> SEQUENCE: 28
cggactcctg agcaagacta gaccaagagg ccggtatgtg gacaccccg                50

<210> SEQ ID NO 29
<211> LENGTH: 50
<212> TYPE: DNA
```

-continued

```
<213> ORGANISM: Homo sapiens

<400> SEQUENCE: 29
tgtggctaga agcagcccgg actcctgagc aagactagac caagaggccg                50

<210> SEQ ID NO 30
<211> LENGTH: 50
<212> TYPE: DNA
<213> ORGANISM: Homo sapiens

<400> SEQUENCE: 30
cgcggacacc taccgcgggg acgccccgac cccatcctac ctgctgcgcc                50

<210> SEQ ID NO 31
<211> LENGTH: 51
<212> TYPE: DNA
<213> ORGANISM: Homo sapiens

<400> SEQUENCE: 31
cgccccgacc ccatcctacc tgctgcgccc cgcgccgcgc cccgcacccc g             51

<210> SEQ ID NO 32
<211> LENGTH: 50
<212> TYPE: DNA
<213> ORGANISM: Homo sapiens

<400> SEQUENCE: 32
cgcccgccac ggcctgcgtc cgccaccgga agcgccctcc taatccccgc                50

<210> SEQ ID NO 33
<211> LENGTH: 50
<212> TYPE: DNA
<213> ORGANISM: Homo sapiens

<400> SEQUENCE: 33
cgccaccgga agcgccctcc taatccccgc agcgccaccg ccattgccgc                50

<210> SEQ ID NO 34
<211> LENGTH: 50
<212> TYPE: DNA
<213> ORGANISM: Homo sapiens

<400> SEQUENCE: 34
cgccctccta atccccgcag cgccaccgcc attgccgcca tcgtcgtggg                50

<210> SEQ ID NO 35
<211> LENGTH: 47
<212> TYPE: DNA
<213> ORGANISM: Homo sapiens

<400> SEQUENCE: 35
aaggctggca tttctgaacc ttgcccctct gcaaacacaa gggggcg                  47

<210> SEQ ID NO 36
<211> LENGTH: 50
<212> TYPE: DNA
<213> ORGANISM: Homo sapiens

<400> SEQUENCE: 36
ccaagcaaag gggcgtgtgg gtgctgcagg aggagcacag agcactggcg                50

<210> SEQ ID NO 37
<211> LENGTH: 50
```

```
<212> TYPE: DNA
<213> ORGANISM: Homo sapiens

<400> SEQUENCE: 37
cgccctgcag atgccggagg ccccgcctct gctgttggca gctgtgttgc            50

<210> SEQ ID NO 38
<211> LENGTH: 50
<212> TYPE: DNA
<213> ORGANISM: Homo sapiens

<400> SEQUENCE: 38
cgagttcatc ctgcagccca tccacaacct gctcatgggt gacaccaagg            50

<210> SEQ ID NO 39
<211> LENGTH: 40
<212> TYPE: DNA
<213> ORGANISM: Homo sapiens

<400> SEQUENCE: 39
actggagcgt gtactacccc aggacgcatg cagggccccc                       40

<210> SEQ ID NO 40
<211> LENGTH: 2304
<212> TYPE: DNA
<213> ORGANISM: Homo sapiens
<220> FEATURE:
<221> NAME/KEY: CDS
<222> LOCATION: (250)..(1065)

<400> SEQUENCE: 40
cggcctgcgt ccgccaccgg aagcgccctc ctaatccccg cagcgccacc gccattgccg    60
ccatcgtcgt ggggcttctg gggcagctag ggctgcccgc cgcgctgcct gcgccggacc   120
ggggcgggtc cagtcccggg cgggccgtcg cgggagagaa ataacatctg ctttgctgcc   180
gagctcagag gagaccccag acccctcccg cagccagagg ctggagcct gctcagaggt    240 gctttgaag atg ccg gag gcc ccg cct ctg ctg ttg gca gct gtg ttg ctg    291
         Met Pro Glu Ala Pro Pro Leu Leu Leu Ala Ala Val Leu Leu
           1               5                   10 ggc ctg gtg ctg ctg gtg gtg ctg ctg ctg ctt ctg agg cac tgg ggc    339
Gly Leu Val Leu Leu Val Val Leu Leu Leu Leu Leu Arg His Trp Gly
15                  20                  25                  30 tgg ggc ctg tgc ctt atc ggc tgg aac gag ttc atc ctg cag ccc atc    387
Trp Gly Leu Cys Leu Ile Gly Trp Asn Glu Phe Ile Leu Gln Pro Ile
                35                  40                  45 cac aac ctg ctc atg ggt gac acc aag gag cag cgc atc ctg aac cac    435
His Asn Leu Leu Met Gly Asp Thr Lys Glu Gln Arg Ile Leu Asn His
            50                  55                  60 gtg ctg cag cat gcg gag ccc ggg aac gca cag agc gtg ctg gag gcc    483
Val Leu Gln His Ala Glu Pro Gly Asn Ala Gln Ser Val Leu Glu Ala
        65                  70                  75 att gac acc tac tgc gag cag aag gag tgg gcc atg aac gtg ggc gac    531
Ile Asp Thr Tyr Cys Glu Gln Lys Glu Trp Ala Met Asn Val Gly Asp
    80                  85                  90 aag aaa ggc aag atc gtg gac gcc gtg att cag gag cac cag ccc tcc    579
Lys Lys Gly Lys Ile Val Asp Ala Val Ile Gln Glu His Gln Pro Ser
95                  100                 105                 110 gtg ctg ctg gag ctg ggg gcc tac tgt ggc tac tca gct gtg cgc atg    627
Val Leu Leu Glu Leu Gly Ala Tyr Cys Gly Tyr Ser Ala Val Arg Met
                115                 120                 125 gcc cgc ctg ctg tca cca ggg gcg agg ctc atc acc atc gag atc aac    675
```

```
Ala Arg Leu Leu Ser Pro Gly Ala Arg Leu Ile Thr Ile Glu Ile Asn
            130                 135                 140 ccc gac tgt gcc gcc atc acc cag cgg atg gtg gat ttc gct ggc gtg      723
Pro Asp Cys Ala Ala Ile Thr Gln Arg Met Val Asp Phe Ala Gly Val
            145                 150                 155 aag gac aag gtc acc ctt gtg gtt gga gcg tcc cag gac atc atc ccc      771
Lys Asp Lys Val Thr Leu Val Val Gly Ala Ser Gln Asp Ile Ile Pro
            160                 165                 170 cag ctg aag aag aag tat gat gtg gac aca ctg gac atg gtc ttc ctc      819
Gln Leu Lys Lys Lys Tyr Asp Val Asp Thr Leu Asp Met Val Phe Leu
175                 180                 185                 190 gac cac tgg aag gac cgg tac ctg ccg gac acg ctt ctc ttg gag gaa      867
Asp His Trp Lys Asp Arg Tyr Leu Pro Asp Thr Leu Leu Leu Glu Glu
                195                 200                 205 tgt ggc ctg ctg cgg aag ggg aca gtg cta ctg gct gac aac gtg atc      915
Cys Gly Leu Leu Arg Lys Gly Thr Val Leu Leu Ala Asp Asn Val Ile
            210                 215                 220 tgc cca ggt gcg cca gac ttc cta gca cac gtg cgc ggg agc agc tgc      963
Cys Pro Gly Ala Pro Asp Phe Leu Ala His Val Arg Gly Ser Ser Cys
            225                 230                 235 ttt gag tgc aca cac tac caa tcg ttc ctg gaa tac agg gag gtg gtg     1011
Phe Glu Cys Thr His Tyr Gln Ser Phe Leu Glu Tyr Arg Glu Val Val
            240                 245                 250 gac ggc ctg gag aag gcc atc tac aag ggc cca ggc agc gaa gca ggg     1059
Asp Gly Leu Glu Lys Ala Ile Tyr Lys Gly Pro Gly Ser Glu Ala Gly
255                 260                 265                 270 ccc tga ctgcccccc ggccccctc tcgggctctc tcacccagcc tggtactgaa     1115
Pro ggtgccagac gtgctcctgc tgaccttctg cggctccggg ctgtgtccta aatgcaaagc     1175
acacctcggc cgaggcctgc gccctgacat gctaacctct ctgaactgca acactggatt     1235
gttctttttt aagactcaat catgacttct ttactaacac tggctagcta tattatctta     1295
tatactaata tcatgtttta aaatataaa atagaaatta agaatctaaa tatttagata     1355
taactcgact tagtacatcc ttctcaactg ccattcccct gctgcccttg acttgggcac     1415
caaacattca aagctcccct tgacggacgc taacgctaag ggcggggccc ctagctggct     1475
gggttctggg tggcacgcct ggcccactgg cctcccagcc acagtggtgc agaggtcagc     1535
cctcctgcag ctaggccagg ggcacctgtt agcccatgg ggacgactgc cggcctggga     1595
aacgaagagg agtcagccag cattcacacc tttctgacca agcaggcgct ggggacaggt     1655
ggaccccgca gcagcaccag cccctctggg ccccatgtgg cacagagtgg aagcatctcc     1715
ttccctactc cccactgggc cttgcttaca gaagaggcaa tggctcagac cagctcccgc     1775
atccctgtag ttgcctccct ggcccatgag tgaggatgca gtgctggttt ctgcccacct     1835
acacctagag ctgtccccat ctcctccaag gggtcagact gctagccacc tcagaggctc     1895
caagggccca gttcccaggc ccaggacagg aatcaaccct gtgctagctg agttcacctg     1955
caccgagacc agcccctagc caagattcta ctcctgggct caaggcctgg ctagccccca     2015
gccagcccac tcctatggat agacagacca gtgagcccaa gtggacaagt ttggggccac     2075
ccagggacca gaaacagagc ctctgcagga cacagcagat gggcacctgg gaccacctcc     2135
acccagggcc ctgccccaga cgcgcagagg cccgacacaa gggagaagcc agccacttgt     2195
gccagacctg agtggcagaa agcaaaaagt tcctttgctg ctttaatttt taaattttct     2255
tacaaaaatt taggtgttta ccaatagtct tattttggct tatttttaa                2304
```

```
<210> SEQ ID NO 41
<211> LENGTH: 271
<212> TYPE: PRT
<213> ORGANISM: Homo sapiens

<400> SEQUENCE: 41

Met Pro Glu Ala Pro Pro Leu Leu Leu Ala Ala Val Leu Leu Gly Leu
1               5                   10                  15

Val Leu Leu Val Val Leu Leu Leu Leu Leu Arg His Trp Gly Trp Gly
            20                  25                  30

Leu Cys Leu Ile Gly Trp Asn Glu Phe Ile Leu Gln Pro Ile His Asn
        35                  40                  45

Leu Leu Met Gly Asp Thr Lys Glu Gln Arg Ile Leu Asn His Val Leu
    50                  55                  60

Gln His Ala Glu Pro Gly Asn Ala Gln Ser Val Leu Glu Ala Ile Asp
65                  70                  75                  80

Thr Tyr Cys Glu Gln Lys Glu Trp Ala Met Asn Val Gly Asp Lys Lys
                85                  90                  95

Gly Lys Ile Val Asp Ala Val Ile Gln Glu His Gln Pro Ser Val Leu
            100                 105                 110

Leu Glu Leu Gly Ala Tyr Cys Gly Tyr Ser Ala Val Arg Met Ala Arg
        115                 120                 125

Leu Leu Ser Pro Gly Ala Arg Leu Ile Thr Ile Glu Ile Asn Pro Asp
    130                 135                 140

Cys Ala Ala Ile Thr Gln Arg Met Val Asp Phe Ala Gly Val Lys Asp
145                 150                 155                 160

Lys Val Thr Leu Val Val Gly Ala Ser Gln Asp Ile Ile Pro Gln Leu
                165                 170                 175

Lys Lys Lys Tyr Asp Val Asp Thr Leu Asp Met Val Phe Leu Asp His
            180                 185                 190

Trp Lys Asp Arg Tyr Leu Pro Asp Thr Leu Leu Leu Glu Glu Cys Gly
        195                 200                 205

Leu Leu Arg Lys Gly Thr Val Leu Leu Ala Asp Asn Val Ile Cys Pro
    210                 215                 220

Gly Ala Pro Asp Phe Leu Ala His Val Arg Gly Ser Ser Cys Phe Glu
225                 230                 235                 240

Cys Thr His Tyr Gln Ser Phe Leu Glu Tyr Arg Glu Val Val Asp Gly
                245                 250                 255

Leu Glu Lys Ala Ile Tyr Lys Gly Pro Gly Ser Glu Ala Gly Pro
            260                 265                 270

<210> SEQ ID NO 42
<211> LENGTH: 28236
<212> TYPE: DNA
<213> ORGANISM: Homo sapiens

<400> SEQUENCE: 42
cggcctgcgt ccgccaccgg aagcgccctc ctaatccccg cagcgccacc gccattgccg      60
ccatcgtcgt ggggcttctg gggcagctag ggctgcccgc cgcgctgcct gcgccggacc     120
ggggcgggtc cagtcccggg cgggccgtcg cgggagaggt gagagcgctg gctagaccgg     180
ggccgaatgc ggccggattc ggggcggggg ccttcagacc tagggtggaa cactgggata     240
gggtgtgggg aattcggacc gctgtgaagt gatctgacgt tgggtgggag tctccggact     300
tggggtgggg aatctggatg ggaactgggg aattcggacc ttgggtgggg atctttggac     360
cggggtgggg tccccagact ccttgtggaa agctgaggtt gaagatctgt gctgtgatga     420
```

-continued

```
ggggctccag atagcggtga gagatcccgc ttcaagactg ggttgggggt ccagaccagg     480
aggataagcc tctccctgga gtagggcttg acctggtgag ggtgtggtag agtcacaggg     540
gagggtccca cttggtcctt gggctgggat cagactctca gagctggaga gttgcaggag     600
gcctggggga gggtctgtgg agccccagac tcagagggcc ttggtgactt ctccaacagg     660
ctccctgttg gaggccttgg ggtaccccag ggcctttccc tgcaagagag aggctgctcc     720
accaggaagg ggcccaggac tccccagggt cggggggatg tgtggtgtgc aggaccacgt     780
gggaatgtta gagaaagggg aagtcactcc gggcctgccc tgctaacaga cctgcttttt     840 ggattttttcc agccagggat tttgtgtcc tgttgctttt tattgtttaa agtgaccctc     900
caagcctgag ggaccgtagg agctgccctg cagagcccag tgagacacta gttaatgcag     960
aaaaaacaga ttttacttgg taactactga caacatgaga aaaagctggc tccatgctga    1020
tttgtctaga tgtgcctgga gtttaaaggg agagtgaggg agtgggaagg ggtgggggact    1080 cagtagagtt agggaaacag aaaatcacca aaactgggaa gggagggttg gccctgtga     1140 aaccaactga tctgggtttg ccactggggc ttaccgaagt caggccccca acctcccaca    1200
gagactggga gacaggggcc ccatcctcag gtgttggctg aacacacag gaaattcttg     1260 tggcagcctt gaacttctca ggcaggcact ttagagggg ctaggatcgt tctgggaatg    1320
tggccttgag ctgttaggag ctatgttagt gttcgttcca gcctagatag gccagggtga    1380
ggcccagtgg agaaggggac tctaaggagc ctggctggag tgtggggagg gagggtcttt    1440
gtcagcactc cccctgtgca agaagagcag agacctgctt ctttcctctc aacagtcccc    1500
gtccattttc tgttctgtgt tgtgttcata aactaccagc gggaccatct gttgagactt    1560
ggtagcaaag gatttttgct ggatgatgca agcagtcaag catttaatga ggaaacaaaa    1620
ataacaggcc aggcacagtg gctcatgtct gtaatcccag cacttttgga ggccgaggag    1680
gatcacttga ggccaggagt ttgaaacaag cctgggcaac ataaagaccc catctctaca    1740
aaaaatttaa aaattagccc ggcgtggtgg catgggccta tagttccagc tacttgggag    1800
gctgaggtga aaagatcgtt tgagcctggg aggcggaggc tgccatgagc catgatcttg    1860
cctctatact ccagcctgag caacagagag cccctatctt taaaaaaaaa aaataataat    1920
aaaataaaaa aataaaaaga aagaaagaaa taaaaacaaa gatgaatgga ctgttgata     1980 aacccagttt ttgagcctac agggcagcag ttgaggtttc tggccgttgg gccctaacaa    2040
ggccagcagg ggcactcagg gacttcctgg tgtgtggtgt gaagtctgtg atgatggcat    2100
aggcattggt atcccagttg tggttacttt ctggagagag catgtggcat gcaggagctg    2160
gagggggggt cttcctgggc ggcctgtgta gcagcagctc caggcacaaa ggctgcccct    2220
ggagaatctg ttgtggttct gagttctttc aagtttatat caagtttttcc ggcttcagtc    2280 tgcagggctg tttttttcag atcctggggg caaagggcag ctacaagacc acctgagtcc    2340
caatagggat ttgagttctt ggtgacacca agtcagggag gagacaaatt agaaatgtca    2400
gtctgaagag agtggtaggt agccagatac tgaaggaaag tagatgggag gatttggtaa    2460
gggctgacgt gtaggaaggc agtgacagtc caagtgacag gcagatcata aaacctcaag    2520
gataggccgg gccggtggc tcatgcctgt aatcccaagc acttcgggag gccgaggtgg    2580
gcaaatcacc cgagtccaga agttcgagac cagcctggct aacatggcaa aaccctgtct    2640
ctactaaaaa tacaaaacat tagccgggcg tggtggtgca ctcaggaggc tgaggcggga    2700
taatcgcttg aactgggagg tgggggggctg cagtaagccg agatcgcacc actgcactcc    2760
```

-continued

```
agcctgggca acaagagcga aactccatct caaaaaagaa ttaggccggg agcggtggct   2820
cacgcctgta atcccagcac tttgggaggc cgaggcgggt ggatcacgag gtcaggagat   2880
cgagaccatc ctggctaaca cggtgaaacc ccatctctac taaaaataca aaattagcca   2940
ggcgtggtgg cgggcacctg tagtcccagc tacttgggag gctgaggcag gagaatggtg   3000
tgaacccggg aggtggagct tgcaatgagc cgagatcaca ccactgcact ccagcctggg   3060
cgacacagca agactgcgtc tcaaaaacaa aacaaaacaa aacaaacac ctacaaaaga   3120 cagtgaacta gactaggatc tgataactcc caagggggtg ttatatttct ccactgaagc   3180
atagcatttc tctttacaaa cccttcccctt ttgattgaag ataatcaaag tgagattatt   3240
cttatttacc aaataattct ggtctcatta aatttggcct gattatttac ataaatgcag   3300
cacgaacagt aattgaccac acaggccttt ttaagtttgc tgaaactttt aatagggaat   3360
cttagattga gctttttaaa gcctttcgag gttaggaagc caagccaaga acttccaacc   3420
agacttcacc tgcagtgtct atagatttgg gtgaattcct ctcttctcga ggtccctgaa   3480
atatcccaag gttcctgggc cttagaacct tgggatattt ggaagtgact ttccttactc   3540
acatgtaaga ccaagaaccc cgtaagccac ataccaggcc aaattttttca agagctcttt   3600 gtaagcaatg gctccacaaa gtcaacctga aagccatctg gtcatagctg attctatgtg   3660
catcatcctc aaacaggaca ttccagtcca aaccttggta atagaaccag tgtttccaat   3720
tgtgtcctgt tacaaggaga acagattctt attgaagtta ttcaataact atattgccat   3780
gaaaatagaa tactcaataa tagtttctga tttttggagg ggtcaggccg gaagaaaaag   3840
ataattgctt caattttgtt tagagaagta tcatttacta taatattacg agtcattgat   3900
aggttaagag aaaagggaaa ggtttctttc ttttttttctt ttttgaggca gagtctcact   3960
ctgttcccca ggctggagtg cagtggcgtg atctcagctc actgcaagct ccgcctcctg   4020
ggtttacacc attctcctgc ctcagcctcc cgagtagctg ggactacagg tgcctgccac   4080
cacgcccggc taattttttg tgtttttagt agagatgggg tttcactgtg ttagcaagga   4140
tggtctcgct ctccagacct cgtgatccac ccgcctcggc ctcccaaagt actgggatta   4200
caggcgtgag ccaccgtgcc cagccgggga aaggtttctt tttttaatat tcagaaaata   4260
aaacataaag agccaacaat attctgaaca aaagtcataa aaagactgta atcatccttc   4320
agcagtttac tcagttgcat gcaggtactg aattcttgtt ctgcttgatc ttgggctagc   4380
aggtacatga acccatcttt tctcaaccag tggagatcct ggctcagtgc agtcatgtga   4440
tctcaaagtt aagaaatgct gtcacgccca ggtgcagtgg ctcaggcctg taatcccaac   4500
actttgggag gccaacgtgg ctatatcact tgaagtcagg agttcgagac cagcttggcc   4560
aacatggtga aaccctgtct ctaccaaaaa atacaaaaat tagccagttg tggtagcaga   4620
cgcctgtaat cccaactact cgggaggctg aagtgggaga atcgcttgaa cccgggacat   4680
ggaggttgca gtgagccaag atcacgccac tgcactccag cctgggcaac acagtgagac   4740
tccatctcaa aaaagaaat aaagaaatgc tgtcagaagc ctaccccatg gtacctgtca   4800
tgggcctttt cattggtccc tttttgttga agatgaagca ctttgccctg tagctgattg   4860
caagagattt caggaaagca tcagagtaaa actctaatga caaaagactt aaaatagtgt   4920
agttaaatat ctaatgagag atcattacaa aatcaaacga tttacaagga atgttggttg   4980
tttatgacac atagcatttt aaataataac cagaatgatg attgctgtta tatgaggaca   5040
tgtcattggc agaagggtat tcaccagttt gtgggaactt tatacaatat ctggaatcct   5100
tatattaaca tttaccaata tgcatgtaac tcaaggaagt ttaaatagca ttaaaaaaaa   5160
```

-continued

```
tttttttttta gtttttttttt ttttttttttt ttttgagaca gagtcccact gtgttgctca      5220
ggctggagtg cagtggcacg atctcggctc actgcaacct ccgcctcctg ggctcaagcg      5280
attctcctgc ctcagccc
cc caagtagctg ggattacagg tgtgcaccat cacacccagc      5340 taattttttgt atttttagta gagatggggt ttcgccacac tggccaggct ggtcttgaac      5400
tcctgacccc aggtgacctg cccaccttgg ccttccaaag tgttgggatt acaggcgtga      5460
gtcaccgcgt ccggccctaa ataacatttt ttatttgaca gcaccttgca tgaaattctg      5520
tagggtccag ccctacaggg tctgtgggtt tttctccccg tgtgcagaga tgagagatcg      5580
tagaaataaa gacacaagac aaagagatag aagaaaagac agctgggccc ggggaccact      5640
accaccaaga tgcggagacc agtagtggcc ccgaatgcca ggctgcgctg ttatttattg      5700
gatacaagac aaggggggcag ggtaaggagt gtgagctatc tccagtgaca ggtaaggtca      5760
catgggtcac gtgtccactg gacgggggcc cttccctgtt tggcagccga ggcggacagc      5820
gagaggagac agcttatgtc attatttctg tatttcagag acctttagta ctttcactaa      5880
ttttgttact gctagttaga aggcatagcc aggtacaggg tggaacatga aagcggacca      5940
ggagcgtgac tgcttaagca cagcatcaca gggagacggt taggcctccg gataactgtg      6000
ggcaaacctg acactccaca agaggtggtt gagcagagtc ttctctaact cccacaggga      6060
aagggagact tcctttcccg gtctgctaag taacgggtgc tttttctagg cactgacgca      6120
actgctagac caaggtccgc taagtaacag gcgtcttccc aggcgctgac gttaccacta      6180
gaccaaggag ccctctagtg gccctgtccg ggcataacag aaggctcaca cgcttgtctt      6240
ctggtcactt ctcaccgtgt cccttcagct cttatcactg tatggcctgg tttctcctag      6300
gttataattg tagagcgaag attattataa tattggaata aagagtaatt gctacaaact      6360
aatgattaac aatattcata tataatcata tctatgatct atatctaatg taactattct      6420
tattttatat attttctttta ttatactgga acagctcgtg ccctcggtct cttgcctcgg      6480
cacctgggcg acttgctgcc cacaaaattc accattgaaa taaacctaat tagtttaaca      6540
tctctcttat aaggtcacag gacagatcct ttgaggtctt ccaggggccc tccaggaaat      6600
ctcaagtcag tctgagatca agacaatgtc acaggccaca tgcagtggtt cacgcctata      6660
atcccaacac tttgggagtc cgaggaggga ggactccttg agcccaggag tttgagacca      6720
gcctgagaaa catgctgagg ccctgtctct acaaaacaaa aagttgaaaa attagctggg      6780
catggtggta catgtctgta gtcccatgta ctctgaagac tgaggcggga ggatcacttg      6840
agcccaggag ttcaaggttg cagtgagctg taattgcacc actgcactcc agcctcagta      6900
acagagtgag actctgtcac taaaaaaaat ttaggctggg tgcagcggct cacgcctata      6960
atcccagcat tttgggaggt caaggtggac agatcacctg agatcaggag ttcaagacca      7020
ggctggccaa catggcaaaa ccccacctgt actaaaaata caaaaattag ctgggcgtgg      7080
tgccatgtgc ctgtggtccc agctacttgg gaggctgaga cagcagaatt gcttaagcct      7140
gggaggcaga ggttacagtg agcccagatc acaccatggc actccagcct gggtaacaga      7200
gcgagactct gtctcaaaaa aaaaaaaaaa aaaaaaaaaa tttaaagaaa ctttatacat      7260
aaatccattc aatgattatg aggtcaattc tagccagctt tgacctcata acataaaatt      7320 tctttttctgc agactttctt gaggccagga gttcaagacc agcctgggaa acatagggat      7380
aactttctgt atccattcac agttgctttt gttttgagac agaatctcag tctgtcaccc      7440
aggatggagt gcagtggtga gatctcagct tactgcagcc ttgacctcct gggctcaagc      7500
```

-continued

```
gatcctcctg cctcaccctc ccaagtagct gggactacag gcatgtacca ccatgccagg    7560
ctaataattt ttgagttttt ttatagaaac agggtttcat catgtttccc aggcttgtct    7620
cgaattcctg ggccattcag gctttgtccc atatttttcc tctttttgta attttacttc    7680
aggacaaaat tacatccctt tctttaacaa aaacactcta cattctttgc atacttttca    7740
tataaaaaca catcctatct tcctcccata ctttgtatag gaaattgttt ccctcattct    7800
tattgtttct aggagttttg ttttcatata ttgattataa tttttaacca ttagtaaccg    7860
gtattttttt tttaaagaga cagcgtcttg ctcttttgcc caggctggag tgcagtggca    7920
caatcaggac tcactgcacc cttgaactcc cgggctcaag taattctcca acctcagccc    7980
cctaaagcac tgagattaca ggcatgagtc accacgcccg gccataactt gtattttaca    8040
agtaaaactg ggaagaagac aattggaaat tgtctgtcat ttaccagttt gttggcaaat    8100
tttatgaata taccatctta taatctctag aggtatatcc tttttatagt acaatgtttt    8160
taagtgccaa gtacatgttt attaacagac cagaatacct ttagccagtc tgtaccatat    8220
aaaaataaga agccaaaaag tacaaaaagt tacgcttaat aatgaatgtt tcagcacttt    8280
cttctcttca ggtattattt agatattcaa tgaatgtcta ttatttaact tcacttagta    8340
tgactctgag gttgaaagtt actgaaaaca tcttgtaagc tttttttaggc caatatatta    8400 tcaaacgcaa ttaacaaaac acaactcact agtttatata agagctagtt ctcactttt    8460 tttttactct attttatata tttttttcttt tcttttcttt tctttttttt tttttttttt    8520
ttttctgtag agacaaggtc ttgctgtgtt gcccaggctg gtcttgaact cctagcctca    8580
agtgatccac ttaccttggc ctcccaaagt gctgggatta caggtgtgag ccaccaccca    8640
gccctatttt atattttat ctgaactgtg tttctggcaa attggacaag ttaagggtca    8700
cttgctccat gtgaggggaa ggctttctac ctgtatttgt ggataagacc tttacgactt    8760
gttttgccct gatggatgac tacatgtttc cagtgagctc agctggttgc ttttgtgggt    8820
ccctgaggca ctgcgagccc ctgatggggc aggaagccta aagttccagg accgtgggg    8880 agttgagggg ctggaggggg aagagagagg cctgcagcgg ggatccacag gtggaggagg    8940
ccagacttga aggggtgtc tccttcaaga gaaagtaggg aagtatggag gtgataggaa    9000
gggagaggcc tgagaggagc tagtttgggg agatctcaag tatcccaaag gagccactga    9060
tgttccaaat tatccttggt aaagtcacat caacaaggaa ggaagcagac agaggcgcac    9120
ttgttccttg cagttttgtt ttgatgtgct gattaaagta gcgcagaggg catgatcagc    9180
agggctccag taagacgctc ccacgggagg agcaagaaca cagaacagag ggggcaagac    9240
agctccacca ggagtcagga gtgaatcccc tctgggaacg aggcactagg aagaagaact    9300
tccagcccag gaggtaggta gcgttcagaa gaagcctggg gcgggcgcgg tggcgcacgc    9360
ctgtaatccc agcactttgg gaggccgagg cgggcgaatc acgaggtcag gagatcaaga    9420
ccatcctggc taacacggtg aaaccccatc tctactaaaa atacaaaaaa ttagccgggc    9480
gttgtggtgg gcacctatag tcccagctac ttgggaggct gaggcaggag aatggcatga    9540
acccggggga cggagcttgc aatgagccga gattatgcca ctgcactcca gcctgggcga    9600
cagagcaaga ctctgtccca aaaaaaaaaa aaaaaaagc ctgggactct tagcgcctca    9660
gagccttact cagaatcata aaatcattag aagcaatgtc tgtcctcact gctgcatccg    9720
atattcttcc ggaccactgg atcacaaatc aaaccatgtg actcccgcat gagcaggcag    9780
agtggagata acacggatcg ctgtgtacac tgtgtgctcc ggttgttgca tccgagggtt    9840
gatcggatgg tggttcccat ccagatccaa gtcctggccc ctgatcacag agaaacacag    9900
```

```
ctggacatta aagtggtgag gacggaaatt ataatatttg gtgaccagtg acaggagggg    9960
agagagccga gctccgctcc gagttgtgca aagaagtggg gagtggggag gaagaacagt   10020
ggggactcag tggagtgagg aaagtggaaa attaccaaaa gcaggaaggg agggttagcc   10080
ttgggaaacc aatctgggtt tgccacgggg gcttactgaa gtcaggcccc cagtcccaca   10140
gaggctggga gacaggggcc ccatcttcag gtgttggcca gaacacagga aattctcttg   10200
gtagccatga ctttctcagg caggcgcttt gaaggggggct gggatcattt taggaatgtg   10260
gccttgagct gttagaagcc atgtgcagta tggcttacac ctgtaatccc agcactttgg   10320
gaggctgagg ctggagaatc acttgaggcc aggagtttaa gaccagcctg ggcaacatag   10380
caagacgctg tctctacaaa aataattttt aaaaaattag ccaggcactg cggcatgccc   10440
ctgtgtagtc ccagttactc aggaggctga agcaggagga ctgctggagc ccaagagttc   10500
aaggttgcag caagctgatt gcaccactgc actccagcct gggcggcaga ggtgatcacg   10560
ccactgcact cccgcctggg cgacagagca agaccctgtc tttaaaaaca aaaaggccag   10620
gcaggtgcgg tggctcatgc ctgtaatccc agcactttgg gaggccaagg cgggcggatc   10680
atgaggtcag gagatcgaga ccatcctggc taacatggtg aaaccccgtc tctaccaaaa   10740
acacaaaaaa gttagccggg cgtggtggcg ggcgcctgta gtcccagcta ctgggaggct   10800
gaggcaggag aatgccatga acccggggga tggagcttgc agtgagccga gattgcgcca   10860
ctgcactcta gcctgggaga cagagcaaga ctccgtctca aaacaaaaca aaacaacaac   10920
aaaaaaaaaa cagccgagcg cagtggctca cgcctgtaat cccagcactt gggaggccg   10980 aggtgggcag atcacaaggt caggagttca agaccagcct gaccaacatg gtgaaacctt   11040
gtctctacta aaaatacaaa aattagctag gcgtggtggt gtgagcctat aatcccagct   11100
actcaggagg ctgaggcagg agaatcgctt gaacccagga ggcggaggtt gcagtgagcc   11160
gagatcgcgc cactgcactc cagtctgtgt gacagagtga cagcccgtct caaaaaataa   11220
ataaataaat aaataaataa ataaataaat aaataaataa ataaataaaa tgaagcagca   11280
gcagctttgt tagtgtttgt tcaaggcctg ataggccaag gtgaggctca gccgagaaac   11340
gtgctcagag gagcctggcc ggagtgtgat gggggagtct ttgtccaggc tgctgccacg   11400
gtgggcctca ggactcatgg cctgggcgct gggggtgggg ctgccactca gccttgagga   11460
gagcaatgag gaggtcagat tccactcaca tccagtgcgg tctggatgca ggcctggccc   11520
agagcctggt ccagatgctg gggctttgtt tttttgttgt tgtttttttg agacagagtc   11580
tcgctctgtt gcccaggctg gagtgcagtg gcactatctc cactcactgc aacaacctcc   11640
acctccacgg ttcaagcgat tctcctgcct cagcctcccg agtagctggg actacaggca   11700
cccgccacca tgcccggctc attttttgca ttttttagtgg aaacagagtt tcaccatgtt   11760
ggccaggatg gtctccaact ccagaccttg tgatctgcct gcctcagcct cccaaagtgc   11820
tgggattaca ggcgtgagcc actgcaccca gccggctttg tttacagtac tcagcagctg   11880
ccaaaatagt ccccattccc aggcagggca ggctcccggg ctcagtccag cggggcagat   11940
ggccagcctg cacgtcaccc cactaggcat gtccaggccc tttctgcccc tccctaaagg   12000 caccccctgtc ctttctgtcc cctccacact gagccaagcc agcctccact cttgccccag   12060
gcctgccctc tgctgggagc cgggacactg agctcctgcc acatgagcag gttgacctgc   12120 aggggggcctc caagcaggtg ccaaggcaga atcggatgtg accaggagaa caccccttgaa   12180 ggataaagcg aatgtgcgac caccatgcag gtctggccca tggaagggag gggaggggc   12240
```

-continued

```
cccgacgggg ccacagtaaa ggagtggagg ggccccacag gcagggatgg cccagctggc   12300
cccctggggc tgtgaatctg caggtgcagt gcagcctctt gcctctctca gcccagccct   12360
tgcatctgcc tcttggtgtg tctgtgaaga caaagtcacc gtggtccctg cagcacctgg   12420
cttgaagcag gtgtgcagtc cgtgtgaaag ccttcccttt agctattagg tattgagtca   12480
aaaaaaaaaa aagccttccc ctgagcctgg gggcctggcc ccactgagga taccaggcgg   12540
gggaggctac aggaggctgc cctctgcctg gccatctgac cttccattct gaccccttcc   12600
cttccacacc agcccctttc cctatgtagg gtgcagtctt tgttgcaact gctcacctct   12660
gccatggtcg gatgagagca gccacggaca atgtctgtgc aattgtgcgt tttttgtttt   12720
gttttgtttt gagatggagt cccactcttg ttgcccaggc tggagtgtaa tggcaccatc   12780
tcggctcact gcaacctcca cctcccgagt tctagcgatt ctcctgcctc agcctcccaa   12840
gtagctggga ttacaggcat gcatcaccat gtctggctaa ttgtgtattt ttaatagaga   12900
ctggggtttc accatgttgg tcaggctgtt cttgaactcc tgacctcagg tgatccaccc   12960
gcctcagcct cccaaaatgc tgggattaca gacgtgagcc accgtgcctg gttgattgtg   13020
cgttctgata aagcttcatt tacagaaata gcaggtaggc ccctcgcagg gtgcccagag   13080
caggtgcact gtctcacctc ttctcaggtg tcaccggggt gagaggctag tcctctgcct   13140
cctccttcct ctctgcaggt tggagaaatg acagcttctt gtactggggg ttatgagaca   13200
gtggcaggag ggggacactc ccagagtgct gccagaaaga ggcgaggccc catctggatt   13260
tgatggcatt tttattgtgg tgttgtttta gagacagtgt ctgtcgccca ggatggacga   13320
catggtgcaa tcatggctca ctccagcctc caactcctgg gcccaagcaa tcctcccact   13380
tcagcctcct gagtagctgc agctataggc acaccaccat gcctggctca atgggtattt   13440
tgtggccatt aaacttctgg tcattccttt agattcccag aggctggatg gaggtgagtg   13500
gccagcccct gggtccagag atgagcgcgg ggcctggctg cagcctgtgg ggtctcccag   13560
gctggcctcc aggtgtcctc tcagcctgtc cacaggcgct gcccaagcgt gtggcctacc   13620
tggtgctgcc tggcctgtct ctacgcacct gtactggctc tccctggatt actggatcgc   13680
agtcgaatcc cctgccagaa tcctggtccc cctttatcac accggatcag ccccaaaggg   13740
cagggcttct tgcagcagtt ccagcctttg ctgggggttt ccagccctgt tgagcaagcc   13800
ccaggtaggg ccctctgcag cccccgtggg ggacctgtgt gccgagcaga gctgccccgt   13860
gtgtaaacgc ttagaactgg cctccttcct gccatctgtg tcctgtttgt catcacgcct   13920
gtggctctat gcttgtctcc ccgactgggc caccagccct gtgagggcag gatgaggcac   13980
gtccaagcca cagtggctct cagtgtgcag ggtgctgtta gcattggttc tgtgttctgg   14040
aatagtgaga acagtgtgcc ccaaatggcc agtggccttt ccgagggtca ctgcagccgc   14100
atgttggccc tctgtggaga acggaggatg cacagccatt tcagagcaca acctgaggtc   14160
tcctgagctt gctgtgcagc ccagtctttc tctccgtggc ccctggtagc tgtctttctc   14220
ccaggaggag gagaaagaca ccttcctgag caggaggatg tgggtgaata gagaccaaag   14280
tgtcaatcac tcttctgaca gaggtgatag cagaatgaaa aactgatgga ccccagatct   14340
ttgcaaagaa aacaaagtca gtttctagtt atctttcttt cttttttttc ttttttttct   14400
tttttttttt tttttttttt tttgagatgg agtctcgctc tgctgcccag gctggagtgc   14460
agtggtgtga tctcagctca ctgcaaccgc ctcccgggtt caagtgattc tcctgcctca   14520
gcctcctgag taaccaggac tacaggcaca caccaccacg cccagctaat ttttgttatt   14580
tttagcagag acagggtttc accatgttgg ccaggatggt cttgagctct cttttttttt   14640
```

-continued

```
tttttttttt tttttgagac ggagtctcgc tctgtcaccc aggctggagt gcaatggagt   14700
gatcttagct ccctgcaacc tctgcctccc aggttcaggc tattctcctg cctcagcctc   14760
ctgagtagct gggactaaca ggtgcttgcc accaagcctg gctaattttt gtatttttag   14820
tagagacagg gtttcaccat attggccagg ctgatctcga aatcctgacc ttgtggtctg   14880
cccgccttgg cctcccaaag tgctgggatt acaggcgtaa gccaccacac caggcccatt   14940
ttctagttat cttttacgga ttttttaaaa tgagcctaga aaccaggtca tataattagt   15000
ttatttttta atttcttata gagacagggt cttactatgt tgcccagagt ggtcctgaac   15060
gcctgggctc aagtgatcct cctgcctcag cctcccaaag tattgggatt acaggtgtgg   15120
ccactgttcc agccatagtt catattttaa aggattttta agagtctcat ttcactgatg   15180
ttacttgcag tatatttatg gaaaacattc ctgtcttttt ttttttttg agacggagtc   15240 tcactctgtt acccaggctg gagtgcagtg gcgtgatctc ggctcactgc aagctccgcc   15300 tctgggttc acgccattct cctgcctcag cctcccgagt agctgggact acaggtgcct   15360
gccaccacac ccggccaatt ttttgtattt ttagtagaga cagggtttca ctgtgttagc   15420
caggatggtc tcgatctcct gacctcgtga tctgcccgcc ccggcctccc aaagtgctgg   15480
gattacaggc atgagccacc gcgcccggcc agcattcctg tcttttaaag aaagatgaga   15540
ccagatgcag tggtgtgcac ctgtggtccc agctactcag gaggatgcct tgagcctggg   15600
agttcaaggc tgcagctgca gtgagccttg atcacgccac tgcactccag cctgggcaat   15660
tgaacaggac cctgtctcta aagaaataaa ataaaggcag atgaatgtca tctagggtgt   15720
gtccaatgtg agagagaata ctgaccaggt gacagaggtg atggactctc tagctctgca   15780
gcagactgct gggcagagaa gcttgggcag gcctggcact gaggcccaga agcttcatgc   15840
tctttagagc cagaggtgtc aagcccagct gcctgtgtcc tggccgcact gtgaggcact   15900
gaggatgccc tcacacgtgc atctgcatgt ggcgtgcatg tggcaagcat gtgcaggtgc   15960
tgtgtgggca cgatcatgcc tgccctctac tgtgctggag aggtaagacc atcagccgtt   16020
tcacagagga gggaatgtgg acctcacggg ggtctcatga gcttgcgagc cgatggccag   16080
gcagccggtg cagaaggttc atccattttg atgaaccgtg aattcatctg tactttattc   16140
attttaataa ctgaatcata cctcattgta tggctctacc atgtttt att atccattcag   16200 gtgctaacgg atggaagggt tgtttctacc tgttggccat tgtggatgat gttgctatgc   16260
atattggggt acgagtatct ggtttagtcc ctgttttcaa ttcttggtat acacctagga   16320
gtagaattgc tgggtcatat ggtagttcta ttttaacttt tttttatttt taattttgt   16380 gggttttaa gaatttttta atatttgtgg gtgcatagca tgtttaattt tttttttttt   16440
tttgagacgg ggtcttgctc tgttcccag gctggagtgc agtggcagga tcacagccct   16500
gtgcagcctc aacctcctgg gctcaggtga tcctcccgcc tcagcctccc aagtatctgg   16560
gactacacgt gcggaccacc acgcctggct aattttaag tttttgtag agatggggtc   16620 ttgccatgtt tcccagactg gtatgggact cctgggctca agcaatcctc ccatcccaac   16680
ctcccaaagt gctggaatta cagtcatgag ccaccaggtc tgaccacatg tttaactttt   16740
tgaagaacta ccaaactgtt ttccacggca ttcacaccag caatgcaaga gggttcccat   16800
ttcatcacat ccttgctaac acttgttatt ttccttaaaa aaaaaaaaaa aaaaagcca   16860 gctgggcacg gtggctcatg catgtaatcc cagcactttg gaaggccaag ggggtggagc   16920
acttgagctc aggagactag cctgggcaaa atatcgagac cccacctcca ctccatctct   16980
```

-continued

```
accaaaaaaa aaaaaaaaaa aaagctgggt gtgcggtggt gcacatctgt cgtcccagct  17040 acttggggggg gctgaggcag gaggatccct tgagcccagg aggtcgagac tgcagtgagc  17100
tgcgaccgcg ccactgcact ccaggctgag cgacagagtg agaccctgtt tcaaaaaaac  17160
aaaaaaaaag cacatttcaa acatacacaa aagcagagag aattcccctc ggtcctccgg  17220
cctgcacccc accgcccccc accacagggg cattcaaaac tgtctttttg cctctctgta  17280
aggtaagggg ggactcttga cgctccccag accacacagc caaagtaggg cgatcggatc  17340
atagggggtc ccgagtcgga cactgagctg gcgtgcccac tctcgagtcc tgggacccca  17400
aactaaagga gctgttcctt ttccccatgg agggctgacg gggcaaaatc ccagggctgg  17460
gaacatccga gcagctttga gtagcacagg tgggtttcta cgtggctttc tttaaaggga  17520
ggcctgattc tcggcttttc aggacccgcc ctccattttc tcacttgcct gctctttcgt  17580
cctgcgaaac tgggcagtgg ccggtgacag cgcagggtca gccctcggat ggccaggtgg  17640
gcgtgatccc accctcctcc gtggctgggg gggcgtggtc ccaaagtcaa ttggatgtgg  17700
tcccgcgtcc ctcccggccc agtgggcggg gcctcccctt ctggggcctc ccatcccaca  17760
ccagcgagca gagaggaggg tgggcgggga ggccctacgg ggctggggcg gggcggagcg  17820
gaggtggtta gctgtcggga ggtgggggtgg gcagggccca gggctctgtt ggtggcccgg  17880
ggcagccagt ccctctgctc agggcttcag ttcacactca caagggaatc ccagcgctct  17940
tctcctctgg cggttgctgg agggccttgt gaggtggccg tgggcactgt agcccccagg  18000
cactgcattg tggcctgggc gtgttggcct ttgagccttt ggccttgagc acttccccat  18060
cccccatggc tcttggccgt tggggcccag ttggccgcag agcctttggc cttgagcact  18120
tccccagccc ccatggctct tggccattgg accccagttg gccacagagc cgcgggcagg  18180
tgggacaggc gggcactggg tgcctccttg caccagccag gcccagcctg cagagtggag  18240
tgggccggtc cctcctgcca ggcaaaggaa gggggcttcg ggcccctccc tgctgtggcc  18300
tcctcccctc tgctgcctcc cactaggccc tgggagacac tgcctgcaga tttatgaaca  18360
gacagaccta gagattagag attcaaaagc caaattctta cacaattcaa gtattaacgc  18420
agatttggat ttataatttg ggactccaag gtctaccaag taatttgctg tttcagaata  18480 gccctttta tttggggtat atatttctaa cactgttttt taaatatgga gagtaaacaa  18540
aatggcccat tatctgacca cacaaatact agtagtcatt atagataaac catagcagat  18600
aaataatagt aaacaaagca acaggctgtg tcataggaaa tccccaccat gaagaaagga  18660
gcaaggtgga aagttctggc tgcttcaggt ctgcatggtc cctctccacc atggttcccc  18720
ctgtcatctt cctgccagaa taaggacact gtccttaggg aagcaccatc tcttgttttt  18780
tccccacgag ccctgtgggt catggcacgt cctgccccgc tgggaaacac agtgggccac  18840
gggtttccct gcaggcctgg gacccttccc aagggtagca gcagaaggca gcacgattcc  18900
cactcctgca gctgtggaca ggggcacccc cactgtcact gagccctgca ccgggttcca  18960
tcacctgctc ggggctctgg cctttggcct tttcctgtga gctgcatgtt ggccactgtg  19020
acctatctgt ctcatcatct ttttcttact ggtttgtgta tgttcttggt aaactagccc  19080
ttggtcttac acatcatttc caaggtacta aggactcttc aggggaaata caacttgagc  19140
agagtggttc cctcctcttg tggttcacaa ggtgcaggtg cacacacaca tagcccacag  19200
ggcagtgtgg acagggacca ggagactgcc cctgggggtcc ctggctgggg gacactagta  19260
gggatgtccc ttggcctctc tgaggccttc tgctgtctct tctgaggccg gaaaggcgaa  19320
gcactgccct cgccctgcta gggaaggctc aggccaggct ggccctatcc ggggaagggg  19380
```

-continued

```
ctcaggtatc tggaccttgg tcatcgccag gttagggttt atgttgatga ttatccaaag   19440
gcaaaattga tttccacaga aataacatct gctttgctgc cgagctcaga ggagacccca   19500
gacccctccc gcagccagag ggctggagcc tgctcagagg tgctttgaag gtgagttggc   19560
caacggaagc cggggcagtg ccagggtggg tacagattcc ggcccggtgc atgggcacag   19620
gtctgctgag cacatgtcca ctctgcctgt gtaaataggc cacatggcct gaaatcccct   19680
agaagcctgg tgtccgcatg acctcccct agggcggagc ctctgcttcc ctgttctctt   19740
ctgctctgtc ctctggtgcc ctgaggctgg cctccagggg tgtccctct gtggccctag    19800 gcctgcctcc ttgcctgggt gtgcctttct aaaatggagc gtccagcaga gagtgggatc   19860
tcctatgcca ctgggagccc agggccccat cccagaaaga cctctgagtg agcacagggg   19920
ccctagaaga agtttccttg tgtccttccc gtttttagggt ctgtgacctg aacccctggg  19980
cttctgcctc aggcctcctg tgctctgctc tctgcctgct gggtcccctc accaggcttc   20040
tgtctggttc ccaggctacc tgcctggagg gtcacaccag gaggatttca aacaggtttc   20100
aagtggggtc acttgccatc actgtgcccc acgaggtaca ctgttgtggg cggcagggct   20160
ggcctttctc atctgggaca tgccacgttg ctgttcccaa ggggagtggt gagtgggtct   20220
gtcctggtgt gcctggcctg gggactgcca gtgtccttac ttggacactc aatgaaaagg   20280
ccacatgaat ccctggggcg tccagagcat gggtgaccag cacgggctca ccacatgagg   20340
ccaaggggct gcaccataca gcctctcctt tggccacccg tgactacccc caactccggg   20400 ccatgggct tccctacccc tgggtgtcct ctaagccagc tgggagacaa cagcctgagt    20460
ccgtgtctgc ttctgtattt tgtgtggttt tagaggatcc ctgggctgcc tggggaagca   20520
cccagggcca gggagtgtga ccctgcaggc tccacacagg actgccagag gcacacacct   20580
gctctgtcta cccgagggca ccagagggca cgagaaggct ggctccctgg cgctgacacg   20640
tcaggcaact gaggcacaag gctggcattt ctgaaccttg cccctctgca aacacaaggg   20700
ggcgatggtg gcactccaag caaagggggcg tgtgggtgct gcaggaggag cacagagcac   20760
tggcgcccct cccctcccgc cctgcagatg ccggaggccc cgcctctgct gttggcagct   20820
gtgttgctgg gcctggtgct gctggtggtg ctgctgctgc ttctgaggca ctggggctgg   20880
ggcctgtgcc ttatcggctg gaacgagttc atcctgcagc ccatccacaa cctgctcatg   20940
ggtgacacca aggagcagcg catcctgaac cacgtgctgc agcatgcgga gcccgggaac   21000
gcacagagcg tgctggaggc cattgacacc tactgcgagc agaaggagtg ggccatgaac   21060
gtgggcgaca agaaggtgg ggtccgggcc agcaggtgct cagctctggg acagggaccc    21120
aggaccaggc atcaaagccc ttacaggaga agctgttatc accccatttc caggggggctg  21180 ggaaccctgg gatatgccca gatagggctg gggggctcct ctggagtccc agggtgccag   21240
ggtccctgat gacccctgca ggccctgctg cctgctgccc caggacaaca ggcccccaca   21300
ctcacagggt ctgacggtgg tgcagttccc cttgaactct gttctggcca ccatgggacc   21360
tgcctgggga ccagtcagac aggttctcct gggcccgcct cccgcttgaa cttcagcctg   21420
gggcacagga tgtgttaccg ggctcacgga gtgactcagg gaactagtgc cgccccaggg   21480
ccccaaggtg ggcggttcgg tgattcagag agggcagctc tgtgttagga cacactgggg   21540
ccagccagga agggtggaaa agatagggac cagcgtgagc atagaggcta agggaccatg   21600
ggagctccaa gcgcgctcac agtggggacc aggtcctggg ggctggggac accagggagg   21660
tgaaataccc ctccagcggg tagggagggt gggcagagga gggccagcgg ccaggcattt   21720
```

-continued

```
gggaggggct cctgctcttt gggagaggtg gggggccgtg cctggggatc caagttcccc   21780
tctctccacc tgtgctcacc tctcctccgt ccccaaccct gcacaggcaa gatcgtggac   21840
gccgtgattc aggagcacca gccctccgtg ctgctggagc tgggggccta ctgtggctac   21900
tcagctgtgc gcatggcccg cctgctgtca ccaggggcga ggctcatcac catcgagatc   21960
aaccccgact gtgccgccat cacccagcgg atggtggatt tcgctggcgt gaaggacaag   22020
gtgtgcatgc ctgacccgtt gtcagacctg gaaaaagggc cggctgtggg cagggagggc   22080
atgcgcactt tgtcctcccc accaggtgtt cacaccacgt tcactgaaaa cccactatca   22140
ccaggcccct cagtgcttcc cagcctgggg ctgaggaaag accccccag cagctcagtg   22200 agggtctcac agctctgggt aaactgccaa ggtggcacca ggaggggcag ggacagagtg   22260
gggccttgtc atcccagaac cctaaagaaa actgatgaat gcttgtatgg gtgtgtaaag   22320
atggcctcct gtctgtgtgg gcgtgggcac tgacaggcgc tgttgtatag gtgtgtaggg   22380
atggcctcct gtctgtgagg acgtgggcac tgacaggcgc tgttccaggt caccttgtg   22440 gttggagcgt cccaggacat catcccccag ctgaagaaga agtatgatgt ggacacactg   22500
gacatggtct tcctcgacca ctggaaggac cggtacctgc cggacacgct tctcttggag   22560
gtgagcccca accaggatgg catccgtgcc agctgctgcc cagagcccat tcagtcagcc   22620
tcagcctctc caaagagcca ggcattccag tagagccctg tgtggacaca gctcgctctg   22680
gaggcaccac ctgaggtctg ggagtgtggg ggactgagga ggccctgtgg tgggtggaga   22740
tgggtgggga gctgggccag gggcctggct gggtggcctg ttgggaactg gggagccagc   22800
tgcctgtgca ggtgcaaaat gggtggcaga agtggggtgc acaccccaga ccagacacca   22860
gggcagaaac ggcacaggac caaggagatg gggtggggaa gggccgctct gggcccagcc   22920
tgctctcccc caagcaagcc actgctcgtg caaagaaagc atgtgtctcc tgcagatctt   22980
cctcctgagg ccccatcttg tgcattcccc caacccagcc ccactggcga ggaccctgag   23040
tgccccgagt gaggctagac agcgggtggg gctgtcctcg cttccctggg gggcgtgggg   23100
cactggtggc ccttcacaga ctgatgctta aggagcctca catcagtgac acactgcccc   23160
atccctccct ggtggtcagc gacactgagt ggctctgtga tcctccactg ggcttgggac   23220
acccaccctc acggcctccc cacctggtgc tcgctcacct gcagctctcc cagaaactgg   23280
acactgctgt tagcagccgg actaggagca cgaggggcac agcccccatg cctggctagg   23340
tagggccgct ggaccctgga cacggattgg aaggaaccag cactagcaga agcctgaggt   23400
gtgaaagggc agagaatgtt ccaggaacaa tgggagtcag ggcacacagg actttgggca   23460
ggtgaggatg aggttagacc tgtcttctgg agctgggctc aggggctcat gcctgtaacc   23520
cttgcacttt gggaggctac ggcaggagga gcgcttgagg ccaggagagt tcgagaccag   23580
cctgggcaac atggcaaaag aaaaaatata tatatatatt ttagatggag tcttgctctg   23640
tcaccaggct ggagtgcagt ggcacgatca cggctcactg caacctccac ctcttgggtt   23700
caagcgatta ccctgcctta gcctcctgag tagctggac tacaggcgcg cgctgccaca   23760
cccggctagt tttttgtagt ttagtagaga tggggtttca ccacattggc caggatggtc   23820
tcaatatcct gacttcgtga tccgcccgcc tcggcctccc aaagtgctgg gattacaggc   23880
gtgagccact gcgtccggcc gtattccagc tttcaaaaca acaaaaaaca acaaaaactt   23940
ttctggaaag atccctgtca gccttgtgga gtgtggagag ggctgtgggg agggcatttc   24000
agatgccctg aactcacgag gaggcactga accctggccg tggagaggga ggacctgtag   24060
tggccaaggg ggtgggcatt gggagggtgg gagggagacc tacaggccaa gacagggtag   24120
```

-continued

```
ctggaggggg gctcacccct gacaaaggag catgatgctg gcaattgggt attgatggca    24180
gagagctggc actcagccag atgggcttca cttgggcagg aaagacaccc acagctgggc    24240
ctgcgttact gcggccgagt ttcagcagct gtgatgtggg tgctaattac aggggcctgc    24300
cttcatagaa aagtagcaaa cattgcagtt tagtaactag gaaactaata gttttctcag    24360
tgctgcttgc gcaaagctgg taattatctc aaaagaagca aagtcatgaa gtgggaagtc    24420
atgaattggg aatgggtgtc cttgttaaac gcacatctgc acactcaggg ctggggccct    24480 gtgcccctt gtggagggtt aggggacaac ctggctcttg tgagggtcta gccatcccct    24540
cagtgggttc tgtgagcatc ggaggcacga ggggtgaggg gctcaggagc aggttgcaat    24600
tcaaaatcaa gggctgcttt gaggaggcct ctccaccggg ctgctgtagt caccaagtcc    24660
agcccatgcc caaaggaaga ggaatgagtt cccccttaaa aaaaaaaaa aaaaagaaa    24720 aagacagagt cttgctctgt gcccaggctg gagtgcagtg atgacatcat agctcactgt    24780
agcctcaaac tcctgagctc cagtgatcct cccacctcag cctcctgagt agctaggact    24840
aaaggcatgc accactacac ctggctaatt taaaaatttt ttgtagaaat ggggtctccc    24900
tatgttgccc agactggtct caaactcctg gcctcaagcg atcctcttgc ctcaacctcc    24960
caaagtgctg ggagtacagg tgtgtgcttg gtctgaggct ccaactttt gttgttgttt    25020 ctcgagacag tctctcgctc tgtcgcccag gctggagtgc agtggcgcga tcttggctcc    25080
ctgcaacctc tgtgaggctc caactcttga agggaggaga gtctaaggag ggtgggccag    25140
atgaaaacca cctcagcata gtgtcacctg ctcctctgac actgtcgctt ctccacggca    25200
ttagattttc agtcctgctc agacgctgat gcatgtttag ccagttctcc aggtggtctg    25260
agtagctggt aggaggcttg cagtgtcggg cgacaggcag acaggtgct gccttctttc    25320 ccctcttgac cagtttcgta aaggagtggg cccctggcag cctccaaagg tgacccatgc    25380
tcctttctgc ccttccctcc ttctttcctg tttaactcgt gcaggtgcag tggtctggtg    25440
tctttcagtc cgctgacgtc ttctgtatcc ctgatgacca gattgggctc ctgagtcccc    25500
tggcgcaacc cgagaagtcc aggagcccag gccctcact catgcattcc ctggcccaga    25560
ctggaaggca gccgccctgc tcaaggccta ggccattgtc ctcctcccgg gtggcgcttt    25620
gttctacgtc ttttcagctg acattgctag gacattttt ttttttta aatgaaaaca    25680 catcatgatt catggtggta cttcctgctc aactccggac cttggggctg tcccctgacc    25740
tcactgacct tgcagccgtg tggtgtccat actgtcacat gaaagccccc tgctttctct    25800
gcagcataca ggctggaaac gaccgccacc caccaccagg acagctgcaa gccctgtggg    25860
actctccagg cccatcccag aggcatgtgg ggtcggatac cagtgtttca aggcacctgc    25920
ctgcaaattg attttattat actttagatg tttgagattg cttgttaact tttgtttggt    25980
gactaagtca aatttccaag acaaggtgac tggggtgtcc cttgccctgg taggtccttc    26040
ctccccatag gcaaacactt cctctcaagg tttcttgttt atgtgatgta agcaaaccct    26100
tttctgatag catagatagg caagcatcct atgaggtttc tcccgatagt ggaccccacg    26160
ggccatgccc tatggctgcg tgtccagtaa caactccttc cttctgcaca gaacccaggc    26220
agaggaactc tgtgtcctcc cagggcccag gcactggtga agatggggg tctgcaaatg    26280 caggagcttg gggatgtcca gaactgaccc caaggggcag gcttgttgat gggaggtctg    26340
ccccacctca gccctgcagg gtcaccctgg tcaggccaat attgtctcca gggaccatac    26400
cagcaacccc tctccttggg tgcctctccc tcataggcct gagttcctgg cactgggtgt    26460
```

```
tgagggcccc attgtttcca ctcacccagc tagcatttat tgagcaccta ctgtgtgcca    26520
catgctgttc taagggatgg atactcctga gatggataca ggagttgatg agagaaaggt    26580
ccctgtcctc acggggccca tgttctgaag gtggcaccca agtcttgtac agtcctttcc    26640
tgcaggagtc acgctgggca gaaagtggaa acctggcccc aggggctagg cacaggcgtg    26700
gtgccgtggc ctagtgagga gcacccatcc tggtttgggg caggttctct gggcacctct    26760
gaccctcacc tccccaccc cccggtctgt ttgcaggaat gtggcctgct gcggaagggg     26820
acagtgctac tggctgacaa cgtgatctgc ccaggtgcgc cagacttcct agcacacgtg    26880
cgcgggagca gctgctttga gtgcacacac taccaatcgt tcctggaata cagggaggtg    26940
gtggacggcc tggagaaggc catctacaag ggcccaggca gcgaagcagg gccctgactg    27000
cccccccggc cccctctcg ggctctctca cccagcctgg tactgaaggt gccagacgtg     27060
ctcctgctga ccttctgcgg ctccgggctg tgtcctaaat gcaaagcaca cctcggccga    27120
ggcctgcgcc ctgacatgct aacctctctg aactgcaaca ctggattgtt cttttttaag    27180
actcaatcat gacttcttta ctaacactgg ctagctatat tatcttatat actaatatca    27240
tgttttaaaa atataaaata gaaattaaga atctaaatat ttagatataa ctcgacttag    27300
tacatccttc tcaactgcca ttcccctgct gcccttgact tgggcaccaa acattcaaag    27360
ctccccttga cggacgctaa cgctaagggc ggggcccta gctggctggg ttctgggtgg     27420
cacgcctggc ccactggcct cccagccaca gtggtgcaga ggtcagccct cctgcagcta    27480
ggccaggggc acctgttagc cccatgggga cgactgccgg cctgggaaac gaagaggagt    27540
cagccagcat tcacaccttt ctgaccaagc aggcgctggg gacaggtgga ccccgcagca    27600
gcaccagccc ctctgggccc catgtggcac agagtggaag catctccttc cctactcccc    27660
actgggcctt gcttacagaa gaggcaatgg ctcagaccag ctcccgcatc cctgtagttg    27720
cctccctggc ccatgagtga ggatgcagtg ctggtttctg cccacctaca cctagagctg    27780
tccccatctc ctccaagggg tcagactgct agccacctca gaggctccaa gggcccagtt    27840
cccaggccca ggacaggaat caaccctgtg ctagctgagt tcacctgcac cgagaccagc    27900
ccctagccaa gattctactc ctgggctcaa ggcctggcta gcccccagcc agcccactcc    27960
tatggataga cagaccagtg agcccaagtg dacaagtttg gggccaccca gggaccagaa    28020
acagagcctc tgcaggacac agcagatggg cacctgggac cacctccacc cagggccctg    28080
ccccagacgc gcagaggccc gacacaaggg agaagccagc cacttgtgcc agacctgagt    28140
ggcagaaagc aaaaagttcc tttgctgctt taatttttaa attttcttac aaaaatttag    28200
gtgtttacca atagtcttat tttggcttat ttttaa                               28236
```

```
<210> SEQ ID NO 43
<211> LENGTH: 3952
<212> TYPE: DNA
<213> ORGANISM: Homo sapiens
<220> FEATURE:
<221> NAME/KEY: CDS
<222> LOCATION: (127)..(1989)

<400> SEQUENCE: 43
```

```
cgctgcggag cgggagggga ggcttcgcgg aacgctctcg gcgccaggac tcgcgtgcaa     60
agcccaggcc cgggcggcca gaccaagagg gaagaagcac agaattcctc aactcccagt    120 gtgccc atg agt aag agc aaa tgc tcc gtg gga ctc atg tct tcc gtg      168
       Met Ser Lys Ser Lys Cys Ser Val Gly Leu Met Ser Ser Val
        1               5                   10
```

-continued

```
gtg gcc ccg gct aag gag ccc aat gcc gtg ggc ccg aag gag gtg gag    216
Val Ala Pro Ala Lys Glu Pro Asn Ala Val Gly Pro Lys Glu Val Glu
15              20              25              30 ctc atc ctt gtc aag gag cag aac gga gtg cag ctc acc agc tcc acc    264
Leu Ile Leu Val Lys Glu Gln Asn Gly Val Gln Leu Thr Ser Ser Thr
                35              40              45 ctc acc aac ccg cgg cag agc ccc gtg gag gcc cag gat cgg gag acc    312
Leu Thr Asn Pro Arg Gln Ser Pro Val Glu Ala Gln Asp Arg Glu Thr
            50              55              60 tgg ggc aag aag atc gac ttt ctc ctg tcc gtc att ggc ttt gct gtg    360
Trp Gly Lys Lys Ile Asp Phe Leu Leu Ser Val Ile Gly Phe Ala Val
        65              70              75 gac ctg gcc aac gtc tgg cgg ttc ccc tac ctg tgc tac aaa aat ggt    408
Asp Leu Ala Asn Val Trp Arg Phe Pro Tyr Leu Cys Tyr Lys Asn Gly
    80              85              90 ggc ggt gcc ttc ctg gtc ccc tac ctg ctc ttc atg gtc att gct ggg    456
Gly Gly Ala Phe Leu Val Pro Tyr Leu Leu Phe Met Val Ile Ala Gly
95              100             105             110 atg cca ctt ttc tac atg gag ctg gcc ctc ggc cag ttc aac agg gaa    504
Met Pro Leu Phe Tyr Met Glu Leu Ala Leu Gly Gln Phe Asn Arg Glu
                115             120             125 ggg gcc gct ggt gtc tgg aag atc tgc ccc ata ctg aaa ggt gtg ggc    552
Gly Ala Ala Gly Val Trp Lys Ile Cys Pro Ile Leu Lys Gly Val Gly
            130             135             140 ttc acg gtc atc ctc atc tca ctg tat gtc ggc ttc ttc tac aac gtc    600
Phe Thr Val Ile Leu Ile Ser Leu Tyr Val Gly Phe Phe Tyr Asn Val
        145             150             155 atc atc gcc tgg gcg ctg cac tat ctc ttc tcc tcc ttc acc acg gag    648
Ile Ile Ala Trp Ala Leu His Tyr Leu Phe Ser Ser Phe Thr Thr Glu
    160             165             170 ctc ccc tgg atc cac tgc aac aac tcc tgg aac agc ccc aac tgc tcg    696
Leu Pro Trp Ile His Cys Asn Asn Ser Trp Asn Ser Pro Asn Cys Ser
175             180             185             190 gat gcc cat cct ggt gac tcc agt gga gac agc tcg ggc ctc aac gac    744
Asp Ala His Pro Gly Asp Ser Ser Gly Asp Ser Ser Gly Leu Asn Asp
                195             200             205 act ttt ggg acc aca cct gct gcc gag tac ttt gaa cgt ggc gtg ctg    792
Thr Phe Gly Thr Thr Pro Ala Ala Glu Tyr Phe Glu Arg Gly Val Leu
            210             215             220 cac ctc cac cag agc cat ggc atc gac gac ctg ggg cct ccg cgg tgg    840
His Leu His Gln Ser His Gly Ile Asp Asp Leu Gly Pro Pro Arg Trp
        225             230             235 cag ctc aca gcc tgc ctg gtg ctg gtc atc gtg ctg ctc tac ttc agc    888
Gln Leu Thr Ala Cys Leu Val Leu Val Ile Val Leu Leu Tyr Phe Ser
    240             245             250 ctc tgg aag ggc gtg aag acc tca ggg aag gtg gta tgg atc aca gcc    936
Leu Trp Lys Gly Val Lys Thr Ser Gly Lys Val Val Trp Ile Thr Ala
255             260             265             270 acc atg cca tac gtg gtc ctc act gcc ctg ctc ctg cgt ggg gtc acc    984
Thr Met Pro Tyr Val Val Leu Thr Ala Leu Leu Leu Arg Gly Val Thr
                275             280             285 ctc cct gga gcc ata gac ggc atc aga gca tac ctg agc gtt gac ttc    1032
Leu Pro Gly Ala Ile Asp Gly Ile Arg Ala Tyr Leu Ser Val Asp Phe
            290             295             300 tac cgg ctc tgc gag gcg tct gtt tgg att gac gcg gcc acc cag gtg    1080
Tyr Arg Leu Cys Glu Ala Ser Val Trp Ile Asp Ala Ala Thr Gln Val
        305             310             315 tgc ttc tcc ctg ggc gtg ggg ttc ggg gtg ctg atc gcc ttc tcc agc    1128
Cys Phe Ser Leu Gly Val Gly Phe Gly Val Leu Ile Ala Phe Ser Ser
        320             325             330
```

-continued

```
tac aac aag ttc acc aac aac tgc tac agg gac gcg att gtc acc acc    1176
Tyr Asn Lys Phe Thr Asn Asn Cys Tyr Arg Asp Ala Ile Val Thr Thr
335             340             345             350 tcc atc aac tcc ctg acg agc ttc tcc tcc ggc ttc gtc gtc ttc tcc    1224
Ser Ile Asn Ser Leu Thr Ser Phe Ser Ser Gly Phe Val Val Phe Ser
            355             360             365 ttc ctg ggg tac atg gca cag aag cac agt gtg ccc atc ggg gac gtg    1272
Phe Leu Gly Tyr Met Ala Gln Lys His Ser Val Pro Ile Gly Asp Val
            370             375             380 gcc aag gac ggg cca ggg ctg atc ttc atc atc tac ccg gaa gcc atc    1320
Ala Lys Asp Gly Pro Gly Leu Ile Phe Ile Ile Tyr Pro Glu Ala Ile
            385             390             395 gcc acg ctc cct ctg tcc tca gcc tgg gcc gtg gtc ttc ttc atc atg    1368
Ala Thr Leu Pro Leu Ser Ser Ala Trp Ala Val Val Phe Phe Ile Met
    400             405             410 ctg ctc acc ctg ggt atc gac agc gcc atg ggt ggt atg gag tca gtg    1416
Leu Leu Thr Leu Gly Ile Asp Ser Ala Met Gly Gly Met Glu Ser Val
415             420             425             430 atc acc ggg ctc atc gat gag ttc cag ctg ctg cac aga cac cgt gag    1464
Ile Thr Gly Leu Ile Asp Glu Phe Gln Leu Leu His Arg His Arg Glu
                435             440             445 ctc ttc acg ctc ttc atc gtc ctg gcg acc ttc ctc ctg tcc ctg ttc    1512
Leu Phe Thr Leu Phe Ile Val Leu Ala Thr Phe Leu Leu Ser Leu Phe
            450             455             460 tgc gtc acc aac ggt ggc atc tac gtc ttc acg ctc ctg gac cat ttt    1560
Cys Val Thr Asn Gly Gly Ile Tyr Val Phe Thr Leu Leu Asp His Phe
            465             470             475 gca gcc ggc acg tcc atc ctc ttt gga gtg ctc atc gaa gcc atc gga    1608
Ala Ala Gly Thr Ser Ile Leu Phe Gly Val Leu Ile Glu Ala Ile Gly
    480             485             490 gtg gcc tgg ttc tat ggt gtt ggg cag ttc agc gac gac atc cag cag    1656
Val Ala Trp Phe Tyr Gly Val Gly Gln Phe Ser Asp Asp Ile Gln Gln
495             500             505             510 atg acc ggg cag cgg ccc agc ctg tac tgg cgg ctg tgc tgg aag ctg    1704
Met Thr Gly Gln Arg Pro Ser Leu Tyr Trp Arg Leu Cys Trp Lys Leu
            515             520             525 gtc agc ccc tgc ttt ctc ctg ttc gtg gtc gtg gtc agc att gtg acc    1752
Val Ser Pro Cys Phe Leu Leu Phe Val Val Val Val Ser Ile Val Thr
            530             535             540 ttc aga ccc ccc cac tac gga gcc tac atc ttc ccc gac tgg gcc aac    1800
Phe Arg Pro Pro His Tyr Gly Ala Tyr Ile Phe Pro Asp Trp Ala Asn
            545             550             555 gcg ctg ggc tgg gtc atc gcc aca tcc tcc atg gcc atg gtg ccc atc    1848
Ala Leu Gly Trp Val Ile Ala Thr Ser Ser Met Ala Met Val Pro Ile
    560             565             570 tat gcg gcc tac aag ttc tgc agc ctg cct ggg tcc ttt cga gag aaa    1896
Tyr Ala Ala Tyr Lys Phe Cys Ser Leu Pro Gly Ser Phe Arg Glu Lys
575             580             585             590 ctg gcc tac gcc att gca ccc gag aag gac cgt gag ctg gtg gac aga    1944
Leu Ala Tyr Ala Ile Ala Pro Glu Lys Asp Arg Glu Leu Val Asp Arg
            595             600             605 ggg gag gtg cgc cag ttc acg ctc cgc cac tgg ctc aag gtg tag        1989
Gly Glu Val Arg Gln Phe Thr Leu Arg His Trp Leu Lys Val
            610             615             620 agggagcaga gacgaagacc ccaggaagtc atcctgcaat gggagagaca cgaacaaacc    2049
aaggaaatct aagtttcgag agaaaggagg gcaacttcta ctcttcaacc tctactgaaa    2109
acacaaacaa caaagcagaa gactcctctc ttctgactgt ttacaccttt ccgtgccggg    2169
```

-continued

```
agcgcacctc gccgtgtctt gtgttgctgt aataacgacg tagatctgtg cagcgaggtc   2229
caccccgttg ttgtccctgc agggcagaaa aacgtctaac ttcatgctgt ctgtgtgagg   2289
ctccctccct ccctgctccc tgctcccggc tctgaggctg ccccaggggc actgtgttct   2349
caggcgggga tcacgatcct tgtagacgca cctgctgaga atccccgtgc tcacagtagc   2409
ttcctagacc atttactttg cccatattaa aaagccaagt gtcctgcttg gtttagctgt   2469
gcagaaggtg aaatggagga aaccacaaat tcatgcaaag tcctttcccg atgcgtggct   2529
cccagcagag gccgtaaatt gagcgttcag ttgacacatt gcacacacag tctgttcaga   2589
ggcattggag gatgggggtc ctggtatgtc tcaccaggaa attctgttta tgttcttgca   2649
gcagagagaa ataaaactcc ttgaaaccag ctcaggctac tgccactcag gcagcctgtg   2709
ggtccttgcg gtgtagggaa cggcctgaga ggagcgtgtc ctatccccgg acgcatgcag   2769
ggcccccaca ggagcgtgtc ctatccccgg acgcatgcag ggcccccaca ggagcatgtc   2829
ctatccctgg acgcatgcag ggcccccaca ggagcgtgta ctaccccaga acgcatgcag   2889
ggcccccaca ggagcgtgta ctaccccagg acgcatgcag ggccccacct ggagcgtgta   2949
ctaccccagg acgcatgcag ggccccaca ggagcgtgtc ctatccccgg accggacgca   3009
tgcagggccc ccacaggagc gtgtactacc ccaggacgca tgcagggccc ccacaggagc   3069
gtgtactacc ccaggatgca tgcagggccc ccacaggagc gtgtactacc ccaggacgca   3129
tgcagggccc ccatgcaggc agcctgcaga ccacactctg cctggccttg agccgtgacc   3189
tccaggaagg gaccccactg gaatttt att tctctcaggt gcgtgccaca tcaataacaa   3249
cagtttttat gtttgcgaat ggcttttt aa aatcatattt acctgtgaat caaaacaaat   3309
tcaagaatgc agtatccgcg agcctgcttg ctgatattgc agtttttgtt tacaagaata   3369
attagcaata ctgagtgaag gatgttggcc aaaagctgct ttccatggca cactgccctc   3429
tgccactgac aggaaagtgg atgccatagt ttgaattcat gcctcaagtc ggtgggcctg   3489
cctacgtgct gcccgagggc aggggccgtg cagggccagt catggctgtc ccctgcaagt   3549
ggacgtgggc tccagggact ggagtgtaat gctcggtggg agccgtcagc ctgtgaactg   3609
ccaggcagct gcagttagca cagaggatgg cttccccatt gccttctggg gagggacaca   3669
gaggacggct tccccatcgc cttctggccg ctgcagtcag cacagagagc ggcttcccca   3729
ttgccttctg gggagggaca cagaggacag cttccccatc gccttctggc tgctgcagtc   3789
agcacagaga gcggcttccc catcgccttc tggggagggg ctccgtgtag caacccaggt   3849
gttgtccgtg tctgttgacc aatctctatt cagcatcgtg tgggtcccta agcacaataa   3909
aagacatcca caatggaaaa actgcaaaaa aaaaaaaaaa aaa   3952
```

```
<210> SEQ ID NO 44
<211> LENGTH: 620
<212> TYPE: PRT
<213> ORGANISM: Homo sapiens

<400> SEQUENCE: 44

Met Ser Lys Ser Lys Cys Ser Val Gly Leu Met Ser Ser Val Val Ala
1               5                   10                  15

Pro Ala Lys Glu Pro Asn Ala Val Gly Pro Lys Glu Val Glu Leu Ile
            20                  25                  30

Leu Val Lys Glu Gln Asn Gly Val Gln Leu Thr Ser Ser Thr Leu Thr
        35                  40                  45

Asn Pro Arg Gln Ser Pro Val Glu Ala Gln Asp Arg Glu Thr Trp Gly
    50                  55                  60
```

-continued

```
Lys Lys Ile Asp Phe Leu Leu Ser Val Ile Gly Phe Ala Val Asp Leu
65              70              75              80

Ala Asn Val Trp Arg Phe Pro Tyr Leu Cys Tyr Lys Asn Gly Gly Gly
                85              90              95

Ala Phe Leu Val Pro Tyr Leu Leu Phe Met Val Ile Ala Gly Met Pro
            100             105             110

Leu Phe Tyr Met Glu Leu Ala Leu Gly Gln Phe Asn Arg Glu Gly Ala
            115             120             125

Ala Gly Val Trp Lys Ile Cys Pro Ile Leu Lys Gly Val Gly Phe Thr
        130             135             140

Val Ile Leu Ile Ser Leu Tyr Val Gly Phe Phe Tyr Asn Val Ile Ile
145             150             155             160

Ala Trp Ala Leu His Tyr Leu Phe Ser Ser Phe Thr Thr Glu Leu Pro
                165             170             175

Trp Ile His Cys Asn Asn Ser Trp Asn Ser Pro Asn Cys Ser Asp Ala
                180             185             190

His Pro Gly Asp Ser Ser Gly Asp Ser Ser Gly Leu Asn Asp Thr Phe
            195             200             205

Gly Thr Thr Pro Ala Ala Glu Tyr Phe Glu Arg Gly Val Leu His Leu
            210             215             220

His Gln Ser His Gly Ile Asp Asp Leu Gly Pro Pro Arg Trp Gln Leu
225             230             235             240

Thr Ala Cys Leu Val Leu Val Ile Val Leu Leu Tyr Phe Ser Leu Trp
                245             250             255

Lys Gly Val Lys Thr Ser Gly Lys Val Val Trp Ile Thr Ala Thr Met
            260             265             270

Pro Tyr Val Val Leu Thr Ala Leu Leu Leu Arg Gly Val Thr Leu Pro
            275             280             285

Gly Ala Ile Asp Gly Ile Arg Ala Tyr Leu Ser Val Asp Phe Tyr Arg
        290             295             300

Leu Cys Glu Ala Ser Val Trp Ile Asp Ala Ala Thr Gln Val Cys Phe
305             310             315             320

Ser Leu Gly Val Gly Phe Gly Val Leu Ile Ala Phe Ser Ser Tyr Asn
                325             330             335

Lys Phe Thr Asn Asn Cys Tyr Arg Asp Ala Ile Val Thr Thr Ser Ile
            340             345             350

Asn Ser Leu Thr Ser Phe Ser Ser Gly Phe Val Val Phe Ser Phe Leu
            355             360             365

Gly Tyr Met Ala Gln Lys His Ser Val Pro Ile Gly Asp Val Ala Lys
    370             375             380

Asp Gly Pro Gly Leu Ile Phe Ile Ile Tyr Pro Glu Ala Ile Ala Thr
385             390             395             400

Leu Pro Leu Ser Ser Ala Trp Ala Val Val Phe Phe Ile Met Leu Leu
                405             410             415

Thr Leu Gly Ile Asp Ser Ala Met Gly Gly Met Glu Ser Val Ile Thr
            420             425             430

Gly Leu Ile Asp Glu Phe Gln Leu Leu His Arg His Arg Glu Leu Phe
            435             440             445

Thr Leu Phe Ile Val Leu Ala Thr Phe Leu Leu Ser Leu Phe Cys Val
    450             455             460

Thr Asn Gly Gly Ile Tyr Val Phe Thr Leu Leu Asp His Phe Ala Ala
465             470             475             480
```

-continued

```
Gly Thr Ser Ile Leu Phe Gly Val Leu Ile Glu Ala Ile Gly Val Ala
            485                 490                 495

Trp Phe Tyr Gly Val Gly Gln Phe Ser Asp Asp Ile Gln Gln Met Thr
            500                 505                 510

Gly Gln Arg Pro Ser Leu Tyr Trp Arg Leu Cys Trp Lys Leu Val Ser
            515                 520                 525

Pro Cys Phe Leu Leu Phe Val Val Val Ser Ile Val Thr Phe Arg
        530                 535                 540

Pro Pro His Tyr Gly Ala Tyr Ile Phe Pro Asp Trp Ala Asn Ala Leu
545                 550                 555                 560

Gly Trp Val Ile Ala Thr Ser Ser Met Ala Met Val Pro Ile Tyr Ala
            565                 570                 575

Ala Tyr Lys Phe Cys Ser Leu Pro Gly Ser Phe Arg Glu Lys Leu Ala
            580                 585                 590

Tyr Ala Ile Ala Pro Glu Lys Asp Arg Glu Leu Val Asp Arg Gly Glu
            595                 600                 605

Val Arg Gln Phe Thr Leu Arg His Trp Leu Lys Val
    610                 615                 620

<210> SEQ ID NO 45
<211> LENGTH: 52579
<212> TYPE: DNA
<213> ORGANISM: Homo sapiens

<400> SEQUENCE: 45
agcccaggcc cgggcggcca ggtgaggcca gcgtcgctcg cggcatcggg gcgccccgct      60
ccttccgcag accccgaagt ggggcgcagg ggcggggggcc ggggaccggg cacagtctgg     120
ggtccccgcg tcccgcagac cgcgccgtct ccaaagtcgc caacagtcgc gggtgccgag     180 cgcccccga tagcgccaca tgggaccctg aggccgtccg aggcgcgagg agggtgcagg      240 gctgccctg gccccgctcc aggctcagaa ccgggtgggc acctggtgca gtcaccggct      300
taggggacgc gtgggtgtct atggctgtga ctcgggggtc ctggtttctt ctcgtggaac     360
ttaaccctac taggggtgcg cgcatcccca gatccgatcg gagtgggttt tgtacaccgc     420
cgctccatct cgcgggggct ttgtctgtgt tggggtggt ggcgggcgcg ggctgcgcgc      480
tggtgctctg ggcagggcgg ggaggccggg cgaggactcg ccaggcagcg ccgcttcttg     540
ttctgggcgc ggtgaggaag gacgctttct aacgggccac attttgctgt gtagacccaa     600
aactcgcctc tgaggccccg cgttcaggag cggggtcagg tggccccagg gcggcggcgg     660
cttgccggag actcgcgagc tccgcacccg acgccctctc ccaacgcggc ctcctgctcg     720
cgccgcggaa ccccttcgtc gggtgtttta cccaccggag gggtcgtgcc ggttgaggtt     780
gtcaccgggt gcgtggcata gctcgtgata gctcatgggt gaggtttgt gcaaacttgg      840 atgcagggaa agttgcctgt tagagcctcc acctgcgacc tgcttcagtc gttgtgtgtg     900
tgtgcgcacc tgtgtgagtg tgagtgtgta tgtgtgtaag tgtatgtgct cgcctgtgtg     960
tgtgtgagtg tgtatgtgtg tttgtgagtc tgtgtgtgtc tgtgtgtctg tgtgtgcgtg    1020
cgctcgactg aaacacgctg ctgctggatc caaatgacag aagtcgccct ggctgggggcg    1080 gtgtagacgc tcctgctctc ctgctcagcg ttgcaggggg gtttatgtag ccgtttggac    1140
aggatttccc gggttacccct gctggcccag gagctagttc ccgcgatgaa gccctgtcca    1200
tcctccgccc agctctctca cgcggggtgg tgccacctgc cctaggtgga gtgtggcttgt    1260 acagacactt tttgaggaag cagttgtgat ggttatgtct aaactctctt tacagtggct    1320
```

-continued

```
gattttgctt atataaattt tgctctttat tactgagtat aaacaataca agcccaggct   1380
tggtggctca tgcctgtcat ctcagcactt tgggaggctg aggcaggagg atcgcttgag   1440
accaggagtt caaaaccagc cttggcaaca atagtcagac cctgtctcta caaaaaaaca   1500
acaacaacaa caaaaaaaca cacacaaaaa taacttagcc ggtgctgtgg tgcacacctg   1560
tagtctcagc tgctcaggag gctgaggtgc aaggatcact tgaacctagg aggttgaggc   1620
agtgagttgt aatcacaact gtattccatc ctgggtgaca gagcgagacc tcatgttaaa   1680
aaagaaaaaa aaaagaaaaa agaatacaga tgaacagtca tgaagacatt attgaatgct   1740
cttagaagat tgtaaaattg ctctctggaa gtgtgggggga aggtggaagt gatatccatg   1800
cattgttagt agaaagccac gctagagctc acacagcctt gcactttgat aggagtgggg   1860
aggggtgcag gggaaggagg agcaaaccag agtgtctgtc ttgaggcctc catgggccag   1920
tgccccagcc ctgtggtgag ggctggcact tcccagctcc cgtgccccag ctgtaccatc   1980
tcaggcgctg agaacgcacc catcccttcc cagaggaatg cccgtgaatg cctcggggct   2040
ctgccctccg caccaggtat gtccctagcc ctggctgctg aattgttgcg ttcctgttgt   2100
gtgtttattt ttcatattgg ctgaagacca agagggaaga agcacagaat tcctcaactc   2160
ccagtgtgcc catgagtaag agcaaatgct ccgtgggact catgtcttcc gtggtggccc   2220
cggctaagga gcccaatgcc gtgggcccga aggaggtgga gctcatcctt gtcaaggagc   2280
agaacggagt gcagctcacc agctccaccc tcaccaaccc gcggcagagc cccgtggagg   2340
cccaggatcg ggagacctgg ggcaagaaga tcgactttct cctgtccgtc attggctttg   2400
ctgtggacct ggccaacgtc tggcggttcc cctacctgtg ctacaaaaat ggtggcggta   2460
agtcccatct cagcctccct gagcatgctg gccgggcggg ggtcgtaggg gcagccgggg   2520
ccaaggcacg tacggaaacg agatgaagct gttcccatgc gtgaagacgg agctccctgt   2580
gagagctcac ggccggtgca gatcctccca gaggatgtca caaaaccatt gagcaggact   2640
cggagctgcc ttgtcccacg cctgcatttc agagtttagg aaagggaggc ccgcgaagaa   2700
gctggggggt gggggggcggc agacggggca gcttggctct gcctcctgtt tccagaggct   2760
atcttcgctt tggaaagaaa attctcaaag gtccaaagaa cagcctgcgg ctgactttgg   2820
cagcctttgc aaagcatgtg gaggccctgg agcctggagt ggcagaggag gcccctggaa   2880
agtgactgtg tccctgcac cctccagaac ccagccacag agccagaaag cgaagatcga    2940
ggcagggcca ccggggacgt ccaagaacat tggtgatccc ttcccaggag cctctttggg   3000
cctcccagcc tccctgcctg gcctccctca ttggcctcta tgctaggtct gggaagggag   3060
gcctggggaa gaatctgggg ggaagcctca caggatgcct gcgaggaggc tggcattttt   3120
atgcccatct tgaagagggg aagacagagg cctcagcagg tacaggaagt tgcccaaaga   3180
cagagctgag gggcccccatg cctccccctc cccttcccca ggagagagag tggcaaagct   3240
ctccctcact ccagtcagac caggggagca gaggggaattt aggaggttga gaccaggggtt   3300 ccctgggctt tgtgctgggg gtgggggagg tgcaggtttc agaggaacta ggccttaccc   3360
tggaggggct cccagcacct ggggcagcaa agaccctcag ccacagtcaa taggggcagc   3420
ctctgagggc cccagaagct ggggacagga cggcagggcc cactcagctc aggggcagag   3480 ttgggggggtc acagattcac aactcaagag gcaaagagga tcagggcaaa gtggggggac   3540
gcaggccagg gaagggcacc ccgaaccacc acggggaagg atagtaccta gagcaccgct   3600
gagcatgggc agggcctccc tgtgctgctc ttgggtttga cttcatggct cgaggtgcgc   3660
aatgacaagg ggatccagga gggacgtgtc aggcactgac agcagtggag ggcgggcttc   3720
```

-continued

```
gggactcatc tacccctagcc tgggacttcc cgttggagag tggggtgaaa cggtcgggcc      3780
aggacatgga tggttgactg gggtagccgc ccaagctccc acgaggagag atgggccctt      3840
ccgaggcccc aaactaaagg tgcttttctg ccccacaggt gccttcctgg tcccctacct      3900
gctcttcatg gtcattgctg ggatgccact tttctacatg gagctggccc tcggccagtt      3960
caacagggaa ggggccgctg gtgtctggaa gatctgcccc atactgaaag gtaatatgcg      4020
ggtgcctccc ttcaccctgg cgcagcgcgg atcatggtgg tgacgctgga gctttcaaag      4080
caagccagcc gcatcatggg catccagccc tgctttgcta agacacaggc atggcacacg      4140
ccacttgaac ttgggtccca ccttaaagat ctgcagtgac aaggactgga tagttcattc      4200
ccttgctcta ggtgagggtc ctgcaattca tttgtggtgt tactttgtca agatgctaaa      4260
atgtagttaa gataaaacac atgtctatct atggatctgc catctaccta tcatccatcg      4320
gtccatccgt caatcatctg ttatctatct atccattatc tatctttatt attggtcttt      4380
atatcaatca ttcacccatc tatctaccta tctacctaat ccatccatct atcatcatca      4440
tctatctgta tctgtttcct gtggctgctg taacaaatga cacaaactgg gaggcttaaa      4500
aggcacacgt ttattgtctc acagctctgg aggctggaag tccaagatca aggtgtctgt      4560
agggttgatt tcttctgagg ctgtgaggaa gcatctgttc tagcctctct ccttgtctca      4620
gagattgtct tctccctgtg cctctttata cttcttgctt ctatgcatat ctctgtaacc      4680
aaattccccg tttttatgag gccagaagtc ctgttggatt agggacaccc taatgacctc      4740
actttaactt gatcacctct gtaaagacct tgtctctaaa taaagtcaca ttctgaggtt      4800
tgcggggtta gaacttcaac agatgaactt gggggaggga cacatcccac aattctatct      4860
atctattatc tgtcaatcat ctattcaccc gtctgtcatc tacccattca tccatctatt      4920
ttcttttgat ccatccacct atcaatccat tcatccaccc atccagtcat ccatccattc      4980
atctatctat ggatctatca tccatccatc catccatcca tccattatct attgatccat      5040
ccatctacct atcgatccat ctatctatcc atccatccat tcattcatcc attcatctat      5100
ctatggatct atccatccat ccatcttcta tctattcatc tatccattca tccatctgtt      5160
atccattgtt ccatccatcc atccattcat ctatgtatgg attaatccat ccatccacct      5220
atcgacctat ccacctatct actagctatt gatccatcta gttgtcactg aacctttccg      5280
gctgctgatg tcctgctctg gcaccatgaa atggacacac ctcgtgttga gtgcaggtgg      5340
cctgcccagc accaagccct ctcccagcat ttctgactcc atcttcatga gaccctggga      5400
agggcacaca ctaggtctct gtgttggaga tgcagatgct gaggaccaga gggccggggt      5460 cgttcccct ggtgtcccca tcagagcaga gtgggatttg atcccagacg tttctgactc      5520
cccaatccct gcacgcaggt cacacttgcc cagtgggcca aagccacctc tcaggggctg      5580
gtggttcagg gaggattcag gcatttactc agaggcacca ctcagaaaat tggcattaag      5640
aaaatgacta ctagaaggtc agcctctgga tactcataga agttctggaa aagctgtgtg      5700
tttagaagac agccgagccc agcacggccc caggacgcat taccaatggg tcaggggtgg      5760
gccttcagag gcgagccgct gacctccctt aggagaggga acagatggca tttcacagct      5820
gctgaggtca ggctccagga ggagaagtca gtctcgcagc cgtggaaatg ctgagactgg      5880
acaggtgtga tggttcttcc caggcacgag actcattcgt tcttaatggg ctgcttagtg      5940
aatcttatga cttcagtaat ttcttcctgg gctccacatt cactggactg cactgaaatg      6000
gagctacaaa aagaggcctc cctccccacc cccaccccca cccccacccc acacacatct      6060
```

-continued

```
tcagagtgag agacagatgc tttgggcatg cactggtgcc agacgacccc ttggcgggat    6120
ctgcaggtag aagtcaaacc gtacaagaat tgctcagaac atgcctccgt ccccgtcgtc    6180
aggtccctga tatcaggtcc ccaatggaag aatgcagcag ccaacggaag acccaggcct    6240
gttgttacag acagacaggg gcgcgtgtca aatccggcgt tgcagtgaac ccaggctaac    6300
agttcaagac acacgcgtta cctgtgtcct gcctggccct ggccagcggc acggacgtgt    6360
ttcagagagg agtgctgcct ctgagcctgc agtcgtaagc gatgctgagc ttgcaccgtg    6420
gtccgtgttg gagagtatct gagggctcag agccttggga tgctgagtca gagatgaagc    6480
cggcccactg gggtagggga aactgaggaa agatgacatt gtgctctggc acaggctgca    6540
gcgacatcca actgtgcttt gctggatttt caagagccac cctggagtct gtcacaagtg    6600
tcttacaagg cacagccctg tgccccactc ccgccagtga gcctggtgtt ggagcaagtt    6660
aaatcacctc ttcacgtgca ggattcaggt gaggagggca ggagaaaaag ggacctgtag    6720
gtccgcagat aagagctcat ttccttccgt ctgtcacaca gaaaggatgt tcaccaacaa    6780
agctgccgtt gtgggtcttc atggtgtagt ccataaaatg tcaagaagca atttctaaga    6840
atttcagagc accaactcaa cttgggctag tagagaacct ctgacttcca tcagcgtgag    6900
cagtggcacc tcgttctgaa gaaatgcagc cggcggatgt gggcatatca tcgtgttctc    6960
cacaatgcgc agccggggta agctgggcag tcgtctcctc tgtgtcacag accctgtgcc    7020
cacaatcccg cattccatgc cgccagcttc gttctgaaga ctagtcccag aggagggctg    7080
caaagtgtgg ccgcaggaag gaaggctcgt ggccctgcgg gcggatcttt ggaagagctt    7140
gttcacactc acctagtcct ggtgaggaag gaaaattgca aatcacagaa agtgaactgt    7200
tcgacccacg aagggataga tgaatcagtg caagaaagct ggacttcttt ttagagacga    7260
gacaccttga gttgttgaat ctcagtaacg ctgcaggttc cggtgccagc gtcccgtttg    7320
ttctgcctac ctgtcaagcg caggatgcca gtttagagga gactgacatt gcttatgaaa    7380
tcagatgtac accatgcacc cccggcaccc tgatacatgt gcctttgtcc tttttaaaaa    7440
tctggttaat aaaaatgcat acgttttcat gtctcattga atagaagtgc cacgtggtaa    7500
attaagacat cagctaaagt gcccacaaca atcattgtgg agctaaaagg ccatccagcc    7560
ctgagcaggt ggcaattcca tgggggaatg aagccagctc tccaggaagc ctggttgttc    7620
ctggcccttc ccctcctgca gacctgcgag ctgctccctg ctcctaactg ggagccaaga    7680
tccacccttg aaagccagag ggcggagttc atggtgaggc ccagctgctc agcagccatg    7740
actcacgtgc atttcccgta gtctcaccag agcagcttgg gatgggcacc acagccagag    7800
gggcctctgg ggccttcagc cccgcagtgc accccagggt cctgagaggt gggtctttaa    7860
aactctccgt ctcctccctt cccctcgctc tctttccctc tccctgtgtc tctttctgtc    7920
tctctccctc ctttcctctc tgtgtctctc ctgttctgtc tcttctcctc tctgtctctc    7980
tcctgttctg tctcttctcc tctctgtctc tcgggtacat gcacacacag caagcacata    8040
ctaaagacac ccagactgac acagagaggc gtcctctccc ctctttcttt tcttttcttt    8100 tcttttttt ttttttgtg agacggaatc tcgctctgtc accaggctgg agtgcaaagg    8160
cgcgatcttg gctcactgtc acctgcgcgt cccgggttca gcgattctc ctgccccagc    8220 ctcccgagta gctggggcta caggtgcgtg ccaccacgcc ccgctaattt tttgtatttt    8280
tagtagagac ggggtttcat cgtgttagcc aggatggtct cgattgcctg acctcatgat    8340
ccgcctgcct tggcctccca aagtgctggg attacaggag tgagccaccg tgcccggccc    8400
tctcccgtct ttcttccaaa gacctgcttg atgcctcctg tgaggtatgg aggggctgct    8460
```

```
ccaccagagg cttcctccag cgggatccgt gcatgcgttg acaacaccct ctcctgaagc   8520
cagctctcgt gggtgccctg gggtgtactg gtgttcaggg gtggggcagg gtggccgtgc   8580
tctggtgggc gaagcaccat ttgcaggcac gaccctcagc cagcttctgt ttgtcaggtt   8640
tcggtttcat tgccaagggc aaccccattt tacagacgcc ctggaaaccc caccattcga   8700
ttgtattgaa tataaaatat tttatagtca gtcatatttt agtgtgattt ctcaaacaca   8760
aaacaaacta cacacaaggt taatataaag aaaaagatac taagcaaaaa taaatttaag   8820
gaaatgggcc ttaaaagcta tgcttgaaat tcacacttag cgccgagctt cctgggagtc   8880
agacaggagg gaagggaagc gccatgttct catgaatgtt ttccctggaa acgcgagcag   8940
ggactttgcc tgccacctcc ttggggagac agtctcccgt gtcactaaat ggtgtttaag   9000
aaatgtgtca ggtgaagctt catctggagc ccacagtgat gtcatgagca gagatcacta   9060
gaaggttctg tagccaacag ggtagtgggt ttcctgcgtc tgggccttcg gtgagcttga   9120
ggagctcgtg gtgaagttgg ctggttggtg aggggctaca cgtcagtggc ccaggtcacg   9180
ggctctgcct tcctgaaggg cagggcttgg agcaaccgaa tgcctggcca gtgctgacag   9240
tggccactac cgttcaaggg agccatttcc tcacccaggt gcccagggaa gcatccagga   9300
ggggactggc caccaccgtt caagggagcc atttcctcac ccaggtgccc agggaagcat   9360
ccaggagggg actggccacc actgttcaag ggagccattt cctcaccgag gtgcccaggg   9420
aagcatccag gaggggactg gccaccaccg ttcaaggctg tttcctcacc caggtgccca   9480
gggaagcatc caggagggga ctggccacca ccgttcaagg gagccatttc ctcacccagg   9540
tgcccaggga agcatccagg aggggactgg ccaccaccgt tcaagggagc catttcctca   9600
cccaggtgcc cagggaagca tccaggaggg gactggccac cactgttcaa gggagccatt   9660
tcctcaccca ggtgcccagg gaagcatcct caaccaggag gggtcctctt ggtaaggggg   9720
actctggtgt gggggctgca ctgtcccatg gatcagagca ggcccatttg ctctgggagc   9780
cgcatcagcc agtgtggcca gtggtgatgt catgcacagt ggccatggtg atgtcatgct   9840
cccatggtgg ccctgccaat ctgtggtgca gggcaggaaa caaaagcagt ggctctggaa   9900
ggacccaggg tacactcagc ccttccttcg gactctggat tgggatccac tctggtgttg   9960
tttgatcaag gacttcccag ggtttcaagc taaggacttg atacagaaag ttttaacctt  10020
gaaaaatttt caaattgggc atccattgtc agttaccacc atggaaaacc ctccacagtg  10080
ctctctggaa acaatgtggc tcaccgacag tgtggctccc aacctggctg cctgggtgag  10140
ttcactgtgg atcacaaccc agcctctctc ctaagggact ccggacagac ggtaatatag  10200
aattatttaa tatggaccag atccacgtgg gagaaggcct tccaaaggca atccgtgaca  10260
gactgcaata cagaattatt taatatggac cagatccata tgggagaagg cttttcaaag  10320
gcaatccatg acagactgca atacagaatt atttaatatg gaccagatcc acataggaga  10380
agaccttcca aagcagcag cttggctttc atcgtcacca ctactgagca tgctttccaa  10440
gggggattac ccgcactcct gatcttagat ttgtttaaaa caaagttttg agtcttcttt  10500
ttgctttcaa ggtaggaaga gaactttact gaggtgccct gagcatgaga acagcttctc  10560
ctaaggattg agactataaa aagcaaccca ggccacccc tgcaaaagtc accttgaagg  10620
tatgctccta ccccggccat gaacaggcaa gacggcatgg tgcctactgg gttttaataa  10680
agtaaatcaa agttgtaccc aaaactaatca tgtcagtaaa ctgagaagaa atgtggaaat  10740
gaaaaaaatt cttcctggag cttagtaaag tgaaccccag tagcaagaac gtgatggtgc  10800
```

-continued

```
ccatccagca gtgaacaagg aggaagtcat ctgaccacca ggcccatctg cccaccagtc   10860
aggctgacac cactccaaag actgctgacc actgagttct gttccagttt accaggagac   10920
cccataaatg atggatccca aattccaggt ctgtgatcct ggaaaggaca ctctaaaaga   10980
ccgtggatgg cattgcatgg ccatggatgg ccctggctgg tccttgatgg tcttgcatgg   11040
ccctggaagg cctcggaagg tcaaacatgg ctctgagtag tccttcatag tcatgcaagg   11100
ctctgggtgg cccaaggaag ccctggatga tcttacctgc cctgggtgga ccctggtggt   11160
cttacgtggc cctgggtgat tctaggaaac cctggatggt catgcatggg tagtgtgacc   11220
ttggatggct ccacatggct gtaaatgagc tcagatgact cttctgagta gtcttgcagg   11280
agaggcatga gcagctatag atggccacag atggccatag atggctatgg atggctctgg   11340
atggccatgg gtggctgtgg atggccatgg gtggccgtag atagttatgg gcaaatgcag   11400
atggctgtgg atggctgtgg atgtctgtag atggctgtgg atggttttga atggcaatgg   11460
attgttgtgg atggccgggt ggatgtggga ggttgtggac agccatggat gactatggat   11520
ggctgtggat ggatgtggat ggttgtggtt gggtgtggat ggttgtggat ggttgtggat   11580
ggatggatgg ttgtggatgg ccgtggatgg atgtgggtgg ccatgaatgg ttgtggatgg   11640
ctatggatga ccatggatag ttgtggatgt ctgtagatgg ctgtggatgg ttgtgaatga   11700
cagtggattg ttgtggatgg ccaggggtgg atgtggatgg ccatggatga ctgtggatgg   11760
ctgtggatgg atggatggtt gtggatggct gcggatggat gtggatggcc gtggatggcc   11820
atgaatggtt gaggatggct atagctgacc gtggatagtt gtggatgaat ggagatggct   11880
gtggatggcc atggatggcc ctttgcgact caaagtggcc ctggattagc ctgggtggcc   11940
atatgtggtc ctgggtgccc tccatagtcc tgaatgagcc tggtggctgt ggatggctgt   12000
caaggacccc aggtgtccct tagtgactat tggcagtctt gatggctctg ggagacactg   12060
ggtgttcctg ggtaaccccta gacgaccttt gatggccta tttgcatggg ctccctaggt   12120
agccctgggt gcttctgggt ggccgtggat gattctgatg gtttcacatg ggcctgatag   12180
ccctggttaa ccatgagttg ggttgccctg ggtcacccag agtacccct agatggcctc   12240 aatgatcctg gatgactctt atggatcctg agtggctgtg gtggggatgg atgaccatat   12300
gtggctgggg gtgaccttgg tgtccctggg ggtctctggg tgcataaggg tggccctgga   12360
tactcgccat agctctgggt gaccttgctg gctctggatg tctctcagag acaccctgaa   12420
agtccttgtg taggagtgca tggttttggg gagtgggcag cttcttctct gtggtcacag   12480
tgtgaaatct ggtctcaggc ctttcacggg ccttccctgc atgtttgaag atgctgtctg   12540
gcatcagggc tgtccaggag ttgtgggctc agggtaatgt ctcccgtgag gggaggtgga   12600
agggacacgt tgctgatggt ggctctgtgc tccacctgcg tgggctccat ggcctccccc   12660
ttcccgctag gtgtgggctt cacggtcatc ctcatctcac tgtatgtcgg cttcttctac   12720
aacgtcatca tcgcctgggc gctgcactat ctcttctcct ccttcaccac ggagctcccc   12780
tggatccact gcaacaactc ctggaacagc cccaactgct cggatgccca tcctggtgac   12840
tccagtggag acagctcggg cctcaacgac acttttggga ccacacctgc tgccgagtac   12900
tttgagtaag tgggagtcgg gtcctcggga acgggagaga tggcgcagcc aggtccccca   12960
tggtagcccc ttggttggac accagccctt gctgactccc agggtgcggg gagggggaat   13020
ctgttcctgc actccatccc tttagtgctc tggagggggca catttctgaa tcactgtggt   13080
ggtctccagg agctcagcaa agctcctgta gggcgagccc tcagcaagga tggggcactg   13140
agcagctccc ttggctgctc ccagcggcag ctcagggtgg gaggggctg atggggaaca   13200
```

```
cagcagaccc tgtgcagaag gtgggcaagc tccagtctct gggagctgca gtggcgcctc   13260
tggagtgagt cagccccatg tctgggctcc cttcctccct acccttcctc tgtgcatagc   13320
atggggccga actgcctcac tccggccctt gccctctcca gaaaagataa ctttctgggt   13380
gtcactgcgc aagaagtctc tggcttcagt aggcagcccc tgtctccagg gtgacccagc   13440
cgtccgcttt tcacaagact ttgttttgtt gtttacctgc atggctttat ttctgtctct   13500
gggcctcttt ccacctccca tgccagcgta tcccatgtcc agcagcctcc tgggtctctg   13560
tctccttctc cctttgccct ggccaggcct gacctgcaca gtcctcccca gccaggccag   13620
ttcctcactg cccaccccag ccaggcccaa ccctcactgt ccaccccagc caggcacaaa   13680
ccacaaagtc caccccagcc aggcccctcg ctcactgtcc acctcggcca ggcccacccc   13740
acaccgtcca ccccggccag gcccgcccct catggtccac cccggccagg cccacccctc   13800
accgtccacc ccggccagac ccaacccaca ctgtctaccc tggtcaggcc catccctcac   13860
tatccacccc ggccaggcct gatcctcact gtccatccca gccaggccca acccatacag   13920
tccaccccga ccagccccaa cccgcacagt ccaccccatc caggcccgtc cctcactgtc   13980
cacccaggcc aggcccgccc ctcaccatcc acctgcagca cctgctttcc tggacccga   14040 tgtctccgat gaagtccttt tgggccccgt gccagctcct gctggccctc cctcgtcacc   14100
aatggcctgg cccagcctgg aagggtcgtt actgacaccc aggggttccc tgtttcccct   14160
ggacccctcc cggaatctgg atctggcggg tgccatccac atcttcctgc cctcgccagc   14220
cgggcctggg gcctcgtgcc gggtcgccgt tctgacaggc ggactcttcg actcagccgt   14280
cattttggag aggaggagag gacgtttgcg cgattctccc cagatccagt gtttcccgtc   14340
agccagggcg ctcctgtttg gggggctcgc ttgcctggtt agacgcatct tattcacgtt   14400
tatatgccaa aatgagtcca cttcaaggta ggaaaaggaa ctttgaccag taagactaat   14460
tccagtttta acagccagta ggtgcctttg caaaatttgt tttgagtcag aaaacaggga   14520
gcttgaaagc aaatgaagca tctcatgtta agtttgtaca agtcacggtg agcagagaag   14580
cccccacctc gcctctgctg ggggaggatc atccccgaga actttggtct tggtctgcaa   14640
gggcaccttc ggggcgcaca gcctcccaga gagatgcttt ctatatctga aaaccgtatc   14700
aacagacatc actgaggtct tttcctgcaa ggaagggacc ttcgccctct cctgggggtc   14760
ttgtcagaga tggctgagat ggagccttcg ggcaggccgg agggtgtggc ttggagaaag   14820
tagggctgat gctgccggaa agggaccagt tctcatggtg ggcaggcgtt cggtctctca   14880
aactgctctg cactcagata ttcagaaccc aagtgcttgg ttctagaatt cctcctcggg   14940
catggaagca tattgccggg actggccttg gaggtgagga gccggggcgg aggcaggttt   15000 tgggggggcca cccggcgttt ttcttagagc atgaggaaga ccatgggtcg cgtgggtga   15060 gcgttgtgtg ggcctttctt gtggtttggg agtggacaag agtgacgaac tctgaggagg   15120
acggtgccac gatgggagag agtggcccac caagtaccca gcaggaggag agagagtcca   15180 ggctgggcg ccaggaagac gctcatggga ggagggctgg tttcagaagg tggggcaggc   15240
gggagagaag atgcacccgg gatgagtcct ggttgtttgc ctgaagacac ttggacgagc   15300
atcgccatag gaagcgcagc tgcaggcaag gtcgtgggag agtctgggca ggactctcgt   15360
gggtgacagg caagcgggaa atgataaaat tgtccaaata atgcacagtc acaccatttg   15420
tccaagtaga tttttaacatt ctcgagggag aaaactccca ttgcgtgtgg atggcctgtt   15480
cacacctaca tttccctaat taaacaccct atgaacaccc caggcctggg ctgcatgtgc   15540
```

-continued

```
tcttgctgtg tgcccagctc tcagggttag catgtgatca aagagagggg acagcaggag   15600
aaagtggggg gcacacagag ccaggggcag tggccgcaga ggtgccacca gggcaagagc   15660
ctgagagttc ccggtaccca acgccctgtt aaagctgcca agtgctgcca tgtgggact   15720 gccttccttt tgtttgggca gtgtgggaaa tgttgactca ttgaagtgat gttcagataa   15780
cagaattgga gaggaaaact tagtgtagtg attagtccag tgattcgttg ttaagaatgc   15840
tagaaggaaa gaacacgtgt tattatttta aacgatcaga ctagcgaagt ctatttggaa   15900
gttctcagtc tggaaggaag gaaggaaaca gaaaggtgcc cagcccttca ctcagaagcc   15960
ctgtccgcac tggcacgtgg tacactttag ctggcggcag ctcaagagca gacgtgggga   16020
gttggagaag gtttaagatc aattcacaaa tgattaatga cccaaggcac tgaggtgctt   16080
ggcactcctc ccacaccttc tgaaggtgat tttcccacca gtgggactga ggttccctg    16140 aaacaggccc cagtgactct tggggagcag ggaggacagt cataacgtac tcaggtctgc   16200
caggggtgtt ctggatttca aacctgcttt ataaagcaga tcactggaca aaggatgtcg   16260
ggttcctgcc agcgcatgta atcagggagt ggatgtctca ctgtgaaagg ccataaaggc   16320
cagagtggct gtgatgtgtg acagtgcagc tctttgtcct agataatggg catgcctgac   16380
tttgtcagta aacacaaaag ggattgagtt tcctacacaa tgtacgaaac atgacgtgtc   16440
ataaatttga caactaagat gttagcaaga gtagatctga aagggcttta tcgtgcgttt   16500
ttactacagg tcctcaggaa gtaaccgtga ggcctgggtg agacgctggc catgtcttct   16560
gggccctaag tcagaaaaga ctgctgagct gccccactaa tggtgcttcc tccatgtgcc   16620
atgaatgccg tgtgcagtgc tggctcctac acccagtgtt cctcagggtt ggcaaatgaa   16680
acgtatcctg tgggagttgc tggcacccct ggcccccagg ggtcccagcc agccttcctg   16740
cattgccact tccttcttgg gcagcagccc acccaccaga gggaggtggc agaaatggtt   16800
cctggagaga aataaaagga acccttcctt gtaggaacct ggagattatt gattggctgc   16860
atcccacaca tttgatatgc tgtgtttttca tttcaaaacc ccaacacagg accacataac   16920
tgtgaccagt ttacagtttc cccacttcca taaatactta tcgacactgc ctaatataaa   16980
ttataaagtt ataaattaaa gctattaatt tgcctcaaat ggactgcatt agctgcatcc   17040
cacaaagttt gatatgctgt gttttcattt cattcagttc aaagtattcc ctaatctttc   17100
ttttgatttc tatttgacta acagggcatt tttagaagtt tgttgtttaa tttgaaatat   17160
ttggaagttt gctaggtatt tttgttattg atttctaatt taattctgtt ttggcaagat   17220
gatatgctta tacatcttta atattttaaa atatattgag acttgtttat gacctactag   17280
atggtttaca ctggtgaatg ttccacatgc acctagaaag aatatgtatt ctgctgtctt   17340
tggttggaaa gttgcataaa tgtcagagag gttatgttag gtcactgtgt ttttcaggtt   17400
ttctacatcc ttactggttt tctgtccact tgctctatca gttactgaga aaggggtact   17460
gaaatctcaa ctgtaactgt agatttgtct atttctttc acttctatca gtatttgctt    17520
cattcacata ttttgaaact ctgctatgaa gtgcatacat gtttattatt attagtcttt   17580
gaattgaccg ctttaccatt tgaactatcc ttctgggtta gatttctcat tctgaagtct   17640
actttgtctg atagtaatat ggccacccca actttcgtat cattactgtt tgtgtggtat   17700
tatcttttcc agccttttat ttttaaacta tatgtgtcat tatatataaa atggatttat   17760
tgtagacacc atcgagttgg ttgtgctttt tatccaatat ggcaatctct gttttttaat   17820
tagagtttcc attcaataat tgtcagcatg gctggcttta agtctttcat tgtgctaatt   17880
ttttgccccc tctcttcttt gtttcttgtt tcctctattt attccctgtt ttgaattaat   17940
```

-continued

```
tttttaggct ttcattttat caacactatt agctaataaa ctatagcttt ctgttttcat   18000
ttcttcgtgg attttatagg gtttacaaca ctgaccttca agtgacatga taccgtttca   18060
cagagcagaa gggcctacaa cagtagactt ctgttttcct cacatccttt gtgcaattgt   18120
tgtcatagat tttttctaca atatgtatca actccatgat accttgctgt tatttctgct   18180
ttaagcattt acattttaaa taaatctaac aaagaaatgt tttatattta cctgcatagg   18240
caccatctct agtgctgtcc ggtcctgtat gtagattggg gtttccattt aagaccatct   18300
tccttccatc taaagaattt cctttaacat ttctcatagc gtagacttgc tggcagtgat   18360
tcagcttggg ctttacacaa aagtattttg ccttcttggg gggctattgt ggtaagctat   18420
acatagcatt gcttttacca ccttagccat ttttcagtgc acagttcagt ggcattaggt   18480
acaatcacat gttgtgcaac catcaccatc atccattgga actttctcct cctccaaagc   18540
tgaaattttg tccccattaa atactaagtc cccatcctcc ctcactgcag cccctggcag   18600
ctaccattct actttctgtc tctgtgaatt tgtctactct aggtccctcc tctgagtaga   18660
atcacttatt tttttgtgac tgccttattt tccttagcat atgtcttcaa ggtttattga   18720
agaatttcag aaccagaatt tcattccttt ttaaggccaa ataatatttc aattccattg   18780
tatggatata tcatgttttg tttatccatt tatctttttc cttttttagag acaggatctc   18840 actctgttgt ccaggctgga gtgtgcagtg gtatgatcac ggctcactgc aggcttgacc   18900
ttctgggctc aagcaatcct cctgcctcag actcccaagt agctgggact acaggtatgt   18960
gacaccacat ccagctaatt ttttaaaatt ttttgtaaag tggggtcttg ccatgttgcc   19020
caggcctgtc ttaaactcct gggctcaagt aatcctcccg cctcagcttc ccagagcact   19080
gcaattacaa atgtaagcca ccacacctgg ccagatctat ttatcttttg atggacattt   19140
gggttgcttc cacattttgg ctactgtaaa aacatgctgc tatgaacctc aatattgagt   19200
acctactttt gagtagatac ccagaagttg aattgctgga gctatgtgat aattctgtgt   19260 ttaattttt gaggaaccac cacactgttt cccacagtgg atgcaaatcg gaacaagggt   19320
tctgatttcc ccacatcctt gacaacactt actttctgct tgtttgtttt gatcatagcc   19380
atcctaatgg gtgtgaagtg gtctgtcatt gtattttga tttgtatttc cttaatgatt   19440
agtgactgtt gggcatctct tcatgtgttt attggccatt tgtataccat ctttggagca   19500
atgtctattc aagtcctttg cccattttg aattgggctg tcagtttttt tgttgttgag   19560
ttttaggagt tctttacata ttttagatat tattctcttt tcagattaat aggtgatttg   19620
cgaatatttt ctctcattct gtagtttcc tttttactct gttgatagca tccttcagtg   19680
cacaaaagtt ttaaattttg atgaagtcta attcatcttt tgtgtcatat ctaagaaacc   19740
attgccaagt ccaagattgt gaaaatttac cctatgttct cttccaagag ttttatggtt   19800 ttagcccta tatttggctc ttttatccat tttgggttaa tttttctata tcatgtgaag   19860
tagctgttca ctgattttcc tctggttgta gatcacattt cttgcttctt gtcatgtcta   19920
gtaatttttt attagatgct agacttggtg agttttatac taatgggtat ttagctcttg   19980
tcgtctttgt ttagagagtg ttagatttgt tctaatagga agttaacgtg ctttggcaca   20040
attttatcct ttggaagctt gtttcaccac ctcactgcct tggctccctc ttggtaaaac   20100
ggggtgagag ggctgctgtg aggtcatcac aatgatgcat gggaggcctg agcatgcctg   20160
gatcaccacc agtggctcca ctgtcaccca attgaatcat ggccaggaat tcaccaggaa   20220
aaagagccca gtagaaattg ggaggtgctg tgtcttttcc acgcctggtg aacatcctgg   20280
```

-continued

```
gccaacactt ttctggtcct cccaactatt atggcttatg aaacacctgc acgtaggcct   20340
gcacttatgc cccttcccgg atgtcctttg atggtctcgc ctgccctgcc ctcagaagca   20400
tggacatgct gggagacgca cagctttccc ctgctcctgg catggctggt tcccatgctg   20460
tggtcagctc tggggacccc tcttctcagg ttgacagcac tcaggagtgt ccggttctct   20520
aaattgtctg tgggttttca aataacctca aagcacagtg actttctaat ctcgagaagg   20580
ggctcgaccc agtgtgtcaa ggtgctgcgt ctgaagttgc tttcatgttt aatgctgagc   20640
cagctgtgtg tgctgtggac gcaaccttgt gagaaggccc tgagtggggc agcgcacttt   20700
ccctgggcct ccccctctgg tccaggaggg cctgtgccat gtatgggcat tgactgagtt   20760
tgccttttct ccaggcacct gggcaagggg agagggtgtg ctgtctggtc tgggtgtata   20820
attcatgcac gtgtgtgtgt gaggcactga ggctgccaag gcgtgggcgg gtggcatgct   20880
ggggtcagtg acaccatggg cagtgaggga ggagtggtcc gggctgcaca aagttgctgg   20940
gaggcctcag aagctctcag tgatgagacc ttgctggggg agcagaacga cggggactgg   21000
ccagcagggg cagagcctgg tgtgtggcag gaggagtgag aagaaggccc tgggagtccc   21060
cactgcccca ggaagggcag gcgtgacctc caccagctca gacaactttc cctgcacagt   21120
gcgggtgacg gatagcctct tgactgagcg gcttgccctt ggagaagagc agagaatggt   21180
ggcgatggtt tcagtggtgc agccatctgc ccacccggcc aacctggggc ctgtgccaac   21240
ctggggcctc tgcctgggcg ccctccagga taggacggag gcactgtcca gcgctttcag   21300
ggctcgtggg gccttccctg ttggcaacag ccagggtgtc tggagtttga agagccgaat   21360
tcctgggaca tggccctgga atgccttgca gctggtggaa agctccccaa ggctgcattc   21420
ggccgggctc caccatgggt gtcaggtttt atctcctggg gacctcagtg gacccacaac   21480
agaagcaaac ctgggcagtg ggagctcctt tcataacgcg gcttctgtct gtcacagctc   21540
ctgactctac ggtggcagcg gcacggctgt tacagttgtc ttggccccaa gtcacagtct   21600
gcagtggtga cgcagctgac tgcatgtagc ctggtgcatg ttctcccaca gagagtgtca   21660
ccaggatgga atgagttccc acagacaggg gcccaggac ctgtgcctgg ggcaaggagc   21720
acagccgatg gtcagctcca tccctcaccc tctgttctgc cctttctgag ggatccttca   21780
aaaaacagtg gaactgcgag tgattcctgc tggagcagag tcatccactg aatctgttcc   21840
ttgtggaatc ctcatagcag caggggctgt gagcaggtgt cgtgagccat cccctcagaa   21900
aacagtgctg gctggtgcct gtgtgcctgg cattattgct agagtttgct cggcctcatc   21960
cctggagagg gaccctgggg ctgtcttgtg ggcagcagtg ggtacccagc agcgtgggca   22020
gcactgtggg cagcggtggg tacccagcac catgggcagc actgggcagc ggtgggtacc   22080
cagcaccgtg ggcagcactg tgggcagcag tgggtaccca gcaccatggg cagcaccgtg   22140
ggcagcggtg ggtacccagc accatgggca gcactgggca gcagtgggta cccagcagcg   22200
tgggcagcac tgtgggcagc ggtgggcacc tagcaccgtg ggcagcactg ggcagcagtg   22260
ggtacccagc agcgtgggca gcactgtggg cagtggtggg tacccagcac cttgggcagt   22320
actgtgggca gtggtgggta cccagcacct gggcagcac tgggcagcag tgggtaccca   22380
gcagcgtggg cagcactgtg gcagcgtg ggcacccagc agcgtgggca gcactgtggg   22440
cagcggtggg tacccagcac catgggcagc actgtgggca gcggtgggca cccagcacca   22500
tgggcagcac tgggcagcag tgggcaccca gcagcgtggg cagcactgtg gcagcggtg   22560 ggtacccagc accgtgggca gcactgtggg cagcggtggg cacccagcac cttgggcagc   22620
actgggcagc ggtgggcacc cagcaccgtg ggcagcactg tgggcagtgg tgggcaccca   22680
```

-continued

```
gcaccatggg cagcactggg cagcggtggg tacccagcac catggcagc actgggcagc    22740 ggtgggcacc cagcaccatg ggcagcactg ggcagcggtg ggtacccagc agcgtgggca    22800
gcactgtggg cagcggtggg cacccagcag cgtgggcagc actgtgggca gcggtgggca    22860
cccagcagcg tgggcagcac tgtgggcagc ggtgggcacc cagcagcgtg ggcagcactg    22920
tgggcagcgg tgggtaccca gcagcgtggg cagcaccgtg ggcagcggtg ggcacccagc    22980
accttgggca gcactgggca gtggtgggca cccagcattg ctcagcaact tccttttggt    23040
ttctgtggct ccttttcttc aaagacccaa ggtgccctcc gcctccgcag ctccagtgag    23100
caggggtgcc aagggcagat ggtgaggcag ggcttcctgg gcctcccacg tgctccacgg    23160
gtttcaaggg cggccctgac acctctgcca gggcctgtgg gccagacctc cctggaaggc    23220
atctcttgtc catcagactg gatgctttct gccctgctga gatggggagg gcaggtcccc    23280
ggacaagctc agccgtccag ttccaggtgg gttgacagcc acccacagag tcccccgctg    23340
actcccctct gcagacgtgg cgtgctgcac ctccaccaga gccatggcat cgacgacctg    23400
gggcctccgc ggtggcagct cacagcctgc ctggtgctgg tcatcgtgct gctctacttc    23460
agcctctgga agggcgtgaa gacctcaggg aaggtgaggc tcgggggtca ccaattgggc    23520
ctgtagacat ggggccacca agtggacatg tggccgtggc tggacaggag gtgcacgtgt    23580
ggcctcagtt gggttttgtg ctaccaatgt ggccatggcc aggttggggt ggacacatgg    23640
ccatggttga gtttgggaga ctcatatggc cataatcagg ttgggagtgt acacgtggcc    23700
atgattgagg gtacacctgt ggctgtgccg ggttggcttg ggtagacgcg cggccatggg    23760
tgggtggggg gacacgtggc cgtggctggg ctgggcggac acacggcaca gttgggtttt    23820
gggtccacgt gtggctgtgt ttggggaagg gcctcaggag ggaagcactc acagcagtgt    23880
ttctggcagg aaggcacaca caagatgatt tttttgttga taaaaatact ttgggaggct    23940
gagacgggca gatcacctga ggtcagggt tcaagaacag cctggccaac atgatgaaac    24000
cccatctcta ctaaaaatac gaaattagcc aggcacggtg gcacgtgcct ataatcccag    24060
ctacgtggga ggctgaggca ggagaattgc ttgaacccag gaggcggagg ttgcagtgag    24120
ccaagatcat gccactgcac tccagcctgg gcaaaaagag caaaactcca tctcaaaaaa    24180
aaaaaaaaaa ctttggttgt tatatgggcc aaaaccagtt ttgaccaaga tacgactcct    24240
cccttggaaa agtgcgtgta gtatggcacc agccacggga gcctcccgca gggacacagc    24300
ccagagcagc ccttcatcgt gccacagtgc cgttcaccag tgtgaatcca ctcacgtccc    24360
acgcatcaga aaaccccat cagccactcc cagctactct ggcggaccga atgcagaaaa    24420
ggaatgtgct ttccctgcca agttgttctt ccctttccat ccctggggag ggtgtgcagg    24480
acagaaagtg tctgaccttc tcactccaag gagcatttgc tgagctggcg tcccaggaaa    24540
tgtttgggaa ttgggcctcc caatcagagg acaagccgtc agggcaaccc ggtgcccttg    24600
tgccagtgtc tgctcccacc aagggccctg cctgtgcagc ctggtgacac tgtcctctcc    24660
tgcaggtggt atggatcaca gccaccatgc catacgtggt cctcactgcc ctgctcctgc    24720
gtggggtcac cctccctgga gccatagacg gcatcagagc atacctgagc gttgacttct    24780
accggctctg cgaggcgtct gtgagtacag tctgctcact gcttcacagt ccacagggc    24840 tctggcattc ccaggtttcc atatgcattg cctgccaggg ctgagaggtg tcagagttgc    24900
agacaccagg gttctttcct cgggaagcca aatcccaagt acctgtgata cagcacgagt    24960
catctaaatc aaattacatc agaaactcca tctagactca ggctgcagct ttggtcagca    25020
```

-continued

```
aaagaagaca taattcaggg ttaaaatatt tggagaaagc ctcccggaga gaggagactc    25080
agctgggcca tggggatgg gaccccttgtc cagaaaggga ggagaaaggg ctgcacccctt   25140 cctggcaaac aggcccagaa acagaagcag ctgttggcgg aaggctggca tgacaaaaat   25200
ggcagctccc ttggggcatc gttggaaatc aggtggacta agtggggggag gtggcaggcc   25260 ccaaagccgc ccaggggcat ccatgttgct gtgggaggac aatgcagcaa gaggggaagg   25320
gccatctcag ctggggtatg aggcaggagg ccgttgagag gtgctgccct gtgtgggtgg   25380
gccggtggag ccaggtctgg gggtcatgag gcaagtgtaa acccaaggca gaagtgggaa   25440
ggaaggggag aagggatggg cgggcatggc tgcaagcctc ccaggaagcc ccagggaggc   25500
agcagctgac aggtgcagtg agagagggca cctggacatg gcacctatga ggctgcaaag   25560
cagttgggtg ggggtggggg tggaagtgtg cctgcagcac tgaaggggaa gccctgtgga   25620
gacaggagcc atgggtgcag caggcgtgtg gcccacggga gccaaggaag agagaggagg   25680
acaaccaggg cagcaaaatc agctgtggcc ggggggcccac aagtgcagag ctggagccag   25740
acaaaccatg aagtcagcag ggcgtctgga ccccagaaag gccaaaatga agccaagggg   25800
tgtgtttgca ggaccatggc atgttacaga atcaaagaaa aataccacaa ggacaacgta   25860
gagcctagtg ctccagctag gaagaatagg cagccccagg aggaggcaaa acaaacacca   25920
gtgcatgtga aaagatgctc actggagaac aaattacaaa gatgagatgt cagaaattag   25980
gtggagacag tgaatagatt ggatggatgg atggatggat ggatggatgg atggatggat   26040
ggatgaatgc taggtaagta ggtggatagg atggatggat gataggtggg tagatagaat   26100
ggatagatag gatgggtgga tggaaggctg gctggctgga tgtatggata atggatgggt   26160
ggatggagga atgatgata ggtaggtagc tggatagtat ggatggatgg atgatggatg   26220
gatggatgga tggatgaatg gatgatgcat gggtgaatgg gtggatgaat gataggtagc   26280
tagataggat ggacagatgg ataatggatg gatgatggat gggatggatg ggtggatgga   26340
tgatgggtgg attgctggat gatggatggc tgggtggatg gatgaatgat aggtaggtag   26400
ctggatagca tggatggatg gatggatgga tgatgaatgg atgatggatg ggtgaatggg   26460
tggatgaatg ataggtaggt agctagatag gatggatgga tggatggata atggatggat   26520
gacgggtggg tggatggatg atgggtggat tgctggatga tggatgtttg ggtggatgga   26580
tgaatgatag gtaggtagct ggacagcatg gatggatgga tggatgatgg atgggtgggt   26640
ggatggatgg atggatggat gatgggtgga ttggtggatg atggacagat gggtggatgg   26700
atgaatgata ggtagctgga tagcatggat ggatggatcg atgatggatg ggtggatgga   26760
tggatgatgg atgggtggat ggatggatga taggtaggta gataggatgg atatacaata   26820
ggatggatgg agatagatac atacacacac atgtacttca tatattcata gatgatagac   26880
agttgataga ttatagagat gacagataga tgatagattg gtgatggatt gatagatgac   26940
agtgatagat gatagatara tagatgattg attgatagat aatagatgat ggattgatgt   27000
atagtgaaga gaaatcagga aagaaatgga aggaaaggac aattgcaggt cctggagtga   27060
aagtgcatga ggtgaggccc agggaggcag ccatgggcac tggctctggt gtggcactgg   27120
gcagaggcct gagctgcaca cacagatcag ggtgaggagg aggcaggcgc tcccctgtga   27180
cacctgatcc agcctgcagc tacctggcca ggcaggtggc tgatgaccag catgggagcc   27240
acatcagggt atgagcctct ccacccactg cccacccagc cactctcggc ttggctcctc   27300
ccctcatgct gaaacactgg ccacctgcag agtcctgact gcgggggcctg gccatctgcc   27360 tccaaacaca ctgtcccagg aactgggtt gccttgaggc tctgacatgc tgcccaaagg   27420
```

-continued

```
acagagggcc ccgcccccctc tgcagcaccc agttcccttg ctcagtcaag ctcaggcaag   27480
cttgacctgg gacctgggat gccctgagac ccacctggcc tccccagcag gagcatctgg   27540
tgtctctgcc tcagcatcct ggcccacagg cctgtaccat gggctccagg gacttgcagg   27600
aacagcccta actgaccagt ccctcaaatg cctccaaggg ggggttggct gctccttctc   27660
ccccatccaa ggcccaggga agggcaaggt gggcatctga gtcactgaat ggtctccgca   27720
gtgccctcac cttagcaggt tgtggctgac tttttaaaat accacaatgg tccaatcgtg   27780
gacccaccca cctttccttt cacgtccaga gttgtgggtg ccatccaccg agttgggcag   27840
gcacagcacc agtgtctaag ctgcaggtgg gctcctggcc atgcccaggt gccactgtgc   27900
acctgtactg ctcatgtttt gggaaggata caaagcaggc attgctggtg tgcgtccaat   27960
caggacacca tcatcatgta gcatgtggat gggtccatgc ctttctgagg gttatcaggg   28020
tgctgccatc atgcagcatg tggatgatcc atgctgttct gagggttgtc agggcgccac   28080
catcatgtag cctcaggatg agtttatgtt gttctgaggg ttatcagggt gccgccatca   28140
tgcagcttgt ggatgatcca tgatgttctg agggttatca ggaagccgcc atcatgtagc   28200
ctgtggttga gtctgtgctg ttctgagggt ttcaggcac tgccatcatg cagcagggcg   28260
cacatgggat gggggggacac actcaggggg ttgtgaagct ggaccctgat caagggagga   28320
tggagacccc gctagggctg gtgtgagtgt ggataagtcc atgctgttct gagggttatc   28380
agggcgccgc ggtcatgttg tgtgtggatg agttcatgac tttctgaggg ttatcagggt   28440
gccaccatta tgcagcatgt ggatgaatct gtgctgttcc gagggttgtt aggacgctgc   28500
ggtcatgtca tgtgtggatg aggccgtgct gttccgaggg ctattaggac gctgcggtca   28560
tgttgtgtgt ggatgagtcc gtgctcttct gagggctatt aggacgctgc ggtcatgttg   28620
tgtgtggatg agtccgtgct gttccgaggg ctattaggac gctgcggtca tgccgtgtgt   28680
ggatgagtcc gtgctgttct gagggctatt aggacgctga ggtcatgctg tgtgtgggtg   28740
agtccgtgct gttctaaggg ttattaggac actgtggtca tgttttgtgt agatgaggcc   28800
gtgctgttcc gagggttatt aggatgctgt ggtcatgccg tgtgtggatg agtccatgct   28860
gttctgaggg ctatggagca gggcacctct ggttctgtgg aatcgctgcc ttgatactcc   28920
atggggaatc ccagatcaat gaacacagac agcccctgc ttctcaggct cttccaggcc   28980
gctggcccgg gagggttcac ttcctgaggc tgcatcttcc accagtcgtc tgctgccatt   29040
tacttcttga ggatggtgtt gagtttagag gcctcagtgt ggggctggga caggaagggt   29100
gctcaggtcc tttgcctgtg gcctgcgttc tcctgggaca gcctctcacc gccctctggc   29160
tctgcaggtt tggattgacg cggccaccca ggtgtgcttc tccctgggcg tggggttcgg   29220
ggtgctgatc gccttctcca gctacaacaa gttcaccaac aactgctaca ggtgagcccc   29280
tagcagggcc aggcaggggc ctcatcaata ctagggagag gtcgctgact tccagaaata   29340
gggtgtccct ggatgagaac agggcggatc cactgaaccc gcaaacctgt gagctgcgtg   29400
gcctttcaga cagaagcgac agcgaggcag ctcccaacac gattttgatt tcaactttaa   29460
agaaggcact gaagccagtg ggtgtgtcgc ctcctgggag ggacctgcct aggtttgacc   29520
tgcggccaga ttccccactg agggccccaa gtggcaaggc cagcccctcc ctccacaagg   29580
acacaccctc ttccctcaca ccagccccgg ggggtctctg tcctccctcg ctcagggtcc   29640
agcttcacaa ccccctgagt gtgtccccc atcccatatg caccccgtgt tacttactgg   29700
caggcacctg aagcccgtg ccggacccca aatccttcta aaaacagaaa cagaattttta   29760
```

-continued

```
tccgggatct gcttgctttg acctttatgg acttgtgctt actttctttc acatcatgag   29820
gctagaaaca cggtaaaaat acaaggacag tgtgtgcagc agaatggcca ggcagaccac   29880
aagcaggctt cactgagagt gggcgctgga aggcaggtcc tgaggcagcg cctgcccgca   29940
gcccacctgc gtccacctgg gtccaggtgc tctgcagatg aagtgtgtgg tccttccacc   30000
ccagtgacag gccacacagg aacccaggag gaggacgctg gtgccctgac cgaccccagg   30060
accctccctc ttcgtcctcg gcttgcctcc agctctctgg tttctcagcc ctcagagtgg   30120
ggcccccagg cccgcagcac cagcgccctt gggagttcat gggaaacaca gcccccgaga   30180
ccccatgaga cccgcccagt caggatctgc atcttagcga ggtccccggg aggtgtgtgc   30240
tcctagagct tctggaagat ctgccctggg tgaggtgtcc acagcaagac tcgcggggca   30300
caggggtggc cgtctgttct gcccaccctg agccttgatg gctgagcctt gagcagctca   30360
gctaggggac caaggtggcc caaggacagc tctgccaggc tgctaaggag ctggccgtgc   30420
tcactgggaa aagtagcccc tccgaagacc tcccgccccc ttcccagac acagtaaatt   30480 aagaataatg actggaaaat tgcagctgct gcagctcagc tggttcctga cacggcgtgt   30540
cttgttctta cagggacgcg attgtcacca cctccatcaa ctccctgacg agcttctcct   30600
ccggcttcgt cgtcttctcc ttcctggggt acatggcaca gaagcacagt gtgcccatcg   30660
gggacgtggc caaggacggt gagccctcc tgctgcacct gggcctgctc cgtgtagcac   30720
cagcgccgag ctctcagcaa agccttttc cttgtgaaag aggaaggaga cgcatgggcc   30780
ctgagcgact tcagtgagag ttgctgcctc actcttgaag gatggtggta cacatcccag   30840
tacagacctg cccccaccca gcgccttccc cgccctgacc ctccaggccc cccacccagc   30900
gccttccccg ccctgcccct cccggcccc cacccagtgc cttctccgcc ctgccctcc   30960 aggccccccc acccagtgcc tttcctgcct tgtgcctctc ggggcctcca ccctgggctg   31020
gggaacctca agcccaaatg cagctgagca gcatagttgg tgcctcagtc cctcgactgc   31080
tccctgcaga tgccacatga ggctgcccca ccagggtctg gcgtagatgc tgtcactgag   31140
ggccctctag atgtttgctt gccacgcggt gtgggaacat gcagctcagg gaaggggagg   31200
aatgagctgt tccagcaaca cctggaggca ggctgggatg ccgcaaacat cagcttggcc   31260
acagagcagc cgggagatcc ctggggcctc cagcacaggg tgtccctgcc cgctccccag   31320
gccgacgcat gacgctgagt gtccctgcac gcctggagtt gtctccgaga gggtggggag   31380
gggtccaggt ctcgggcagg cacaggtgag tggtgggggg aggccttggc cacagcaaga   31440
agtgtgccag gcaggatgga gccggcagga cgggcacaga tgcagggct gagagtgggc   31500 ccaggcactt ggggccacgt gcctggctcc ggtgcttgca gtggaaagct gtggcgttgg   31560
cagccctaac ttgggccaac cgagagctcc agggagtccc aaggcttctc ggtctctgtc   31620
agccagcaga gcccccgcct gcctcccggc ctgctctgcc acatggatgt ggaggaggcc   31680
ctttcgctcc agacacgggc ctgggttggg tgggctccca tgctgcgtcc ccatccttgc   31740
ttcctctgga ctgtcttctc cggggtgg gtgggggcac tacatttgtg aggaatgatt   31800
gtgctcagaa aagcccctgt cccgtgtggg tgttgttgct gactgatctc tgcctgggtg   31860
ttgaggctca gtgaaggcgg ggagcgacaa gcaccaagcg gggcagcct tgaccgcacc   31920 tgagtctcac agagtggggc actaggaccc tcgcaccgca ggtaggaaca cgctcagaga   31980
cctgaaaggg cccactccat gcttgcaaca gaaagccagg gtcggggctg gagccacagc   32040
tcagaggtgg gcctcctaag cccatgttct ttccactagg aaaaaaaatt cagtcaaagc   32100
gggagaaagg gaacatctgc aaataaatgc agagcagtga aatttactcg gtgccgcatt   32160
```

-continued

```
tatgcctttt cttcattctt tttgcccttt attatgataa cgagcatagt ttgcaaaaac   32220
ctctattaac ccctgaaaat aaagttgaat gttcttctgt gcatttcatg acaagcaaag   32280
taaatgtcat ttacagcctt aattctcaag aaaatagggt gaaatgttaa cttaggtaca   32340
gaaacgaagg cacgggtgtt gacattacat tccctgagct gatgaatatc ttcccaggct   32400
cctggctggt accatctaag ccccggaaca tctcaggcga gcctgcctcc cccaccccac   32460
gcggaggctg tccccatcca ccagggtatc tgggagctgc gagagcccag gtctgacccc   32520
gctgcttggc tgatagtgag gccctgaaa gacctttagg aacggcccct ggctctggcc   32580
tttgattatt taaaaggcca ggcgcaggcc tattcctgca ggctagggcc agacacgtgc   32640
ctgctgagga cagggggactc tgttgcaggc agattgggct tgggagatgg tgccagccag   32700
tggaggatgc aaggcttctg aactggtcaa aggtcaattg cctatgggac tggttttttac   32760 tttggggtca tcagagacca aactgcgttg acttttggtc gcctgcctgc cacactctcg   32820 tccccctccac ctccatccga gtctgcctgc tggtagcagg aagcacgtgt cgtttcccga   32880
gagagctgtg ggggaacacc tcctccgcct ttgccatgcc gccctcagcc tggcgtgccc   32940
ctcgcttgca gggatagcaa ggtagcaggt ttgtctctta tctccgaagc caccatctgg   33000
gcccctgtat ccatcaggat gtgctgctcc tctgagccct cagggcccca gctgacagga   33060
gcctgtctca atatggcctg cgggacccg tggcagggga ggtggtgaag gagccacaca   33120
ctcctctacc aagcttcact cgcagggacc cgctcactgt gggttcacag cacattggcc   33180
aagtgcagcc acgtctaacc tcacgggagg gtgggaggac ctcagcttcc tcatgtgcct   33240
ggaaggcgga ggtcaggaat gtatccctaa atgtttttgct aattttagaa attaggctac   33300
taaatagtgt ggacgtgtgt gatttgtgtg tgtttgtgta tgtttgtgca tgcacgtgca   33360
tgtttctgtt tgtgtgcgtg catgtggatg tgttcttgca tgtatgagtt tgaatgcaca   33420
aatgagtgtt cgtgcatgtg cgcgcatgtg tctgtgtgtg tatattgcat ggtatgtgtg   33480
tctgagtgtg tatgttgcat ggtatgtgtg tctgagtgtg tatgttgcat ggtatgtgtg   33540
tctgagtgtg tatgttgcat ggtatgtgtg tctgagtgtg tatgttgcat ggtatgtgtg   33600
tctgagtgtg tatgttgcat ggtatgtgca ggaaaaacta actcgaagga cattagcaga   33660
tgtccctggg atgaagggca ggaccagcct ggaagcccct cctgctcctc cttgtttctg   33720
ccccttcctt ccccaagcac ccccatagcc caaaaggacc caggtaattt ggaggagccc   33780
cattgctggg tggtgggcat gaaccaaagc cctctgatca gttctgggtt tccgctttcc   33840
tgagtcccag gcctggtctg ctggacatat agaaggggggc ttttcagcag agccgcacca   33900
gccctagtct ctacaggcct gtggcaggcc atgcttctcg gggcggggtg gggcaggatg   33960
ggcgggagag cacagcgtgg gctctgtggc aagcagggcg ggttctgttt cagggccagg   34020
gctgatcttc atcatctacc cggaagccat cgccacgctc cctctgtcct cagcctgggc   34080
cgtggtcttc ttcatcatgc tgctcaccct gggtatcgac agcgccgtga gtaacccgca   34140
ccgcccggcc ctgtcctcgg cagttgggtt ccttccaccc gagggggccc tgccctccca   34200
gggctaggca agatccctgg gctcacgtac ggccccagga cctcctgtcc ttgacttggg   34260
cgagccccgt gattatttgg gagacctttc tcggggctgg agtgagtggt gactggagtt   34320
tacctttccc tttatccccc tactctgggg tacctgtgtg ccctgccctg agccacctac   34380
agatcctgga aatgtgcaca cacatgcaca cacacacata cacgcacaca catacacaca   34440
tacacgaaca cacacattca caccaccatg cacatgcatg cacacacata cacacatgca   34500
```

-continued

```
cacacgcaca catacatgaa cacacacgaa cacacacatg cacacacgca tgcacacaca   34560
catacacaca gacatgcatg cacgtgtagc agggccccag ccaccaaaga cttggctccg   34620
gacaccagag tggtgggggcc ttggagggca cacagcaggt ccttcatatc tcgtggcttt   34680
ccctggaagc ctcagctacc ccatgaggaa tgaggagggc aacagaagtt cctggcacct   34740
accaatccca ggcctggccc tgaatgcttt gtgtgtggcc cctgcacctc cagctgctgg   34800
gggtggcggg tccagcccett gatcggccct gggcctgctg gactttctca ggctccttct   34860
tccctgtcag ctgcttggga ccaaagaacc cagaatccct tgccttataa acgctggtca   34920
tgcaccgggc cccccactca tatcctatcc acctcgtcca cggctcctgg gttgaccaca   34980
ggcctcatgt tcctgacatg agagcatgaa gagggggtctg gaccgagcaa ggtgaagaag   35040
gtcactaagc aggagtcagg tgcctggacg gtgtcccaca ggaggatgcc aggagtcagg   35100
aggctccgtc gggaaggcgt agccaatgac aaggccaggt gcagctgaaa gctttgtgtg   35160
ggggacgcat cttgctcagg aaaatctggc caagctgagc ccgtgcagca gcagtggaca   35220
gggtggcatt gttttagcca tgccgcatct tacccaccca gagacatcga agaggctgca   35280 aacccctac cgtggataca gtggtccctc tgggtcctct ctcctgcggt cgtgccgcca   35340
tagaagccct cgccaacagc tgtcctcact accaggcatc ctgcaccctg gacggccatg   35400
tggcccctgt tccgtgtcca tcccccgggtg tgcgtccact gggtgacaag taggtcttgg   35460
cccaggctgc ggtcaggagc gccgccagcc tgcagcccga ccctgtgctc tgtgtgcaga   35520
tgggtggtat ggagtcagtg atcaccgggc tcatcgatga gttccagctg ctgcacagac   35580
accgtgagct cttcacgctc ttcatcgtcc tggcgacctt cctcctgtcc ctgttctgcg   35640
tcaccaacgt acgtaccatc gccggcttcg ccttctcctg gtcatgtctc cttagcacgt   35700
ggcacggggc gccctggctg ggactgtcag gccagacaga accgcagcac ttccagggag   35760
ctgcgaaccc acccacccca gaaaatgact cgtagcagtg cacagggtaa ctgcacatcc   35820
agagcttggt cccagagtca cttcagcacc tggacagctc ccccagaagc accccaggct   35880
gaagctgcct ccttctaggg tttggggact gggggacgct gggggtgtgg tggcagagcc   35940
tatctatgtg ggaggggggag cccaggccac tccctctcca agggaggcac tgccaagttc   36000
cgcattcggt tgcttccatt tctaattgca catgaagccc taggaaggga aaggagaggt   36060 cattttatt tttattttt gtaatacacg tggccctaag aagctgcatg tgggttgaat   36120
tttagggact caaaccagag ttttgcagtg agtgaaacaa tttgtgtgca cagtgaatcc   36180
ccaggctggg tttacctctg gggaaagccc ttctgtaggt ccacaggctc ccctctcttc   36240
cagggtggca tctacgtctt cacgctcctg gaccattttg cagccggcac gtccatcctc   36300
tttggagtgc tcatcgaagc catcggagtg gcctggttct atggtgagtc cggggggaagg   36360 cagccaagcc ggcaccctct tgtttggtgg ctgtgccact ccccttctga aaaaggctcc   36420
gtgaggaaac acctttcagc tgcaggaagc ctgggttgtg tcatcacag ctccgcagag   36480 gggagaggct tggcactggt ccctttgatg ggatcagtga ggtgcttagc ttggatggca   36540
gccagaagag gcacactgtg gtcagaggtg ttcacagcgg ctgggcgtct tctgcctcct   36600
ccacgctaga ggcaccggtg agcccatccc acccagggga acacaatcag atccatgctg   36660
gggtttcagc agggatgtga catggtgcct ttcaaaggtg ccgtcatcgc cttccctgct   36720
gaccagagct ccagagcagt cgggacctga tgatcagcgg gcggcgctcg aacggggtgc   36780
agctcctggc ccattgtgct gccccagctg tgtcctggga cttccaccag tggtttaaac   36840
agcaacagaa aacccagcct ggagccaggg ctgcccttttc cccacatgct gacctggcca   36900
```

-continued

```
agtcacctcg actcccctta gttctctctt ctgtaaaatg ggcaggagtg ccagctccgc   36960
ttacctggcc agctcacttc cagggaagtg gcgaggccga gccagggcat ctcgccatga   37020
atgtgtggtc cgggcgcggt gactcacgcc tgtaatccca gcactttggg aggccgaggt   37080
gggcagatca cgagatcaag agatcaagac catcctggcc aacatggtaa aaccccatct   37140
ttactaaaaa aaaaaaaaaa aaaaattagc cgggtgtggt ggcacaaggc tataatccca   37200
gctagtcagg aggctgtaga ttttctgaag acactgatgg tatacttacg atggaatatg   37260
attcagcttg aacccggaag gcggaggttg cagtcacccg agattgcacc actgcactcc   37320
agcctgggca acagagtgag actccgtctc aaaaaagaaa aaaaaaaatg tgtggatccg   37380
gctgaaagct gaatgtctgt ggtgctgcgt gagccccggt tttggaggac gcccagctca   37440
cctgcaaaca agggggtcat tttctctgcc tcagagccat ggaatttata gccagataaa   37500
cgccctgact ttgagacaaa taggacaaat agctcctatt ctgagaacat tgttttcagt   37560
gttgctctac agaaaacgga aatatcaacc tcgtactttc acgggtgtct ggaatcaata   37620
ctttgtctat cactttcatt gtcatcttcc ctgaacaaaa catagacctt cacagaggaa   37680
gggagaaagt gccttgaatt gccatggcct ccggaaccac gggagatggg gagaagccgg   37740
ccctggcgac ctgcacctca gaagaccgag atctgtgtta tttttccaaa gagaaatcca   37800 cgccctctc atctaaatga aacaaaacct gtgctctaat aagatgtgcc ggaatacgcc   37860
gggcttccag cacgctgcgg tcctgtaggt cttggagctg atgactcctg ctccggcagg   37920
ggccctggga cctgctggtg ggaggcaggg tctgggggcc gaggggcctt ggggacgccc   37980
ctcttggctt cttccggcct cacctctctg catccccgct gcctcccacg tccatctctc   38040
atgttcagag ctcggatgcc gggtgggtgt gaagaggggga ttctgtgtgg aggcttcttt   38100
ctgatgggac acgggacaac cgcaagactt gccccaaatc tcagcagatc agccgcggtc   38160
acacgagtca cagaccaggc cagatgtggg gggagaaacc actcttaagg tcttagggtc   38220
agttcctaga agaagttaga taataccagt gaaagaaaaa tatgcatttc taaagtggac   38280
tgctggtact tgcttttggg gagaaaaaat gtttattatg tttctagaaa tagcttttct   38340
gaagacacag tgacggtata ctcatgacgg aatatgattc ggccttaaaa caaaagggaa   38400
tgctgatgtg ggccgcagct taggtggcct cagggacact ctacaggag taaaccagtt    38460 gcagaggccc cgtgccacgt gactccactg acgggaggtt cccacaggag tcacattcat   38520
tgagacaaaa agcagatggt gctggggcct ggcgggggtt gggggtcggg aggagttggc   38580
gtttcatgag ggcagaattt cattttggag gatggagttc tgaagatgga cggtggtgac   38640
ggttacacag tatgtgaatg tattgataca ttatgaactc tacacgtaaa aatggctaaa   38700
atggtaagtt ttatgttatg tgtattttac cataatcttt ttaagtgaac aagaagtacc   38760
agcagcagag ggagacaggg agagccatgg gatgggagg aggacccgag gggctgttgc    38820
cggggcgcgg ggagcaccca ccggggcacg gctcttcctg gtgcatctcc agggtggagc   38880
aggcacgtgg gctcccaccc gtcagcgagg cacccagtgg gctggggtgt ggcctggcct   38940
cctctgcagg aggctgggtg cagccgaagc ctggggccgg taggtggggc ccttgggagt   39000
cagcgaggac ccccacacgt gtccagcatc ggggaatgc gctgccctga tggacactga    39060
tgccacctct tctccctcag gtgttgggca gttcagcgac gacatccagc agatgaccgg   39120
gcagcggccc agcctgtact ggcggctgtg ctggaagctg gtcagcccct gctttctcct   39180
ggtaagggac ctcgggccac ctgcccttcc cccgtctgcc cactgccccc actctggcac   39240
```

-continued

```
ctgccccgag gtccagcgcc cgcatgtggg ttgtcactgt ggctggagtc aggggcctca   39300
agactcggcc cagaaggaca ggctgatccc tgaactcatc tatagtctcc ttaaggtggc   39360 ttccacccto ccctctagac ccaccgaaaa aacctcacat ggtcttggac ccctgtcaca   39420
gtccgttgtg agtcctgcac ttgggccgcg cctctgtgtt gggaggggaa gctggaggtg   39480
agtcgggctg tccactcacc tctgcctgtg aggatcaagg tcgaagttag agcttccggg   39540
gcagtgggga caaaggatgc cgagtgctgg atgagagcag caggggcctc ggccctgtcc   39600
cgttgctcac gcaagcctcc ctctggctca gcagcatcac tgtgtccagt aggcacttgc   39660
ttctgtcatc cgccaccgag tcagggccca ccgggcaagg ccgtcggacg ctggtgtttg   39720
taaatagagt tttgttggaa ggtggccgca cactttcatt agggattgcc tgcagtgctt   39780
cccccactga accacagagg cctggaggct cacaaagcaa agctgtgctg cctgatctgg   39840
gcaggcaacc taagagctgt ccaagtctaa gcagagtgtc ccgtgagctg ctcacgtaga   39900
gaagcacctc ccgagtccag caggcacgag gtggggactg aaacagggca ggggactcag   39960
gccgcaccct ctcatggacc aagggctggt cccggagtca gcagggcccg cgtgcgtgga   40020
gacccctcgt cacctgcaca cagcaggtgg gacagccccg tagttgccag cagaggggtt   40080
ccggggtaca ggaaagagat gagagacagg ccctatcccg gaggagctca acatagtgtg   40140
agagaacctg cccggcatct tgtagaaatt ccaccgtgtc tgagctccag gccgcgtggt   40200
gtggctgcac gtaagtgttc caagtccagt taactgcgct tgtgaaggct cccgttgaag   40260
gttcctggat tcatggggcg ggcttttaat agcacacaga ctacatggct gttcagaggg   40320
gaaagtgagg aagccctccc agaaagtcag cctcctgccc acctcccgct ctcccccgcc   40380
attagttgaa actgagctgt tttgcatgag gacgttggct cccttgagg gggtgtctcc    40440 tcttaacacc cagagggctg acctcgatct taggagataa aatgttctac tgatcttaga   40500
ctaaatcttc gaacttcata cagaaacaca cttcgtagac ttttagataa aactacaaac   40560
tatacgaaac aggacttcat tttgccaagt tgagagaaac atgacaattt cattgctcta   40620
tgtcattttg tatttaatat gacagcacaa ttcctatgaa gttctgattt cagcagaaac   40680
ataacgtctg tgttatcatc tgtttcttca ggctgcggca tagtcccctg ccctctggcg   40740
tgtgctaacc tctggtcgta aggggtgtac acgccccagt ctcgttcaga tgactctgtg   40800
gcagatgatg ccacagcact gctaaaggga aattatgccg gagcaaaggc aacttacatg   40860
ggcagactgt ggcctgggga ggcatagttc tttctaagaa aggtggtatc tagcaagaag   40920
ttgaacaata acagagagca cattacagca atacctccat gtcagatagg caagcccgac   40980
atgtccaggg atgcacgcgt ggctctttaa agcatgctca gggctctctg tgcagccaag   41040
gcagccgccc ctgatcccag atgctgcagg ccactggctt tgctcgccaa agtgctgctc   41100
accctggctc tggtcacgtg acagacacaa ccccagcccc catcccagtc ctccgctagc   41160
cggctccaaa cctacaagtg gcccgaagta gcgcatgaag aagatgctga gactggcatg   41220
agacacgcgt ccaacatgct tttcaggtgg aaggcttgga tgttttaact tttctgaaat   41280
tgaggaaaag tggacaattg ggaaaaaatt gcattttaag ctacatcata aaccatatct   41340
atcagagctt cacttgtgtc cttgggaagg acccaggtac acagaacaca tatgtaggcg   41400
tgcagtacac atgtgggtgc acagaacaca ttcaggtgtg aggtgcatat gtaggcacat   41460
ggaggatctt tttagatggt ggtgcatgtt tgtggagtgg atgaacaaat gcatgagctg   41520
cctcaggaga agcctctgga gagtgggaag cttccctcc aagtggcatc caccccaccc    41580
tctgttacct ttgtggtggt ggttctgaga caggtctgtg actttatcag atttgcttct   41640
```

-continued

```
agaatgagta gagatacgga gctcagatgg ccctagggtg gtcccgcatg ggtcacagtt   41700
gtgtcttcag gccatggatg atcatagatt cagtgtactg ggtggtggtc agttttgttt   41760
ttgttgtgat ttcaagcaag gaatagaaca aggtgggata cagcaggaag ggatgggatg   41820
ggatgagatg ggatgggata gagccggatg tgatgtaata gaacaggatg ggatggaata   41880
gaacatgatg ggatgggatg ggagggragg ggtggagagg ggatagaaca ggatgggatg   41940
ggaggggaag ggaggagagg ggatggaaca ggatgggagg ggaggggagg ggacagaaca   42000
ggatgggagg ggaggggagg agaggtgatg gaacaggatg ggatgggagg ggaggggagg   42060
ggagagaaca ggataggaca ggacaggcta gatcatgctt caggaggaca tggcttgccc   42120
gggatgccca gctgccatgt ctgcaggcct ggccggggtc tgcacctgca cagctgtggg   42180
ggctgagaga cgctctgcca tgaagtgcct gcccgctccc tgctttgtcc tggcaccgcc   42240
ggctgagagc tgcctgacct ccgtatctgc tggttgcagt tcgtggtcgt ggtcagcatt   42300
gtgaccttca gacccccca ctacggagcc tacatcttcc ccgactgggc caacgcgctg   42360
ggctgggtca tcgccacatc ctccatggcc atggtgccca tctatgcggc ctacaagttc   42420
tgcagcctgc ctgggtcctt tcgagaggtg ggtatttgga cggggcgcct tcacccgagt   42480
gtgaggccac cagaaaggct ccgtgggtgt ccatggcccc agtcctcacc tgcctgggtc   42540
atctgtgacc aagaggagga gactggaggt ggccaccaca acactgtgtg tgtgtgtgcg   42600
tgtgtgtgtc cacctgcacg cccgggccca tgggtgtgcg tccatatgtg tattcatgtg   42660
tgtgtcttta agtatgtcca catgtctgtg tgtgtctgtg tgtgcatgtg tctgtgtgtg   42720
cttgtgcctg tgtgtacatc cactgtatct ctgtgtctgt atgtgctgtc tccgtgtgca   42780
cgtgtgtgtg ggcctgggtc tgtgctcaca ttcgtgtcca agtgtttgtg tgtactgagt   42840
gcatgcatgc ctacacacta tggtatgtgg tgtggtggac acagaagcca tctgagggcg   42900
gtagaatcag gggtgatcta ggtccccca gggccgagcc caactttggc tgaacagggg   42960
cagctggagc cccaggcagt ggaggaagct ttgcggagtc actgatatgc atctcctttc   43020
ttctgcttgg ttttgccgcc tttgtgtaga agaaaggcag gtggaccagt cacagggccc   43080
tgtttaacac cctggctctg tggttccagg aagagacaag gacactccct ccttggaaga   43140
gggtcgccct cacctgagat cccaccactg ggaactcccg gaagctgctt cctcaaatcc   43200
cagcctttct cagaaagaag tcgcttggcc ctgggcatca aaaccccaga gcagcaccag   43260
ctgtgttcaa ggattccacc ttagggccac acggtgtccc ctgggctcag acatgtggca   43320
gatgctctca ggctggcact gagccagtct ctccagcagc ctggccaggc caaggcccag   43380
tgcaggcaaa gcacagtgtg tggctggggg cttctgtgga gtgggaggag ctctggggct   43440
gccatggccc caggaaagct gatggcaccc tgctgtggac agtccctctc agaccccac   43500 gggctgacct gccaggaccc agcacagggg aagagcaggc agccgggcag tctctgcagg   43560
gagagagctc ctctgggagg ctggatggac gtggaggcg gggcccaggt cagcgcagag   43620
ctggaggatg cctacagccc ggcggacctg aacagccagc gcccttaccc ctcgcatggc   43680
caaactctga acgtaagcca agtaaaaacct cagcagctga gccaggtaca agtggaattg   43740
tggtgatgac gtggggtggg gccacgcaca ggggtccctg tgagaggtca cctggcctca   43800
gagatccaga tacaggcatc caggcccgag agggtgagct cctgaagatg ctgcctgctc   43860
tgggaggact tggtgctgtc caggccccag gagctgccgc agcgggcagt ggaaggaagg   43920
cacgttcagc gttcactctc ccaagagctg caggtgacaa aaagcaagtg ctcccggaat   43980
```

-continued

```
atgtcagctg caggtggccc cgaggcagcc cacctgggtg tgggcacttt cttactcaga   44040
gcccagcaca cgtggtagct tagactcaag agccatctcc aggaccacgt tttattttca   44100
agcgagtgct caaatgctga tgttctgctc tgcgctagac tttaagggga ccgtcaggat   44160
gttggcttcg ggcctgactg gctgtctggt cggcatgggc actggcagtg taagtcagtg   44220
gtgggcgctg gtgatatgga tgccagcggg tgggcattgg caggtgagga gggctggtgg   44280
tgagggtgct ggtaggtgag ggtcctggca gtgtgagtca gtggtgggtg ctggcagtgg   44340
gtactggtct gcactgaccc ctgcactctc tttctctttc agaaactggc ctacgccatt   44400
gcacccgaga aggaccgtga gctggtggac agaggggagg tgcgccagtt cacggtgagg   44460
tcgaggtccc tgctgggcct ctctcggggg aattcagaat gatcccaagc tcagtgttct   44520
tagcccccag ggggctccga ggctggtgta gatggtgctc atttactcag ccagcatgtg   44580
ctctatgagg acaggcagcc agtggtggca ggtgacagtg gagacgtgtg cccgggacgg   44640
ggggcacatg acgcagggc cctgggaggt gcggctgcac agacgcctga ggaaagcatg    44700
gtccctgcaa agacctgggc atgtcccaga ccacgggagc agtgccctgt ggggccagct   44760
gagccaggtt aaggaccagc aagggaccac cacccccgc ctcacggggg cacaagggac    44820
agtgccagga ggggaggcct gggcctggcc atgggaagcc acaggagcc ctggaggggc    44880 tgggagaggc ctgggagcct ggggctggct tcgagtgaga ggatggtcac gccaggtgtt   44940
tcctgcaccc tgggagccat ccagctgtgt gcgaacatgt tcatgacatg ccgtggagca   45000
ggtgcattcc cggggggcaca cagtaaacac ttgacgtgtt tttactccca caaccctaag   45060
aggcagccca gcactctctc tacaccaggg tccctgagac ccagagaggc cccggaatgt   45120
gcccaagatc acagagctgg ccagcaggag aggagcctgg gctgtgccct gggcctgtgg   45180
cactgtcctc ctccaccca gagtggcctc agccccgacc tgattccata cactaatgtc    45240
agcctaatgc cgacagcaga gtccaatgca cagcaaaagg gagagaaggc catagtgtgg   45300
agggcaccgc ggccccacct cggacctgcc tcttccctct ggccacctct ctgtggctgg   45360
ttctcgtaaa cagtcctccc agcaggggtc tcatgagctc atgcctgagg agcccagcat   45420
ggacctgcac atggggcagg agcaaggata caggcagagg gaggggggctc tgcgtgcctg   45480 ggaggtgggt ggtgacgtca ggcagaacaa gacgctgagc agggaacagg ccgggaggca   45540
gtggggagaa gccgcctctg agcacacatc tgcacagctt gttcctccta cctgcaagtc   45600
aggttctggt gtgggctctg cctccctccg ttggcaccct ttcctctgtc ctcccagtga   45660
cttgcctgct ccaaacacag gaggcgtgtc caggcatccc atcccatcca tccagaggat   45720
gccagcccct ccccactggg cctccggtcc tgctccacca gagcctctct cctctgagag   45780
tcctatacct gggggtctta cactttgtac aggatcttgc tagtcttctc aaatatccaa   45840
ctttgacttc atgtgagatt cttgctgtgc ttcctgtcac attaatctca gctcctgtat   45900
ttatcatttc ttcctctctt tttcttggat ctactctgtt gtagttttgc taactttta    45960 atttggactt taggttatta atttgcatcc ttcgttcttt tctaatgtaa gcactcaagg   46020
ctatgaattt ccctcaaaat actccatgtg ctacattccg tattttttc atagtatttt    46080 tctttatctt ttagttctaa gtatatttta atttccattg tgactttgtc aactcataac   46140
ttgcttaaaa gtctgctttt aaattgccaa atatatgggg atgttttact catcttttg    46200 tttttaattt ccaaattaat ttcattgttc tcaaacacat atgataccta ttatttaaaa   46260
tgtattgaga cttcttagg gccttatacc tgatcaactt tgataaacgt tgcacatctt    46320
ttagatgaat gtgctattct ctaattgtca atacacagtt ctgcttctgt ccatttgagt   46380
```

-continued

```
agggttatat attatgttac ccacattgtc tacactttgt caactttagg ggtgcttgac   46440
catgagtaat tgagagatgc ctgtggcata ttcttcctcg atagtatatt tgtttgctgt   46500
tcccctcagt tctatcaggt tttgctctct gtagtctgag gctgttttct gaggttgatc   46560
catgtccaga atgatcatct cttcctggtg acatgaaccc atcttcactc cctaatgatg   46620
cttttggtct taaagtctga cttgtctggg acaaatatag ttgcaccaag gtgtcttttg   46680
agtttgcctg aaatatcttt tgcaatctgt taactttcaa ctttgcagta accttaagat   46740
ttaagtgtct tttgcaaacc cagcatacac ctagaatttt ttacgctgac agttggacag   46800
gttaatccat ttacatttgt tgtgattatt gatatatttg aacttgattc tactatcttt   46860
ctattccatt tgtcccattt ttagtgtttt tctcctttat tgccttttta tagattgatt   46920
tttcttggtt cactcatttt tattattccg tttatttctc tctacttgct tagaacttac   46980
atactttatt cttttttttt tttttttttga ggtggagtct tgctctgtca cccaggctgg   47040
agtgcagtgg catgatctct gctcactgca acctccacct cccaggttca agcaattgtc   47100
ctgcctcagc ctctcaagtg gctgggatta caggtgccca gcaccacacc tggataattt   47160
ttgtgttttt agtagagaca gggtttgacc atgttggcca ggctggtctc gaactcctga   47220
tctcaagtga tctgcccacc tctgcctccc agagtgctgg gattacagcc gtaagccact   47280
gtgcccggac ttattctatt cctttaatag ctactcttga ggttgtacca tacatatttc   47340
acttaaactc tacagagaaa ccatatttta accccatccc attataagga cttaaatctt   47400
cctcctactg atgaacatgc tatgattgtt caaatctatt tctctctttt taacccacaa   47460
attagacact gtcattgttc ttgttcctgt tattattttg tacggactca tcatgttcct   47520
tggactaatg tgcatgcttg gtgtttgttg gttcccatac ttttgttata gacttctttt   47580
cttctaggac cattttcttg ctttttcaaaa agcatccttc agacattcct ttgaggaggt   47640
ctcttgctaa cctccctcac tattggtgtg tgggaacatc tttatgctgc tctcattcac   47700
gaaagcactg ttgtgggctc agggctctag gctgacaggg actatctctg cgttttggag   47760
gcagcagtgt tccgtggctg tgctgagatg tgtggcctgt gagcctgctc tgtggtgggc   47820
tctgtcctca cccctgcact cggccgagtt tcttctgctt tcggtgtctc gggttcactg   47880
cggagtgtcg ggacctgggt ttctttttttg tttgtttgtt tgtttgtttg tttgttttga   47940
gacggagtct cgctctgtag cccaggctgg agtgcagtgg cgcaatctcg gctcactgca   48000
agctccgcct cccgggttcg cgccattctc ctgcctcagc ctcccgagta gctgggactg   48060
caggcaccca ccaccgttaa tttggtttct ttttatttt cctctctgga tatgttttgt   48120
ggccagatct gtggattcac aaatcttgtc attctgtgaa ttttgcagcc acacactgaa   48180
agattgcctt ctgcctttct gtgtttttcca ttatgaggct ctggtgtgtc cactttgccc   48240
caggtcctcc aggtctctta cctcacttag attttgtttt catttgaatc ttaggtgcac   48300
agttgagtaa cgcatcttat cattaatcca catgtggcca tttttaaatt attaatttgt   48360
caccgtaaca aacagaccct tgtgagccca cagcaggaaa actaggcact gtggaaactg   48420
cctgcccctc acccattctg tatctgcgtc tagcttgatc tttcccttgc ccttcttaca   48480
atttcatttg ttgcatctct agatatttct agcttcctaa aaagtgtatt atttggcttc   48540
agcatttggt gtagccctaa ccaacccta ctgaagcaag accttatgca caccccatgc   48600
agatccccga gaatcatgac attctcctgg ctggggaac aggcaccgtg cccagccctg   48660
tgtgggcatc agaggtggtt ccctctggtc ctgtcggcgg atctctcccc agcctcctca   48720
```

-continued

```
ttcacagcgg gatgtgctcg tctgaaccct cagcaggggt cctgggccat tgtcccgggt    48780
cttctctctg tgtggccacc tcctctctgg cgctctggcc tgcaaactgc agccacctcc    48840
gtttccctcg ctctcctttc cagcgtctca gctcagggag tccaccaggc tgcaccctcc    48900
ctgtgctgca atctagaaac tccctcgagg cagcgagcag ggtggcaggg gggcctcctt    48960
gttggcttcc ctcagggacc actgaccctt acggtctggt gtccatggtc tggaaggtca    49020
tcggcacgtg tgttttgttt atttgggggct tgtttcggac agtagggtaa attcgatccc    49080
tattattcca tctaggtcag aaatgtttgt atccatagct acgtttcacc taccgtgact    49140
ggtccctgac cgtccgtcac gtgaacaaac cacagctcag ctatggacgc tccgcattcc    49200
actgccctgc ccctggtctg cagcccagcc attctctttt ctacttcatc tctggaagct    49260
gcgtgtgctc tgctgtttct tgtgaaattc tcatcactgt gatgtgcgtg tgtcactttt    49320
ctgagagtcc cctatgtggc catcctgtaa tctgttgcaa cagctctggt cctttggggt    49380
caaattgagg tctggtttct ggggactcac ttagagtggg ctgctgtctt ctgtttctag    49440
tctttatttt acatttatgg cttgatctta atctgtggga atctgggagc ccccaagcac    49500
acctccctcc agaggggacc ttctgcttct gtcagcgggc aggacagaga actgcttcac    49560 cctggggggga acaggactca cagctgaagt cccaagcatg gcttcttcat cgctggcctg    49620 aagtgggggct gccacccaga gcctctgctc tagggctctg gccgctgggc cacccgtggc    49680
tgtgggtcct ggccgggctc cctgacccca gcttccttca ctgagccccg agctgcacct    49740
ggatgctgcc tgtgccggca tcagctgtgg ctgctccagg cccccggtag accctggcc    49800 tgcagtgtga tcccaccctg gctgaggagg tccctgcagg ctcttggtgg agtggccaga    49860
ggagcctgtg gtgtggccag tggtagcttc agtggctttc catggccggc gtggttttgt    49920
cagaagcaag ccccgcatgc ccctgtttgg aaatgtttat gaagcacact tcttgccatt    49980
tagtgctatc gaggggcttt gacgctcaca aacaggctga actaacagct gcataatagc    50040
aggcgatgac atttgctggt ggtgtaaata gctgctcttg tctatctcat cagtccctga    50100
gcagtcagta cacgctgcac ttgcgcccgc gcgggtcgca gagagcaaga tggagctgca    50160
gaggtagcgt gtcactcaga tggagcatct gaggcccccca ggaaggtgga gggacgtggg    50220
ggagaggtga catcaccacg tcacacccaa gtcgctgggg tacaatctgg aaccagcccc    50280
ggactgaggg tgcccggcat ctctcagact cagcatctga tcaatacgcc ccagaggcca    50340
ccatggccac cacgccaacc acagtctcgc ggcttttttaa aaaatcaagt aatgattgat    50400
ttgtaggagt ttgagtgagg catcggatcc ccggcacctg tcaagggtgt gttggtccag    50460
gcccccagtg agcctcccct tctcccaggg cacatggcca ggaggctgca aactgtctgc    50520
tcactgcctt cagctgctct tagccaccctt cagctgctct taaatggggc atcgccccag    50580
ggtttctgac taaacctgtt ttctttccag ctccgccact ggctcaaggt gtagagggag    50640
cagagacgaa gaccccagga agtcatcctg caatgggaga gacacgaaca aaccaaggaa    50700
atctaagttt cgagagaaag gagggcaact tctactcttc aacctctact gaaaacacaa    50760
acaacaaagc agaagactcc tctcttctga ctgtttacac cttttccgtgc cgggagcgca    50820 cctcgccgtg tcttgtgttg ctgtaataac gacgtagatc tgtgcagcga ggtccacccc    50880
gttgttgtcc ctgcagggca gaaaaacgtc taacttcatg ctgtctgtgt gaggctccct    50940
ccctccctgc tccctgctcc cggctctgag gctgccccag gggcactgtg ttctcaggcg    51000
gggatcacga tccttgtaga cgcacctgct gagaatcccc gtgctcacag tagcttccta    51060
gaccatttac tttgcccata ttaaaaagcc aagtgtcctg cttggtttag ctgtgcagaa    51120
```

-continued

```
ggtgaaatgg aggaaaccac aaattcatgc aaagtccttt cccgatgcgt ggctcccagc   51180
agaggccgta aattgagcgt tcagttgaca cattgcacac acagtctgtt cagaggcatt   51240
ggaggatggg ggtcctggta tgtctcacca ggaaattctg tttatgttct tgcagcagag   51300
agaaataaaa ctccttgaaa ccagctcagg ctactgccac tcaggcagcc tgtgggtcct   51360
tgcggtgtag ggaacggcct gagaggagcg tgtcctatcc ccggacgcat gcagggcccc   51420
cacaggagcg tgtcctatcc ccggacgcat gcagggcccc cacaggagca tgtcctatcc   51480
ctggacgcat gcagggcccc cacaggagcg tgtactaccc cagaacgcat gcagggcccc   51540
cacaggagcg tgtactaccc caggacgcat gcagggcccc cactggagcg tgtactaccc   51600
caggacgcat gcagggcccc cacaggagcg tgtcctatcc ccggaccgga cgcatgcagg   51660
gcccccacag gagcgtgtac taccccagga cgcatgcagg gcccccacag gagcgtgtac   51720
taccccagga tgcatgcagg gcccccacag gagcgtgtac taccccagga cgcatgcagg   51780
gcccccatgc aggcagcctg cagaccacac tctgcctggc cttgagccgt gacctccagg   51840
aagggacccc actggaattt tatttctctc aggtgcgtgc cacatcaata acaacagttt   51900
ttatgtttgc gaatggcttt ttaaaatcat atttacctgt gaatcaaaac aaattcaaga   51960
atgcagtatc cgcgagcctg cttgctgata ttgcagtttt tgtttacaag aataattagc   52020
aatactgagt gaaggatgtt ggccaaaagc tgctttccat ggcacactgc cctctgccac   52080
tgacaggaaa gtggatgcca tagtttgaat tcatgcctca agtcggtggg cctgcctacg   52140
tgctgcccga gggcaggggc cgtgcagggc cagtcatggc tgtcccctgc aagtggacgt   52200
gggctccagg gactggagtg taatgctcgg tgggagccgt cagcctgtga actgccaggc   52260
agctgcagtt agcacagagg atggcttccc cattgccttc tggggaggga cacagaggac   52320
ggcttcccca tcgccttctg gccgctgcag tcagcacaga gagcggcttc cccattgcct   52380
tctggggagg gacacagagg acagcttccc catcgccttc tggctgctgc agtcagcaca   52440
gagagcggct tccccatcgc cttctgggga ggggctccgt gtagcaaccc aggtgttgtc   52500
cgtgtctgtt gaccaatctc tattcagcat cgtgtgggtc cctaagcaca ataaaagaca   52560
tccacaatgg aaaaactgc                                                52579
```

<210> SEQ ID NO 46
<211> LENGTH: 15143
<212> TYPE: DNA
<213> ORGANISM: Homo sapiens
<220> FEATURE:
<221> NAME/KEY: CDS
<222> LOCATION: (306)..(1508)

<400> SEQUENCE: 46

```
ctccctccct tccagcctcc gaatcccgca tggcccacgc tccctcctg cagcggtgcg    60 gggcaggtga tgagcctctg tgaactacta aggtgggagg gggctatacg cagaggagaa   120
tgtcagatgc tcagctcggt cccctccgcc tgacgctcct ctctgtctca gccaggactg   180
gtttctgtaa gaaacagcag gagctgtggc agcggcgaaa ggaagcggct gaggcgcttg   240
gaacccgaaa agtctcggtg ctcctggcta cctcgcacag cggtgcccgc ccggccgtca   300 gtacc atg gac agc agc gct gcc ccc acg aac gcc agc aat tgc act gat   350
      Met Asp Ser Ser Ala Ala Pro Thr Asn Ala Ser Asn Cys Thr Asp
      1               5                  10                  15 gcc ttg gcg tac tca agt tgc tcc cca gca ccc agc ccc ggt tcc tgg   398
Ala Leu Ala Tyr Ser Ser Cys Ser Pro Ala Pro Ser Pro Gly Ser Trp
            20                  25                  30
```

-continued

```
gtc aac ttg tcc cac tta gat ggc aac ctg tcc gac cca tgc ggt ccg        446
Val Asn Leu Ser His Leu Asp Gly Asn Leu Ser Asp Pro Cys Gly Pro
            35              40              45 aac cgc acc gac ctg ggc ggg aga gac agc ctg tgc cct ccg acc ggc        494
Asn Arg Thr Asp Leu Gly Gly Arg Asp Ser Leu Cys Pro Pro Thr Gly
        50              55              60 agt ccc tcc atg atc acg gcc atc acg atc atg gcc ctc tac tcc atc        542
Ser Pro Ser Met Ile Thr Ala Ile Thr Ile Met Ala Leu Tyr Ser Ile
        65              70              75 gtg tgc gtg gtg ggg ctc ttc gga aac ttc ctg gtc atg tat gtg att        590
Val Cys Val Val Gly Leu Phe Gly Asn Phe Leu Val Met Tyr Val Ile
80              85              90              95 gtc aga tac acc aag atg aag act gcc acc aac atc tac att ttc aac        638
Val Arg Tyr Thr Lys Met Lys Thr Ala Thr Asn Ile Tyr Ile Phe Asn
            100             105             110 ctt gct ctg gca gat gcc tta gcc acc agt acc ctg ccc ttc cag agt        686
Leu Ala Leu Ala Asp Ala Leu Ala Thr Ser Thr Leu Pro Phe Gln Ser
            115             120             125 gtg aat tac cta atg gga aca tgg cca ttt gga acc atc ctt tgc aag        734
Val Asn Tyr Leu Met Gly Thr Trp Pro Phe Gly Thr Ile Leu Cys Lys
            130             135             140 ata gtg atc tcc ata gat tac tat aac atg ttc acc agc ata ttc acc        782
Ile Val Ile Ser Ile Asp Tyr Tyr Asn Met Phe Thr Ser Ile Phe Thr
            145             150             155 ctc tgc acc atg agt gtt gat cga tac att gca gtc tgc cac cct gtc        830
Leu Cys Thr Met Ser Val Asp Arg Tyr Ile Ala Val Cys His Pro Val
160             165             170             175 aag gcc tta gat ttc cgt act ccc cga aat gcc aaa att atc aat gtc        878
Lys Ala Leu Asp Phe Arg Thr Pro Arg Asn Ala Lys Ile Ile Asn Val
            180             185             190 tgc aac tgg atc ctc tct tca gcc att ggt ctt cct gta atg ttc atg        926
Cys Asn Trp Ile Leu Ser Ser Ala Ile Gly Leu Pro Val Met Phe Met
            195             200             205 gct aca aca aaa tac agg caa ggt tcc ata gat tgt aca cta aca ttc        974
Ala Thr Thr Lys Tyr Arg Gln Gly Ser Ile Asp Cys Thr Leu Thr Phe
            210             215             220 tct cat cca acc tgg tac tgg gaa aac ctg ctg aag atc tgt gtt ttc       1022
Ser His Pro Thr Trp Tyr Trp Glu Asn Leu Leu Lys Ile Cys Val Phe
            225             230             235 atc ttc gcc ttc att atg cca gtg ctc atc att acc gtg tgc tat gga       1070
Ile Phe Ala Phe Ile Met Pro Val Leu Ile Ile Thr Val Cys Tyr Gly
240             245             250             255 ctg atg atc ttg cgc ctc aag agt gtc cgc atg ctc tct ggc tcc aaa       1118
Leu Met Ile Leu Arg Leu Lys Ser Val Arg Met Leu Ser Gly Ser Lys
            260             265             270 gaa aag gac agg aat ctt cga agg atc acc agg atg gtg ctg gtg gtg       1166
Glu Lys Asp Arg Asn Leu Arg Arg Ile Thr Arg Met Val Leu Val Val
            275             280             285 gtg gct gtg ttc atc gtc tgc tgg act ccc att cac att tac gtc atc       1214
Val Ala Val Phe Ile Val Cys Trp Thr Pro Ile His Ile Tyr Val Ile
            290             295             300 att aaa gcc ttg gtt aca atc cca gaa act acg ttc cag act gtt tct       1262
Ile Lys Ala Leu Val Thr Ile Pro Glu Thr Thr Phe Gln Thr Val Ser
            305             310             315 tgg cac ttc tgc att gct cta ggt tac aca aac agc tgc ctc aac cca       1310
Trp His Phe Cys Ile Ala Leu Gly Tyr Thr Asn Ser Cys Leu Asn Pro
320             325             330             335 gtc ctt tat gca ttt ctg gat gaa aac ttc aaa cga tgc ttc aga gag       1358
Val Leu Tyr Ala Phe Leu Asp Glu Asn Phe Lys Arg Cys Phe Arg Glu
```

-continued

```
                    340                   345                   350
ttc tgt atc cca acc tct tcc aac att gag caa caa aac tcc act cga      1406
Phe Cys Ile Pro Thr Ser Ser Asn Ile Glu Gln Gln Asn Ser Thr Arg
                355                   360                   365 att cgt cag aac act aga gac cac ccc tcc acg gcc aat aca gtg gat      1454
Ile Arg Gln Asn Thr Arg Asp His Pro Ser Thr Ala Asn Thr Val Asp
            370                   375                   380 aga act aat cat cag cta gaa aat ctg gaa gca gaa act gct ccg ttg      1502
Arg Thr Asn His Gln Leu Glu Asn Leu Glu Ala Glu Thr Ala Pro Leu
        385                   390                   395 ccc taa cagggtctca tgccattccg accttcacca agcttagaag ccaccatgta      1558
Pro
400 tgtggaagca ggttgcttca agaatgtgta ggaggctcta attctctagg aaagtgcctg      1618 cttttaggtc atccaacctc tttcctctct ggccactctg ctctgcacat tagagggaca      1678 gccaaaagta agtggagcat ttggaaggaa aggaatatac cacaccgagg agtccagttt      1738 gtgcaagaca cccagtggaa ccaaaaccca tcgtggtatg tgaattgaag tcatcataaa      1798 aggtgaccct tctgtctgta agattttatt ttcaagcaaa tatttatgac ctcaacaaag      1858 aagaaccatc ttttgttaag ttcaccgtag taacacataa agtaaatgct acctctgatc      1918 aaagcacctt gaatggaagg tccgagtctt tttagtgttt tgcaagggaa tgaatccatt      1978 attctatttt agacttttaa cttcacctta aaattagcat ctggctaagg catcattttc      2038 acctccattt cttggttttg tattgtttaa aaaaataaca tctctttcat ctagctccat      2098 aattgcaagg gaagagatta gcatgaaagg taatctgaaa cacagtcatg tgtcagctgt      2158 agaaaggttg attctcatgc actgcaaata cttccaaaga gtcatcatgg gggatttttc      2218 attcttaggc tttcagtggt ttgttcctca gtttttaaatg tgcaatttttc ttgctcctat      2278 ttaagtgttc acaaaaggta atagtcaatg agctcatcac ttcatccatg caggaagtca      2338 agcattaaaa tgtactcttt atttctcact ggtttctcca tactgcaggc tccccacata      2398 ttattttctt tttttaactc agctcagaat ccttatgcct tttgaatcag tgtgataaaa      2458 tgacagatgt ttttgttgat tgccagaaca gtttaaactt tttttaaaca ataaatccaa      2518 taaacataat ctcaagacag actcatatga ccatacagaa aagtgtgtca tctatttttc      2578 aatcctgtgt agttacttgg atgtgaaata ttaacaatgg cccaaaaata ttttcctgaa      2638 gattgtgttt atataatgtc atcaccaata ttttggtctt tttgatctct gctaaatgtc      2698 aagatttcct ttgtaaagtg tcgatcttct aagtagtttc tttaagacaa ttctccgctt      2758 taactgattt tctttgttgt gaaacacagt agagatttgg caatcaacca ttttacttga      2818 tctaggtaga cagccaagtc agatggccca tgcctagaag ctctccattt tgaacttttg      2878 tcagcattga ttaaaagaat caaatacctt gtagttatct atgatgatac aagtaaaaaa      2938 ctaggctgct gacttctgag tattcctgag cctacaattg taaaattgta gactccattg      2998 taaaatttgt attttttcat caatctgaca aggcacaaat atgtgccaga tatacaaaag      3058 caatgtttct agaaaacagc tatcatggat cagaataact gaatttactc tcagatctat      3118 tggctatagt tatgtggact caacccacgt atccagtaga tgggaaaaaa caaaagccaa      3178 aataagtttt ttagtgtttc cttctgatga gtttcatgt ttgcttgtaa taatctccat      3238 ttctcaaata ttatgttcca aatagacat acattatgtt taattttta tattttctga      3298 caaaagtaac taaaactagg accttaaaaa gatttagaat gttaaataag tgtactaggg      3358 tgtatatatt tacatatata cactactaga gcttccaaaa gtaaaatgga taattcaaac      3418
```

-continued

```
agaacacaat gtaatatttg tatgtaaata actgaggagg aaaatccatg cttttcatgg   3478
gctaggatgg tttctcccaa gagatgacat agtattgctt ttgctcatca ggctgtttct   3538
cagcaatcat tgtttctgct taataccagc tcctagtacg aattatctgg catgttgaga   3598
gcaactttgt cttcaagtag gacctgatct atctttttcc acaaatgtca tgtgtgtgaa   3658
caagtttctt ccatgtcatc tttgagactc tacacagaat acacaataaa gggagttatt   3718
tttaaaataa gacattctaa agtaaataat aaataaggtc attgtcaacg tttttcattc   3778
aaaaccattt tttaacgtaa atttgctaga accaccttcc aattccaagg caaggagaga   3838
cattacaacc ctgactcaac tggatgggct aaggtttctg ataaaatctg aagataaaga   3898
aaatggaata ttctgctttt ttcttccttc taatttcacc cttgcctaag gatgagattt   3958
cttcccaggt tggtatccca gaaatgcaga ctgtagctat ggggcggaag ctttgtttct   4018
ttacctgatc acttgctgtg gaaattctag cttattgtgt tccaagtagt tagtggtttt   4078
tctccttcag tctccactgt tattttgctc cttcatccct ctttccttgc caatcattag   4138
aaaggaaaga agaggaaaga gactcgctgg agcactggtg agtctctagg accctgctat   4198
cctatcccaa cagggctgtc agacggagaa ctcctaatgt ggccatttga aacacttctc   4258
aacattgaaa tagacagttg aagttttaaa ataacctctt ctaagacacg gctatgagta   4318
ggtaagagag cattcattcc cttcaataat atgactgtgt tgataaaact gataaccatt   4378
cacttgcaaa tgttattatt gaataagtct cacttagctc atttaatatt acccaaaaga   4438
tgctaacaaa ttctgtttcc cacattgtca cagcatgccc tttacatctc aggatccagg   4498
caaaagttga aattcagaaa catagatatg aaatgtaaga tacaagaaa acacctctgc    4558 aaagattccg accacattta tcaaaaagtc cccaaagcat tcaaaatctt tacttaagtc   4618
aagtctattt atacgtttaa aagctaaaaa caagatcttt ttggtaatgc ttcaattaaa   4678
tgttttatct aaatatgtgg aaatgataag atgcgtactg catctctcat ataataaaga   4738
taatcagttt tatacagaca tattctccat ctactggcaa ttaccaagat aagatggcac   4798
tagaaatttc tccagcttac gccatgaata ctgcagaagc tgatactatc cgttgtggtt   4858
ttacaaattc tagagggttc tagccaaagc aacctaagaa taggacatgg tagcttaagt   4918
ttttcagctt cttaactggc cacacacaca caagttgtgt ttgtacaatt cttgaggtca   4978
atcagaacca aaaatctgt tgctggaaga aatattatcc tcttcataga aatatccacc    5038
agcagaaaat tggtttctca aggaatccct actgcccttg tagaaacatc aagattcttg   5098
cctggattct caacataagt ctttactcac aggcctattg cttggtttca gaagagtgag   5158
aacatgaaag ttcataaatg cctgggccac tgcaactcta accactgtgt ttcccccagt   5218
ttgatatggt tcaggataca tagtcataga acagggcatg cagattgtat ttaagaccac   5278
tgcaagtaag gtctaaggca aaagtaaatt aatgagtcca actctggggc atccatttaa   5338
gagccattta atccatttaa ttacaaataa tttcaaccca tagtcagtgt tcttcactgt   5398
cttcaaaaat ataaaaagta caaggaattg tgtacattac aaactgctcc agaaacaaaa   5458
ccaaatgtgg atagctttgt gagctgcagt gtgtggcaaa tgttcaacct tttgttatgc   5518
aatatcaccc atatcaaata ccattcttaa agcagtagac agatgagtca agttcaattt   5578
aatgcaaaca atattactgt gttctaagcg cttctgttac tcgaaagggg tctgatccag   5638
accccaaaag agggttcttg gacctcatgc aagaaagaat tcaggagtaa agtgaaagtg   5698
aaatgggtca ggatcaatgg tctcattgtc taaggtgtta tccgagctcg ttgtctcaca   5758
```

-continued

```
accaagaaaa ttaaggagca tggacacaaa gggtgaggtt ggagcaaaag tttaataagc    5818
aaaagaggaa agctctctgc agcagagacg ggagcccaag tgggttgctg tttttacagc    5878
tgaatccaaa agcttttata agaaactcct ctcatctctg cagctatttg agtaacttct    5938
cttatctgaa aagctgtctg tacaactgcc tctatctatg cagctatggg gtgtctctag    5998
gcgagcacaa agcatagctt ctcttgttgt ataattgtgg gtttgtttta agtaagccac    6058
tttcctccct gcaagttccc acggagcaga aaaaaggagg aaactttttc ctgggagccc    6118
actaatcaca cagtgaacaa aaggcttcta tgctgggcct tactttctaa cagtgcagca    6178
gttatagtct gagttttctc caggctgctc cattttttgcc tgtagctatg atttttcagg    6238
cagcctgctt ctccgaggac tagtcttagc tgtttaccta actgattggt cctttttcttc    6298 tccctgaaaa gcaagtttat taagaaagca aaggaataaa gaatggctac tccataggca    6358
gcgtagcccc aagggctgct ggttggctat ttttgtggtt atttcttgat tatatgctaa    6418
acaaggggtg gattattcat gggttttctg ggaaaggagt gggcaattcc cagaactgag    6478
ggttcttccc cttttaagac cgcatagggc aacttcctga cattgccatg gcatttgtaa    6538
actgtcgtgg tactggtggg aatgtttttt agcatgctaa tgcaatataa ttagtgtata    6598
atgagtagtg aggacaacca gaggtaactt tcattgccat cttggtttta gtggggtttg    6658
gccggcttct ttaccacatc cttttatcag taagatcttc gtgacctgta ccttgtgcca    6718
acctcctatc tcttcctgtg acttggaatg cctaacctcc tgggaatgca gcccagtagg    6778
tctcagcctt attttacccca gcctctattc aagatggagt cgctctggtt caaacacctc    6838
tgacacttga attacaaata taaggaccat tgacactgag attttaaggg aggaaaaaca    6898
gattgacagt ggactaaagg tactttgta gcaaggtact ttccacacaa tattgaataa    6958
atgcagtgta tacatttta aaggaatttt aagagctcgg aaatcattaa aattaagttt    7018 atcaatttt gaaagcatct tctgactcaa atatatgaaa agattattct agaccttagg    7078
cagatattca gagaaagatc agttttctat gggttttttc catcatgcat tttatacaaa    7138
tttaatatac ttttttcaact cactttgcat ttcctgttac cttgtactga gaacttcatt    7198
aaaacctgca cttgaaattg cacttaaact ttacaaaatc acagaagaag ttgtttttcca    7258 taggtgtggg gtgggatgtt agagctctag acattaattc ctaggaatcg catacctacg    7318
gaaaacagtc ctctgacctc ctgtgacaca tggggtgagc ccttcctttt tgtctcaatc    7378
tcaaaaaaca gtaagtcttt aatccatttg catcaaaaag tacttcatat gctcgaaact    7438
aaagtaaaac tttattgaaa tacattaata tgctcctgga acatactact gggtctcaga    7498
cagtgcagaa gctttattgt ttatttggga agagcaaggt aagaatcaag tagaaatgat    7558
aaagggcaag gaaaaaagat gaaagcttac tcatattaac cattctacca ttggaattat    7618
ttgccaacac accttgctgc tacttagaga aagtagttca cctcactacc ttttatccaa    7678
agaaattatc tctaaaagca ctcagacatt ttgtagagca agtagcaatc tattcaaagt    7738
tgtaaaggtt ctgtagaatc tctcagacca ggtacaggac ctaccaaagg ccacagccaa    7798
gcacaagcag ctacattaga cagttttaca gctctgtatt tcaggaaaac ttctgtcctg    7858
tgggagcaat acaaaactat accagttttt tgttagtgta aaaattgccc aatattaacc    7918
agagcagccc aaaatatttc agggtaagaa tagatatatt tatattttc agatgatata    7978 tcttcatttt cgattttgaa agaacagtaa tactaattat atcccatgta aggggctact    8038
gacaattttg atggtacctg aatttgcctc tatcatgcat ctcaatgatt tgttgtcatc    8098
caaagctatt tcatgaatca aatatcgttt tctacctgcc ccacaactgt gtacataaaa    8158
```

-continued

```
cctaaacctc tgaagcaata aacctcttcc attacacagg tttagattca gagttttctt    8218
gcttaagttc caactaaaag tattacattc ttagcataag tatactcata aagaaaaata    8278
agtatttgtt ttaggtttta gagagagagc acagagtccc tttgagacag tggggaaaat    8338
tcatcttcat attgtcacat gcactgtaat aggaatgttt agcaaaaaaa accttccaga    8398
gaaaggtggt ttccaatatt acctacaact tcctttgcaa tttgatttttt gaaaggacct    8458 aaaagttgaa aacaggctat cacatcccat ttgcttaaa gtctcttaaa cttacgctct    8518
ttcgcttcaa atgcataaat gttttattta agtttgcatt gcccactaag gctagacatt    8578
tttttttttt tttttttttt tttttttttg agacagagtc tcgctctgtc gcccaggctg    8638
gagtacagtg gcgggatctc ggctcactgc aagctccgcc tcccgggttc acgccattct    8698
cctgcctcag cctcccaagt agctgggact acaggcgccc gccactacgc ccggctaatt    8758
ttttgtattt ttagtagaga cggggtttca ccgtttttagc cgggatgatc tcgatctcct    8818
gacctcgtga tccgcccgcc tcggcctccc aaagtgctgg gattacaggc gtgagccacc    8878
gcgcccggcc cggctagaca ttttttgata aattcacagg gttacaaaat accaaacgga    8938
aatgagataa gtggtataaa ccacagaaga tataggagaa gagaaaaaaa aaagaggaaa    8998
taaagaagac aactcttttc ctaagagtct gggtaaaatt gaacatagcc atattcactg    9058
aacaacatga gtgagcttca ttaatttaag cacagcaaaa ctgctttaat taacaagacc    9118
agagagaagg gagaggagac tacatttgtg tgacctaatg gttgtgattt cactgtccaa    9178
gaggacaaag acaaagaaat tctgggaagg agaacaacaa ttatattccc ccatttcaag    9238
aagggcagaa gtgtcccaac actacccaat atttgcaaaa ttcaaatgtc tcataggctc    9298
ttcttccctg gttccctcag gagctggggtt tctgggttgc agaagtgctt ttcatattct    9358
gtatctggtt gtggtggcaa tgtcaccacc ctacactgct gtgacaccga aacaaccaag    9418
cctagaatca gctggtgcct cttttcatct gcagggtaga tttggcttcc atggttgttc    9478
actgctctgt gttaggaagg ctcagtgaca ggtgtacagc cttcagtaat gcctcaaagg    9538
ttctccaagc agaggtaaac atgtgggtcc tgctggtgac atattagact tcttactttc    9598
cccaaataaa aaagtgcctg ctgggcgcgg tggctcacgc ctgtaattcc agcactttgg    9658
gaggccgagg cgggcggaac acaaggtcag gagatcaaga ccatcctggc caatatggta    9718
aaaccccatc tctactaaaa atacaaaatt aggaaggcgt ggtggtgcac gcctgtaatc    9778
ccagctagtc gggaggctga ggcaggagaa ttgcttgaac tggggaggcg gaagttgcag    9838
tgagccaaga tcgcagcatt gcactccagc ctgggcaaca gaatgagatt gtctcaaaaa    9898
aaaaaaaaag tgccacatgc catgctatgt gcccaaagtt tccttcacac aacacagcct    9958
tgagatgcag tattaaattc tacactttc ctaccatagt gatacatgtg ctttttcttt   10018
gctgtgttct gagatgtcat gctttgaaat cagtggccat tatcatctaa ggattccgcc   10078
agagacttcc aaaagaagag gtctcattta taaagtgaat ttgaataaaa tgaccagtta   10138 ggtgtttttca gaaacaccta tgccctactt gcctactctt caagggttta ggggcttagg   10198
gggaggtttt gtttgggttt tttgttgctg ttgcttgttt atttgtttgt tgtgtttaag   10258
acgttttact tgtccctgaa atgtttgtca tcacacagat acacgctcag gataagaact   10318
accagactag attaggaggt ccacaccacc aattgagatg tacctgtgct catgacttga   10378
cattgtggtg ggccggctac aaccctcccc acccctcgct ttcactaaat aacaactctc   10438
ttctctccat cattttgact tagagccagt cagaattcaa tctccaatat cctgactagc   10498
```

-continued

```
acaagaaatc cataggttga ttcttgttct cctgcatctc tgcaggtggc aaacctgatt    10558
cctaatgcct gttcctgcct ctgcaggggt tcattcagaa aacaggaaaa taacaaaggc    10618
ttcctgtaat tctctttggc tgtaatacaa tttgttcccg tctgccccca ggctcaccca    10678
gtgctctgtc tcagtggtaa gctgtaactg atcactgctg tattaactca aaactcattt    10738
gctttatgga aattcatggc ccttatttct caagggacca gagaaaacca ataggcctac    10798
tccccagctg agtactttcc atgcaagcta ccgcatctgt ataaattagg ttcaaataac    10858
agagtatttc caggatttat aaattcagta ttacaaatag taatctggca agtgttctca    10918
ggatcccctt gctacctgta attcaatcat ataacttctg aatgggctgg gggaaaataa    10978
caataagaaa aactggtgtt tacctgaaga tctgcccagt gatttgtgtg ttttcttaat    11038
aaactttacc cacttattaa aagaataaaa tgaaggtgga gttaattctg actacgggat    11098
tcctttttca cttttataat gaactccttc cttctaacta aatcttatca taagcaaatc    11158
tatgcaccaa attatttagt acaattccta ataacagctg aaggaccatt tatttgaagc    11218
aatgttcacc atagcaaaat tccagtgaag tctaagaact gggacagtcc gttgaggatc    11278
cttgtgccag gatgtatgtt gccccatgaa tgtgcacatg catattaaaa tatgggcacc    11338
tcttttaatt ctttttttc tcataataag tttgaaactc acagtaggaa attgagagat    11398
caatttggtt actgttttat cattgatcct gaagacagtt gaagcaatca tactggttgt    11458
tctcgaacta gctggtttcc cagagacagc tggagactga gcacataaag acatcattga    11518
ggaaaaaggc taccttgtac ctcatggaga gctgaaggtc tgataaatgg gaactgccag    11578
gtaatagcta tgctatttct gacataaatt taaaaactag tattgtttct tctagctctg    11638
tttttgcata gtgcacagag atctttgtaa aaaacaggaa attaatgtta aattggatct    11698
ataaacataa gtcaatttgg ctctattatg tcaaaagaga ataggagttt taacttatat    11758
ctgtgtttta ttaatatttt gaagtatagg aacctcatgg tgtagcagga tgagccacag    11818
acaaaacctc tcagacaccg agttgtagaa ggaagggctt tattcagctg ggagcatcga    11878
ccagctactg tctcaaaatc caagctccct gagtacacaa tttctgtccc ttttaagggc    11938
tcacaacact agatttcaca tgaaagggtc gtgattgatt tgagcaagca aggggtatgt    11998
gacaggggct gcatgcaccg gtggtctggg aggaacagaa caggacaggg agttcttcta    12058
tacaatagag aacagaacaa tgttcttcta tacaatgtaa ggaatctatg aataacatcg    12118
gcttctaaat cataagttga ttttttaacta ctgggtttag gccaggcggg cccaggcctg    12178
gtttcgggcc tggcgctgag ctgcctgtat ttggtttttac ttccttgttg tttttactga    12238
atatgaaaca atataaaaca atgtgagagg gtctttctct cctctcaatg tcaacatcat    12298
atatgattgg agacttccac ataattgagt tttagtgccc actgttacag aaaatcataa    12358
tggaaaaact aaaatgtcaa taataatttc agatgtgtat tttagttctc ataagaacat    12418
ctacattcat ttgaaaaata gttctatatc tattcttgaa acatatttct ttagttcaag    12478
gtctgatgag ctcccagact gttggggatt gctctacagc tgctcaagct tttgaagact    12538
cctgtgattt ttttaaatgg ctggtttggt tgaagtttct cttatcagtc aggcactttg    12598
cattttaagc gtactttacc accgacaccc tccccccca gcacacacac acacacac    12658 acacacac acacaacata gtgaaatgga cccgtgggaa ttatatgata gttgtaatca    12718
aaataaaatg caatcaatac taaaatacaa tttaccaaag gcttacctcc ttatttgaaa    12778
ctccagcatc aataatttac ttgcactctt gttatttaca tttgtactct ggaagtaaac    12838
ttaaaatgaa aattagaatt tgctttcaat tatactatct ctatctaaat cttaatttga    12898
```

-continued

```
aatttaaatt attttgtctc tacccaaacc atcgatttca tggaaatgtt taaattttct    12958
tttttttttt ttttttttgat ggagtctcac tctgtcgccc aggctggagt gcagtggctc    13018
aatcttggct cactgcaacc tctgcctccc gggttcacac cattctcctg cttcagcctc    13078
ctgagtagct gggactacag gtgcccgcca caacacctgg ctaatttttt gtattttttag    13138 tagagatggg gtttcaccac gttagccagg atggtttcga tctcctgacc tcgtgatctg    13198
cctgcctcgg cctcccaaag tgttgggatt acaggtgtga gccactgcgc ctggccagaa    13258
atgtttaaaa tttcataaat cttgaatcca taaaattcaa tgctaccatt tataatttaa    13318
tactcctacc ataaaaattt ctgtgttagg catagctata tgaatatttg cctataaatc    13378
cccatcaatt taataggaat taagttagaa atactagtat atatattccc tttatatact    13438
aattgtatat ccatataaaa gcattagtac cattatatga aagtatatat gccattccat    13498
aaaaatatat ctaccaatat aaatagaata tataaaggga atatatatat accaatataa    13558
atgggaattt atattggcac atacatttcc attattttaa tgggaattaa agaaaaaatg    13618
cctgttttca ctaagtcatc cttcccctgg caatacattt cctgaacttt tacatactta    13678
aatagccagt tatgaaaatg taaaacaatg agtgatcttg ttgttttcat tttattatgt    13738
tatatgaaaa aaagaaacct tgtaagtgca gatttatttt aaaaaattga aaaactactc    13798
tgtcaaacat agcaaatagg aaagttaaaa aaaagtaagt ctaaagatta ggtgctctgt    13858
cacttgtcat tacatttttt tataacatta atgacacatt ttttgctatc caaatataat    13918
ttccactaga aaagaaaaga tgtcctccat gttttaaatt gcatttgaaa ttcaggtaac    13978
taataaccct tggtttttaaa agatacatat aatgtttccg taggaaaaaa atcaaaatat    14038
tgtaaagaat ctgagtaaat gagagcctct catggttgat taagttcaga cattttaaac    14098
agactcctgc ccacaaacta ttttttcctct ccaggaataa gaatggcaac tgaattgttc    14158
cttctttatt ctatagcttt aagtcaaacc taacataagc aatcaaccct tccacccatt    14218
gtcctctttc tagctgctta tattcctgag tctgaaagaa gggcagaatt aattcgtttc    14278
cttgacagtg ttgggggtga aataaaagat agacccctgc tgctctgcac gtagattcag    14338
tttgtatgcc agggtgacat tttaatttac agtagtccag acacctaaac aggacataga    14398
aatgtcaact ggtcatatta aaataaaaaa gtatagaata gtttctgttt tacggatttt    14458
gtatccaagt aaatgaaaac acaatcacct ttcaaaacat ggtatgaaat ccacagttgt    14518
aacagtgagc acaacatgct ttctgtgtgt gttttttaagc tctttcccca catctgcttt    14578
tcaaaaatat ttgcctggaa acctgtattt cgcctataga gacaaataca tatattgttt    14638
gttgtgataa tgcacaaaaa ggaatgttaa aaaaaaacac acaacattgt tttccttttg    14698
atggtctggg agtttttcta taagtttttg gtttttttttt ttttttctct tcattagtgt    14758
gttagttcca tcatcatgtc tgtttactat tgaaaaataa atatcttcat ttaaagtaga    14818
gacaaagcta ctatttcaca tttccaggta ggacaggatg atcagatgca gcttccaaaa    14878
gaactacctg ctaaatcata atggtctcat gtgcagatca aaatgtcaac tagtatatca    14938
aacagtgagc aattcactaa attatttta cattactcct atttgactgt ttcagatagt    14998
tgtatataaa aaatataaat ttttgcattg tattgttctt gatgtaccag catacataaa    15058
catattaggc tgtattgtaa gtttcctgca tgtaatatgt aatgtgtaat tatatgtgat    15118
aaataaaacc taaaactgat acaaa                                            15143
```

<210> SEQ ID NO 47

-continued

```
<211> LENGTH: 400
<212> TYPE: PRT
<213> ORGANISM: Homo sapiens

<400> SEQUENCE: 47

Met Asp Ser Ser Ala Ala Pro Thr Asn Ala Ser Asn Cys Thr Asp Ala
1               5                   10                  15

Leu Ala Tyr Ser Ser Cys Ser Pro Ala Pro Ser Pro Gly Ser Trp Val
            20                  25                  30

Asn Leu Ser His Leu Asp Gly Asn Leu Ser Asp Pro Cys Gly Pro Asn
        35                  40                  45

Arg Thr Asp Leu Gly Gly Arg Asp Ser Leu Cys Pro Pro Thr Gly Ser
    50                  55                  60

Pro Ser Met Ile Thr Ala Ile Thr Ile Met Ala Leu Tyr Ser Ile Val
65                  70                  75                  80

Cys Val Val Gly Leu Phe Gly Asn Phe Leu Val Met Tyr Val Ile Val
                85                  90                  95

Arg Tyr Thr Lys Met Lys Thr Ala Thr Asn Ile Tyr Ile Phe Asn Leu
            100                 105                 110

Ala Leu Ala Asp Ala Leu Ala Thr Ser Thr Leu Pro Phe Gln Ser Val
        115                 120                 125

Asn Tyr Leu Met Gly Thr Trp Pro Phe Gly Thr Ile Leu Cys Lys Ile
    130                 135                 140

Val Ile Ser Ile Asp Tyr Tyr Asn Met Phe Thr Ser Ile Phe Thr Leu
145                 150                 155                 160

Cys Thr Met Ser Val Asp Arg Tyr Ile Ala Val Cys His Pro Val Lys
                165                 170                 175

Ala Leu Asp Phe Arg Thr Pro Arg Asn Ala Lys Ile Ile Asn Val Cys
            180                 185                 190

Asn Trp Ile Leu Ser Ser Ala Ile Gly Leu Pro Val Met Phe Met Ala
        195                 200                 205

Thr Thr Lys Tyr Arg Gln Gly Ser Ile Asp Cys Thr Leu Thr Phe Ser
    210                 215                 220

His Pro Thr Trp Tyr Trp Glu Asn Leu Leu Lys Ile Cys Val Phe Ile
225                 230                 235                 240

Phe Ala Phe Ile Met Pro Val Leu Ile Ile Thr Val Cys Tyr Gly Leu
                245                 250                 255

Met Ile Leu Arg Leu Lys Ser Val Arg Met Leu Ser Gly Ser Lys Glu
            260                 265                 270

Lys Asp Arg Asn Leu Arg Arg Ile Thr Arg Met Val Leu Val Val Val
        275                 280                 285

Ala Val Phe Ile Val Cys Trp Thr Pro Ile His Ile Tyr Val Ile Ile
    290                 295                 300

Lys Ala Leu Val Thr Ile Pro Glu Thr Thr Phe Gln Thr Val Ser Trp
305                 310                 315                 320

His Phe Cys Ile Ala Leu Gly Tyr Thr Asn Ser Cys Leu Asn Pro Val
                325                 330                 335

Leu Tyr Ala Phe Leu Asp Glu Asn Phe Lys Arg Cys Phe Arg Glu Phe
            340                 345                 350

Cys Ile Pro Thr Ser Ser Asn Ile Glu Gln Gln Asn Ser Thr Arg Ile
        355                 360                 365

Arg Gln Asn Thr Arg Asp His Pro Ser Thr Ala Asn Thr Val Asp Arg
    370                 375                 380

Thr Asn His Gln Leu Glu Asn Leu Glu Ala Glu Thr Ala Pro Leu Pro
```

-continued 385              390              395              400

<210> SEQ ID NO 48
<211> LENGTH: 93117
<212> TYPE: DNA
<213> ORGANISM: Homo sapiens

<400> SEQUENCE: 48
ctccctccct tccagcctcc gaatcccgca tggcccacgc tcccctcctg cagcggtgcg      60
gggcaggtga tgagcctctg tgaactacta aggtgggagg gggctatacg cagaggagaa     120
tgtcagatgc tcagctcggt cccctccgcc tgacgctcct ctctgtctca gccaggactg     180
gtttctgtaa gaaacagcag gagctgtggc agcggcgaaa ggaagcggct gaggcgcttg     240
gaacccgaaa agtctcggtg ctcctggcta cctcgcacag cggtgcccgc ccggccgtca     300
gtaccatgga cagcagcgct gccccacga acgccagcaa ttgcactgat gccttggcgt     360
actcaagttg ctccccagca cccagccccg gttcctgggt caacttgtcc cacttagatg     420
gcaacctgtc cgacccatgc ggtccgaacc gcaccgacct gggcgggaga gacagcctgt     480
gccctccgac cggcagtccc tccatgatca cggccatcac gatcatggcc ctctactcca     540
tcgtgtgcgt ggtggggctc ttcggaaact tcctggtcat gtatgtgatt gtcaggtaag     600
gaaagcgcca gggctccgag cggagggttc agcggcttaa ggggtacaa agagacacct     660 aactcccaag gctcaatgtt gggcgggagg atgaaagagg ggaggtaaac tgggggggact     720 ctggaggaga ccacggacag tgattgttat ttctatgaga aaacctactt ttctgttttt     780
tcttcaactg ataaagaaag aattcaaaat ttcaggagca gagaagttgc tttggtaaaa     840
gctacaaatg tctaggggtg ggggcggag ggaagctata gcatagactt ggagcgcttc     900
cttatactga gcaaagaggg ctcttggcag agtcctacac tcagtccctc tgcaggagct     960
atggaaagag taagttgtga ataatgggag agaaattcta gttagctttc ccaaatttgg    1020
ttggggccgg tgtgtgtgtg tgtggcgggg ggagcagtct caagtcttct caattgtttt    1080
gagatggacc ttggcaactt tcctactcct gctggtttag tacttccctg taccacaacc    1140 ccacccttc ttctcccctg ccatagcagc ccttacccaa ctcttccttt catcctgagg    1200
caacactagg tagaggaagt tttcctagca tctctccatg acagttttcc tctgttataa    1260
caaacatgac aaatgtgttg cctagaccag tttgccgtta gtagcttcag atcgcctaag    1320
tcacaaactg catctggaat gggtaggttg gttcaggaga accgcaggac atggctgtat    1380
ttcattgcct tcacaagttg gagctaatta ggagtgacca aaagcatcat aattccacat    1440
tagaaactgc agaaactctt atacaggaag ttgtgatggg tgctctagac aaagtgttct    1500
tatcaagtaa aattaattca aaagagttgt agtccacttt ctgtttaccc agatgttccc    1560
ggtatatttg gcagagtgtg gaagctctca gtattgactg agattgatat tgattgtgtt    1620
ggtgttgatg tgtatattca aatactacat gtgaatgtga aatgccatat atctgttttt    1680
gttaaagaag ataaatattt taacacttta aaatagttcc taattcgagg gttttttttt    1740
ttaaccaggg gtatgtgtat atagggaaca tggcatttc atatttagtt acaatgtttg    1800
tttcacctat tcagcaagta ttgcaggttt cagcggagct cttaaatcat ttaagaattg    1860
ctctctccag tatgctttca ttacccaggt gctgcaaatt gcttataagc aattctttct    1920
actcatctgt ctgatttctt taattaatga ttttttaaaga gtaaagctaa tttccctgat    1980
cttttgatga ggaataagat aagtattgtc tgtaagaaaa gagcaccatc tattgagagg    2040
aaggctaaca acagaaggaa aaatgcaaga agatcgatgg aagtatttat ttttaaaaac    2100

-continued

```
atttacttta agtaattcaa tacaatgatt cacattgaag attaaaaacc aagtttaatt      2160
ttgcagttat gacaataaaa gttataatta aaggcctgtt ttgtgaaggg aaaatatgtt      2220 tctcatttt tctaaaagaa attcatagaa tcataaacta atcaagctag aagggactct       2280
agagattatc tatgctaagt aaatTaaactg aggcacagaa aatgtaaatt attttctcta     2340
agaacagata gttcattaat tcagtgccac taaatctctc ctagctaaca tatttttttt      2400
ttttattgtg ctggcaaatc atgatttgag ttaattcgac tattaggttg acagagtggg      2460
ttgatatagc aataataact tgggaataac aaattatccc caaattctat gtgaaatcct      2520
gaaggaaaaa agcatgaaac aaaaatacca aagcatctag gaatcctgcc atctgaaaca      2580 taatattta ttccctttta ttgcttcttg atattttcct tcctcatttt tctacccttt       2640
agtttatgct ttgcaataca gagagagcca atagagtggc aactggctgt gaaatgagca      2700
gattggtctt attccagtgt agaagaggtt gctggttggg tgagttagtt ttaaaggcat      2760
tacctctggc ctcttgttga cttggagaaa catggtgacg gtgcatctta ctgagaacat      2820
gttattatgc tttattctcg gtactgaaag ttcttacaaa atgcagtact atttgaaagg      2880
tcatcccaaa cacccacctg tggcaggctg ggtttttaatc gcagggttag gtaaccctct      2940
tggaatgtga ctgtgaaaca gaaaaatggg caagttagtg acagatgaag cgacagggaa      3000
agcatctggg gactgaagca agtatgtcta tttagctgag aacatttaac tgactgtctc      3060
caggctgcgg tgtttaaact acaaaatgat cagttcaggg atgtattgtc cttgctaaaa      3120
tgctggatat aatgttgcat ctattaagta ttgaggagaa atgttcactt ccttccctat      3180
ttaaaattca acaaatgcta ttgaatgatc aagtagttgc agttttctga ttatattaag      3240
gtaatattta ttaaaatgtt ttagtacatt gagtgaatca tgaggctcag atgactatgg      3300
caacaacaac aacaaaaata actgctaaca tggacgctgt gattaactct ttggttctgt      3360
ttgtaacacc atcatcatca tcccctcatc aacaacatta ttaagtagta taacttaaat      3420
gagattctta aacagggcta ctctaaggaa tacaagggag gaaaggagaa actgtaatat      3480
gttctaaaga ttttaagtcc agatgttaag tgataaaaat gttatcagta accatcacct      3540
gaaagctttt ttggttttaa agaaaaataa tgcttggaga ataaccttat gaaaattatc      3600
acaaagattt tagaaaatgt gatgaaaata ctacaaacag tagcaatcac ttaaaatggg      3660
atgatagtat ttcattgtca agaactgtaa agaaaaaaaa tcaaaacaaa aagtaacagc      3720
caccagagat gtttcacttt tgggaaaata tttaataact gaaccagact atagaattac      3780
ccataactgc aaaaactaat ataatcccag atgtgtttat gttgggaaat tcttttttcca     3840 aggtttgttc atgtagctat gaacatggta tgtacagaca ctgttgaaaa gtggagggct      3900
agaaactttg agatttctgt gggctgcgta aaccatcctt ccagtaaatt tccaatgaag      3960
agtgccaagt aatagtacct tcatttttaa gattatttct taatgtggtt agataaattc      4020
tcaatataac taattatcag agaagagcat ttaaatacgt gcaagatgtt attgtcattt      4080
ctccttccta acaagtattt ctgattttag aaaaagtcct gtgagcttat acttgttcta      4140
tatactaaat atttgattca ggtttaaatt taaaaatgat cagttatact tgattgaaac      4200
agaagtataa gcttttaaac ttaatctaga ttcaggtagc tacaaattag tgaacaataa      4260
tgttttatct aatataagga tatatatgtg tgtgtgtgta tatatatata tatataaatt      4320
cacacacaca catacatatt tgaatcaatt tgaatgcatg tcactaaata tgatcattag      4380
taattttcat aaaataaaaa gataatagtt tatttactca aatattaata aaattcactt      4440
```

-continued

```
ttctaaaacc cacaaaatat cctaattaga ggatggattt aaagtgaaaa acactaaata   4500
aaattcagtt ctcaatttaa tggcttacat taaaaaatac taacttaatt gcatgccttt   4560
cacttagtaa gggagagctc ctggtaccta ttacaatttg aactttaagt gctatttttcc   4620 atatagaaac taattcagag gagaacaact cttcttctgt gtcttctaaa cacactaaat   4680 tgctttttcct ttccttggtt gtaagctgtg tctttgtcat ttgcatgaca ttaccaatca   4740
acgagtttcc tatattcttc tctctctctt ttctttcttg aaagaatgac ctatctgata   4800
ttttatgaaa catctccaaa gataaaaaat atataattac agaacaattc ttctcttaaa   4860
ggatggatgg atagatagat agagagagag agagagagat agacagactg aaacagttga   4920
agtctcttct ctgctcctaa taccctcctg tcactgagac taccactatc ataaatttag   4980
tggtgagtta ttcacatgca tgttttaaa catttactac atatggaaac acatatatat   5040
atagtaaaca tatggaaaca cacatacata gtaaatgttt ttgtatgttc tcataacttt   5100
ttataattgg taccatatca tatgtttaag cttaaacaca taatttccct aattactcca   5160
agttgttata gttccagtag gccaatgcta gaaaatagat gtcaaataaa accaacaaac   5220
ataaaagaaa acaaacaaac attcgggcca ttaactcttc tgagtacttt taactgatct   5280
tatttttttt taaatgtgtt aaaaattatt tgtaaaaatt tatttgcaag cattttttcta   5340 agctaattgt tttaattaat atttaggtat aatactcaga aaaaaacctc agctactgct   5400
gcaaaaaaaa taaatcggtt aataaattta aataaagcat aatttctcta ctgctaagaa   5460
gaaaatacaa ataattaatt ggtgtctgta ggtattcaaa taataaatgc tgacaatatt   5520
tactttgaga ttttgaacat ctaataggat ctcttacata taaaagttga aaatattatt   5580
tctcctagga ttccgtttaa ggcagtagtt gaaacagata ttttaaggtc agatgcaaga   5640
aaaaataagc tcattttgag aaataacata caactatatg agatttaaaa atgtactagt   5700
ggtggtcagg cactgtagct cttacttaca atgccagcgc tttgggaggc tgaggcaggt   5760
ggatcacctg aggtcaggag tttgagacca gtctgggcaa catggtgaaa tgctgtgtct   5820
actaaaaata aaaaaaatta gccagactgg gtggcgcatg cttgtaatcc caactactgg   5880
ggaggctgag gcacaagaat ttcttgtacc cagaggcaaa ggctgcagcg agccgagatc   5940
gcaccactgc actccagcct gtgcaacaca gtgggactcc gactcaaaca aaaaaaataa   6000
attaaaaaaa aaagtactag gggtaaatac caagactaaa tggtgcatgt cattttaaaa   6060
tacaagaatt ccaagtcttt agtcctcact aagtttaatg tttatctgac tgaaataatt   6120
atctgtgaca gcagtcttca aacttgtttt tagatgtaga cacttatttc aagaacttgg   6180
gacccaatat ataaaacaga tcacagaaca actgtccaga tgtaaccaca tgttgagacc   6240
aagagcactg ctcaccttgc accccatgc cacccaccag tgctgtcccc aagggaccac   6300
catagaattt ctagggctcc accaggcaaa atttgaaagc aatggctttc acgttgtttc   6360
atatccttct cgtgcccacc tcatgtcctt cacctcgcct tctacctcag ccgttgatat   6420
ggcagtcagt ttccagacat aactgagtaa cacttcacct tggctgcatc taaatcactt   6480
actttctgcc ctagggcttc tctactggag taattgccct ccataggaat cagcctggca   6540
ctcacaaagg cactatttgg aagttcagga aagttcccctt gaccaggaaa tggaagcctg   6600
tggaaaaatg ctgcccttgc tcccctctct cctgaggtgt acaattctga ggtgccaact   6660
acaaggcaca tcagaaggcc ccgcccacat tgtgaccgtc tcaaaaacat gcctcgtttt   6720
cctcttccct ggtttactct tctagtttcc cactccttgc caagcaacca cttttcaaaa   6780
tggttcacct tcacacaagg tcgtatctca cactctgctg aatatccttc ctgttatttt   6840
```

-continued

```
ataattggtg actatacgtt agcacagtaa aatctgttta ataaatagag ctcttacaga    6900
cctatcaata aaggttttct cttaactatc aaaaactcgt aagaaaaatt ctgataggca    6960
gcaccagtta gaactaccaa gagagttcag aagctaagct tttccttcca tttttgttcc    7020
tgccttggga tttaggaaag gctttttggg gtaggtttgg ctgaatggag agagagtggg    7080
caccagtcat gtccagtgtt cagtttactt cttcttgagc tcaggataat aggagcagaa    7140
ttgtgtgtgc catgtaaagg aaataaagcc tcctgtgcct tctggcaaat tatctgaggg    7200
tataagaaaa caaacaaaca aaaaatcctg ccactccctt ttccattaat ttcatgttat    7260
atagtaacgt taagagtatc ttgtgattaa ttgagctcaa gaaaatttca gtcttcaaaa    7320
gtgagctgaa gcatcaaatg caggaaacgt catatacaac aagcatcata tactgagctt    7380
accaagcaac tcctttcttt acccatcctt tcttgcctca ggtaactttt tttctttccc    7440
catcaatttc tcagatacaa atttagaaag gaagaacagc aaggaagaga aaccttgccc    7500
tggctcaggg ccccaagtgt cagttgtggc tcgacttcaa ggcactctgc gcctcactct    7560
ccttatctgt aaaaaggtgc gaattggact aaaaaaatct taaacgcttt ctagtactaa    7620
aatgtcctat ggcaacttca atgactatta agagcatgtt tttcccagca atacaatctg    7680
gaggaaaaga ggaatcatcc acaaaactaa acaatcgtgg ttgccattcc atcacagccc    7740
tttggattct atataagctc aaataggttc tgtcaaaggg agaaagagtg agtgtgctct    7800
gaactgccag gtgtggtgtt tatgattagg acaataaggg aaacagaaag ttacagtcaa    7860
gcctttattc atatgcttcg agagtacagg caagtggtta agtgggaaaa ggtgcaaccc    7920
catcatgttt cattcccccc acccccaccc cacagaagcc accaggtgag catcacatgt    7980
ttgagcagaa atgcaggaag gagagggaaa agtcatcttc ttactgcact gggaggccca    8040
agcaaaaggt cctgctgttt tgtgtacctg agggcctggg tgcaagatgg ggaaagacaa    8100
ggaatgaaaa acagtgagtc agagtatgtg ctgcctcctt aagggttagg aacgcataac    8160
ctaaaagcgt gactggcaaa ggtggagcgt gggcaaaatt ctctctctct ctctctctct    8220
ctctctctgt ctctcattct ctgtttaatt tttaggagat ggttttaata tttgccttta    8280
ggtattagtc ctatcctgga tgttgtattc caaatctgat gcaaagaggt tccaccaaat    8340
ctaatcaagt gaactttcgt aaaccaatgg atagggcttt cccataagat gaagtgtgtg    8400
atgggtttaa atgagagaga gatcattctg ttctggatat gtgtctgtcc aggcaaaaat    8460
gttgttaagt acaatttttg tttgtttgtt ttttgtttgt tttaaataat atgttagctt    8520
atgcactgta tgtaagtagg tgtcttcgtg tgttcaggct gctataacaa agtaccatag    8580
cctgggtggc ttacaaacta cagaaattta ctcttacagt gctggaggct tgaggagttc    8640
atgatgaaag caccagcaga ttctgcattt gctgaggacc ttcttgcaga gacaactaac    8700
ttctccccat ttctccacaa ggcaaagagg caaggaagct ctctagggcc tctttcataa    8760
gggcattaat agtgttcata atggctctgc tctcatgacc taatcacctc ccaaaggccc    8820
cacctccaaa taccatcaca ctggggaata ggttttcaac atgtgaattt gaggggaaca    8880
cattcagttt acagtaggtg tcctaagtga ttcaaatatt aaccactcat attcactgaa    8940
aaccattagt gtgatttaaa ttaacgttta cgtaaattag gccaacctga ttccttcact    9000
atcttccaat atgcttcatg tttatctctt ctatactgtt tcctttattt ttctttctct    9060
ctgttttcct gtaacgtatc tctcattctt ttcctatcaa aatgtttctt gttcttcaag    9120
tatcaactta aatccatcct ttcttacagc ctctccaaag tactcctaca accaatttcc    9180
```

-continued

```
ctgcaatata acccaaaata catgctacca ttgttaaaaa aaaattatgc attttctcat      9240
ggccttataa aatgtcactt gataaaactt aaagacttga actatatcta tctctttgtg      9300
tttaggtgag aaatccaaca ttcaaagttg accaacagaa ctgaatatct tcaaaatact      9360
gtacaattct aagctattag caattcagat gtacctcaaa ttattcaagt ataaaatcta      9420
atttaaataa ttttctcaat tcactttgtt catgcatatt tagcttttat cacttgagtc      9480
atgaaaagtg atctgtacca tagatacata ttagcaaatc ataaattcaa atacaaacac      9540
atacatgtct atatatgcat atattcctga gtttacaaac tttaaaaagg gaatatatgg      9600
ttactcttat aataaaaact cagaaagtaa aatttgaaga agtaaaaaca taaaaagtta      9660
atatagtcaa ttcccattat tcatgatagt tatggtccat aaagtcatta tgactacaga      9720
attcgtgagt actgaagctt tgcttctagg ggatatatag ggcaggttcc tgtgagcctc      9780
tgattataaa attttcatca gctaatgcat tcgtaacctt gttttatgtg tgtttctgtt      9840
taaagacgct ttatttaata tatagctgat tcactaacgt tgaactcatg gttaacagca      9900
ctataaatca tgcctgaaca aagcttctgt aacacaagta ctttcctcat aagccacatc      9960
acagtcttct tggcttaggg acactaagca gaacttccac actatgtttg agaccatttt      10020
aaacagtgaa gtcaccacca ccaccaacaa caacaacaaa aaaacacaga aatgtgaaaa      10080
atgtggcaat aaatagattg tgaaaaggac acgtgtttat agtacaagct gaaagaagac      10140
agcagagcat tgccttgttt gaccttacct gggaacctgc acagagagca actcaaattt      10200
tttgctgctc tatacatgtc cacacaggtc ctcaaatgac tgcaaaagcc aagtattatt      10260
ttgcgggtaa atattaatag attttagtga agaggccaat tttcaaatac agaatcctca      10320
aataatgaga atcaaatata tataaaatgt tcctcaagga aatattttg aaacactagt       10380 aaagaagaaa atcaggaagc tatgttccaa attaaaatatg gtagcaaatt catgacatga      10440
tgacaagttg tatgtttat tataatcagg tagaatcgtt tgaaaacaaa atggattccc        10500
atataactca ctcatgagtc accagatacc caaccacatc acacaaattt aaaatatata      10560
cagcgcattg attgatttgc atatgttgaa ccatccttgc atcccaagga taaatcccac      10620
tgggttacaa ggagtgattt ttctaatgtg ttattgaatt ctgtttgcta gtattatgtt      10680
gaagattttt gcattaatat tcatcagaga tattggcctg tattttctt tttttgatat       10740 gtctttggtt ttggcatcag ggtaatactg gcctcacaga atgagtttgg atgtattcct      10800
tcctcctcta tttcttagaa tagtttgagt aggaatagta ttagttcttc ttcaagtatt      10860
tggtagaatt cagcagtgta gccatcaggt cctgggcttt tctttactgg aagacttttt      10920
attatggctt agatctcagt acttgttatt gatctattca gcttttggtt ttcttcctgg      10980
ttcaattttg gtaggttgta tgtatatact caaaacaaag gaagttagta tatcaaagag      11040
atatctgcac tcctatgttt gttgcagcag cactgtctac aacagctaag atttggaagc      11100
aacctaagtg tccatcaata gattaatgga taaagaaaat gtggtacata aacacaatgg      11160
tatactacta ttcagccatt aaaaagaatg agatccactc atttgcaaca acatggatgg      11220
aactagagat tatgctgtta agtgaaataa gccaggcaca gaaagacaaa ctttgcatgt      11280
tcttacttat ttgtgttatc taaaaatcaa atcaattgaa ttcataaact tagagagtag      11340
aaggatggtg accagaggct ggaaagggta gtgggggctg atgggggggct gggaggaggt      11400 ggggattgct aacaggtaca aaaatattag aaagaataaa taagacctac tatctgaaag      11460
cacaaaaggg tgactataat caataataag ctaattgcac attttaaaat aacataaaga      11520
atgtaattgg attgttactc aaaggataaa tgcttgaggg gatggatacc tcattcctca      11580
```

-continued

```
tgacatgttt atttcacatt gtctgcctgt atcaaaacat tccaagtacc ccgtaaatat   11640
atacacctac tacatagcca caaaaaacaa atatttttaa gattaaaata tatattagca   11700
tgttttattt tgcatattga aataaaattt tcaaaactaa attgattcct gtatatttct   11760
aaaatagaag tttaagtaaa attgtgatta tgtaatataa gtatgtgaac atcaaaatta   11820
tccttacaat gtaggatttc atttatctga agtcttatgc ttttttcagt aaagctctaa   11880
aacatggaaa ggaaacttt acctaataag taataaccat gctatagcta taaaatcaca   11940
acaattactt gatatttaca attagcaaac tttggaaaaa tttattaagc cacaaaatcc   12000
ttactctaat ttttggtaaa caactaaaaa gggctctgcc taaaattgaa tggctctagg   12060
accgtgaatt agcctgctcc ctccaaactg agaatggcga aaatgcacaa gtaaactaga   12120
cattccatct ggaaagtaaa atcctatttt ataccaaaat acttttatta gccaacataa   12180
aatttggatc taaatgattc tgaggtaaga ctctcatctc attttactat agttagatgc   12240
atataagacc ccttcattgc atgaagagtg atggctttgc tcagtctttc ctataagagt   12300
tacaaagtat ttatgcaacc aataagcata tgagaaaaag ctcaacatca cagatcatta   12360
gagaaatgca aatcaaaact acaatgagaa ccatctcatg ccagtcagaa tggcgattat   12420
taaaacatca agaaacaata gatactggtg aggccatgga gaaagaggaa cgctttttaca  12480 ctgttggtgg gaatgcaaat tagttcaacc attgtggaag acaatgtggc aattcctcaa   12540
ggatctagaa ccagaaatat catttgaccc agcaattcca ttactgggta tataccagaa   12600
ggaatataaa tcattctact ataaagacac atgcacacat atgtttattg tagcactgtt   12660
tacaatagca aagacatgga accaacccaa atgcccatca atgataggtt ggataaagaa   12720
aatatgttac atatacacca tggaatacta tgcagccata aaaaagaata agatcacgtc   12780
ttttgcaggg acatggatga agctggaagc catcatcctc agcaagctga cacaggaaca   12840
gaaaaccaaa cactgcatgt tctcactcat aagtgggagt tgaacaatga gaacacgtgg   12900
acacagggag aggaacagca cacactgggc cctgtcgggg gttgggggc aagggggacaa   12960 ggagcattag gacaaatagc taatgcatga ggggcttaaa acctagatga caattgatag   13020
gtgcagcaaa ccaccgtggc acaagtatac ctgtgtaaca aacctgcatg ttctgcatat   13080
gtatcttgga acttagagta aaataaaata aaataggtag aaagtaaata tttctggttt   13140
ttacaatcag ataatctctg tcataactac tcagttctgc tgttgcagcc tagagcaagc   13200
catagacaac acatagatga atggatatga ctgcatttca ataaaacttt atatggacac   13260
tgacatttga atttccatat aattttcaca tgcctcaaaa cattattttt cttttgattt   13320
ctttcaacca tttaaaaatg taaaattgtt cctagctgga agaccacaga aagaagtggt   13380
aggctgggtt ctgcccacaa gctgtcattt gccaaactct gacacagaac atcttaaata   13440 aaatttatt cttgcagtgg tcatgaaata ggaacacatc atcttcttta gaaaatttga   13500
ttacatattg tttactacat gaaggcaaaa cattttgtta aaataaccta gtacttagta   13560
ggtgtgtata tttatggggt atgtatatac ccacaaaaat taaaaattaa caaaaaccta   13620
gaccaactca cagtattttt caacatcaga aaatagcaac acaaatatga agttaccaca   13680
aaccagaaca gttgccatag attgctatga cagagcatat tgctcttctg gaactgaggt   13740
tgaagttgtg ctataataat caccacacaa aattatctct atttcacccc aggcctccat   13800
atctaacccc caaccctttta tttgactcag acaatcagca aggtttatta ccacccttag   13860
ccagtgatta aggagtaagt gcttagaaaa tagcatttct gaagaattta tctttattgg   13920
```

-continued

```
atatgctttg tggttatctt aagtaagtgc agtttgctag gcttgtcaca gtattttcgt   13980
cttcaatctt ttggaagctt tcaggaaaaa tggaaactgt catctgcaaa ttcatattaa   14040
cttcttggca aatataaaat ctgtcttcca agatacctat gcctgcacac ctgccaccct   14100
gcacccactg catgtgacca gatagtgagt ggcagcttca aactctatgc catttcaaac   14160
ataaaagctc attgcttgga tcttttttct tttctgtctg acttacatat tgctcattta   14220
aaaaaaatgt tttctgcagc tctcagaagt tgctttggaa aatgctatta cttattcttt   14280
agaactcaga ctgtctagct gggtaaaaag gagtgctagg gtaggccaag gtattctaag   14340
gatgcttata atcccttgac ttcttgtcta cagttttgtt caatgatttc cttaagactc   14400
actgaaatct cctccctgcc tgactctaca tctttaattt tgtccccatc catccatatc   14460
taaatgactg ccctttgatc tgccatgctc agaggaaact ttctcccatg tacaggaatt   14520
ctttagatta gccagatgac catcaggaaa aagttcgcaa gaagagttaa gttaaaggag   14580
agtttaaact gggtgacata gagtccactg caaaattta taattcccag actctcttaa   14640
gcgagaattg gatctaaatt ctagcaagga acccagacag gataaaatga ataataattg   14700
agtctccttc caattaactc atggaacatc agagccatta tataaatccc cacaatatgc   14760
ttagacatgt agaagaagag tactttcaga tcgtctagtc cagtgattct gaatcctggt   14820
ggtaccttag aattacctgg aaagcttaca ccggtctcgg tggctcacgc ctgtaatctc   14880
agcactttgg gaggccgagg ccggcggatc acgaggtcag gagatcgaga ccatcctggc   14940
taacacggtg aaaccccgtc tctactaaaa atacaaaaaa ttagccgggc atggcggcat   15000
gcacctgtag tcccagctac tcgggaggct ggggaaggag aattgcgtgg acccgggagg   15060
cggagcttgt agtgagctga aatcgcgcca ctgcactcca gtctggtgac agagcgagac   15120
tccgtctcaa aaaaaaaaaa aaaaaaaaaa aggaaacccg cctaaggtta attgaatcag   15180
aatctccagg ggcagctcct gggcataagt aagtgtaaaa gttccctgg tgactctacc   15240 atgcagccaa gatcaagaag gacaggtctg gtccaaccta tccattttat ggatgagaaa   15300
actgagtcct gtttgtgaaa aatatttaac ggatctgtcc ttatatttta cttccctgaa   15360
ctttaagggg ttatttatag aacaagtagt aaattaaatt atcttgcaga aaagcgaaag   15420
ctcaggatgt tttgaaaatt tctctaaatt tgaccaatca tctctcttca gagtaggcat   15480
agtggagtag acagagtagt aaacatgtaa tgaaagacat gtttagataa atgcttgaga   15540
ggatgcatac cccattctct gtgatgtgat tactatgcat tgcatgcctg tatcaaaaca   15600
tctcatatac ttgataaata tacacaccta acacctacta ggtcgcccac aaaaatttaa   15660
attaaaaaac ttgaaaagca gacatgttta gatgtctgcc ccttactagt gactacacta   15720
gacacctaac ctacttgaat ctcattagtt aaaccttaat aaaggaaaaa tagccatatt   15780
caacctcaca tgggttttag gtccaaatag ataagatttg gataataaaa aatatgtggt   15840
caactctaaa gtgctctgta aagcttggct gggcgcattg gctcatgcct gtaatcccag   15900
cactttggga ggctgtggcg ggcagatcac ttgaggtcag gacttcaaga ccggcctggc   15960
catcatggtg aaacctcatc tctactaaaa atacaaaaat tatccgggca acatggcttg   16020
tgcctgtaat cccagctact tgggaggctg aggcaggaga atcgcttgaa cctgagaggt   16080
gaaggttgca gtgtgccaag atggtgccac tgcactccag tctgggtgac agagtgaaac   16140
atcgtctgaa aaaattaatg aataaacaaa aaaaaaaaa taaaagctag agagttttat   16200
tagctcctaa ttttcttccc tcccactgca ctcacaccat cagtatgcaa cctaccaaca   16260
ctcactcagg gcttttgcct ttccctaggt cagatatatt atccattata atatttctaa   16320
```

-continued

```
ttacagttta tctttctaga ctcctaagtt ctgcagagaa gaagctaggt tttgcatgag   16380
tatcactgtt tcttgtcatt cttctcttca ttcccatcaa ctccttctac atgcactggg   16440
tcattccaaa accatcgtgt caaggacatg atgatgtgaa gaaaattcta aggacaggca   16500
actgcaactc atttggttcc ctactgttaa gtctttttat attgtctaat aaagtgagta   16560
ggggaaaaat atgcaaacca gtgatgttcg aacaaaacag catttttgtt acttaaatct   16620
tggtgtgaaa gaatctcaag caggatctaa gtctaaatgc taactgcatg tgacaaaact   16680
cctttgtccc cagcagcact gttcatttga ataagaagaa ataacttata acaatggcat   16740
tctctgaaca ccagctttga gaatttaggg atttctaatt tcatccctat aaagagtcat   16800
cctgacccct gttgagtctg attctctaat cacagtaaaa ttggtcaaat gatggagctc   16860 ttttctttc ttttcttttc tttttctttt ttcttttttgt tttgagacgg agtcttgctc   16920
tgtcaccagg ctggagtgca gaggtgccag ctcggctcac tgcaacctcc gcctcccagg   16980
tttgagtgat tcttctgcct cagcctcctg agtagctggg actacaggtg ctcaccacca   17040
tgcccagcta attttgtat ttttagtaga gatggggttt caccacattg gccaggatag   17100
tcttgatctc ttgacctcat aatccgcccg cctcagcctc ccaaagtgct gggattacag   17160
gcgtgagcca acgcgcccgg cctgatggag ctcttttctg catgaaggac acattaatga   17220
cgattctgtg gctatttcta acaccttcac gatggatttt tccaggactt gcaatgcgat   17280
gtctgtcaac ttcctaactc aggacagtaa actctataaa taaagcaagc agaggatgca   17340
gcagagaatg acaacctgga atcttacggt gcccttgaaa actaagactc ttccaagtac   17400
agaagctgtg ggaacaagga gatcaatgga agggaaggcc tctttgtttc cgagcatttt   17460
ttcaccgaaa tgctgggttc agtgccagtg agaggttgag cttttttccgg gggagtatta   17520 aatgttaatt gaaaaacgtt gccagcagta taacctgaac atcagagcct cattgtgcct   17580
gccaagaaga acaagggaaa ttattatcaa cattataatt tcattcttac tcagcccccca   17640 taagctctgg aaagaaaacc acatgggctg aataaaatta aatatgagca tgttaaagat   17700
ccaaggccac tgaaattggt agtcctatta aaagcagata gcattaattg aaatccttca   17760
aatagtcttt ccttctgatg acaaaaggaa gcctttttcaa cttccttata aaataaataa   17820
aacacatatc taaggactaa agatattctt tttgtccttt taatttttata gaactttaca   17880 tttttcccta aattgagcag tttgagtctc ataacatttt tgtgagtcta aacagggaag   17940
acattgaaca gactcatttt aaagaaatag actaatttta aagaataaac atgaactacg   18000
tttgttgagc actatgtaca aagcactctc ttaggagttt cagatatcag tgagcaaaat   18060
agacacagtc tgacttttc ccaaaggtac agtccagtgg atgagaaaat taaacaattt   18120
taccagttaa taaatgccaa gaataggact ataataactg actttgtgtt ctttccatca   18180
cagtatcaga aaaacactgt tctcaaggtt tattgccatc aattactata gctcaccta   18240 ttccatcacc aagcccatca atgtgataac ttcttaattt aagtctttat tccatttctc   18300
aaattttgtt aaaggtatta tttatgtctc agaggcaaga tagtagtgag tggaaaaggc   18360
ctgcgttcat tttcataaaa gaatgaaaaa aagtgctatt gaccataatt tataagtatt   18420
tttctcaaag tagatattgt aaaaatttta caaatagtaa ggatatcggc acagaagagc   18480
agagtcctgt atgagtggaa tttgtaggaa gaaaatctca ggagtcattc ctttcggaca   18540
tttgttactc tcactgtaat ggaacgatga ccagtctact tatgaatacc ctgtcacacg   18600
aagacaggca agagaaaaat caagccggaa gtccaacctg aaactttcac attttaaaaa   18660
```

-continued

```
gttttgtatc agttttgtga tatttaagat gtaactatca aaagagaaat tgacactatc   18720
ttttagaaaa gggccactat tctgaacaaa gaagaaattg tctgcatata aacaaatgca   18780
tcacatttcc acaaaagact ttggtatatt tgtcaatgcc acaaagcata acttaaaaca   18840
tataaagcac accagtgatc atttccacag gagtattatt ttctcagcaa tttagaaact   18900
taaaataaca gcatatgaat gaaagaatta acatgctttc tacacaccct tgcttttatg   18960
catctttaaa aaaaattgta tataaagata tatgccttct gctatatcaa aaaattctaa   19020
cactattaaa aagatgaaaa atgatgtttg gtatagctct catgtttta ttcacacatt     19080 tgtttgaagt taagttgata ttaaaacaga atatattggg tcagcattct agttgaaata   19140
gatgaagtta taaaatttag ctgaccaaaa cattttggga aagataattg gtcaaagaag   19200
ccctttgaaa acagttgtgt tttcagaaca atcacaggtc agaatgcatc aattatcttt   19260
agcccacatg agaaacatct agaagcaatg ttagtacagt caaaacaaaa agtaacactt   19320
tagtaaatat gaatgcttaa tctgggctca tattctaagg acaaataaac atgaacgtag   19380
tagaatattg gtccctagca atgtgccttg gagaataaat tagcacccat taaattggaa   19440
acccatagaa agcattatca tcatcaccat cttcattatc atcatcaccg tcttcattat   19500
catcatcatc actgactttt actgaaagta actacagttc agattccata ctaacaatcc   19560
ttaaatacac tacattaaaa aattttcatc tttacaccaa ccattaagga aagtattaat   19620
attttccaac tattacagac aggaaaaata gaattcagaa aatttgtgta ataagcccaa   19680
atttgtccaa ctagtaaatg atggaagtca gatttgaatt gagagctaca ttaccctgaa   19740
acctaagtgc ttaaaaattg ttttattcaa ttgcatcaag gagaggtttt caaaccagtt   19800
attgagggtt catttggatg gctgacaggt atattaaggt agcttttata tcttactttc   19860
cagaattgtt ccctaattgg cagcctattt tccttattga taggctctac cttgtggaaa   19920
tcggaatgaa ggaaatgaga tgcctgtctc cttgcaagtc aaaccctgca gattttcctt   19980
catattaggc ggtgacattt tgaattgacc ttttgtctct aggataactc aatctaggtc   20040
tgtaattgag tcagcctttt aacctggtaa aatagaaccc atcaattatt agtggaactt   20100
ctatttacaa agcctcaatt gtgatctaaa ggtgctgtca taatctgtcc tcgacagcat   20160
cattactcaa tgtgtgacta gtgagtgcta ataattccta tcaggaaact ggtcaagaga   20220
cagccactct gccaggctca gtgctgaaag ctggagatct agtcaggctt cctggatgtg   20280
ttattcagcc aagcactgtg acatttgcat atctccactt acattcatga tcctttttta   20340
cacttaaaaa aaaaaattcc ggttttaaga atgcaagctc cttgaggaca gactgtgtct   20400
ggtatttttg ttgttgtttg tttgcctgtt ttaattcttt tatctcagaa cctaacaaag   20460
taacaaatac tcatgtgaca tacagtagct gaaatgttcc actacactga atttattaca   20520
atgttatgtt aatgctacat ttatttcagc cctttgtgtc tcagtgttcc atttctaatt   20580
tttgaaagta acttttaagt cattgttcca ctgagagcta atgtttcaaa gaaacttgaa   20640
attcccaaga ttaaaattat tgtaaaagag ctttttttaat tattttgatg caaagatatt   20700
ttccaaggtt attttctaca ttcgagttga gaagagaacc taagcccatg aagtgtctgc   20760
cttttcctct tcccaattta ttgccgcaag gaatccaaat gggagagggg ttatagcaag   20820
ataatagtaa ccgagaaaaa ttgaatctag aagaggaatt aaatctggaa gactctaaga   20880
agaatcaatc tggaataaaa ggtacaactt tactcaagga ttttattttt gaagcagcac   20940
taatgaaatt caagaaaagg catcctgctc catatccttg catccctacc ctagcgacca   21000
aaacaccaga tggacaggct gaaggcagat tagctggaat tactgccaag tgcaagtaac   21060
```

```
caggcatgtc ggtggtactc cagcgagcct aaataaatag accaaaagaa ccaaaagtac  21120
ccagcaaagt agtggaaact cccacatttt attcatgact cttatctgta actctttctt  21180
tgcttctcaa atggttaatg gggtcactta tgaaaagtat ggaaacctag tccattcaac  21240
tcccatgcca aattcttccc atagactact ccagtccatt ccatattctt tgtcttagaa  21300
acagattgga aaagaataag gtatctgcgg agacttccag taaatgagat ttttgcttat  21360
tgtatcaata tgatagtctg aaaactgaca aacactgaga gaagaattct tagttgtatg  21420
agttttttcc cccgaaaaat cagtggattt ctgcctccct gggagaaaaa gatgaggtga  21480
cactagccat aataacagga gaacaatagg ggcagaatgc ttccctagaa aatgggaaga  21540
aagaagtcac aagacaatgt gtcattaaga aatccagatt catcttagag atgtatccca  21600
caaggaggtt atactgggtg acacaagaaa atttctagcc tctactctgc accaattatt  21660
tcacaaatat ttaaaagtac aaagtttatg tcaagaaaag aaattcttac ttcatggagc  21720
agaaatacac tggtaataaa atattggcaa atatctcact ctcactaaaa tgggtagtaa  21780
aatttgtgaa tttaaacata tttaacagtg gtgtatattc acttctggaa actagataca  21840
tggcaggcta attggagata cttgatttat attagtttct ggaaaacttt ggggcccacc  21900
ctaaattaat ggctttctgc taccatcaga gacaaaatcc ttggcaaaat gggccaggaa  21960
catgtcccca gtaagtgaat taaatacttt cacagacact ctccatctag tagaacaaat  22020
ttggaataat tgcaacattc ctgtcaccta catgagcatt aagtactcct ctcaacactg  22080
ccatgttacc cgcactgcgc tgtaacatct aacacaccat ttagaaatcg cttggttctg  22140
gtttgtcacc agacttagga gagatatatc tcactgtaga accagtgcct atcatgtgct  22200
tggcaaaaat aaaaataaga gaggtgttat tatggaatac tatgcagcca taaaaaagaa  22260
tgaaatcatg tcctttgcag caacatggat gcagctggag gctattcttc tgaggcaatg  22320
tatgcaggaa cagaaaacca aataccacat gttctcactt ataagtgaga gctaaacatt  22380
gagtacacat ggacaaagag gggagcaaca gacaccgggg cttacttgag ggtggaaggt  22440
gggaggaggg taaggatcaa aaaacttta tcaggcacta tgctcactac ctgagtgaca  22500
aaatcatttg aacaccaaac tccagtgaca tgcaatttac ctatgtaata aacctgcaca  22560
tgtactccct aaaaaaaaat aatagttgga aaaaaaaaag gtgttaagga aatgtatgtt  22620
gactcaatgt tgacactaag aagattttat ggcgaacaaa agtaattatg aaaatataat  22680
gcgttctatg aaaattaaaa acatgcccat aattcttaag atgctttaat acataaagct  22740
caataacatt tttgtcttta gctaggaaaa gtgtgaaatg tataactttg atcacgaagt  22800
tagagtatta aatataacaa aatgttccca gagtttggct gtacttgtta agtttagagt  22860
gatttatatt ttagtttta tatagttcag tgttattcag atttttaaat atgactgtcc  22920
aatagcataa ggaaaaatat aattaatcat atgaaaacaa gtaaaaaggg agaacatttc  22980
agaagtagta gatgatcctg aaaagtaata aagtattgca ttagagagct tttttactaa  23040
aatataaatc aatgtttgga attttcctat taaaagaata gttacataat ttgtggctaa  23100
aaatgttgtt agtgccaaat gactctattc caagtcagaa gacaactcca tattgattta  23160
ataacctgta ttgcactata agactaaaat ttcaggcttt aaaaactaat gggacttctt  23220
tgctttgcca aattactggt ttattcatga atcatatttt ctccttacaa atgctattga  23280
gttttccaca gggaaaggaa aataccttcc aaaaaaactc tctgactgaa aaaaaaatct  23340
caataagctt ctttctgttt cctagaaaaa tctcaagtca gcatgattgt taaattacaa  23400
```

```
ataattgtgt aattcttgga tggaaaacag tcatcataag tacctaatt  tatataaatc  23460 aagatctaca ggaactaatt gcattacctt tatttttcca tcaattggtc ctaaaatatt  23520
ttggaaacct actgttgcag gaattcatta aatgtcaaaa tattcagaca tcagcaggta  23580
ctaagacaca ctaaaatgga taaacagaaa tgctcatcaa cagtttggac aaatcgaatt  23640
tgaaattaag tctttataga ccttaattaa atctcccttt tgtaaaactt aggagcaatg  23700
agaacatcct tatttcaatt tcagcttcct aaacagtatc ctgacatata attctttcta  23760
atctgttgtg ctattattaa acattccaag tagttaaatc tccagaaaac acacacacaa  23820
aactacaact gaaacaaatc ttaactatcc agatattttg cttgcatagc aacaaatatc  23880
caggtatttc aaatgcacaa tgctaacaat gttaaacatt tttgtctttg acaattgttc  23940
taaacttcag tactcttctc tttaaaatag atacaataat agatacaata atcacggttg  24000
tctaagttac tactagaatt tttgtgaaca tcagttcgca caaacccctg taaagagtta  24060
gtaaagctta ctgtacttta tttattatac agatagctta tgtttcatgg tgcatatatg  24120
gtagcagtgc aatgtagtag taaagagcat taactttatt aaattattaa actttattaa  24180
atttaaatat gaatttaaat tctgcctctg ccattgttat tctttttaa ccctaattca  24240 tattttatt gattcatgca acataaagtt tccattttaa ccgcttgtaa gtatacaatt  24300
cagtggtctg aagtacatcc atgtcattgt gcaatcatta gtatcattca tctctagaac  24360
tcatttcatc ttgcaaaact gaaactctat acccattaaa caataatacc cattcgttct  24420
ttcctcctcc caaaccctgg taatcaccat cctactttct gtctctatga ttttgactaa  24480
tctagttaac taatataaga agaatcatat attatttatc ttttataaat ggtttatttc  24540
atttggcata atgtcctcaa agttgatcca tgttgtagta tatgttaaca ttttcttcct  24600
tttgaaggat gaataacatt tcattgtatg tatgaaccac atttggttta tttattcatc  24660
tattgagtgg ttacatctat gctttagtaa ttctgaataa ttctgatgtg aagatgggta  24720
tataaatatc ttgtggagac cgtgtttcca atttctttgg gtatttggat catatggtaa  24780
ttctgttttt aattttttga gaaactgtcc tactgtttcc cacactgata tgtcatttta  24840
cattcccacc aacagtccat aagggtccta tacgttcttc atatccccac caacacttgt  24900
tattttctgc tttatttaat agtaatattc ctaatgaatg tgaggaggtg tctcactgtg  24960
gtttaatttg cattgtccta atgaatagtg atattttgca tcttttcata tgcttattat  25020
ccattcaaaa atctttttg gagaaaagtc tgaatagact cttgaataag tcctttgtct  25080
attttttaaa ttgggttgtt tgttttctgt tgttgagttt tgggagttct ctatatgttc  25140
tggatattaa tcccttctca gatatatgat ttccaaatat atttctcatt ctgtaggttg  25200 ccttttact acatggatag tgtcctttga ttaacaaaag ttttcagttt ttatgacatg  25260
caatgtgtcc atgtttgctt ttgttgcctg tgcctttagt atcatatcca agaaatcttt  25320
gtgaaatcta atgttgtgta gattttgccc tattttttct cttaagggtt gtataatttt  25380
agcttttata tttaggtctt tgatccatct tgagttaact tctatacatc aggttaggta  25440
aggtgccaaa gttattctct tgcatgtgaa tgtccaattt tcccaacacc atttgttgaa  25500
aagactgttc tttctccatt gaaaggtctt ggaactcttg ttgaaaatca tttgggcatg  25560
taggcaaggg tttatttctg ggatctctac tctattccat tggtcaatat gtatggcttt  25620
atacaagtac catgctgttt tgattaccat tactttaaag taagtttga attcaggaag  25680 tgtgagtcct ctgcctttgt ccttcttttt caagattatt ttggccatag tgtttaactt  25740
aagattccat atgaatttca ggatgaattt gtctatttca gcaaaaactt cattgagatt  25800
```

-continued

```
ttggtaaaga ttgcattgaa tctgaagatg acattgtatg acatcttaac agtattacat   25860
ttccaatcca tgaacatggg atgcctttcc atttatttat gtcttcttta attttttttt   25920
tttttttttt agacagagtc tcactctgtc accacactgg ggtacagtgg cacgatctcg   25980
gctcactgca acctccacct cccgggttta agtgattctc ctgcctcacc ctcccaagta   26040
gctgggacta cagctgtgtg ccaccatgcc tagctaattt ttgtattttt agtagagttg   26100
gggtttcacc atgttggcca ggatggtctc catctcttga ccttgtgacc cacctgcttt   26160
ggtctcccaa agtgctgggg ttacaggcgt gagccacaat ttcctttagc aatgttttgt   26220
agattttgta cacatctttc acctccttgg ttaataccta agtgttttat tacatttgat   26280
gctatcataa attaaactat ttttctaatt ttcttttcag attgttcatt gtgaatgtat   26340
agaaatgcaa ctgattttta tatgttgact ttgtattctg ctacttcacc aaattcatta   26400
ttagttctaa cagtttttttt tgtgtgtgga atctttagta ttttctactt ataagattat   26460
gtcatctgca aacatattca ttttacttct tttctaattt aggtgtattt ttttttcaaa   26520
tttatttctt ttacctattt tctctggtta gaactctcat gctacataga acagaagtgg   26580
ggaaagcagc catcattgtc ttgttcctga tattagagaa aaagctttca gcctttcaac   26640
attgagtatg atctctgctg tggaattttc atatacagct tttaatatgt tatggttgat   26700
tctttctatt ttgattgttt tgagtatttt atcatgaaag tgtgttgagt tttaacaaat   26760 acttttttctg aattaaatga gattatcatg tggtttattt tcttcgttct gttaatctga   26820
tatattacat tgattggtat tcacatgttg aaccatcctt tcattccaga aataaatccc   26880
agttgattat aatgtataat cctctcaata tgctgtagaa tttagtctga caatattttg   26940
ctgaggattt ttgcttcaat ttttataagg gacattggtt tactgttttc ttttcttgta   27000
gtatctttgt ctgtctttga tgttagggta atgctggcct tatagattta attaggaagt   27060
gctctctcct cttcgttata ttgaaaaatt ttgagaagta ttggtatttg attttttttta   27120 agtgtttggt acaattcacc aatgaagcca tcaggaccag ggcttttgtt tattgggaga   27180
tgttttattt actggctcaa tctcctatta ttgatagttt ctattacttt gtactttagt   27240
cttgagaggt gttatgaatt gaattatgca ccctcccatc ccccccaaaa aaaatcattt   27300
gttgaaaccc taactttgat gtgactgtaa ttggaggtaa ggcctttagg agataattaa   27360
agttaaatga gatcacaatg atggggtact aatgaggtta gtgcattaat ggaattagta   27420
gtcttataag aattgagaga gagagagaga tctcctttaa gcaaagagga aagatcacag   27480
gaggacacag tgagaaggct gcacctgcaa gccaggaaaa aaatccctca ccaggaatta   27540
aatcagttag catcttgatt ttcaattgac cagcctccag aactacaaaa aacattttg   27600 ttgttaaaac cactcaatgt atggtatttt attgtagtag cttaagtaga ctattacagt   27660
agtttttatg ttttttacgaa cttggtcatt tcatccagat tatccaattt gttggcatat   27720
aatttgtcca tagaactctc ttgtaaacat tttatttatg tacaaaaact agtaatatgc   27780
ctacttcaac attttattgt agtgatctga ttattgtcta ttttgttatt agccaatcta   27840
gttaaagatt tgccaatttt gctaatattt ttggaaaacc aattttttgtc ttcgttcact   27900 ttctctattt tttttttagtt tctatttcat ttatctctgc tccaattttt ccttccttct   27960
gctagctttc tgcttacttt gttctttctc tagttcctta agtttttaag ttgttaactt   28020
aagattttta aatttaagca tttatacata caaattttcc cttagcactg tttttgctgc   28080
atcataaaaa tttcagtgtg ttgtgcttta attttcattt atctctaagt attttctaag   28140
```

```
ttctcttgtg attttttctct ttgaaccatt gtttatttaa gagtgttctt aattttcaca   28200
aacctgtgaa ttttccagtt ttctttatgt tattatgtta ttgatttttt ttaattttat   28260
ccaattttgg tcagagaaga tactgtatat aatatttatt tttttaattt attaagattt   28320
aatttgtggt ctaacatata gtctgtcctt gaaaatgttc catgtgcatg taagaggaat   28380
gttttctgtt gttgttgggt agagtagtct gtctatatct gttaaaccta gttggtttgt   28440 tgtgtttttgt aagtcctcta tttccttact tatctcatct gattattcta tcctttgttc   28500
agagtaagat attggcacta cctccttccc tcttcaattc tgtccacttt tgctttatat   28560 gtttttttaat ggtctgttgt tgagtactgt ttgtaattgt tatatcttct tgctgtgaaa   28620
catttattga catataatgc ctttctttgt cacttgtaaa cttttttttat ttacaaaaag   28680 ttaaattaca aattattttt gcaataatac tagcatttat aattgtcaat gtatttacct   28740
ttactgagac ctttattttct ctgcatgact ttggatattg tctactgtac tttcctttca   28800
acctgcaaga ctcccttttag catttttctta aattttaata gtatatttta cttaatccca   28860
tatatctata ttatcatttc aacaagtaat cgatgtaaat ttcttaaatc atgtaccaca   28920
tgatattttg aagtatacat gcattctggg atggttaaat ctagctagtt ataacttctg   28980
taatgaaaac acaacattca ctctcagcat ttttcaatag taccatattt caatattaac   29040
tatagtcacc atgttgtaca atagatctct tgaatttatt cctcctaaca gtaattatgt   29100
cttctttgat ctatataacc tcaaccccaa ttcaccctaa ccaccccagc ctccattcta   29160
ttctctactt gtgtgagatc aattttgtag atttctcatt tgagtgaaat aatatggtat   29220
ttgtctttct gtgcctggct tattgcactc aacattatgt cctccaggtt gacccacggt   29280
cacaaatgac aggactccct tcttttttat ggctaagtcg tatcccattg tgtatatata   29340
ccacattttc tttatccatt catatattaa tggacactga gatttattcc atatcttggt   29400
tattgtgaat agtgctgcaa taaacatggg aacgtagcta tctcttcaac atatttattt   29460
tgttcccttt ggatatatat acctagtagt gagattgcta gatcatatgt tagttgtgca   29520
attagttttt tgaagcacct ccacagtgtt ttccataatg gctctactaa tttgcatttc   29580
caccaacatt gtgtgaggat ttccatttct ctccatcctt gccaccactt accttttgta   29640
ttttttgtaa tcatcattcc aacaggtaca agctgatatc tcattgtagt tttgactcgc   29700
atttccctga tgattactga tgttaaacat ttttttcata tacctgttga ccatgtgtat   29760
gccttttgag acatgtccat gcaggtcttt tgcccatttg ttaattaggt tatttgcttt   29820
cttgctattg gtttgtaaga gcttcttatg tattttggat atcagcccct tatcagctgt   29880
ataatttgca aatattttct cccattttga atgttgtctt ttcactctgg taatttgtct   29940
cctgcagtgt gcagaagctt tttagtttga tgtaatctta tttgtctaat tttgtttttg   30000
tggcctgttt tattttttga gatggagtct cgctctgtca ccaggctgga gtgcagtagc   30060
cagatcttgg cttactgcaa cctccacctc ccaggttcaa gtgattctcc tgcctcagcc   30120
tccccagtag cagggattac aggtgcatgc cgccacaccc agctaatttt tgtattttta   30180
gtagagacag ggtttcacca tgttggccag gatggtctcg atcacttgac ctcgtgatct   30240
gcccacctcg gcctcccaaa gtgctgggat tacaggcatg agccaccgcg ccgagccctg   30300
gcctgtgctt ttaaggtgat agccagaaaa tcattgcaga aaccagtgtc atgaagcttt   30360
ttcctatgtt ttcttttagc attttcatag tttggggggtc ttacatttaa gttgctaact   30420
tactttgaat ttatacttta tctggtgaaa gataagggtc tcattttatt ctgctgcacg   30480
tggaaatcca gttttcccaa cattatttat tgaaaagact tcccttttccc cattgtgtttt   30540
```

-continued

```
acttagcacc tttgttgaaa gtcactgaga tataaactta aggtcttctc aggctttttt   30600
ctggcctgtg cctctccctc ggcttgttag tgactttctg attttccttg tatatgcagt   30660
tgcttttgaa tatcctagtc tttaatgtct gacccccaaa aaaggataag aaggaaaaac   30720
aaatgaagta gggggggaaat ggtcctggta atttaaattc cctggaagtt gcttcagcta   30780
tagggaaaga aatttgtaat attcggaggt gaggggggtac aacaatgact atctgccttt   30840
gtgtctgcct tccatgatca gaagcaacag tcagcactca gaacacaggt tctgctattt   30900
ggatgacatg gttcttattg cctaccctgg ctcccacaag ctgcatgcaa gctgctcctg   30960
cagctcatgc actgcctccc accaggctcg tgtgggagat agaaaactgt tagccaggta   31020
agagcagaaa ttaaccaaaa taaaccaagt ttactgtcaa gcattcccct ggaagttgca   31080
agccttccac aacactccaa agttcaaaaa tatttacaac agacagacta tgccaatgca   31140
gtttttatct agatggggag acagattctt gatgcttcta ctcatccatc tgcccagaat   31200
ctttgccact gttatttaag aggtgcatct tgaaaggctg tgatgaagat caagtaagaa   31260
aaatccaagt aaactcttta gagcaatgcc tggcattcaa caaatgttgg ctctaattat   31320
aatgctcaaa aacagtatct atctccatta ttatttaatt tgttttaaag ataatttttt   31380
ggtaatatct tcgccacttt acatttatgg aaattgggac tcagcaactt gactaacatc   31440
acagacacag ttctcagatt tatatatcct aattccaaac ccaatattct tactactaga   31500
atatgctgga ccgtttttact cctaacttgg ttaagaagcc aaatatagga ggaaattaac   31560
aaatcaaggt agttttagtt actcattggt ctgtgggttc acagcatttt aatggagcca   31620
actttgctct taagatgagt aagcagttgg tatgactcag gaatctctaa gaatgtttct   31680
accttaaaag gcaggttttt gtttcttaat cctttaacaa ttaatatttt aattaaggga   31740
acattggata gacattgtaa ggtgcaaaat acctctagaa ggtattgaaa atactcactg   31800
taagtataag ccatttgatt acaactgagc aagcaggtct tcactttgat aacttctaga   31860
cctaaagacc atggttaact gatatttgaa ggtatggaat gcataatatg gaaagagact   31920
taacctagat catggtgaag atccagctaa aggcacagtg tgtagtcata gctgctgaag   31980
gaaggaagca gctcattaaa aaggtgagat ggtatccaac actagctttc ataccccag    32040 gtctgcctga ggtgggtttc tgcctgctac agatagatgc tggataagta tatatgccaa   32100
gatttcagtg aggcagcagc tgatgtagct acaatgcccc ctaagtggcc tgtacccatc   32160
tgtcagcatc actggaaaat gtctaatgct tccctctaat tgctgatttt tgtcagcttg   32220
ctcatcatga agcctgatcc tcatttgtta tcttcaagta cactctatta tccatgctca   32280
ccagcgaaaa ccccccaggaa tatccctgta gttttaaaaa aaaaataggt gtattgatct   32340
tgctacagca aggaatacaa aacacccagg gatttcagtt tatatttggt gatttgggaa   32400
aggattcaaa gaaacaaagg tctatctaga cagtgtgctg tcctaaagca agagaaatct   32460
gatgaatgag catcagtaat tttttatcta ggaggaagaa ttaagcatgt aaggctagag   32520
ttgtcattga gcagtggtca atgacaataa gaagcagtgg ttacttaatg ttaaccagga   32580
aagggagatg cttggcattt ttatggttgt gggtgatttt ggttttatct cttttccagg   32640
catggttaca aagttaactt gttttttgtct tgttgcatca catcatggag agtcctcatc   32700
tgatgtttat attctatgga attttgttcc acagaggaat accacagact gatggttagc   32760
aaccaggctg cttcccaaaa gctgtcaggg actttttttt ggtctttctc gcaattactc   32820
aactattata tactgtccct tctccttctt tggcaatagg agagggataa aaatgagaat   32880
```

-continued

```
caacgtggga atggtaagat aacaagagct gggaaggtat ggtttattct tattggaggg   32940
aaatctccta agaatgtgag atgatcagga atgtcataat taaacaaata tataaatgtg   33000
gccgttagga tcaagagaat gcatcatgtt gctcaggcat agcaaggtag gcagttgagt   33060
gcagattgaa ggtggtctct gaactccaga agcttataaa ccaatagata aaacagatac   33120
tactactata atcatcacat atgttacata gcactaagat ttcatgtgca agaatgcaaa   33180
aggttgaaat gtattttcaa attcattgat agcacaagat ttgctttat tcaatactaa   33240 aactaagtac ttgcttaaag tgaatgcaat ctttcatttt caagatagct aattgagaac   33300
aagcatgaga ctccactcct ggtccccaag ctccagaaca caatagaaac tatttttag   33360 agaatataaa gcaataaatc aatggacagt catacattag tttatgaaaa tgacagaaaa   33420
attcttacta aacaatgtga tattttaaag ggccctatta aaggttattc ctgtttctc    33480 tgccattttg aaccaactga gagataagac aaaatgaatt aacaacgtca ctactgataa   33540
atatctttat gatggaaagt tgtgcagtaa caatggcttc ccaattctaa tcccagaatg   33600
cagcatactc aaccacctga ttgcctgctt gaaccactgg tgacctctgc acacggatac   33660
cagccccttt aaaatttaga aaatagagta cttttatgtt ttccttggga agctgaatct   33720
caaagaaaga gagaaatgga gaaagctata tatatcctat tctttaaaca tataaaatag   33780
ctaagtcact cctccttttg aaaggagtga ataatggaac tgagagaaat caaagcagag   33840
aaatggtgga tgactttact catgaaacat gaactcagaa gaaaggaggt tctcccattg   33900
cagataaact aagatgctga aagaataacct gaaactaaga acagccaata taagctgcag   33960
gtagtggagc aaactccact gatgttccat aatgaggcag acttccacag tggtagcagg   34020
catgttagtt tactctttta tatcttccag gctagacata agcaacagtg tcctcatgca   34080
tacttagggc agagatacta ggctatacct gggaaactag cacttctcta caggattaga   34140
aggaaagata agtaatcgaa atcagatgac cagccactaa tgtattatgt ctactgcaag   34200
ccatctcatc ctctgttttt attgaaaact gcatagtgtg taaactcagg agctaattct   34260
aacctttatc cccagccagg ctgcacaagc agaagcagtg aacagtctac cagggaatat   34320
taacttcaag gatcatctca aagccaataa tcatcacact gttgaagagt gactgcacca   34380
ggaaagagac agggcagcag tgggaacaca gcaaacagaa gaatttacac ttgaggaaac   34440
agaataaaaa agcagtcaca caaggacttt aaaataagtc atatcaggca tggtggctca   34500
tgcctgtaat cccagcactt tgggaggcca aggcatctgg gtcacttaag gccaggagtt   34560
caagaccagc ctggccagca tggcaaaaac tggtctctat taaaaataca aaaattagcc   34620
agtgtggtgg tgatcccagc tactcgggag gctgaggcag cagaatcatt tgaacctggg   34680
aggtggaggt tgcaatgagc caagattgtc ccactgcact ccagcctggc caacagagca   34740
agaccctgtc tcagaaaaac gaatgataat aagtcatatt ttacatcttc agatagataa   34800
aagagagaat tttttctatg aaataggagg aagcaattca aaaataataa gagatggtta   34860
ttaacaagca aagcatagca accaaattcc cagacaacct gggtttcaat cctggctctg   34920
acaacaatca ctagttggat gtctccaggg caaattactt aaccaatctg tgtcttcatt   34980
ttttcatctg taaaatgaag atagtcatag tatatacctt atatatgtgg tatgaggatt   35040
aaataattta gcattagtaa agcactctga acagtatctg acacataagt gtttgttaaa   35100
taaacgaaca aattggaaat tctaaaaata acaacttaa ttttttggcgt tcaggatttt   35160 atgggtgagc cgaaaagcag aaagagagaa ggcgaagagc atgttaatga gctgaagaa    35220 catagaaaat gggatggagg ccaggcacag tggctcacac ctgtaatcct agcactttgg   35280
```

-continued

```
gaggccgagg caggcaaatc acctgaggtc agaagttcaa gaccagcctc gccaagatgg   35340
tgaaacacag tctctactaa aaatacaaaa attagccagg cgtggtggta cactcctgta   35400
gtcccagcta cttgggaggc tgaggcagga gaattgcttg aacctgggag gtgggaggtt   35460
gcagtgagct gagatcatac cagtgcactc cagcccggag gacagagcaa gactccaaat   35520
aaaaaaagaa aagaaaaaca aacagaaaaa aaagacaagc aaagaagaaa agaaaatggg   35580
atggaaatgg agagtatgaa gaaacacaaa agatactaga aggatagaca cggaaaaact   35640
aaaatgtatc tattaaaggt agagaacaaa agcaatggaa gagaggcaat attggaagaa   35700
ataatagccc caaacatcct ataactaaag aaagggatga gactgaactg atgtctctgt   35760
gttccaggca caataaatat ttttaaaaat tcttgccaca ttttaataaa attcaggaac   35820
atacaaaaga gataagattg caagtactat aagagaagag aaaatgatat ttttaaaggg   35880
aatagaataa gagttttcat caacacactt ggcacaaaga agacaatgaa tagagtaaca   35940
ttttcaaagt gaacaaaaac tactttgaaa attaagccaa actagctctc ttagaggtta   36000
catcctcaac ttacactaga aacatgcttt ttagagacat tgaagtaaat agcaaaataa   36060
tcagttacaa gtattgaaaa tgatacggtg agcaatagga atgagacaaa gtaaaaagaa   36120
ctggcatttt tcattacaag gatgaaatta tgttttttgta ccctttttcat agagattaaa   36180 tctgtttttt atataaccaa ctaaaataag cacttttttt tttttttttt ccagacggaa   36240
tttcactctg ctcccaggct ggagtgcagt ggcgcaatct cggctgactg caacctccac   36300
ctcccaggtt caagcaattc tcctgcctca gcctcccgaa gagctgggat tatgagtgca   36360
ggccaccatg catagctgat tttgtaatt ttagtagaaa tggggtttca ccatttgggc   36420
caggctggtc tcaaactcct gacctcaagt gatccaccca cttcagccta aaataagcat   36480
ttcgagtgct cctatgcaga gggcttgaag acttggaaga ctcaacccca cctctgagag   36540
acttcccatc tgttagaggg aggaagggtg gaacagtgaa cacatctggg gaatcccagt   36600
ctgtcattta ctggctttac aagttgaggg aagggagctg atctctctga gccttagttt   36660
tcttgcctgt aaaatgggga tgatgaaatg cctaccccat caactttatg aattacttag   36720
tgcaatactt ggcatgtaga caacattcat tatcattact cttcttctca tgtataagga   36780
gatgctcgaa aaggctatct ccatgtagta ggatttttact ttatttttat gttattcttt   36840
gtattttcct gtattgtgta tttatacagt aagcatgtat tattttttaca aagtttacaa   36900 aatgcaccct gtaaaagaat caatattttt aaattatcgg aagaaaattt cagagatcat   36960
ttttaataac ctcagaataa gtaagacctt tacgaaaaac atgtacaaac acacccacca   37020
caggtagtca aaatgtaata ctcctaaggg acaaaaacac tatgaataaa gttaaacaat   37080
agcaatcttt gaggaactat ttgcagcata tatcttaaat tttataaat cagtgagaaa   37140 aagacaacct aataaaaatg gtcaaaaaat aaattcatag acgaggcagt acaattaacc   37200
cagaaataga tgaaattatt ttcaacctct aattagtata ttgttaattg aaacaatagt   37260
ggcatattac ctatcattca taatattggt agatatggct agacacggtg gctcacgcct   37320
gtaatcccag cacttttgga actggtcatc aagaactcca aaatctcccc tgtaagaacc   37380
accacctttc agaccagcac ctcttccttt ccagatcctg aatctgacac ctccccaaa   37440 actgagctct tcaatccatc atcctaactc cttttttata aactacaaat ctcaaatgag   37500 cacctaaatac tgccaagcaa atgtttcttt gctaaattta cttttcctgtt ctcttctctt   37560 ctagatctct cacattttct tctctatcat ttcctttcat tgatacttcc gggtttttatt   37620
```

-continued

```
ttatttattc atccaacaaa tatttatttt gttcctttcc aatagaattc aggtccatga   37680
atgtggattc tttcttgaag ttttgctgaa aagtaaaata gaaatgaaaa ttataaaaca   37740
taaaaaattg cggttaagag agggctttca atgaaaaaaa ataaaagcag gcaaaaaagt   37800
cctcaataga tctacaagcc ttttctgtat ctgtgcccat attttcagtc ttcatgccag   37860
taataatcaa gaagaggtca accaatccac atgtgctcca aaccccaccc cctttcagtt   37920
tctcagggac attgcacata ctctattttc cctgcttctt caagtttcca ttgctacaac   37980
ataatttaat agcacacata aattctctag tatatcaaat cataaggggg tggtttctgg   38040
gatttgtttt gttttgtttt tagagacaga gtttcaccat gctcgccagg ctggtctcaa   38100
actcctggcc tcaaatgatg tgcccacctc ggcctcccaa agtgctggga ttacaggcat   38160
gagccactat gcccagcctt caagtcatgt tttttaaaaa acaaaataag gccgtgtatg   38220
gtggctcacg cctgtaatcc cagcactttg ggaggctgag gtgggcggat tggttgaggt   38280
caggagttca agaccagcct ggccaacatg ctgaaacccc atctctacta aaaatacaaa   38340
aattatccag gcgtggtggc acatgcctgt aattccagct acttgggagg ctgaggcagg   38400
agaatcattt gaacctgcga ggcggaggtt gcagtgaccc gagctagcac cactgcactc   38460
cagcctgggc gacaaagtga gattccatct aaaaaaataa ttaattaatt aattaattaa   38520
ctaaaacaaa agaaattctt tcttgaactc acatgtctct ctttccctct tcataccaaa   38580
atatctctaa agagttttct aaatcattgg cttccagatc ctcacacccc atctactttt   38640
ttttttttaa ctcatatcta tttatcatcc aaccctacca ctccaaggaa tttgccaagg   38700
ttattaacag gtattttgcc aaaggcagtg aacatatttc tgttactcag tctctctgca   38760
ttccgcaaat ttgaccacta tagacttcat gataatcttt cctcttttga tttccttaac   38820
cctagctctg ggtttcttgc ttaaattctc tggccattcc ttagttcctc tacctttctc   38880
agagctttaa cctagtccct cttctcttct gtgcatatac tttctcctta agtttttcttc   38940 ctcagttcca tgctttataa actacccata tgtcaactac tcccaaagtc acactctagc   39000
cctgtcctct cttctaaact ccatattcca actgcctatt taatttcctt accagttacc   39060
taataggtac ttagcaaaaa taagaaataa aaataatatc cattgcatat attcccttttc   39120 agtaattcct tttttatactg caggtctgtt acccttaaca ccagactatg agagtaagcc   39180
tgtattccca agaaagggaa aaagaaccca cagggagagc aaatgactgt caattccatt   39240
atagaatttt gaaagcttta gctttaaaat gcaaaactag atgatgaaaa aggaaaatgt   39300
ttttaatgaa ttctgaaatc ttggacttaa ttatgaaaaa cacatcctag gctgcatgtg   39360
gcagctcaca cctataatcc cagcattttg ggaggccaag gagggaggac cacttgagca   39420
caggaatttg agaccagcct gggcaacatg gcaaaacccc atctctcatc tctacaaaaa   39480
atacaaaaga ttagccaggc atggtgatgc atgcctgtgg tcccagctac ttgggaggct   39540
gaggtagagg atcgcttgaa cagaggaggt caaagctgca gtgagtcata attgtgccac   39600
tgcactccag cctgggcgac agagccagac cttatgtcag gaggggggaaa aaaaatcatc   39660 ctaaaagact aaaagaatat ggcttatgcc ataggccata gattagaaaa taaaagctgg   39720
tgaaaatgtt gatgttcctg ccacacagag aggaagagag gagagaggaa aacgttctgg   39780
gctggggaaa gacatttgag aggataggag aaagagagca agagaaatca actcagtgtg   39840
agccctgcct ttaccaactg atcatctcat tccctcactc caggaaaaac tctttatggg   39900
gaaataaaca aaaggaatcc aaaacagtaa gagatgtgac ctctcgcctg actggaattc   39960
tggagacatt tcacagggtg ccccagggtc ccctggagta gctagagggg agtagaaatc   40020
```

-continued

```
tggccaagtg gcactaggca aagagaaact gagatgatct tgcaatatgc aaaggagacc   40080
caaaatgggg tagaggaggt caatggagtt gggaaatttt gtgccagcca gaggcacctg   40140
cactgcatgg gggaagtgag ccctctagat tcctgtggca gaaatccagg gcagagacca   40200
gagagataat caggctcagt ccaggaacag ctctgagagc cagagctgag aagtgagcag   40260
gcaggggctc gaaatatgtg ggatgaggct caagactcat acacactgga gtgctctgta   40320
agaagacgat agaaaatcac aagtaaaaat aagaaactaa agcagataat tcaatggaaa   40380
aatcatttag aaatataaag tattaaaagt tgacaaatac cacaaatatc acaaaatcca   40440
aaaaagataa tcttttaatt tatctttta attagttttc attttttaga ggtgagatct   40500
tgctctgttg cccaggctgg agtgcagtgg catgaccgta gctcactgca gccttgaatt   40560
cctaggctct gtggatcctc ccaccttggc ctcccaaaga gcttaggatt acagacgtga   40620
gcaactgcac ctggtcagaa aaataataat attttgtta gttaactccc tgccatacct   40680
ctgtaatgct ttcttaaatg gtaggccgca tactttagga atgcctgatt atttgataac   40740
aatttcagat tatcatattc tatatggaaa agggaatact aattagtttc tctagcatgg   40800
ttaatgaaaa atttatttat ttttattgat attttacata atttttttagt ttgcaaattg   40860 atcctggaat tctcatttaa atgtttaaga ttgtcacatt tggggacatt tctatcaaga   40920
tcatttctta tatgagctat aagatttatc aggaaagttt gtatcacata agtgaaatgt   40980
aattcaatat gttaagatgc atgaaatatg tgatttcact tacaaacata ctcatggcta   41040
tagtactgca gcaaacttaa cgccttcaaa tgcaagaatc ctgataaatt gtatttcaga   41100
cgattgccat gaaaaagtta tagtccatga ataattgcat gttacatgta taatcagcta   41160
tagtcagacg agaattgata aaaaccagat cctctactta caaaaatgtg tgtacgatga   41220
ttaaaaaatt tcccacagat tggcttctac ctctgacatt tcaaacctca tttctctcac   41280
actcacttat ttctgacgta gcctgcaaag tgcattccta tctttcctcc ctgtctcgct   41340 ccctctttc ctctctgttt ttttctggaa cttgatcctt ctctgccttc agcattcttt   41400
ccattctgca tcacagcaca gagccatccc atctgctcac atgattagaa tcatctagag   41460
tctggtgacc cgtacgtgag tggctccggc taaactgtag acatttccaa tggcttaatg   41520
aacagtctcc tttgtcccac aacaccatac atccaaagtg tcaacaccaa atctactttt   41580
cctctctgcc ttctctgtta gacaatgata ttatcatcta tccattctcc catgctggaa   41640
gtgcagaagt cacattacat ccttctttta ttccctcctt ccaaaaaata agtcttgttg   41700
atccttcttt ctaacaatcc caattctcca tttgttgtat ctttgtaagt gacgtcactg   41760
attattgcgt tgttctcatt gtggtggtgg tgggtgaaga ggtgagaaag aataagtgta   41820
ttttgagaag tattgtctct gagaaaccaa cacggcaagc aagcacagat gtccaaacaa   41880
aaggagaaaa tgtagtcacc aaactgggaa cagagaggtt gtgagtcagt ttacatagaa   41940
ctgataggtt caaaccatgg attgtaagaa aataaagcaa agggcctggc gcggtggctc   42000
acgcctgtaa tcccagcact ttgggaggcc gaggcaggca gatcacgagg tcaggagatt   42060
gagaccatcc ttgctaacac agggaaaccc cgtctctact aaaaatacag aaaaaaagta   42120
gccaggcgtg gtggcgggcg cctgtagtcc cagctactgg ggaggctgag gcaggagaat   42180
ggcgtgaacc cgggaggcgg agtttgcagt gagccgagat cgcgccactg cactccagcc   42240
tgggcaacag agtgagactc catctctaaa taaataaata aatgaaagaa agaaaagaa   42300 agcaaaggat atggaaaaaa ctcagctttc ctttaaacaa ctatgactgt tacagcattc   42360
```

-continued

```
actataacga gaaaatgtct caagatttcc aagatactct cagcacagtc atatttgaaa   42420
agaagataag aaagctttgc atgcctactt cgacgtggtc agagaggtgg aagagtattt   42480
ctgggaccca ttgcttacaa cacaatcagc aatgcactcc tagaaataca cgtggcccac   42540
aatacaggct agactcctct ttagtttcag atggagtcta gagaaatggg agaaaagcct   42600
caaatacttg taactctgtg tgcctcgggt ccttcaccat caagcaaagg tgcctctttg   42660
cttagtttca tagaggcctc tcccggtctt ctctttttga ggcaaactag caagcaatag   42720
ttcctttcct gcagcaggat tcagaggtct gctatcaccc ctcgttctct tagacaatgt   42780
gatcttgaaa gtctcattgg gatcttctca ttattccatg actttctatg attgaagttc   42840
tttttaattt gatagtgaac tggcacagca aaaacaaata ttccctcttc agtcttactt   42900
caaaaattgc tggttctcta agaaaaaaat gttttgtctt acacacagaa aataaaataa   42960
cccaagccct tatttcttta tttaaattcc attcaacaag catatgctgg tgcccatctt   43020
gtgctgggtt ctatgctgaa tggattattt ttttctattt tattttgtta aattattcta   43080
tccatgttat ttttcatatt ttacttatat tgagtgatta catgtacaat gtcattacca   43140
aaagtgtata ttaagcctca tatttgttgt actaagcgca gtaaaaaata attttactag   43200
tagtctaaac tttctagaaa tttaaaatct acagcatatg tttgcacttc tacaaaaggt   43260
aattttctaa tattgataat gatgaaattg ttttatcata ttttgaagtt gtcttctttg   43320
ttgttccttc cgtattaaag aaatacctag ggctatacta tgatttgaag tcgctagtaa   43380
tgtatacttg attttttcatt tataaaattc ccagatcata aaatataaga aatgaccttt   43440
ccccttagaa gttataagtt tgaaagctaa gctattctta agctctaaat atcaggttct   43500
tagaataaaa gcaaagcagt attctctgta aaccaaaaat ctctagctcc tgagatggat   43560
gctctgatgc tgtttcaaa gtctttagtc caaaaaaata aatattctat atatttgcaa   43620
acaaaaatca aagccacaga taggaatatt tcatctagtt ataactgctt atatatgtca   43680
gagaatataa catagtaaca ttttctata atacataaat actatttatc acagaataca   43740
gaaatcagag aagcaaaaca tgtcatttt atataaactt ctgatacgtg ctatccatgt   43800
cctgaagtaa aattttcaga aatcgaataa tgcaggaaat gggcacttcc ggaaagcata   43860
atacaaaaat gggaaagcaa ggtctcttgg ctataatgga agtatctctc gttccatttc   43920
ctttcctata cccagaggag tagtgcaatg acattcggcc atgttctctc ctcaccctcc   43980
aacccagttt ccaattccaa aataagaatt tgaagagctt tacaaaagtg cataccagaa   44040
aacaagagaa ataaagaaga aggcaggcca atagaaacca agagagaatg aaaccatgag   44100
attagcagga gaggtaacac aatagaaatg tatgccatta gcttctacac aattattatg   44160
gggatacaca gattttcctc tgatatttta agcaccaaat gcaaaaataa aaatacaatt   44220
agttattcat tttatatttt ctatatacaa agttcatcat ggttctgaga aagcaacttc   44280
cccttgctct gtctgaaaga tactcatggt ttgtcatcgg gggacccgaa ggaagaagaa   44340
agcagagaag attgggagag gacaaaagag cgagaggatg tggagagaaa gggtgacatg   44400
ctaccaagaa gactgatagt cagccgggtg cgatggctca cgcctgtaat cctggcactt   44460
tgggaggcca aggtgggtgg atcacgaggt caggagatcg agaccatcct ggctacgaca   44520
cggtgaaacc ccgtctctac taaaaataca aaaaattagc cgggcttggt ggcggacgcc   44580
tgtagtccca gctactcgga aggctgaggc aggagaatgg cgtgaacccg ggaggcggag   44640
cttgcagtga gccgagatcg cgccactgca ctccagcctg ggcgacaaag ggagactccg   44700
tctcaaaaaa aaaaaaaaaa aaaaaaaaaa ggaagaagac tgatattcat cccactctgg   44760
```

-continued

```
tgacacacag gaatggaaac ggccacttgc cctctggatg gaaatgcctc tttgcttaat  44820
ttcatacagg cctctccccg tcttctcttt ttgaggtaaa ctagcaagca atagttcctt  44880
tcccgtcgca ggattcagag gtctgctatc accactcttt tcctttgctg atagtagctt  44940
attagaaatg tcattaacta cataacgtca ccttgaaata aatgtaaatt aaatgtttca  45000
caacatttta tagcaaagtg agaagtcctc cattctcccc ttcactaagc tagtggagaa  45060
tataatacaa aatagcaacc taatatatag tctttctcca tgttaatgcc aatgagagga  45120
taatcactag ttttgattat gcttttctt attttagaac ctcccccccc aacagacaga  45180
cagacacaca cacacacact cacaagtaaa aacgcacctg ggatatcaga atggaataga  45240
tggataataa tggatcaatt aactcaggta gatactcatt tgaccatatt ctttgcctaa  45300
ataattactt gaaatgtagg aaagtatctt tatctcattg gattgatcca attaaatatg  45360
agtattaaag tatgacactc tagggaggat tttttctcg actaaaaagg ttaatttcta  45420
tgtgagggta agtggacata aaagtcatgg caaatgcaag aaatatatct ttccaagcac  45480
attgctgaac atataaaagg ggcttgttga attcttactg aattaggtat ctttcttcac  45540
actacttggt aaaaaaaatg aaaaggcaga aaaattagcc ccaaaagaga tgaaactctt  45600
ccgtccatca ccattgactc tattgtgaac ttatgaaaaa ggtagttgag caatatgaag  45660
gccatgatgt ggaattaaac acacacacac acacacacac acacacacac acatgctgga  45720
ttctaaaatg tgtccttcct cctctcactc tcttgatcag ttttatttct gaactgagac  45780
acgatcacca caattcaaat aattaaccac aaaactaaac agaagtttac aaaacccatc  45840
aggtgtacag aggtaattta tttagtctgg cttcacttaa cacaaatagg tcaaaagcaa  45900
tcacattttg taagtagtaa tagttggaga aatgtgtgaa gaataggtca aaagataaat  45960
aagaattatt ttataaccat aagaaaggaa gaacatctat aaacaaaagt catatatgca  46020
acataaaaga ataggtgagc tgccagcaaa tgggcctcac aatgcctttt ccccaacact  46080
tctggaagtt ccataaaaat cactctaatg ggtcaaacat cgatggttct cagaagaaca  46140
caattttttt caaaaacgaa tagcattgta aattcatttg aattcataaa acaaagagc   46200 tatttaatca tctagaccaa agttaaagaa atacctacta caaaaatttt aatgggataa  46260
ttagaaagaa atagcttggg ccactgcttc gagcagaaga tggagttcag tggctaccat  46320
aggaagggtc aatatcagga tggcctgtga gtccagatga gtctctcttt gcccattttg  46380
ccacagaaca cattcacagc acagtacaaa gcagtaggca tggagtaagg aaaaaggctt  46440
gtgttttaat agccaggagt tctactcgga cccactcagg taaactgaat ggcaaagata  46500
attcttcctg caggtcattt cttttgctag tttgctaact ctgagtccta tgctcctgtg  46560
caaggcccat gatgtgactc tgagcattca ttgaactttg ctgggacaac attcatgcca  46620
ccacatcaga acagaatgaa agcttgccct tttttttttt ttttttgaga cagtgtctct  46680
ctctgttgct caggctggaa tgcagtggta cgattctcct gcctcagcct cccaagtagc  46740
tgggattgca ggtgcctgcc accaccccca gctaattttt ctaattttag tagagacagg  46800
gttgaccagg ctggtctcct tccctgccc tcaagtgatc cattcacctc agcctcccaa   46860
agtgctggga ttataggctt gagccaccag gcccagccca cattactcct tttctgatta  46920
gaccatctct tcagattaaa gcctttgggt atatgctgga ggcaattgga attcttaatc  46980
ctttagcttt gtataatttt ctttcacata tttagaagat cgttgagccc cctttttatat 47040 gttgctgtga tccaaagcat gagtaactgg ggtaagaatg ctggctatct ttagaggaag  47100
```

-continued

```
actttttaaa taaattgaga aaaattaaac agcatcattc ctataaaatg cccgttgaaa   47160
gaatttttat agataaatat tcactttttt ttggtaaatt gatgataaaa ttatgtatat   47220
ttaccatata caacatgatg tttttgaaatg tatacacatt gtggaatggc tagcatgcta   47280
attaactatg cataaccacg tttcctttca ccatgttgaa ccctgacata attttttttt   47340
ccacaaacac ctcactctgg agaaggaaat gatttttttt aattaaaata aacatacatt   47400
ggaaatactt agtgctaaaa taagcctgaa ggaaaggttg gaagtatgat gagtcagaaa   47460
actgactgta aagaaaccaa ttacttaaca taaaacacca ttaaagataa gccacgaaat   47520
gtaaggtctg ctgggtagga aagtggcaaa tgcaatgaag catgtcttta gatcatgcag   47580
gtctataacc aacggtgaat ctagcaaaag ttattttctc ttttggggag aaacttcttc   47640
ttattaaaaa aataaaaaat gtttcaactt cttgagcacc aaggtcaatt attctaaatc   47700
ttaaaaccac agtttttaatt ttgctttttt gttggttttt gtactttgga gtatttgtct   47760
acattatcct tttttatattt gccatattta aagtccaaac taaaagcaaa ttattttctc   47820
tcctcaagtt aaatggctct atctttttct ttaaaatcca ttaagaaagt gaaactccca   47880
aagtaagtcc aaaaaaaagc ccccaagtct gaaaatgtgg agctttttctg gcagtaatgc   47940 agcttctgca agtattgcag accagatcag gtatcagaat tttaaagctt cagtaacaaa   48000
gctgtcctat tgaccctgag gagatttatg aaatcacttt cctgatgtta ttgaaaccaa   48060
aacactttcc tggacactga attcagtcct aaacaaaggg cctccaacca acagctgtct   48120
tgggctgaat gagttagact caacctcgtg tgacggaaaa acagtaaaca caagctaaca   48180
tttaaaagga attgatggca ccgtgtaaat cagaagccca aggagggcct ggcttcaggt   48240
gtggggttct ctctcacgct ctcaaatcca catcctccgg attaggtcca ttttcagaca   48300
agctcctcca gcaactacat accatgcgtc ttctcaggtg tgggtcctgc aggaaaacta   48360
atacactctt tgtccataag tctcaaaata aactctcact ggctctggtt ggaacatgag   48420
agcatccttg ccattcacca tggccccggt cactaaacgt cttcacgccc tggactggta   48480
atacagccta tcccaaagca cctggactga gaacgggaaa tgagtggttc ccagagtgaa   48540
actgaggtac tattactaaa ttaaggtaaa tatatgtgga atgttaaaaa aaaaatgatg   48600
tccaatgttt acaaggtata cttctgccat cagatataat gtattattgc aagtgtacct   48660
gcttatattc tactatcata tttctaattt ctgcaggcct tgaaaacata taacactcct   48720
agatacttac ccaggaggaa gaaaagcata tgtttatata aagacttgca catgaatgtt   48780
cgtaacagtt catttgtaac atccaaaagt tgtatgcaac tcagttccca ttaataggtg   48840
aatggattaa aaaaaaaaac agatgaatgc ataagtaata ctacttgtca ataacaagga   48900
attaattctt gttatatgca accacataga tgaatctcaa aataatgaca ctgagtgaaa   48960
gaagcagcac aaaaaaagag tacatactga atgattctat ttgcatcttc taggaaatgc   49020
aaactaatct ataagaacag aaagcaaacc aagatcagca attgcctgag gaatagtgag   49080
ggttggatat gaggacaggg aggggcaaac aggaaagatt aaagagctac acaaagacac   49140
ttttgggagc aattgatgtc attatcttca tcagaggttg acatttttttt ctgtaaagtg   49200 caagatagta aataacttag gctttgcatg tcatctgatc tctgttgcaa ttattgaact   49260
ttgccattgt agcatcaaaa cacttatggg ttttttaaata ggtgtattta tttataaaac   49320
aggcaacggt ccaattgggt ctacacacca tagtttgcca atctctgatc ttaattatgg   49380
tggtggtttc acaggtgtac acacgtatca aagcttatca aattgtatac tttaattatg   49440
cgttatttat tataggtcaa ttccacctca ataaagcatt aaaaaataaa aacaaagcaa   49500
```

-continued

```
acacacttgg gttcctcatc atggattgga tagagtctaa tcttaccatg gcatacaagt   49560
tcttcatgta ctggcctctc ttcttcccca gtcagatccc ttgccattcc ctggtagaat   49620
gtgcttgaca cacacatcag gccattccaa ctctacatct ttgttggggt tctctctgtt   49680
acctctctgt ctagaatgac ctgctcctac caagtgtcta actcaatcat cctgcttgtg   49740
ctttgagatt aaacttgcac ttccaggatg ccttccacat cttactccta ctattccctt   49800
tgccttatgc tctgtgagat gcctcatctc tgtgccccat aatcgcctgt gtgtttgtat   49860
gtgcatgtgt ttgtgtacat acctatagac acttgcacaa ttatacttct tgataatttt   49920
aactatattt atatagctaa aattttctct tttatattta gaattactat ccagtcgctg   49980
cccctactat ttgactggaa tctccctctt tctattagac ctatcacaat gactgacaca   50040
ttacaaaaaa aaaaattaaa accctcactg cgtgtggtgt ctcatgcctg taacacaaac   50100
actttgggag gccgaggagg gaggactgct tgagcccaag agttcaagac caccctaagc   50160
aacatgtcaa gaccctgtcc ctacaaaagt tttttaaaat taacagggta tggtggcatg   50220
cacctgggat cccagttatt caggaggtga ggcaagagga tctcttgagt ccaggaggtt   50280
aaagctgtag tgagctctgt tcataccatt acactccagc ctgggtaaca gggcaagatc   50340
ctatccaaaa aaaaaaaaa aggaagaaac tcaacaaagc agcatcgttg ctattattgc   50400
agctatttag ccaataggta catcattgac atcattgtaa atagccaagc tgatactgga   50460
aaacaattct atatctaatc tcaaaaaagc tttctactaa ttcatgcaaa tttattattg   50520
gaagcttacc tatattttac actagtgtct tttactgatt ctcactcttc ttcctttatc   50580
tcctagatac accaagatga agactgccac caacatctac attttcaacc ttgctctggc   50640
agatgcctta gccaccagta ccctgccctt ccagagtgtg aattacctaa tgggaacatg   50700
gccatttgga accatccttt gcaagatagt gatctccata gattactata acatgttcac   50760
cagcatattc accctctgca ccatgagtgt tgatcgatac attgcagtct gccaccctgt   50820
caaggcctta gatttccgta ctccccgaaa tgccaaaatt atcaatgtct gcaactggat   50880
cctctcttca gccattggtc ttcctgtaat gttcatggct acaacaaaat acaggcaagg   50940
tgagtgatgt taccagcctg agggaaggag ggttcacagc ctgatatgtt ggtgatgtca   51000
taagcaaagc agtatttatg gagtgcccca ttgtcttagt cacattgtaa ttttaattat   51060
tcttcctagc aaaaaaagcc tttgaatact taaaaatagg aattttcctc ataattttag   51120
gcctattaaa tcctttaaag agaatgtaat ctatttattt ctgatttctc tgtatttact   51180
tcataaaaat ggtgtgtaaa ttagtacata gctctcccaa gagtaattgg agcttaaacc   51240
caaagagtat tacactgagg cttgtttaaa attatcaagt ggctgactac atggcaaatg   51300
tatctttcta cacctaatat cagaatattg aacaatccat caaaaaatga agtgaaaaca   51360
tccattacct ggagccgcct agagactttg dacaattatt acattttta tatcaatata   51420 gacctcatgg aggatctagc tcatgttgag aggttcattt ttgttccctg aacgaaagct   51480
taatgtgatc gaagtggact gcaaaatggg aaatttagaa aaaaacaaaa aacattagaa   51540 gtaaaactt ctttgaaaag taacaaacaa ctgagtttct tccacaattt ctttatagcc   51600
ttaagttagc tctggtcaag gctaaaaatg aatgagcaaa atggcagtat taacacctta   51660
tgacataatt aaaatgttgct gctaattttt cctttaaatt cctttcttct aggttccata   51720
gattgtacac taacattctc tcatccaacc tggtactggg aaaacctgct gaagatctgt   51780
gttttcatct tcgccttcat tatgccagtg ctcatcatta ccgtgtgcta tggactgatg   51840
```

-continued

```
atcttgcgcc tcaagagtgt ccgcatgctc tctggctcca aagaaaagga caggaatctt   51900
cgaaggatca ccaggatggt gctggtggtg gtggctgtgt tcatcgtctg ctggactccc   51960
attcacattt acgtcatcat taaagccttg gttacaatcc cagaaactac gttccagact   52020
gtttcttggc acttctgcat tgctctaggt tacacaaaca gctgcctcaa cccagtcctt   52080
tatgcatttc tggatgaaaa cttcaaacga tgcttcagag agttctgtat cccaacctct   52140
tccaacattg agcaacaaaa ctccactcga attcgtcaga acactagaga ccaccectec   52200 acggccaata cagtggatag aactaatcat caggtacgca gtctctagaa ttaggtatat   52260
ctactgggga tgacataaaa attataaggc tttgtgctaa actaggagtt taatccatta   52320
tagaggatga gaatggaggg aagaggggaa gcaaattgtg gttctagtgt tagagaagag   52380
gtttgttata taaactgtgt tctttatatt tgactgtaca tattcattta ggtataaaga   52440
tacaccaatg agaaatccat gaaactattc aaaataacta tttttatggc ctttacttct   52500
atgcaaaatt tatgacttta gcacattata gaaataattc tgatctagaa tccttttcat   52560
tttccccaga attattatat aattcataga tgttgctgca ataccectct tatttctcaa   52620 aagccagtct tgctctggtt ctgtgattaa agagagaggg tgagtgcctt gcccactgtg   52680
gtcatggatg caagatattc acagaaaatt agcatcatgg aaaaggagaa aagattaaaa   52740
aatgaccatc cctaactttt cttaagctat tggtttgcta cctgaactct agcacaaata   52800
tcaaacatat tagactgaat aatatattat taatatgtga atattaatct aataaattt   52860 attagattaa acaatttta acagacctca tgcttgttgg agataatagg gtgaatagcg   52920
actagctttt ggaaggtgta tttctgtgcc cagacctaca cagaaaattc aagacttata   52980
cacactatta taatcatatg ggaaatcaac aaggaggaaa gagaaaaggc tgtctccaag   53040
ttagtattac ttgattaagc cactggttgg ctaaatttga cctctgatct ataaaatcaa   53100
tcaaatacat ggcttaattt ttaatattaa tctaagtaag taaatttaa ataatgatgc   53160 cagcatccaa aaatcacagc ctgtataatt tttttaacag tgaattcaaa ttcaaacttc   53220
ctatgaagta aaggctggag tcagaatctt ggctaaagtt cctagagtca ggcgtcagga   53280
ctgtgaggac agatggctcc ggagaaatga atagcaagtc aaatgattga ggagctaggg   53340
gaggcctttg ccaccacagg gtgcagtggc ttcctcctgc tgtctcttga ccacaccctg   53400
tctctcactg tcccctcttt accccactct gccatccagc ccagcccagg ctcaacecttt   53460 ctaattgacc agaggactaa tgtaatatgg cccagataca tccgtcatgg gcgacattaa   53520
tcctcatacc cctggtattc agtgatgctc aagggaacac aggaactcac accccctaga   53580
gagcatgagg taatgatggc agacccactt ccagacaaag ggaaattaac ttattatgtc   53640
tcagttctaa ttccatttca gaaatgaatg ccagaaagaa atggttttga ctctgcttct   53700
tttctctacg ttttttttcca catcaagact gctaaaccta ctccttttac taggagctac   53760
ttttaaaaag taattgcaaa aacagcgatt acttttgcac caacctaatg ctaagcagcc   53820
ctcctattca gtggctgcta gaatcttgta agtaacttta aaagggcagg gatttaaata   53880
gattttcacc aacctgggga taacatgtta agattgcaa cttaaaatgc ctagtcctca   53940
gctaaggata aaatatttg ctttgaagta aaatatttcc attggagcaa aataatggcc   54000
attataaagt actgactctt tctcctttag tgcctaccta taccttccct gtcttgctgg   54060
gctctagagc aaggctgctt ggttgtgtac cctggaccac tgcaaggacc tcttgtcaga   54120
tatgacctcc cagctatcct tcactcgtcc tgccttcgtg gaaatactgc tcccagcccg   54180
tctggtggag catttctcct gagttaagca tgattattct tcagttgccc gacactgccc   54240
```

-continued

```
ttgactccct tccaaattcg gcattttcac atcagtatgg ctattgtaca gccagataga   54300
agagaaaaga agctaattgg aggagttctg ttccaagtaa ctaaaaggtt tgctttaaaa   54360
atacatccaa ttaggcctta tcttcatcgc tgcctctatg aagcagtatc agtgtaagat   54420
aacagcagaa acacattagc cctcgaattg gttgctgtcc caaaatgccc aactgagaga   54480
actggacaca gaagagaggc tgccaggaaa agagggaaag atgctctgac atatttaaaa   54540
attaagataa atcaaagctc cctttggcta atctccactg atgtgtcatc attagaatta   54600
aagcagttac aaccagacaa ctggaacaat acataagctg ctagtgatag tttcaataat   54660
atatcaacat aataaaatga cttgaaggag aaattggaga cttgatggct gtgtctatag   54720
gacatgttaa gttagttgta caaatccaga atgtgataaa caggtgtttg gtcgttgttt   54780
cacatcatga cccatcatgt tggaaaacaa agctaatagg atttgcattt aacttttcaa   54840
ctacttgttt gaagtttata ttggttgtgg atgtttatgt tctgccttat gtatttgtac   54900
tttctttgag gaatatatta tactctatat gtcacatttc aagcacatta gtcaacttca   54960
tattctgcag atcagagatc caatatcaaa ccttcccagg gtgtctgtat tctgacaact   55020
gtccactgag gcaatttcca tacagcgcaa agtggagtgg cgatttggca gttatcaagg   55080
taatttgata agccaatgag aaaattctgt gcccaaaata agcttagagt catacttaca   55140
cagttaagag ctgctcagtc agcttttgtt acattacaaa tcattccaaa atgtagtggc   55200
tagaagcaac catttatta gtttacaatt ctgtagaaca gccattggag ctgggcttgg   55260
ctggaccgtt cttccagtat tggctgggct tgctcggagg gcagctgccc gatgggcggg   55320
tggtcagcta gctgatctac atggcctcag caagaatgac tagctccaca tggactctta   55380
ccgtctagca tgttacccca gccttgttct catggtggtc acagattcca agagaaagaa   55440
agagagagag aaaagaggaa agcgtctttt ggcatagagt aggaattggc atacggtcaa   55500
ctctgtggtt ttataggtca aataaagtca tcctgccaac ctagattcaa agggtgagaa   55560
attagactcc atctcttgct gataggatct gcagtcacat tgcaaaagga taggtatata   55620
gggagcgaat aattatgacc acttctgcta acaatccgta gtaaggacat gctgcatgag   55680
acagggaagc cattacttcc tgagggcagg agccgtgtct gtcttgctct cccaagccag   55740
agtctagcac attaaaaaga aagtacttct ggccaggcac agtagctcat gcctgtaatc   55800
ccagcacttt gggaggccaa ggctagtgga tcacctgggg tcaggagttc gagaccagcc   55860
tggtcaacat ggtgaaaccc cgtctctact aaaaatacaa aattagccag gtgtggtggc   55920
acatacctgt aattccagct atttgggagg ctgagacagg agaatcgctt gaacctggga   55980
ggcagaggtt gcagtgagcc caggtcgtgc cattgcactc cagcctgggc aacaagaacg   56040
aaactccatc tcaaaagaaa gaaagaaaag aaagaaagta cttccaaaac atccaaagca   56100
ttggacagat tcatgtctgt tgaataaatg atgagagggc tgaggatatt tcaggagatg   56160
tggcaggcat gaccccttca tcatgcaact gacgaacaac ctaaatgact atgtacccta   56220
accctcttac cgtcagtaat gggaaaatat tcaaaatagg ccttcttcct tttctcctcc   56280
tcagcctttg ctactctgat ccaatgttat ttatacttt caaaaaatca gttacattca   56340
tggttgtttt ctaattttat ttctaacgcg tacttttgat aaggagacca agagattgat   56400
tcagtgccct aaagaggtct ttccctagct gagtatgaaa aaacaaaaaa gatggtctcg   56460 tgttttttt gtgcatgcct gggctcagcc tactgctcca gctgtagcct ctgtgcctga   56520
tttatgttca gcttgctgtc tttatgactt ttagatcttt attaggtaga ctaaggcata   56580
```

-continued

```
ggcattcatt ttccatctgt tctcagtgca atttaatttc tccacacacg ccctacactg    56640
ctgttgtcct attgaactcc actttgcttt caaacccttc ccttgtttat ttcgatcact    56700
tcaggttcaa ctcaaacctg aactgttggc cactgctaac ctgccttgcc cacttggttt    56760
ccacccgcat catattatct aatgcatttt cttttttgttg ttattgttgt tgtttgtttg    56820 tttttttgatt tttagtttga aatggaatta ctctgtcgcc caggctggag tgcagtggtg    56880
cgatctcagc tcactgcaac ctcttcctcc tggttcaaac gattctcctg cctcagcctc    56940
cccagtagct gggattacag gcatgcgcca ccacacccag ctaattttttg tattattttt    57000 agtggagatg gggtttcacc ttgttggtca ggctggcctc aaactcttga ccccaagtga    57060
tccgcccacc tcagcctccc aaagtgctga gattccagac gtgagcccct gtgtctggcc    57120
tctaacgcat tttatatctt gacacgtagg tgattattga aaacgtttag cattatatgg    57180
ggaaaaaagc aacactgtta catcagttga attatcactg aaacggtaga gtttggtgca    57240
aaagtaattg cgggttttgc cattactttc aatggcaaaa accgcaatta tttttgcacc    57300
aggctagtac taacaaccac tataataata atgctgcctt acatttatat ggcaatgtac    57360
agattcaaaa gtgcttttat gggcattatc acatctgctt cctataacaa ctctgatggg    57420
taaatgtaag aaaatgctca gggaagttaa atcattatat aagatcaaac agccaggaag    57480
aggtagaatc cagacaagca cccagggctt cgaatattac tccacagctt ttctctgctt    57540
tcctacacaa tgctactttg cactcaatta ttatcacatg gtctcagcca gattctcaac    57600
atttactatg agctccagaa aatgtaagtt cttaagaact gctctaataa attatagttt    57660
gttatgtgag ggtccaagaa tctgcctttt aaataaaaca ataaactgaa atctcttatt    57720
taaactgtac cttcatctcc aaagtagcac atttactgtt ttgtctaacc tgtctagcca    57780
tttcagtcaa gctgattgac atgaatgttt tcaccaaatg agttatgtgt tttgtgaaat    57840
aatgtaatta tccttggaaa aagccttaat attctgacat atctacccgt gggtcttaca    57900
ggaaaaagca atataatagt gataaagtga acgtcgtggc atgtcctgct aattcctttc    57960
cattaatatg gcaagtccag tcctaaaccc tctaattact attattaaag cactttcttg    58020
acattttaat caaaatagcg ggtcaagaag ttaggagatg ctctgtattt ggtttaactg    58080
tgaactatat tatccccagc taaactaaaa gcagaagcct acttttaaaa taaaatacat    58140
cactctcaaa agttgatctc agtttttttt acaagacatc tgtggagagt taatttggga    58200
aagtaattgt ttcaattcaa tgggaaaaaa aactcaaatg agaatagctc acaaaattac    58260
agcagtggac aacattaatg cttattttgt gaatgaaatc aaaatggcta ttcttttcagt    58320 tctacagttt aaaaagaaaa tggttccgtg tgtgtgtgtg tgtgtgtgtg cgtgtgatat    58380
aggcatgtct cttttttgcat gtatggaatt agagtaaatg taggtttaaa attaatatttt    58440 catgcatagc agaagaaatt agtatgtgtt tctataaatt attgtgatat gtgagagaaa    58500
atgttgttta gttaaaaatg tgtttatccc tagaaaaatt tggcttttttag actattcata    58560 ataacatata ttgaccatttt tgtgtctggg atgggatatc ttatttaatc atattagata    58620
tggattgtaa cctctactct atagttgagg aaactaatgt ttaaggaagt aacttgccca    58680
aggtcatagt taaaatgtag tggctgaggg ttgggtgcag tggctcacgc ctgttatcct    58740
agtactttgg gaggccaagg caggaggatt gtttgaggcc aggtgttcga gaccaacctg    58800
gccaacatag caagaccttg tctctactaa atttataaaa ttttaaaaat tagaaaaaaa    58860
attttaatta gtggctaact attgactcca gttaaattcc atcttataac ccaggctttt    58920
aatcaatgtg ccctgatata ttccagtcta tttttcactc ttctcagcat ggtctcagac    58980
```

```
ctgagaaatt tagggaaatt tagtttaaa gattggatta actaaagtgg tgcagtatct   59040
tcttttcctg actgttctaa ctaatgtaac taactgaaaa acagcaacat atttttcctt   59100
tcaaaactaa caaaatgaga tgtcatctta tttggttaaa cttaagtggt gaattgctat   59160
tttacagcca tttttttgtaa aaatactctc actgagattt agtgttttgg aacatgtcaa   59220
tctttatttt ctacctcatg tagttttgga tgctaaatat gaaaaggtgc atatttttct   59280
cttttaactt tcaacaacac cacgtttatt tttacttcta cctctatgat tttgaaatgc   59340
agtttcacag tatttatttt tgcttttgca ttttctcctt cacactaaag gaaaggatat   59400
ttgaatgtat atgacctatc acaaccagc tgttaacttt tggatgtcat tctgatcact   59460
atatcttttg gcaggttgca aataaatatt tgtaaattgc taaaatttga caaaaatggc   59520
aaaattaatt tggagagtac attatgagaa atagaaattt ctgtggggtg tagaacaaaa   59580
tttgtcttat tgataatttt cctttctaa ttattatttc cctggaaatc aagaatccaa   59640
agccacaatt tcatcagtcc tctcccttca cactcagaat ttgtttcttt atagagtaga   59700
gtttctgagt ttcacgtgaa taggaacttt tcatgatgaa gaaaaaaaat tagagccaga   59760
ccaggtgcag tggctctcat ctgtaatctc agcattttgg gaggccgagg ccagtgaatt   59820
gcttgagccc aggagttcaa gaccagcctg ggcaacctga cgaaagtcga tctctgcaaa   59880
aaacaaacaa acaaaaaaag ccaggcgcgg tggcatgcac ctgtaggtct agctactcag   59940
gaggctaagg tgggagaatt gattgaacct gggaagttga ggctgcaatg agcagtgatt   60000
gtgccaccgc actctaggct gggcaactga atgagagtct gtcgaaagga aggaaggaag   60060
gaaggaagaa aggaaggaag gaaggaagga agggagggag gaagagagcg agagagagag   60120
agagagagaa agaaagagaa agaaagagaa agaaagaaag taaagaaaga aagagagaaa   60180
gagaaagaaa gagggaggga ggaagaaaga aagagagaaa gaaagaaaga aaaagaaaga   60240 aagaagaag gaaagaaaaa gaaagaggaa ggaaagaatg agagaaagag gaaagagaga   60300
gagggagaga ggaagggagg gaggaaggaa accatatcgt ctatgacttc tactctactg   60360
caataaaatc tcttaaataa agatcataca catatataca cacatatata tacacacatg   60420
tatatacata tatacacaca tatatatgat gtgggtaggg gaggctagaa acaagattca   60480
tttcaaatgt taaattgtaa ttgtagtttt taaaaacatg gagagttttc ataataaaca   60540
tgaagagttt cataaaaaca tgagtttca taatatatat caaatatata tcatatcagg   60600
atatatcata atatattata tattatcata tgatatatat cataacatat tatatattat   60660
attatgatat atatcataac atgtattatc atattatgat atatatcata acatatatat   60720
tatcatatta cgatatatat cataacatat tatatattat catattatga tatatatcat   60780
aacatattat atattatcat atgatatata tcatatgata tatatcatga tatatatcat   60840
attatatatt atcatattat gatatatata ttatatatta tcatattatg acatataata   60900
tatattatca tattatgacg tatcataata tatattatca tattatgaca tatcataata   60960
tatattatca tattatgaca tatcgtaata tatattatca tattatgaca tatatcataa   61020
tatatattat catattatga catatatcat aatatatatc aaaaagtcac agagctcatg   61080
caagcccagt catccccatt gccagtggtg tgtgctaaag gaatacaccc ataaatatta   61140
accctaactg gtgtgagata agtatgaatt taaggtagtg cttgttgctt tactgtgtat   61200
gaatcaaagg aaattaacca tcttgtcttt ctataacatc tgaacatatt agaaacacat   61260
gcaaagaaat aaatagcctg ataaattggc tccatatcat tatcagatac caaataaata   61320
```

-continued

```
taggctgaaa atttcatcac aatttgaata ttggtcctct cagtttaaga atgaatatat    61380
agaaaaataa tgtgagcaat ttgtctgtat aaagtgaagt atttcttggg aaagaaggaa    61440
aaagagctaa tgtatagagc acatttttg tgtaaaatca gctaccatct actattctgt     61500
tttctataca gacaccagaa atcccaagaa tactagatat ctacaaaatc tagcaatccc     61560
tacctaggtt ctttctactt ttgtcacatt atccaatatt tataaaggtt aaaaaatata     61620
tatttaggag attttataaa tataaatata tatgtatata taatccagga ttcgtaatat     61680
atatttacat attatatata taaatatata tacacacata tataaaattc aagttttcta     61740
tacctaagtc ccttgaagtg taaaaagtaa atgatttatt atgatgaaat ggattccttt     61800
aagatgtaat agaaaagcaa atcctatgaa agatgatatt aagaaataag aataacttaa     61860
tcaacaaata gcaaaatatt ttttaaaacg ttgacaacca gaaaattcag tgaaaggtgg     61920
atgtgggatg agatatgact actgtacatt tgacaataca atcatctatt taactcattt     61980
cataatttgt cgacttaaga agaatatctc actcttactc ttcttcattc ttctctatta     62040
tattagctaa ggtgttctta tattcaaaat tcctgaagta tcattaaata tgggctcatt     62100
caaattcaaa ccatcaactt ttaaaaacgc tctccttgag ctactctttg gaaatagaag     62160
ggaaatggga ggaacaattc tctcatagaa ttttttaaatg cttcagctaa ggcttgcagt     62220
gtgacttgca tatactataa taactgaatt tctttctgat tgcttcagaa gttcaatatg     62280
acaaatagac tttcaaatgg ctatagtata gcaaatatca acgtctaaat ctcaataatg     62340
taactggata tgtcaagcag atgcaaaatg ttcacagttc ttcgaacact ggaactgaaa     62400
aagaacactg cagactgtct tatccaaaca tcctttttcct ataaatggag aaattgaagg     62460
ccagaaatgt atttttttat tgtgtaccttt ttttcttact aaatgtaaaa gatgatagtg     62520
aaatctttcc aaacacctag ttttcaaata gagtttaaga aaatttgtgt aaataaaaag     62580
tcagataatt gtatttttac ataaacatat gtaaatttaa ttttaaaatt ttcatcaggt     62640
taaggggaag cattacaatt agataagaac agcagatgca agataaaatc ctaaaaaatt     62700
atttatttta ttttttttgga gacaggattt agctctgctg tccaagctgg agtgccgtgg     62760
caccagctca gctccctgca gcctctactt cccaggctcc agtgatcctc ctgcctcagc     62820
ctcctgagta gctaaaacta tgggcacaca ccatcacacc atgctaattt ttgtactttt     62880
tgtagagaca gggtttttgcc gtgttgcgag cctggtctta aactcctggg ctgaagtgat     62940
ccacctgcct tgccctccca aaatcctagg atagccaaaa tcctaaaaat gtaaatggcc     63000
ccagatcata ctactgatgg gctgaatgtt cttgggcaag tttctaacaa tctctgcttg     63060
catttcctca tctgtaagaa aggtaataac tgtagtaact accacttagc tttgatgtaa     63120
gcatgatgta tgattatcca tccaaagtgt caggcaactg gctaatatta ttactccaag     63180
ccatccggtg aggctttact attctcatct tcttcttttc cttttccctc aaaactgaat     63240
ttcatctctt gtaaatagca tttaaaagga atgaaataat gtaccaaaag agatcataaa     63300
gtggactaac ccaagccttc tcaaccttgg cgctagtgac attgtgggca ctgtaagatg     63360
ttcagcagca tcctttgtct caacacacta aatgccagta gcacccaccc atctcccact     63420
gtgatgccaa aatgcctcca gatattgcca aatgtctcct ggagtggagg caggcagcag     63480
aaatcagtca agaaccattg atctaacctg tttaattttg ttcaatagct ggagaaacat     63540
taaggtccaa ttagttgtga tgtttttaaa gcaatgcttg agaaaattgg aaccaaaccc     63600
caggtgtcct gactttagtc tgatcctcct ctgaaaattt ctctaaggaa agctttcttc     63660
tacaccacta accagttgca aaaaaaaaaa aaaaaaacac tccatactca tggaagacaa     63720
```

-continued

```
gagaaaggca caattcttca acccttatat tacttcaagc ttcttttaga aaaaaaatga    63780
ccttcagctt gagacactat taagaaaaaa attaaaggcc aataaagatg aagatattgt    63840
tagagaaccc caggaggctc tgaatgaggt caaatctcat ggcgatatta aaacattaag    63900
aggagttgtg gacaaactac aatgaaacac aaatcataat ctctgaagca aataagaatg    63960
gaaggactcc tggaaaatga gggtaaagaa atagaatccc aagtttaatg ggaatattgt    64020
agcaactgaa aaccacagaa tatttagctt tgtacaaatt gttttttagaa cctggattaa    64080 atcattaaaa tgtattttga aagtacttag aaagaaagca agtaacctct aagaggcaag    64140
ttatcattag ttatggcaaa ataaattta ttttcttaga acattactgg acccggaaat    64200
taggtaaacc ctataccaat tgtgtttcta acaatagatt tgacaagctc ttactaattt    64260
ctgtaatact atactgtgtt tatgatctag gtaaatagtac aatgaggtag gtttataaac    64320
tttttttttc aaagtgaaag caagtttatt aagaaagtaa agaaataaaa gaatagctac    64380
tccatagagc agccctgagg gcttctggtg gcccattttt acagttattt cttgatgata    64440
tgctcaacaa ggggtgtatt attcatgcct cccctttta gaccatacag ggtaacttcc    64500
tgatgtttcc atggcatttg taaattgtca tggtgttggt gggagtgtag cagtgaggac    64560 aaccagggt cactcttgtt gccattttgg ttttcatggg ttttggccgg ctcctttact    64620
gcaacgtgtt ttatcagcaa ggtctttatg acctgtattt tgtgctgacc tcttatctca    64680
gcctgtgact tagaatccct tcactgtcta ggaatgcagc ccaataggtt tcagcctcat    64740
tttactcagc tcttattcaa gatggagttg ttctggttca catgcctctg acatgtcccc    64800
cctccctttt gtaagagaac ccttaatcct aagagttgca gagagatgaa gatccatctt    64860
ccgtaacttc ttcaggctga atagggggcaa taatattcct gcctagctat taggggctct    64920
tgtgtttagg gtagagagaa gctcagtcag aaagcatcag tatggcgagg gccattcatg    64980
actcttgagt ttcaacaaca gatgatatct ggaagattaa taaatgttta gttaaagaaa    65040
acattcagtc agcttgtcct gtattcctac acaaagaata taataggaat atattccaaa    65100
agagtaaagc aaaacaaatg aagttattcc aagtaaacta aattagaatg cttttcataa    65160
actggacaac tgttggaact aagctgatat ggggttgtta gctgattgta atgtgcccag    65220
aattagaata ctcatttaga ttttttacatt acccatccct cttgtttctt ctaagcagca    65280
gtcagacatc actggttggt ttacaggaat aagcaggatt agcctaaatt gcagaaacaa    65340
gcttaaaaac aactaatgag actagaattt aataacaagt gtaccatagt ttttgaaaca    65400
taatatttct ctctctagtt tcccattttt actaaagaca aatcatggta aggctgattt    65460
gctttattat acatgacctg attatttgta taaagtgcag caagaataat tatttttcac    65520
ataagctctt tttaaattgg ctttgatgga atgctgttcc acagaaggaa tttcaggtaa    65580
gatcttttta agccaagccc agccatgggt ttgtaccctc aaatacctat aagttgggta    65640
aatttctttc ctcttgaggt cccaaagtaa cttcagtctt ctggacctga cagaaaatga    65700
cgttctttac ttaccatagg tcagaaaccc tgaacaggga ctgtgtaggc aaggtatgag    65760
gccagttccc caagggactt ttattggctt tataagtcaa gtttaattcc ttaaaggaaa    65820
acacaccatt ccagtcaaag ccttggtaag ataaacaatt tctccaattg tgttgtatta    65880
caaaagaaaa cagattctta ttatgcctat gcaaataact atactaccat aagttaagaa    65940
tactcacaac tagtttccaa attctgtaga aatcaggtag acagaaataa atatgctcca    66000
aattttgttc ataggagtac actcaactgt taaaagctgt aaatagctta aaagaaaagt    66060
```

-continued

```
tttcttgact ctgaaaaaca aaacaaagga tcagcaatgt tctaagcaaa gtttaaaaga   66120 ttagtttttct attggtttac tgaatttagt taactcctgt tttgcttgac attcatgaac   66180
attccatgtc ttcatgagtt ctgaaagttg tttcctctat tctaatgtta caatttccaa   66240
agttatcaga aacttgcatt taagaacacc tgttagagtt ctatagttga ttataaatca   66300
tcttctaaag aggattaaaa caagacaaca attttctgtg gatgacaaaa agtttttagga   66360 cagccactat taaagccaca attgataagg aaatttgctt acttctgtgg cacacagaat   66420
tttacacaac agttataaat aacatacact aagtcatatt agaattatag gagtttccca   66480
taactttgga acatatacca gtaacacatt tatgcaaata tagtctaaag caagcaaaac   66540
atcatttcac atttgataac acttcctcta tgattttat gccaaataag tcaaatttca   66600
ccttttacta ttaatgctaa acctaagttt taataaaacc ttatagacat atttacccaa   66660
ttttaatgtt taaccataag gtaagattct tataaacctt ttataaccat ttacattttt   66720
ttgtgtaaga gcagatcagt gctctaggaa aaagctattg tgatttattc caatgtttaa   66780
tttatggaaa aacggaataa tacccccttt tagccaatat gttcacacac agaatctctt   66840
acaattaatc cttataaacc ttccacagct tgtttaaatc tttagatttt tttcttactt   66900
aaaacaatcc tttaacactt taagcagaaa aaattcacat tcttatgact tcttataatt   66960
tttcaccaaa aacacatttt actttctttta cacaccttgc atgtaagatt gtttctttag   67020 tagtttaat tacatgtgat aatgttaact cttagcaact tctattttg atgaaaacct   67080 tggtaaattt gagattttag ttgtgtgcta ggtgtgaagc ctggcccaga acactccagg   67140
cagaagtgca gataagagct ggctctccag cacagctgag ggcatgacta actccgcatg   67200
tccccagacc ttacctagca gtaaagcagg caagttgtac ggtaagagtc atagtggcat   67260
tttatgaagc atttaggagt ccttacaacc tttgaattac acaacatttc ttgcataaat   67320
tccttttcac aaatcctttc atcactcaca cagaatatct gaggcatttt tggactttct   67380
gacttgccct aaacctccct tcttttaaac aaccagttat tttactttag gacaagaatt   67440
taccatacag gatccttttt tatataaaat ctctttcttt ataatcttct ttgtatagct   67500 aggggggcatg gtaaattcca catatcccca ggccttatct agaatttaat ggctttaggg   67560
taggtagatt gaacaatttt caaaagtcaa agaaacagtt tgaccttaaa gcatttagca   67620
aatctgatat ctgaccttaa tttagaccaa atgtctacat tttttaagatg tttttatttta   67680 ccaataatct ttaaaactgt ctttatttcc aaaatattac taaagtcatg tgaacaaaga   67740
ggcataaaat attctatttt tctgctgaaa tacttcattt aaaggcttat atttctaagc   67800
caattaatca gagcccctttt acatataaac atacaacaca tataaatata gagacagaca   67860
gaagattcag cacttgtaag attttcattt gccagtttct taattggatg actggcttga   67920
ggatggagtc cttggaagaa tggggacagg aaaggggtct ctggtgcctc ctgtttttcc   67980
caaggagtcc agactgttaa gagtttgaat gtccgcttttt aattaaactg attttaacca   68040
tagcactctt taataaagtt cttttagaat ttcttatgcc aaaaggccgg tatttctggc   68100
ttttgaactt caccaaaggc aacctccttg gtgcttagag aaaggaaaat ttcagacagt   68160
ccgcagagga gaagagaata gacgtcttca ctcagatatt aaaccagaag tgacttactt   68220
tctaggtgga attgaacctg gactgtcact gtgaaaatgc aaagccttgg ccactgagct   68280
acaatgcagg gcagtctcca tttcccttcc caggaagagt ctagagcatt aattttgagt   68340
ttgcaaaggc ttgtaactat ttcatatgat ttttagagct gactatgaca tgaacctaa    68400 aattcctgtt cccttgaagg tggagaccaa gagaaggtac tgccgtgtgg ttaaaaggtc    68460
```

```
aagctcccaa ggtggagaga cttcatccag tttttttgtt ggtttcaggg acctccagcc   68520
aagtttgttg ctgaccaact tgccgggtcg tcttgaaaag ggggcttaca ggtgttccaa   68580
gcccgtgttt tatcctgaag tatccctcaa cacagaaaaa cgacctcata acacaaaata   68640
caccagctta aaaatagcct ttgaattatt tttcacatta atcaaaactt tacagaggag   68700
ataaacactg atttttttat tttattttat tttattttat tttattttat tgccattcat   68760
tcaaccgttt gcacagagag aaagaagaca gaaatctgac tggtaagaaa ttgttaccct   68820
tttgccagca tgccaggctt ctgggttccc tttccctgag cggccctagt gatccggctt   68880
gcggcaccat cgcctacggg ccaagctgca tcataaagga aatttttttt tttcattctg   68940
gccagagcaa aacacatgtg ataaaacata ggcattagct actctgctta gcaccaaata   69000
tcagactagc ttaaatttgc ccccagatgg gttccatcat ctttaatccg acctctgact   69060
tgcagtttca acacgtgctc tctgggcaaa acagttgccc tgagtaacag aaaagatagg   69120
aaaggaaaag gagagagaga aaaacgtgcc agtggaaggg tggggaaggt gaaatgatca   69180
aggaggccag agaaagactc acctattgca gcaacactgt agaagttcag gcagctgctt   69240
ctcggtagca aaaggatctt ttccagcaat cctattagct ctcaagtttc ccctttttagg   69300 gaggaaaaag ctccccatgt cccgcgatcc tgtacatgtc caaccctgcc atccacagcc   69360
atcagcaaag agtgcaagac agattaatcc aaagagaata gcaattaata tcccatagca   69420
tcaaagctgt tcttagccaa gagggacttt aacgagaggg gtctctaaca ccctaaatct   69480
tagaagagac tctaaccatc ctaagtaggg cctctaaccc cgctttataa acttttaatt   69540
gactcccatc ttaacagttg caatccatgg aggaatgctt gataacctcg gtgataagat   69600
aaaaaaccaa gcatactaga agtgttctct aaaattaaaa atacagtagt tactagagaa   69660
aaattttagt ccaaaaatcc aactatagaa acatagaatg tgagaggtag cacataagaa   69720
ataagtcatg gggattttat ttcatggacc agcaatatga tgataaaagc catctaacct   69780
gttggaatta taggtcacat caagagaatt ctagtgtcta gaaccaaaga aatgttagcc   69840
tcactctaat agacaataca cttcaggaac gaaataagca aattagattg tgttcagaga   69900
tgaataacca agatggcaga gggaattaaa ataattgctc atgattaccc tgggaaatag   69960
aaggcttaga aaggacaaca cagtttcttc atatgcttaa agcaatgtga atagggaatt   70020
ggactcaacc aacatagccc gacttattaa agccaatggg tagaggttac agagaaagct   70080
attccagtac aaccaaacaa aaaaaataaa atgtaagcca cttcttgag acatgattga    70140 cttacaaaaa gatgtatgta tttaatgtat acaacttgat gagtttagaa ttttctaagc   70200
tgtgagttat agagattttc ttgttactgg aagtctaata ttcaaacatc agcattttgc   70260
ctacatgaaa aggacactga gataattcag atgttaagat ttgatgatta gggaatcaga   70320
gggaatgacc cttttgaataa ggttttcagt tttcacacgc tctaccagct tcttgtagaa   70380
cactactaaa gtgaaatgct aatggtggtc cgtgaatgag aagctctata gacaagtgtt   70440
aggaaatgtg gcctaccta ttttggtcat ggggactgat aatatgtata agcatttaaa   70500
aggctgtgaa aagccctact ctctctccct ctctctctct ctctctctct ctctgtgtgt   70560
gtgtgtgtgt gtgtgtgtgt gtgtgtgtgt gtgttgcata catacacatt tcattttcta   70620
agccaaagtt cagttctcca gttcatctga gctcaggccc agttttcaa gggacacctt    70680 ataacatctc acagaataaa ggtttcacta agcaatgttt aaaagccact gtagatcatc   70740
agtcccagtt aggcatgaat ctattcaaaa ttcaatgttt cactggaata attggcaagg   70800
```

-continued

```
tctcataatt ctaggcatta atcagaatcc taaaattgat tgttgaactc ttattcttac    70860
tcatttaaaa tatatgctct aaatacttca gtatacaaaa agacattaaa atttcctatc    70920
tctgaaaata gagcagggtt ttcccttttg ttttatttgg gttttcactt ttgttttact    70980
ttgttttctg gtgatattac aagaaaaaaa tctatgtacc tttggggtat aaatcattga    71040
attaaactat acattgctaa gaataagcat tataattggt acattgttct gtttttgaat    71100
gaaatatctt tgcagaaaat agatttattt caaaagtcat ctttactcaa ctgtgagcat    71160
accaagggct aataattaca atattttccc gtgaaagaat ataagattgg aagccagaga    71220
gcctgggttc tgctgctagc cctaatggag accatttgtg tgagttttc atcccatggc    71280 ttaagggttg cttatggttg cttaagggat cccttcacaa gcaggagttt ccgagctctt    71340
ttgactgctc aagaattagg actcattggc cgggcacggt ggctcaagcc tgtaatccca    71400
gcactttggg agaccgaagt gggtggatca cgaggtcagg aaatcgagat catcctggct    71460
aacatggtga aaccccatct ctactaaaaa ttcaaaaact tagcaggcgt ggtggcgggc    71520
acctgtagtc ccagctactc gggaggctga ggcaggagaa tggcgtgaac ccgtgaggcg    71580
gagcttgcag tgagcagaga tcgcgccact gcactccagc ctgggcgaca aagcgagact    71640
ccgtctcaaa aaaaaaaaa aaaaaaaaa gagagaatta ggactcattt ctgggtttga    71700
ctgattacac cattcagact ccagggccag cttctgttag tggacaataa atgtaatgac    71760
caacgctttc tcttgtgaaa gaaagatgta ttatattgga caaaataagt ccatattcac    71820
agcagaagaa agcatatggc agatcaagtc tggatctttt gaactaccag attattctac    71880
ctctccttga attcttcttt gctgaagtcg gagcccttgt actatagatt ccatatgtct    71940
gattcaggca atggagcttg gaagaggggga tgagtttcct attattatta tttaggtaca    72000
tggagatctt tgcctatgag tcatcagctc ccaaggtttt ctgtatggct ctgtttttat    72060
gatttctgta ataaatgaga ttttgaagcc tatttctggc tcaaactctg attggcttca    72120
aaagtaccca agcctgttat tgccttcaat tgtaactttg aatggcatca caaagagaaa    72180
agaaaaaaat tgaggtggag gagagtggcc acaaaataaa aatattaaac caactttcct    72240
cctccaatgc acctgggcac accacttcac ctctcaaggt tatgtttgct tccatagatt    72300
gacaaggttg aaaagacaat ctcttcaatt ttctttagtt ccaaaagtgc aggaaataca    72360
caccaacctt tgcgtggata aagattaaaa gtgccttaaa tcagcttcca tttgaacctt    72420
aaaagctttt caaacattta attttttttaa acaggaccaa aaatagccca agggtatttg    72480
ctagttgact tcctggaaaa actatagttt attttttattt atttatttat ttatttattt    72540
attttgagac cgagtctcgc tctgtcgccc agctggagtg cagtggtgcc atctcggctc    72600
actgcaagct ccgcctcccg agttcatgcc attctcctgc ctcagcttcc tgagtagctg    72660
ggactacagg cacctgccac cacgcccagc taatttttg tattttttagt agaaacgggg    72720 tttcactgtg ttagccagga tggtctcgat ctcctgacct tgtgatccgc ccgcctcggc    72780
ctcccaaagt gctggcatta caggctggag ccaccgcgcc tggccaaaaa ctatagttta    72840
aaaaattgtt gacaaaaata gaaaaccgac agcagagagt tgtgttacat ctatgtatct    72900
aacatatgtg tctaagtatg gtatctaatg tcaaatgtca aatctactaa ctgtactgtg    72960
gttatcatca gaaaagaaac ccagctttag aaaatggtag gaagttccaa aactgcaaag    73020
gagatatctt agcaagcaag tagcttggct tttcacaatt ttatgggtgc tagaaatagc    73080
atgactcagt ggaccagaga aaaccactta ttactcacag cacagtaaac agcacaagta    73140
tcagcatgct aatgccagtt cctttgcctt tatgtcttgt gatgtgacac catgaaccca    73200
```

-continued

```
aattgctgct  acacatacaa  tgagttgcac  agcagctgag  gagttcagag  atatgggttc   73260
agtgtctttt  gtagcaagca  gtaaacaaat  caatcctcct  tccccaggag  ccagagtctc   73320
aaaatgccgt  ggtcctcatg  tggtcaggca  gtgaaggttg  ttaattgact  atgactagct   73380
gtagaaagaa  atcagggtga  gaagatgatt  agatcttgca  gttcagctca  gtcagtaaga   73440
atgggcaggg  ttgttcagtg  gactgcctct  cccaataatt  cacattcaac  ctagaatatt   73500
cttggctgaa  cttaaatttt  tatacgatta  tgccaccta  tcagcaactt  gaattagaca   73560
tattgacaag  gactaggacc  aaatctgttt  ccacttattt  cagtcaatac  tagattaggg   73620
ctattgtcag  cagaatccca  tccacaggat  taggtcagtc  tgcagtattg  acctccacca   73680
tgcactccag  gatccccgac  ccaattaaat  aagtcacaga  gaagactaat  aggtcaaatt   73740
tcagataagc  acctagcttc  ctttcttatg  gtatgcatgg  attgctccac  cataccgtgg   73800
atattaatcc  aaacaaaaca  ggaacagttg  gctaccatac  aaattctcct  ccattcagcc   73860
agactgtagt  ctaaggccaa  tcaatgaccc  atttacaatc  agggagctaa  gactgacctg   73920
ctgatcttct  atggtttgtt  ctgtctcatt  ggctagggta  gctaaactta  agaataggtt   73980
cctggcctgt  ctctaaaatg  tggactctga  tgctggggaa  cagtactcac  actgctgtat   74040
ggaaatagaa  aaccatgtat  ccctcaggca  ggacagccct  ctttacctag  gggactaaca   74100
aaggaaataa  aatccaaaga  gtggcgccat  tgccaattat  tgcaaggact  caaagatgaa   74160
ccaaatagca  acctccacat  gctccagtgg  atggatatcc  tctgggccac  tctctcccac   74220
atatgaacat  ataacttgat  ttggatcacc  atgaccttgg  tttggttaag  ctctatgggc   74280
agggtcgcca  agtacttgtc  acctggacag  ccctccatag  catgactcaa  gggcactcag   74340
tgtcaggaga  agcacatgaa  tcagtatgag  ctgtctgagt  gattgtgcag  gtaaaaaggg   74400
tgattaattt  tggggagctg  actttgatac  accaggcaca  gtagaataat  tctgaccaa    74460 gcaggccaac  aggagatttt  ctgatcccac  agcacacgga  tgaggatgat  aaatccagct   74520
gataaatcca  gcagtgttac  gggttggcaa  tcagagctgc  tgcttgtctc  tgatggacca   74580
tgtgattatt  ttgccaagtg  agaggctggg  attcagagac  aaaaagatca  ttcattattc   74640
cctcctctga  gcacctccag  ggtctaaggt  gttctttccc  caatgaagtg  gcgagtggtg   74700
ccagggaagc  agtgagtcca  ggatgccaag  gggtacctcc  aggtggagac  tgtttccctt   74760
tccagaagcc  tggagttgaa  aagggccccc  taggtggtct  gctgcaacag  cctgctcac    74820 tgacccacgt  gtcacctgca  gcttaggtcc  ccagtcatat  atggcagact  ttctaatcaa   74880
cttgtacata  ggactcaaca  agaggcatgc  atagataagg  cacgtattgt  ctctaagatc   74940
taaatagtcc  aattaagtgc  caggcttcct  ttctcttagg  agagccatag  agcaaagaat   75000
attttcttta  ccgtctagga  tcaactttg  agtcttagtc  cacatcattt  tggagatact   75060
gacttgggtg  gctggtcctg  tatcttatca  gaattaagag  cctttctggg  acttcatgtg   75120
atttagcatt  ggctaatttt  attaaggcct  ttcaatagaa  tatcatcaat  acagtaagcc   75180
caatttctct  gcagaaaaaa  aaaagagaga  aagagaaaga  gagagaggct  tgtcctgtgt   75240
tttgacccac  ctattggcga  taaataacag  ggaaattcac  gtagtactgc  aacagcccag   75300
taaacatgtt  ttggagggtc  agccagggaa  ggggtcttaa  tctttgggtg  caaaagggat   75360
tgagaaaaat  acatggccaa  aatcaaaaat  ggcacaccag  gtgctatcac  agggaattga   75420
ttcatttaca  gtcacaatgt  ctgtaacagc  caggactata  ataccaacta  aattcagttg   75480
gcatgatcta  acacaagcct  ccagattccc  attagttttt  tttttcactg  accatacaag   75540
```

-continued

```
gctgctacat tgagatatta cattttttcat tagtcccatt gtatttaagt ccttggtcaa    75600
ggttgtggtt tcattttctc cttctggaat tctaattaaa aaaaaaaaaa caaaaaactt    75660
gaagagaacc aaagccaagt tgtgatcagt tgtgcatgca tccttctatc cctctctaca    75720
aatggctctt ccaatcaaaa aaatctctct tgtacatcat gaacatttac agaacaagaa    75780
tgtaaattat caataccaat tacacattca gccctgggag ccgcaaaagt agtagataac    75840
agggctctaa acagctctgc ctagtggata cagttacttc ctttcctatt tttttggtat    75900
caaatctggg taattaaatg tgtggtcctt acaagagaag gacctcggag aacctagtgc    75960
agtccctcag gagaacctag tacttagtca tttgagcatg gatatcaaaa agagacataa    76020
ggcggcgcag tggctcaagc ttgtaatcct agcactttgg gaggctgagg tgggtagatc    76080
gcttgagctc aggagttcga gaccagcctg ggcaacatcg tgaaacccg tctctaccaa    76140 aaatacaaaa attagccagg tgtggtggtg catgtctgtg gtcccagcta ctcgggagac    76200
tgaggtggga gaattgcttg agcctgggag gtggaggttg cagtgagcag agattatacc    76260
actgcactcc agcctgggtg acagagtgag gctctgcctc aaaagaaaaa aagagagaga    76320
gagagaataa gagttggacc cttccttctc tcctctacct ccattgttcc ccccatcagg    76380
tgtaatgcct ctgattcctc ttgggaatga agagagcttg tccttaaagg agtctaaatc    76440
aggatataga agtttaaagt tagacagtag aggttctgag ggggtgatct gccctggggc    76500
agcaacctgg cttccccctc cattaaagga ggattgatct ccacaaagga atctgtttct    76560
ataaaggaac atagagtttc atctgtgtaa acaactaact gcctccctag ggcccaccgt    76620
cgctagatat ctggactgag tttctttggc gatcatccga tcattcctt ctttgggagc    76680 tcctgtttag taggcatgcc cacattgcct tatgatcagg tcccttggga ggggcttggt    76740
ttttctcatc ctgggctttg ttttggattg cagagacctt acctggttta gggagtggtg    76800
tctttatcct agacatctag aggccctaaa tcagcacagc tgccagtaca ggatctcccg    76860
gcaagaaaag tagtggaatc ctcaaccttg gagggagaaa ctcaatctta aaaatgcact    76920
ggtcgtgctc tgggtgaggg ttcatcatca aagctgtcat tctgtccagg acagaacaag    76980
tctagggcag cttcagccct caggctttaa atagcttcct ccatggggtt tcatgagatt    77040
ttattgactt aagaaaatct tcttcagttg ggcgtggtgc ctcatgcctg taatcccacc    77100
attttgaagg ccgaggcaag tagatcactt gaggtcaaga gctccagacc agcctggcca    77160
acatgggaaa ccccatctct actaaaagta caaaaattag ctgggcgtgg tggcacatgc    77220
ttgtaattcc agctactcag gaggctgagg cataagaatt gcttgaatct gggaggtgga    77280
ggttgcagtc aggcaacatc atgccactgc actctagcct gggtgacaga acgagactct    77340
gcctcaaaaa aaaaaaaaaa agaaaagaaa agaaagaaa aatcttcttg gatttaccat    77400
aatgtagtca ctaaaacaga aatccagggt agcaaacctt attgtgggac atgattctat    77460
ctcaatgaca taatttgcac agtgtttttaa agtataaggt cccacatgag acagccttgg    77520
ttctgcatgc tctaaggcat aacctttctt actccttcat tacaccaatg cagcagccaa    77580
gtgtcgaaca gccctctgt ctgctgatcc aagcacccct ggacttcttt cctttctctc    77640
tccccttgga tctgcatctt ggtactctct gtgggaatgc attgcccttc aggtgtatac    77700
atttgtaact tacaacttga caccgttgtg ctttcctccc taatggaacc cagaatgttc    77760
tctccatcct ccaccccaca gatgagcaaa cagaaaccat ggcagcttct tggatttttat    77820 ccctcacctt tcaacctcca tctattgact caactcttgt tcatcaacag gtaggacaga    77880
ggtggaccac tcgctgccca ccttctgcac catttgggcc agaatatttg ctaccagacc    77940
```

-continued

```
cagggagttc acaaatgtcc ctgaatccag cttatgagtt cttgcctttt tattcttcca   78000
aaaagttgtt gtctgtcttg gcaccctgca ctttgtgcca ctttgagaag aatttcaacc   78060
tcttagaaga tggcaagaag taatagaatt ccaaaagaga tgactaagca agcaagtagg   78120
ttgctttgcc acaactctat aggtgccaaa attagacaaa agacccaggc aattgactac   78180
tcacagcaca gcaaacagca gaagctttag cataatagtg ccagttcccc tactcccaaa   78240
tcccacaagg caatacgatg ggaccagact gcagtacaca cacagtgggt cgtatcacag   78300
ttgaggaacc cagagcttaa gtctcagcac ctggggagc aataaacaaa cctcccctac    78360
gatcaagcag ccacatcatg gtcagtgctg tgctcgcctg tgctttctta attgcctgtg   78420
tgaccagcta cagaaatgat cagagtcaga ggacagttag accttgtaat ttgtcagggt   78480
cagcaagggt gtgcagggac actcctggcc atgatggact gcctctccct aaagtgagaa   78540
tgacctaatc tgttctttat tcttagaaaa aatgtactga gatatttaag ggtaaagcat   78600
caaatggctt aaaaagatgg tgtgtgtgtg tgtgtgtgtg tgtgtgtgta tgagagagaa   78660
aaaaagagag aaaaagcaga tggcaaagca catggataaa gcacatttac taaaataaaa   78720
ttttaaaaaa atgatctttt acccttttac gcttcctata caaacatctc cttttctcct   78780
tagcagtatt ataatgaatg atagcaacaa ttatttgtta attacaaaac ttattctgtt   78840
tccacagtcc tcttttctta cctgaaaata gcaggccaca tttccatgtg tctgagcaaa   78900
tgttattgtt caacacatat gccagcttta cagtggggat caggtagggt gtatacttca   78960
aatcagttac aggaaaaaaa tcattaattt tgagaattgg gtaaaaatag aaatctcttt   79020
atctggaaat aaataagatc agaagtactg aaaaaaacat cgtttttctt tcaaaatttt   79080
gatcaagtca taaatgattt gaggctaaag agggaggaag agggtaaaaa aaggggggaga   79140 aagagtttca attaaaatgt atttttttcaa ggaaattatc aataatctct ctataatgac   79200
tagtatacag ttctttttcag tagcatacac aaatgaagag catattcata atgagccaga   79260
agattattca taatgtctga agagattgat taatgtcttg acatttaaga aaaactgagg   79320
cttgcaggtg aaagtataca tgaaggtctt caatgcagtt cttacgagca gaagatgctc   79380
aacaaatgtg tgttgcaacc gtatctgaaa tgttcactgt ctttgctctt tctctccttt   79440
cagctagaaa atctggaagc agaaactgct ccgttgccct aacagggtct catgccattc   79500
cgaccttcac caagcttaga agccaccatg tatgtggaag caggttgctt caagaatgtg   79560
taggaggctc taattctcta ggaaagtgcc tgctttagg tcatccaacc tctttcctct     79620
ctggccactc tgctctgcac attagaggga cagccaaaag taagtggagc atttggaagg   79680
aaaggaatat accacaccga ggagtccagt ttgtgcaaga cacccagtgg aaccaaaacc   79740
catcgtggta tgtgaattga agtcatcata aaaggtgacc cttctgtctg taagatttta   79800
ttttcaagca aatatttatg acctcaacaa agaagaacca tcttttgtta agttcaccgt   79860
agtaacacat aaagtaaatg ctacctctga tcaaagcacc ttgaatggaa ggtccgagtc   79920 ttttttagtgt tttgcaaggg aatgaatcca ttattctatt ttagactttt aacttcacct   79980
taaaattagc atctggctaa ggcatcattt tcacctccat ttcttggttt tgtattgttt   80040
aaaaaaataa catctctttc atctagctcc ataattgcaa gggaagagat tagcatgaaa   80100
ggtaatctga aacacagtca tgtgtcagct gtagaaaggt tgattctcat gcactgcaaa   80160
tacttccaaa gagtcatcat gggggatttt tcattcttag gctttcagtg gtttgttcct   80220 cagtttaaa tgtgcaattt tcttgctcct atttaagtgt tcacaaaagg taatagtcaa     80280
```

-continued

```
tgagctcatc acttcatcca tgcaggaagt caagcattaa aatgtactct ttatttctca   80340
ctggtttctc catactgcag gctccccaca tattattttc tttttttaac tcagctcaga   80400
atccttatgc cttttgaatc agtgtgataa aatgacagat gttttttgttg attgccagaa   80460 cagtttaaac tttttttaaa caataaatcc aataaacata atctcaagac agactcatat   80520
gaccatacag aaaagtgtgt catctatttt tcaatcctgt gtagttactt ggatgtgaaa   80580
tattaacaat ggcccaaaaa tattttcctg aagattgtgt ttatataatg tcatcaccaa   80640
tattttggtc tttttgatct ctgctaaatg tcaagatttc ctttgtaaag tgtcgatctt   80700
ctaagtagtt tctttaagac aattctccgc tttaactgat tttctttgtt gtgaaacaca   80760
gtagagattt ggcaatcaac cattttactt gatctaggta gacagccaag tcagatggcc   80820
catgcctaga agctctccat tttgaacttt tgtcagcatt gattaaaaga atcaaatacc   80880
ttgtagttat ctatgatgat acaagtaaaa aactaggctg ctgacttctg agtattcctg   80940
agcctacaat tgtaaaattg tagactccat tgtaaaattt gtattttttc atcaatctga   81000
caaggcacaa atatgtgcca gatatacaaa agcaatgttt ctagaaaaca gctatcatgg   81060
atcagaataa ctgaatttac tctcagatct attggctata gttatgtgga ctcaacccac   81120
gtatccagta gatgggaaaa aacaaaagcc aaaataagtt ttttagtgtt tccttctgat   81180
gaagtttcat gtttgcttgt aataatctcc atttctcaaa tattatgttc cataatagac   81240
atacattatg tttaattttt tatattttct gacaaaagta actaaaacta ggaccttaaa   81300
aagatttaga atgttaaata agtgtactag ggtgtatata tttacatata tacactacta   81360
gagcttccaa aagtaaaatg gataattcaa acagaacaca atgtaatatt tgtatgtaaa   81420
taactgagga ggaaaatcca tgcttttcat gggctaggat ggtttctccc aagagatgac   81480
atagtattgc ttttgctcat caggctgttt ctcagcaatc attgtttctg cttaatacca   81540
gctcctagta cgaattatct ggcatgttga gagcaacttt gtcttcaagt aggacctgat   81600
ctatcttttt ccacaaatgt catgtgtgtg aacaagtttc ttccatgtca tctttgagac   81660
tctacacaga atacacaata aagggagtta ttttttaaaat aagacattct aaagtaaata   81720
ataaataagg tcattgtcaa cgttttttcat tcaaaaccat tttttaacgt aaatttgcta   81780
gaaccacctt ccaattccaa ggcaaggaga gacattacaa ccctgactca actggatggg   81840
ctaaggtttc tgataaaatc tgaagataaa gaaaatggaa tattctgctt ttttcttcct   81900
tctaatttca cccttgccta aggatgagat ttcttcccag gttggtatcc cagaaatgca   81960
gactgtagct atggggcgga agctttgttt ctttacctga tcacttgctg tggaaattct   82020
agcttattgt gttccaagta gttagtggtt tttctccttc agtctccact gttattttgc   82080
tccttcatcc ctctttcctt gccaatcatt agaaaggaaa gaagaggaaa gagactcgct   82140
ggagcactgg tgagtctcta ggaccctgct atcctatccc aacagggctg tcagacggag   82200
aactcctaat gtggccattt gaaacacttc tcaacattga aatagacagt tgaagtttta   82260
aaataacctc ttctaagaca cggctatgag taggtaagag agcattcatt cccttcaata   82320
atatgactgt gttgataaaa ctgataacca ttcacttgca aatgttatta ttgaataagt   82380
ctcacttagc tcatttaata ttacccaaaa gatgctaaca aattctgttt cccacattgt   82440
cacagcatgc cctttacatc tcaggatcca ggcaaaagtt gaaattcaga aacatagata   82500
tgaaatgtaa gatacaaaga aaacacctct gcaaagattc cgaccacatt tatcaaaaag   82560
tccccaaagc attcaaaatc tttacttaag tcaagtctat ttatacgttt aaaagctaaa   82620
aacaagatct ttttggtaat gcttcaatta aatgttttat ctaaatatgt ggaaatgata   82680
```

-continued

```
agatgcgtac tgcatctctc atataataaa gataatcagt tttatacaga catattctcc  82740
atctactggc aattaccaag ataagatggc actagaaatt tctccagctt acgccatgaa  82800
tactgcagaa gctgatacta tccgttgtgg ttttacaaat tctagagggt tctagccaaa  82860
gcaacctaag aataggacat ggtagcttaa gttttttcagc ttcttaactg gccacacaca  82920
cacaagttgt gtttgtacaa ttcttgaggt caatcagaac caaaaaatct gttgctggaa  82980
gaaatattat cctcttcata gaaatatcca ccagcagaaa attggtttct caaggaatcc  83040
ctactgccct tgtagaaaca tcaagattct tgcctggatt ctcaacataa gtctttactc  83100
acaggcctat tgcttggttt cagaagagtg agaacatgaa agttcataaa tgcctgggcc  83160
actgcaactc taaccactgt gtttccccca gtttgatatg gttcaggata catagtcata  83220
gaacagggca tgcagattgt atttaagacc actgcaagta aggtctaagg caaaagtaaa  83280
ttaatgagtc caactctggg gcatccattt aagagccatt taatccattt aattacaaat  83340
aatttcaacc catagtcagt gttcttcact gtcttcaaaa atataaaaag tacaaggaat  83400
tgtgtacatt acaaactgct ccagaaacaa aaccaaatgt ggatagcttt gtgagctgca  83460
gtgtgtggca aatgttcaac cttttgttat gcaatatcac ccatatcaaa taccattctt  83520
aaagcagtag acagatgagt caagttcaat ttaatgcaaa caatattact gtgttctaag  83580
cgcttctgtt actcgaaagg ggtctgatcc agaccccaaa agagggttct tggacctcat  83640
gcaagaaaga attcaggagt aaagtgaaag tgaaatgggt caggatcaat ggtctcattg  83700
tctaaggtgt tatccgagct cgttgtctca caaccaagaa aattaaggag catggacaca  83760
aagggtgagg ttggagcaaa agtttaataa gcaaaagagg aaagctctct gcagcagaga  83820
cgggagccca agtgggttgc tgtttttaca gctgaatcca aaagctttta taagaaactc  83880
ctctcatctc tgcagctatt tgagtaactt ctcttatctg aaaagctgtc tgtacaactg  83940
cctctatcta tgcagctatg gggtgtctct aggcgagcac aaagcatagc ttctcttgtt  84000
gtataattgt gggtttgttt taagtaagcc actttcctcc ctgcaagttc ccacggagca  84060
gaaaaaagga ggaaacttt tcctgggagc ccactaatca cacagtgaac aaaaggcttc  84120
tatgctgggc cttactttct aacagtgcag cagttatagt ctgagttttc tccaggctgc  84180
tccatttttg cctgtagcta tgattttttca ggcagcctgc ttctccgagg actagtctta  84240
gctgtttacc taactgattg gtcctttttct tctccctgaa aagcaagttt attaagaaag  84300
caaaggaata aagaatggct actccatagg cagcgtagcc ccaagggctg ctggttggct  84360 attttttgtgg ttatttcttg attatatgct aaacaagggg tggattattc atgggttttc  84420
tgggaaagga gtgggcaatt cccagaactg agggttcttc cccttttaag accgcatagg  84480
gcaacttcct gacattgcca tggcatttgt aaactgtcgt ggtactggtg ggaatgtttt  84540
ttagcatgct aatgcaatat aattagtgta taatgagtag tgaggacaac cagaggtaac  84600
tttcattgcc atcttggttt tagtgggggtt tggccggctt ctttaccaca tccttttatc  84660
agtaagatct tcgtgacctg taccttgtgc caacctccta tctcttcctg tgacttggaa  84720
tgcctaacct cctgggaatg cagcccagta ggtctcagcc ttattttacc cagcctctat  84780
tcaagatgga gtcgctctgg ttcaaacacc tctgacactt gaattacaaa tataaggacc  84840
attgacactg agattttaag ggaggaaaaa cagattgaca gtggactaaa ggtacttttg  84900
tagcaaggta ctttccacac aatattgaat aaatgcagtg tatacatttt taaaggaatt  84960
ttaagagctc ggaaatcatt aaaattaagt ttatcaattt ttgaaagcat cttctgactc  85020
```

```
aaatatatga aaagattatt ctagacctta ggcagatatt cagagaaaga tcagtttttct   85080 atgggttttt tccatcatgc attttataca aatttaatat actttttcaa ctcactttgc   85140
atttcctgtt accttgtact gagaacttca ttaaaacctg cacttgaaat tgcacttaaa   85200
ctttacaaaa tcacagaaga agttgttttc cataggtgtg gggtgggatg ttagagctct   85260
agacattaat tcctaggaat cgcatacccta cggaaaacag tcctctgacc tcctgtgaca   85320
catggggtga gcccttcctt tttgtctcaa tctcaaaaaa cagtaagtct ttaatccatt   85380
tgcatcaaaa agtacttcat atgctcgaaa ctaaagtaaa actttattga aatacattaa   85440
tatgctcctg gaacatacta ctgggtctca gacagtgcag aagctttatt gtttatttgg   85500
gaagagcaag gtaagaatca agtagaaatg ataaagggca aggaaaaaag atgaaagctt   85560
actcatatta accattctac cattggaatt atttgccaac acaccttgct gctacttaga   85620
gaaagtagtt cacctcacta ccttttatcc aaagaaatta tctctaaaag cactcagaca   85680
ttttgtagag caagtagcaa tctattcaaa gttgtaaagg ttctgtagaa tctctcagac   85740
caggtacagg acctaccaaa ggccacagcc aagcacaagc agctacatta gacagtttta   85800
cagctctgta tttcaggaaa acttctgtcc tgtgggagca atacaaaact ataccagttt   85860
tttgttagtg taaaaattgc ccaatattaa ccagagcagc ccaaaatatt tcagggtaag   85920
aatagatata tttatatttt tcagatgata tatcttcatt ttcgattttg aaagaacagt   85980
aatactaatt atatcccatg taaggggcta ctgacaattt tgatggtacc tgaatttgcc   86040
tctatcatgc atctcaatga tttgttgtca tccaaagcta tttcatgaat caaatatcgt   86100
tttctacctg ccccacaact gtgtacataa aacctaaacc tctgaagcaa taaacctctt   86160
ccattacaca ggtttagatt cagagttttc ttgcttaagt tccaactaaa agtattacat   86220
tcttagcata agtatactca taaagaaaaa taagtatttg tttttaggttt tagagagaga   86280 gcacagagtc cctttgagac agtggggaaa attcatcttc atattgtcac atgcactgta   86340
ataggaatgt ttagcaaaaa aaaccttcca gagaaaggtg gtttccaata ttacctacaa   86400
cttcctttgc aatttgattt ttgaaaggac ctaaaagttg aaaacaggct atcacatccc   86460
atttgcttta aagtctctta aacttacgct cttttcgcttc aaatgcataa atgtttttatt   86520 taagtttgca ttgcccacta aggctagaca ttttttttttt ttttttttttt tttttttttt   86580 tgagacagag tctcgctctg tcgcccaggc tggagtacag tggcgggatc tcggctcact   86640
gcaagctccg cctcccgggt tcacgccatt ctcctgcctc agcctcccaa gtagctggga   86700
ctacaggcgc ccgccactac gcccggctaa ttttttgtat ttttagtaga dacggggttt   86760
caccgtttta gccgggatga tctcgatctc ctgacctcgt gatccgcccg cctcggcctc   86820
ccaaagtgct gggattacag gcgtgagcca ccgcgcccgg cccggctaga catttttttga   86880 taaattcaca gggttacaaa ataccaaacg gaaatgagat aagtggtata aaccacagaa   86940
gatataggag aagagaaaaa aaaaagagga aataaagaag acaactcttt tcctaagagt   87000
ctgggtaaaa ttgaacatag ccatattcac tgaacaacat gagtgagctt cattaattta   87060
agcacagcaa aactgcttta attaacaaga ccagagagaa gggagaggag actacatttg   87120
tgtgacctaa tggttgtgat ttcactgtcc aagaggacaa agacaaagaa attctgggaa   87180
ggagaacaac aattatattc ccccatttca agaagggcag aagtgtccca acactaccca   87240
atatttgcaa aattcaaatg tctcataggc tcttcttccc tggttccctc aggagctggg   87300 tttctggggtt gcagaagtgc tttttcatatt ctgtatctgg ttgtggtggc aatgtcacca   87360
ccctacactg ctgtgacacc gaaacaacca agcctagaat cagctggtgc ctctttttcat   87420
```

-continued

```
ctgcagggta gatttggctt ccatggttgt tcactgctct gtgttaggaa ggctcagtga   87480
caggtgtaca gccttcagta atgcctcaaa ggttctccaa gcagaggtaa acatgtgggt   87540
cctgctggtg acatattaga cttcttactt tccccaaata aaaaagtgcc tgctgggcgc   87600
ggtggctcac gcctgtaatt ccagcacttt gggaggccga ggcgggcgga acacaaggtc   87660
aggagatcaa gaccatcctg gccaatatgg taaaacccca tctctactaa aaatacaaaa   87720
ttaggaaggc gtggtggtgc acgcctgtaa tcccagctag tcgggaggct gaggcaggag   87780
aattgcttga actggggagg cggaagttgc agtgagccaa gatcgcagca ttgcactcca   87840
gcctgggcaa cagaatgaga ttgtctcaaa aaaaaaaaa agtgccacat gccatgctat   87900
gtgcccaaag tttccttcac acaacacagc cttgagatgc agtattaaat tctacacttt   87960
tcctaccata gtgatacatg tggcttttct ttgctgtgtt ctgagatgtc atgctttgaa   88020
atcagtggcc attatcatct aaggattccg ccagagactt ccaaaagaag aggtctcatt   88080
tataaagtga atttgaataa aatgaccagt taggtgtttt cagaaacacc tatgccctac   88140
ttgcctactc ttcaagggtt tagggggctta gggggaggtt ttgtttgggt tttttgttgc   88200
tgttgcttgt ttatttgttt gttgtgttta agacgtttta cttgtccctg aaatgtttgt   88260
catcacacag atacacgctc aggataagaa ctaccagact agattaggag gtccacacca   88320
ccaattgaga tgtacctgtg ctcatgactt gacattgtgg tgggccggct acaaccctcc   88380
ccacccctcg ctttcactaa ataacaactc tcttctctcc atcattttga cttagagcca   88440
gtcagaattc aatctccaat atcctgacta gcacaagaaa tccataggtt gattcttgtt   88500
ctcctgcatc tctgcaggtg gcaaacctga ttcctaatgc ctgttcctgc ctctgcaggg   88560
gttcattcag aaaacaggaa aataacaaag gcttcctgta attctctttg gctgtaatac   88620
aatttgttcc cgtctgcccc caggctcacc cagtgctctg tctcagtggt aagctgtaac   88680
tgatcactgc tgtattaact caaaactcat ttgctttatg gaaattcatg cccttattt   88740 ctcaagggac cagagaaaac caataggcct actccccagc tgagtacttt ccatgcaagc   88800
taccgcatct gtataaatta ggttcaaata acagagtatt tccaggattt ataaattcag   88860
tattacaaat agtaatctgg caagtgttct caggatcccc ttgctacctg taattcaatc   88920
atataacttc tgaatgggct gggggaaaat aacaataaga aaaactggtg tttacctgaa   88980
gatctgccca gtgattgtg tgttttctta ataaacttta cccacttatt aaaagaataa   89040
aatgaaggtg gagttaattc tgactacggg attcctttt cactttatatat atgaactcct   89100 tccttctaac taaatcttat cataagcaaa tctatgcacc aaattattta gtacaattcc   89160
taataacagc tgaaggacca tttatttgaa gcaatgttca ccatagcaaa attccagtga   89220
agtctaagaa ctgggacagt ccgttgagga tccttgtgcc aggatgtatg ttgccccatg   89280
aatgtgcaca tgcatattaa aatatgggca cctctttaa ttctttttt tctcataata   89340 agtttgaaac tcacagtagg aaattgagag atcaatttgg ttactgtttt atcattgatc   89400
ctgaagacag ttgaagcaat catactggtt gttctcgaac tagctggttt cccagagaca   89460
gctggagact gagcacataa agacatcatt gaggaaaaag gctaccttgt acctcatgga   89520
gagctgaagg tctgataaat gggaactgcc aggtaatagc tatgctattt ctgacataaa   89580
tttaaaaact agtattgttt cttctagctc tgtttttgca tagtgcacag agatctttgt   89640
aaaaaacagg aaattaatgt taaattggat ctataaacat aagtcaattt ggctctatta   89700
tgtcaaaaga gaataggagt tttaacttat atctgtgttt tattaatatt ttgaagtata   89760
```

```
ggaacctcat ggtgtagcag gatgagccac agacaaaacc tctcagacac cgagttgtag   89820
aaggaagggc tttattcagc tgggagcatc gaccagctac tgtctcaaaa tccaagctcc   89880
ctgagtacac aatttctgtc cctttttaagg gctcacaaca ctagatttca catgaaaggg   89940
tcgtgattga tttgagcaag caaggggtat gtgacagggg ctgcatgcac cggtggtctg   90000
ggaggaacag aacaggacag ggagttcttc tatacaatag agaacagaac aatgttcttc   90060
tatacaatgt aaggaatcta tgaataacat cggcttctaa atcataagtt gatttttaac   90120
tactgggttt aggccaggcg ggcccaggcc tggtttcggg cctggcgctg agctgcctgt   90180
atttggtttt acttccttgt tgtttttact gaatatgaaa caatataaaa caatgtgaga   90240
gggtctttct ctcctctcaa tgtcaacatc atatatgatt ggagacttcc acataattga   90300
gttttagtgc ccactgttac agaaaatcat aatggaaaaa ctaaaatgtc aataataatt   90360
tcagatgtgt attttagttc tcataagaac atctacattc atttgaaaaa tagttctata   90420
tctattcttg aaacatattt ctttagttca aggtctgatg agctcccaga ctgttgggga   90480
ttgctctaca gctgctcaag cttttgaaga ctcctgtgat tttttttaaat ggctggtttg   90540 gttgaagttt ctcttatcag tcaggcactt tgcattttaa gcgtacttta ccaccgacac   90600 cctcccccccc cagcacacac acacacacac acacacacaa cagtgaaatg   90660
gacccgtggg aattatatga tagttgtaat caaaataaaa tgcaatcaat actaaaatac   90720
aatttaccaa aggcttacct ccttatttga aactccagca tcaataattt acttgcactc   90780
ttgttattta catttgtact ctggaagtaa acttaaaatg aaaattagaa tttgctttca   90840
attatactat ctctatctaa atcttaattt gaaatttaaa ttattttgtc tctacccaaa   90900
ccatcgattt catggaaatg tttaaatttt ctttttttttt ttttttttttg atggagtctc   90960 actctgtcgc ccaggctgga gtgcagtggc tcaatcttgg ctcactgcaa cctctgcctc   91020
ccgggttcac accattctcc tgcttcagcc tcctgagtag ctgggactac aggtgcccgc   91080
cacaacacct ggctaatttt ttgtattttt agtagagatg gggtttcacc acgttagcca   91140
ggatggtttc gatctcctga cctcgtgatc tgcctgcctc ggcctcccaa agtgttggga   91200
ttacaggtgt gagccactgc gcctggccag aaatgtttaa aatttcataa atcttgaatc   91260
cataaaattc aatgctacca tttataattt aatactccta ccataaaaat ttctgtgtta   91320
ggcatagcta tatgaatatt tgcctataaa tccccatcaa tttaatagga attaagttag   91380
aaatactagt atatatattc cctttatata ctaattgtat atccatataa aagcattagt   91440
accattatat gaaagtatat atgccattcc ataaaaatat atctaccaat ataaatagaa   91500
tatataaagg gaatatatat ataccaatat aaatgggaat ttatattggc acatacattt   91560
ccattatttt aatgggaatt aaagaaaaaa tgcctgtttt cactaagtca tccttcccct   91620
ggcaatacat ttcctgaact tttacatact taaaatagcca gttatgaaaa tgtaaaacaa   91680
tgagtgatct tgttgttttc attttattat gttatatgaa aaaaagaaac cttgtaagtg   91740
cagatttatt ttaaaaaatt gaaaaactac tctgtcaaac atagcaaata ggaaagttaa   91800
aaaaaagtaa gtctaaagat taggtgctct gtcacttgtc attacatttt tttataacat   91860
taatgacaca ttttttgcta tccaaatata atttccacta gaaaagaaaa gatgtcctcc   91920 atgtttttaaa ttgcatttga aattcaggta actaataacc cttggtttta aaagatacat   91980
ataatgtttc cgtaggaaaa aaatcaaaat attgtaaaga atctgagtaa atgagagcct   92040
ctcatggttg attaagttca gacatttttaa acagactcct gcccacaaac tatttttcct   92100
ctccaggaat aagaatggca actgaattgt tccttcttta ttctatagct ttaagtcaaa   92160
```

-continued

```
cctaacataa gcaatcaacc cttccaccca ttgtcctctt tctagctgct tatattcctg  92220
agtctgaaag aagggcagaa ttaattcgtt tccttgacag tgttggggt gaaataaaag   92280 atagacccct gctgctctgc acgtagattc agtttgtatg ccagggtgac attttaattt   92340
acagtagtcc agacacctaa acaggacata gaaatgtcaa ctggtcatat taaaataaaa   92400
aagtatagaa tagtttctgt tttacggatt ttgtatccaa gtaaatgaaa acacaatcac   92460
ctttcaaaac atggtatgaa atccacagtt gtaacagtga gcacaacatg ctttctgtgt   92520
gtgtttttaa gctctttccc cacatctgct tttcaaaaat atttgcctgg aaacctgtat   92580
ttcgcctata gagacaaata catatattgt ttgttgtgat aatgcacaaa aaggaatgtt   92640
aaaaaaaaac acacaacatt gttttccttt tgatggtctg ggagttttc tataagtttt    92700 tggttttttt tttttttct cttcattagt gtgttagttc catcatcatg tctgtttact   92760
attgaaaaat aaatatcttc atttaaagta gagacaaagc tactatttca catttccagg   92820
taggacagga tgatcagatg cagctttcaa aagaactacc tgctaaatca taatggtctc   92880
atgtgcagat caaaatgtca actagtatat caaacagtga gcaattcact aaattatttt   92940
tacattactc ctatttgact gtttcagata gttgtatata aaaaatataa atttttgcat   93000
tgtattgttc ttgatgtacc agcatacata aacatattag gctgtattgt aagtttcctg   93060
catgtaatat gtaatgtgta attatatgtg ataaataaaa cctaaaactg atacaaa      93117
```

EPIGENETIC MODERATORS OF NALTREXONE EFFICACY IN REDUCING HEAVY DRINKING IN INDIVIDUALS DIAGNOSED WITH ALCOHOL USE DISORDER

CROSS REFERENCE TO RELATED APPLICATION

The presently disclosed subject matter claims the benefit of U.S. Provisional Patent Application Ser. No. 63/192,952, filed May 25, 2021, the disclosure of which incorporated herein by reference in its entirety.

GRANT STATEMENT

This invention was made with government support under Grant Numbers AA017435 and AA017633 awarded by The National Institute on Alcohol Abuse and Alcoholism of the National Institutes of Health. The government has certain rights in the invention.

REFERENCE TO SEQUENCE LISTING SUBMITTED ELECTRONICALLY

The content of the electronically submitted sequence listing in ASCII text file (Name: 1586_24_2_ST25.txt; Size: 285 kilobytes; and Date of Creation: May 25, 2022) filed with the instant application is incorporated herein by reference in its entirety.

TECHNICAL FIELD

The presently disclosed subject matter relates in some embodiments to methods for predicting naltrexone responses in patients diagnosed with alcohol use disorders. The presently disclosed subject matter also relates in some embodiments to methods for treating subjects with alcohol use disorders with a treatment strategy for the subject that is predicated at least in part on the methylation statuses of subsequences of the OPRM1, COMT, and/or SLC6A3 genomic loci in the subject.

BACKGROUND

The opioid antagonist naltrexone reduces heavy drinking among individuals with Alcohol Use Disorder (AUD; Jonas et al., 2014a), but is not effective for everyone. Genomic factors might account for variability in its efficacy. The most extensively studied genomic factor is the rs1799971 single nucleotide polymorphism (SNP) in the gene encoding the μ-opioid receptor (MOR) OPRM1, which is an A/G SNP that encodes an aspartic acid or an asparagine at amino acid 40 of the human OPRM1 polypeptide in the endorphin binding domain and is associated with increased MOR binding affinity for β-endorphin (Bond et al., 1998). This gain-of-function SNP could also increase MOR affinity for naltrexone (Weerts et al., 2013), increasing naltrexone effects. However, meta-analyses of randomized controlled trials (RCTs) of naltrexone for AUD have found only weak evidence in support of rs1799971 moderation of naltrexone response (Hartwell et al., 2020; Jonas et al., 2014b).

Naltrexone is believed to reduce drinking through opioid-mediated downstream effects on alcohol-induced dopamine release (Benjamin et al., 1993; Gonzales & Weiss, 1998), so genomic factors associated with dopamine reuptake and inactivation might also moderate its effects. Accordingly, in a human laboratory study of short-term naltrexone dosing among non-treatment-seeking AUD individuals, it was previously reported that variation at OPRM1 rs1799971, and a 40-base-pair variable number tandem repeat (VNTR) polymorphism in the 3' untranslated region of SLC6A3, the gene encoding the dopamine transporter (DAT), interacted to predict naltrexone effects on alcohol self-administration and alcohol cue-elicited activation of the ventral striatum (Anton et al., 2012; Schacht et al., 2013; see also U.S. Patent Application Publication No. 2018/0371542 A1, each of which is incorporated herein by reference in its entirety). The SLC6A3 VNTR 10-repeat (10R) allele, relative to the 9-repeat (9R) allele, has been associated with relatively greater striatal DAT expression in AUD (Heinz et al., 2000), presumably reducing synaptic dopamine accumulation, and naltrexone, relative to placebo, reduced self-administration and cue-elicited ventral striatal activation most among individuals who carried the rs1799971 G allele and were homozygous for the SLC6A3 10R allele. These findings suggested that the predisposition to greater MOR affinity for naltrexone putatively conferred by the rs1799971 G allele might be beneficial only in the presence of genetically influenced reductions in synaptic dopamine accumulation.

This finding was subsequently replicated and extended in a secondary analysis of a 16-week naltrexone RCT among treatment-seeking AUD patients (Anton et al., 2020; see also U.S. Patent Application Publication No. 2018/0369238, each of which is incorporated herein by reference in its entirety). While OPRM1 rs1799971 genotype alone did not significantly moderate naltrexone effects on heavy drinking, there were epistatic interactions between rs1799971 and both the SLC6A3 VNTR and the rs4680 (va1158met) SNP in COMT, the gene encoding the dopamine-inactivating enzyme catechol-O-methyltransferase (COMT; Anton et al., 2020). The rs4680 val allele has been associated with a three- to four-fold increase in COMT efficacy (Chen et al., 2004; Lachman et al., 1996), presumably reducing synaptic dopamine accumulation in a manner similar to the SLC6A3 10-repeat allele (but possibly in different brain areas, since DAT and COMT expression vary across the brain). As disclosed herein, naltrexone, relative to placebo, most effectively reduced heavy drinking among individuals who carried the rs1799971 G allele and were homozygous for either the SLC6A3 10R or the rs4680 val alleles. These data again suggested that a combination of genetically predisposed enhanced MOR function and reduced synaptic dopamine accumulation was associated with superior naltrexone response.

Although somatically derived (inherited/germline) epistatic genetic effects may have utility in predicting naltrexone efficacy, a more universal mechanism by which genomic factors could affect naltrexone response is epigenetic modification (which might either be inherited or more likely acquired after birth: e.g., by excessive alcohol use). DNA methylation at cytosine residues in CpG (cytosine, followed by guanine) dinucleotides, which are disproportionately clustered into islands in gene promoter regions, influences transcription factor binding and recruits histone deacetylase complexes that compact chromatin, thereby decreasing gene expression (Jones, 2021). Given naltrexone's neurochemical mechanism of action, and our previous observations of the interaction of specific genes variants that influence naltrexone efficacy in AUD, differences in OPRM1, SLC6A3, and/or COMT methylation could also moderate naltrexone response. Methylation of each gene's promoter has been associated with downstream effects on its expression and the function of the protein it encodes. Greater OPRM1 promoter methylation of a neural-derived cell line was associated with decreased MOR expression (Andria & Simon, 1999); greater SLC6A3 promoter methylation in blood was associated with less striatal DAT availability (Wiers et al., 2018); and greater COMT promoter methylation in a human cell line was associated with less COMT expression (Swift-Scanlan et al., 2014). Importantly, SLC6A3 promoter methylation in blood correlated highly with methylation in the substantia nigra (Wiers et al., 2018), and COMT promoter methylation in peripheral leukocytes correlated highly with neural tissue methylation in a variety of brain regions (Murphy et al., 2005), including the prefrontal cortex (PFC; Ursini et al., 2011), where COMT is the primary mechanism of dopamine inactivation (Matsumoto et al., 2003). While most of this work was done in animals and some not replicated in man there is some evidence that peripheral SLC6A3 and COMT methylation could be biomarkers of neural methylation.

OPRM1, SLC6A3, and COMT promoter methylation have previously been associated with AUD and drinking. OPRM1 promoter methylation was greater among AUD individuals, relative to controls (Zhang et al., 2012), and methylation of several individual OPRM1 CpG sites predicted AUD relapse during treatment, although OPRM1 methylation did not independently moderate naltrexone effects on drinking (Lin et al., 2020). Similarly, SLC6A3 promoter methylation was greater among AUD individuals than controls (Hillemacher et al., 2009; Wiers et al., 2015), although some studies found no differences between these groups (Jasiewicz et al., 2015; Nieratschker et al., 2014). COMT promoter hypomethylation was associated with more hazardous drinking, albeit only in rs4680 met-allele carriers (Swift-Scanlan et al., 2014) but has not been previously associated with naltrexone response. So, while there is some evidence that alcohol consumption over a period of time could influence DNA methylation across the whole genome and in specific genes, there is considerable variation/inconsistency amongst individuals. Importantly, there has been no previous indication of any specific CpG methylation pattern influencing/predicting naltrexone or any other specific treatment response.

SUMMARY

This summary lists several embodiments of the presently disclosed subject matter, and in many cases, lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

The presently disclosed subject matter relates in some embodiments to methods for predicting naltrexone response in subject with an alcohol use disorder (AUD). In some embodiments, the methods comprise, consist essentially of, or consist of performing or having performed one or more methylation assays on a genomic DNA sample isolated from the subject to determine the methylation status of one or more regions of the isolated genomic DNA, wherein the one or more regions of the isolated genomic DNA are subsequences of a gene selected from the group consisting of a mu opioid receptor (OPRM1) gene, a catechol-O-methyltransferase (COMT) gene, and a dopamine transporter (SLC6A3) gene, and further wherein the methylation status of the one or more regions of the isolated genomic DNA determined is predictive of naltrexone response in the subject. In some embodiments, the one or more regions of the isolated genomic DNA assayed comprise, consist essentially of, or consist of the promoter of the OPRM1 gene, the promoter of the COMT gene, the promoter of the SLC6A3 gene, and the 40-base-pair variable number tandem repeat (VNTR) polymorphism in the 3' untranslated region of SLC6A3 gene. In some embodiments, the one or more regions of the OPRM1 gene include 130 nucleotides upstream and 600 nucleotides downstream of the OPRM1 transcription start site (TSS); optionally comprising one or more of SEQ ID NOs: 2-10. In some embodiments, the one or more regions of the SLC6A3 gene comprise one or more of SEQ ID NOs: 12-20. In some embodiments, the one or more regions of the COMT gene comprise one or more of SEQ ID NsS: 28-38. In some embodiments, the SLC6A3 VNTR comprises one or more of SEQ ID NOs: 22-25.

In some embodiments of the presently disclosed methods, the methylation status of at least two and optionally all three of the promoter of the OPRM1 gene, the promoter of the COMT gene, and the 40-base-pair variable number tandem repeat (VNTR) polymorphism in the 3' untranslated region of SLC6A3 gene are determined.

In some embodiments of the presently disclosed methods, the methylation statuses of at least one region of an OPRM1 gene and at least one region of an SLC6A3 gene and/or a COMT gene are determined. In some embodiments, the at least one region of the OPRM1 gene is selected from the group consisting of nucleotide positions 274, 277, 357, and 419 of SEQ ID NO: 1, and further wherein (i) the at least one region of the SLC6A3 is selected from the group consisting of nucleotide position 576 and 1102 of SEQ ID NO: 11, nucleotide position 1102 of SEQ ID NO: 11, and nucleotide position 46 of SEQ ID NO: 21; and/or (ii) the at least one region of the COMT gene is selected from the group consisting of nucleotides 46 and 107 of SEQ ID NO: 27. In some embodiments, a positive response to naltrexone is predicted if the subject has a combination of methylation values that are:

(a) lower than 0.147 with respect to nucleotide position 27 and/or lower than 0.488 with respect to nucleotide position 419 of SEQ ID NO: 1 in combination with lower than 0.651 with respect to nucleotide position 576 of SEQ ID NO: 11 and/or lower than 0.648 with respect to nucleotide position 1102 of SEQ ID NO: 11 and/or lower than 0.089 with respect to nucleotide position 46 of SEQ ID NO: 21; and/or (b) lower than 0.147 with respect to nucleotide position 27 of SEQ ID NO: 1 and/or lower than 0.157 with respect to nucleotide position 277 of SEQ ID NO: 1 and/or lower than 0.126 with respect to nucleotide position 357 of SEQ ID NO: 1 and/or lower than 0.488 with respect to nucleotide position 419 of SEQ ID NO: 1 in combination with lower than 0.587 with respect to nucleotide position 46 of SEQ ID NO: 27 and/or lower than 0.546 with respect to position 107 of SEQ ID NO: 27.

In some embodiments of the presently disclosed methods, the genomic DNA is isolated from a cell selected from the group consisting of blood cells, optionally peripheral blood mononuclear cells, and buccal cells, and/or from a biological sample containing cells, optionally, blood, saliva, cerebrospinal fluid, and/or any fraction or component thereof.

In some embodiments, the presently disclosed methods further comprise, consist essentially of, or consist of converting the isolated genomic DNA with bisulfate prior to performing or having performed the one or more methylation assays.

In some embodiments, the presently disclosed subject matter also relates to methods for treating subjects with an alcohol use disorder (AUD). In some embodiments, the presently disclosed methods comprise, consist essentially of, or consist of (a) performing or having performed one or more methylation assays on a genomic DNA sample isolated from the subject to determine the methylation status of one or more regions of the isolated genomic DNA, wherein the one or more regions of the isolated genomic DNA are subsequences of a gene selected from the group consisting of a mu opioid receptor (OPRM1) gene, a catechol-O-methyltransferase (COMT) gene, and a dopamine trans-porter (SLC6A3) gene, and further wherein the methylation status of the one or more regions of the isolated genomic DNA determined is predictive of naltrexone response in the subject; and either (b1) treating the subject with an effective amount of naltrexone if the methylation status of one or more regions of the isolated genomic DNA is predictive of the subject advantageously responding to the naltrexone; or (b2) treating the subject with an effective amount of a non-naltrexone agent, optionally wherein the non-naltrex-one agent is selected from the group consisting of acam-prosate, topiramate, fluoxetine, ondansetron, or any combi-nation thereof. In some embodiments, the one or more regions of the isolated genomic DNA assayed comprise, consist essentially of, or consist of the promoter of the OPRM1 gene, the promoter of the COMT gene, the pro-moter of the CSLC6A3 gene, and the 40-base-pair variable number tandem repeat (VNTR) polymorphism in the 3' untranslated region of SLC6A3 gene. In some embodiments, the one or more regions of the OPRM1 gene include 130 nucleotides upstream and 600 nucleotides downstream of the OPRM1 transcription start site (TSS); optionally com-prising one or more of SEQ ID NOs: 2-10. In some embodiments, the one or more regions of the SLC6A3 gene comprise one or more of SEQ ID NOs: 12-20. In some embodiments, the one or more regions of the COMT gene comprise one or more of SEQ ID NOs: 28-38. In some embodiments, the SLC6A3 VNTR comprises one or more of SEQ ID NOs: 22-25. In some embodiments, the methylation status of at least two and optionally all three of the promoter of the OPRM1 gene, the promoter of the COMT gene, and the 40-base-pair variable number tandem repeat (VNTR) polymorphism in the 3' untranslated region of SLC6A3 gene are determined. In some embodiments, the methylation statuses of at least one region of an OPRM1 gene and at least one region of an SLC6A3 gene and/or a COMT gene are determined. In some embodiments, the at least one region of the OPRM1 gene is selected from the group consisting of nucleotide positions 274, 277, 357, and 419 of SEQ ID NO: 1, and further wherein (i) the at least one region of the SLC6A3 is selected from the group consisting of nucleotide position 576 and 1102 of SEQ ID NO: 11, nucleotide position 1102 of SEQ ID NO: 11, and nucleotide position 46 of SEQ ID NO: 21; and/or (ii) the at least one region of the COMT gene is selected from the group consisting of nucleo-tides 46 and 107 of SEQ ID NO: 27. In some embodiments, a positive response to naltrexone is predicted if the subject has a combination of methylation values that are (a) lower than 0.147 with respect to nucleotide position 27 and/or lower than 0.488 with respect to nucleotide position 419 of SEQ ID NO: 1 in combination with lower than 0.651 with respect to nucleotide position 576 of SEQ ID NO: 11 and/or lower than 0.648 with respect to nucleotide position 1102 of SEQ ID NO: 11 and/or lower than 0.089 with respect to nucleotide position 46 of SEQ ID NO: 21; and/or
  (b) lower than 0.147 with respect to nucleotide position 27 of SEQ ID NO: 1 and/or lower than 0.157 with respect to nucleotide position 277 of SEQ ID NO: 1 and/or lower than 0.126 with respect to nucleotide position 357 of SEQ ID NO: 1 and/or lower than 0.488 with respect to nucleotide position 419 of SEQ ID NO: 1 in combination with lower than 0.587 with respect to nucleotide position 46 of SEQ ID NO: 27 and/or lower than 0.546 with respect to position 107 of SEQ ID NO: 27. In some embodiments, the genomic DNA is isolated from a cell selected from the group consisting of blood cells, optionally peripheral blood mononuclear cells, and buccal cells, and/or from a biological sample containing cells, optionally, blood, saliva, cerebrospi-nal fluid, and/or any fraction or component thereof.

In some embodiments, the presently disclosed methods further comprise, consist essentially of, or consist of con-verting the isolated genomic DNA with bisulfate prior to performing or having performed the one or more methyl-ation assays.

Thus, it is an object of the presently disclosed subject matter to provide methods for predicting naltrexone responses in subjects with alcohol use disorders and/or for treating subjects with alcohol use disorders with a treatment strategy that is predicted to be appropriate for the subject based at least in part upon the outcome of whether or not the subject would be predicted to respond adequately to naltr-exone.

An object of the presently disclosed subject matter having been stated hereinabove, and which is achieved in whole or in part by the compositions and methods disclosed herein, other objects will become evident as the description pro-ceeds when taken in connection with the accompanying Figures as best described herein below.

BRIEF DESCRIPTION OF THE FIGURES

The accompanying drawings, which are incorporated herein by reference and constitute a part of this specification, illustrate several representative embodiments of the pres-ently disclosed subject matter and together with the descrip-tion illustrate the disclosed compositions and methods.

FIG. 4A is a depiction of the nucleotide sequence of the OPRM1 promoter region (SEQ ID NO: 1). Lower-case letters indicate untranscribed nucleotides and upper-case letters indicate the exonic sequence. The transcription start site (GAT) is highlighted in dark gray (black and white version of Figure) and in red (color version of Figure) in line 3 and the translation start site (ATG) in light gray (black and white version of Figure) and in blue (color version of Figure) in line 6. CpG dinucleotides on the Illumina BeadChip are highlighted in light gray (black and white version of Figure) and in green (color version of Figure), and superscript numbers refer to the specific Illumina ID for each site (see also FIG. 4B). FIG. 4B is a Table showing Illumina IDs and chromosomal positions from Genome Reference Consortium Human Build 37; GRCh37. Sites 1-10 highlighted in gray (black and white version of Figure) or yellow (color version of Figure) in FIG. 4B are ones that are the most significant predictors of naltrexone response in combination with other sites as follows:

FIGS. 5A and 5B are depictions of the nucleotide sequences of SLC6A3 promoter (FIG. 5A; SEQ ID NO: 11) and 3' untranslated region (UTR; FIG. 5B; SEQ ID NO: 21) regions analyzed. Lower-case letters indicate untranscribed nucleotides and upper-case letters indicate the exonic sequence. The transcription start site (GAG) is highlighted in dark gray (black and white version of Figure) or in red (color version of Figure). CpG dinucleotides on the Illumina BeadChip are highlighted in light gray (black and white version of Figure) or in green (color version of Figure), and superscript numbers refer to the specific Illumina ID for each site (see also FIG. 5C). FIG. 5C is a Table showing Illumina IDs and chromosomal positions (Genome Reference Consortium Human Build 37; GRCh37). Sites highlighted in light gray (black and white version of Figure) or in yellow (color version of Figure) in FIG. 5C are ones that are the most significant predictors of naltrexone response in combination with other sites listed on site interaction table.

FIGS. 6A and 6B are depictions of the COMT promoter sequences analyzed. FIG. 6A depicts the P2 (membrane-bound COMT) promoter (SEQ ID NO: 26). FIG. 6B depicts the P1 (soluble COMT) promoter (SEQ ID NO: 27). Lower-case letters indicate untranscribed nucleotides and upper-case letters indicate the first exon (top) and third (bottom)

exons of the gene. The translation start sites (ATG) for the membrane-bound and soluble isoforms are highlighted in light gray and dark gray (black and white version of Figure) or in blue and purple (color version of Figure), respectively, in lines 2 and 4 of FIG. 6B. CpG dinucleotides on the Illumina BeadChip are highlighted in light gray (black and white version of Figure) or in green (color version of Figure), and superscript numbers refer to the specific Illumina ID for each site (see also FIG. 6C). FIG. 6C is a Table showing Illumina IDs and chromosomal positions (from Genome Reference Consortium Human Build 37; GRCh37). Sites highlighted in light gray (black and white version of Figure) or in yellow (color version of Figure) in FIG. 6C are ones that are the most significant predictors of naltrexone response in combination with other sites listed on the site interaction Table above.

DETAILED DESCRIPTION

Figure 1:
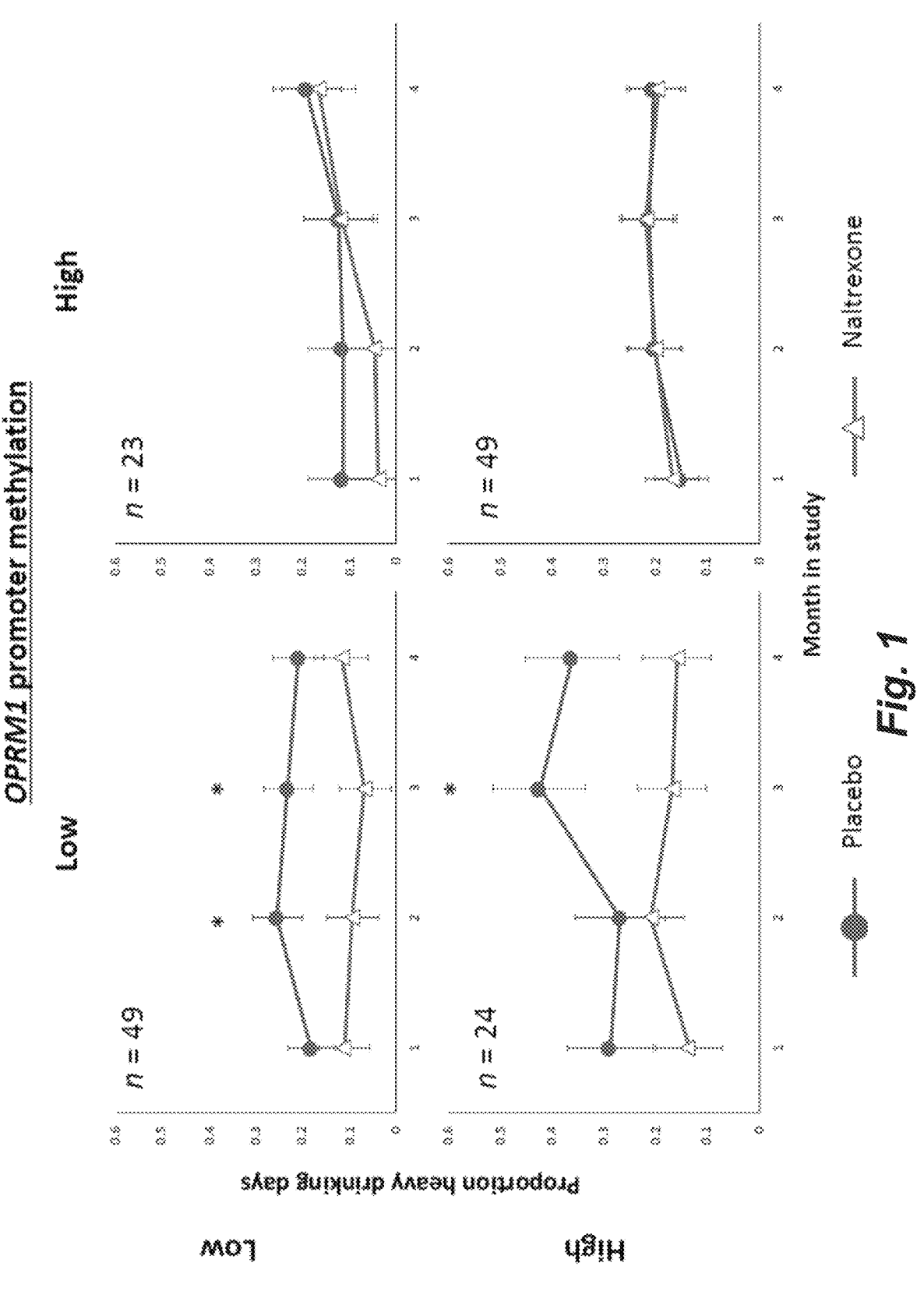
FIG. 1 is a series of graphs showing the effects of naltrexone (open triangles), relative to placebo (closed circles), on percent heavy drinking days (PHDD) during the 16-week trial as a function of SLC6A3 promoter methyl-ation (y-axis) and OPRM1 promoter methylation (x-axis). SLC6A3 and OPRM1 methylation are split into low and high groups (below and above the median methylation levels) for display purposes. Naltrexone, relative to placebo, reduced PHDD more among participants with lower SLC6A3 promoter and OPRM1 promoter methylation. Fig-ures are estimated marginal means (±standard errors) from the linear mixed model where the independent variables were promoter methylation levels (low or high) and naltr-exone or placebo treatment, while the dependent variable was percent heavy drinking days over the treatment period (months).

The current study tested methylation of the OPRM1 promoter and its interactions with methylation of the SLC6A3 and COMT promoters and the SLC6A3 VNTR as moderators of naltrexone effects on drinking. We used genomic DNA extracted from peripheral leukocytes from participants in our 16-week naltrexone randomized control trial (RCT; Schacht et al., 2017), in which we subsequently discovered that SLC6A3 and COMT polymorphisms interacted with the OPRM1 rs1799971 SNP to predict naltrexone response (Anton et al., 2020). It was hypothesized that OPRM1, SLC6A3, and COMT promoter methylation and SLC6A2 VNTR methylation would interact in their effects on naltrexone response in a manner similar to, but different and not attributable to, those polymorphisms, such that naltrexone-treated individuals with lower OPRM1 methylation (and presumably greater MOR expression) and either lower SLC6A3 or COMT methylation (and presumably greater DAT or COMT expression, engendering less synaptic dopamine accumulation) might demonstrate the least heavy drinking when treated with naltrexone.

Numerous clinical trials have tested genomic factors that may moderate naltrexone efficacy in Alcohol Use Disorder (AUD). Epigenetic processes (some of which could be acquired by example by chronic heavy alcohol consumption), such as DNA methylation, which modulates gene expression by inhibiting transcription factor binding in gene promoters and/or at other relevant genomic sites, could also affect naltrexone efficacy. Since naltrexone putatively reduces drinking through direct effects on opioid, and, indirectly, on dopamine signaling, methylation of opioid- and dopamine-related genes might moderate its effects. This study tested methylation of the promoters of the mu opioid receptor (OPRM1), dopamine transporter (SLC6A3), and catechol-O-methyltransferase (COMT) genes as well as the SLC6A3 VNTR as moderators of naltrexone effects on heavy drinking in a 16-week randomized, placebo-controlled trial among 145 treatment-seeking AUD patients. OPRM1 methylation did not independently moderate naltrexone effects, but interacted with both SLC6A3 and COMT methylation to do so ($p < 0.05$ and $p < 0.01$, respectively), such that naltrexone-treated individuals with lower methylation of the OPRM1 and SLC6A3 or COMT promoters (presumably associated with greater expression of these genes), relative to placebo and to those with higher OPRM1 and SLC6A3 or COMT methylation, had significantly fewer heavy drinking days. This effect was consistent with previous pharmacogenetic data from this sample (Anton et al., 2020), which suggested that individuals with functional alleles at polymorphisms in OPRM1, SLC6A3, and COMT influenced naltrexone response. The methylation effects detailed here persisted even when these genotypes were accounted for in the statistical models, and thus represent new discoveries that were not related to the heritable gene variations previously described. Taken together, these data suggest epigenetic modification of genes associated with opioid and dopamine signaling are a novel predictor of naltrexone efficacy in AUD.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

I. Definitions

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, some embodiments includes from the one particular value and/or to the other particular value. Similarly, when values are expressed as approximations, by use of the antecedent "about," it will be understood that the particular value forms an embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed, then "less than or equal to 10" as well as "greater than or equal to 10" are also disclosed. It is also understood that the throughout the application, data are provided in a number of different formats, and that these data represent in some embodiments endpoints and starting points and in some embodiments ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The term "and/or", when used in the context of a list of entities, refers to the entities being present singly or in combination.

The terms "optional" and "optionally" as used herein indicate that the subsequently described event, circumstance, element, and/or method step may or may not occur and/or be present, and that the description includes instances where said event, circumstance, element, or method step occurs and/or is present as well as instances where it does not.

"Probes" are molecules capable of interacting with a target nucleic acid, typically in a sequence specific manner, for example through hybridization. The hybridization of nucleic acids is well understood in the art and discussed herein. Typically, a probe can be made from any combination of nucleotides, nucleotide derivatives, and/or analogs thereof as are available in the art.

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

As used herein, the term "COMT" refers to a catechol-O-methyltransferase (COMT) gene or gene product, such as but not limited to those gene products described in Accession Nos. NM_000754.3 (SEQ ID NO: 40) and NP 000745.1 (SEQ ID NO: 41) in the GENBANK® biosequence database. The human COMT locus is located on chromosome 22 and corresponds to nucleotides 19,929,263-19,957,498 of GENBANK® Accession No. NC_000022.10 (SEQ ID NO: 42).

As used herein, the term "rs4680" refers to an SNP in the COMT gene. The wild-type allele has a G at the nucleotide position corresponding to nucleotide 721 of the human COMT cDNA of SEQ ID NO: 40, which encodes a valine amino acid at amino acid 158 of the human COMT polypeptide of SEQ ID NO: 41. The substitution polymorphism has an A at the nucleotide position corresponding to nucleotide 721 of the human COMT cDNA of SEQ ID NO: 40, which encodes a methionine amino acid at amino acid 158 of the human COMT polypeptide of SEQ ID NO: 41. Hence, this SNP is sometimes also referred to as "Val158Met" or grammatical variants thereof. Similarly, the term "rs4680 genotype" refers to both whether a patient has a G or an A at nucleotide 721 of the human COMT cDNA of SEQ ID NO: 40 as well as whether a patient has a valine or a methionine at amino acid 158 of the human COMT polypeptide of SEQ ID NO: 41.

As used herein, the terms "DAT1", "SLC6A3" and "DAT1/SLC6A3" refers to a solute carrier family 6 member 3 (SLC6A3) gene or gene product, such as but not limited to those gene products described in Accession Nos. NM_001044.4 (SEQ ID NO: 43) and NP_001035.1 (SEQ ID NO: 44) in the GENBANK biosequence database. The SLC6A3 gene is also referred to as the dopamine transporter 1 (DAT1) gene. The human SLC6A3 locus is located on chromosome 5 and corresponds to the reverse complement of nucleotides 1,392,905-1,445,483 of GENBANK® Accession No. NC 000005.9 (SEQ ID NO: 45).

As used herein, the term "rs28363170" refers to a polymorphism with respect to a 40 nucleotide variable number tandem repeat (VNTR; ACTGGAGCGTGTACTACCCC AGGACGCATGCAGGGCCCCC; SEQ ID NO: 39) present in the 3' untranslated region (UTR) of the nucleotide sequences of dopamine transporter (SLC6A3/DAT1) gene products. The 10- and 9-repeat alleles are the most common alleles. (Doucette-Stamm et al., 1995). Similarly, the term "rs28363170 genotype" refers to which allele(s) of the VNTR a patient has (e.g., how many copies of SEQ ID NO: 39 the patient has in the SLC6A3/DAT1 3' UTR).

As used herein, the term "OPRM1" refers to an opioid receptor mu 1 (OPRM1) gene or gene product, such as but not limited to those gene products described in Accession Nos. NM_000914.5 (SEQ ID NO: 46) and NP_000905.3 (SEQ ID NO: 47) in the GENBANK® biosequence database. The human OPRM1 locus is located on chromosome 6 and corresponds to nucleotides 154,360,375-154,453,491 of GENBANK® Accession No. NC_000006.11 (SEQ ID NO: 48).

As used herein, the term "rs1799971" refers to an SNP in the OPRM1 gene. The wild-type allele has an A at the nucleotide position corresponding to nucleotide 423 of the human OPRM1 cDNA of SEQ ID NO: 46, which encodes an asparagine amino acid at amino acid 40 of the human OPRM1 polypeptide of SEQ ID NO: 47. The substitution polymorphism has a G at the nucleotide position corresponding to nucleotide 423 of the human OPRM1 cDNA of SEQ ID NO: 46, which encodes an aspartic acid amino acid at amino acid 40 of the human OPRM1 polypeptide of SEQ ID NO: 47. Hence, this SNP is sometimes also referred to as "Asn40Asp" or grammatical variants thereof. Similarly, the term "rs1799971genotype" refers to both whether a patient has an A or a G at nucleotide 423 of the human OPRM1 cDNA of SEQ ID NO: 46 as well as whether a patient has an asparagine or an aspartic acid at amino acid 40 of the human OPRM1 cDNA of SEQ ID NO: 47.

As is known in the art, in some embodiments multiple gene products can be generated from a particular genetic locus, for example by alternative transcriptional initiation sites, alternative splicing, etc. It is understood that the GENBANK® Accession Nos. presented herein are meant to be exemplary only, and other gene products for which the nucleotide and/or amino acid sequences are not explicitly disclosed herein are also intended to be encompassed by the names of the corresponding genes. Thus, for example, transcript variants of the sequences in the Sequence Listing are also included with the definitions of the genes described herein, as are the amino acid variants encoded thereby.

II. Methods for Predicting Naltrexone Response in Subjects with Alcohol Use Disorder (AUD)

Alcohol use disorder (AUD) is a chronic relapsing brain disease characterized by compulsive alcohol use, loss of control over alcohol intake, and a negative emotional state when not using. An estimated 16 million people have been diagnosed as having AUD in the United States alone. To be diagnosed with AUD, individuals must meet at least two of the criteria outlined in the Diagnostic and Statistical Manual of Mental Disorders (DSM) including amount or duration of consumption, inability to reduce or stop drinking, time spent drinking or recovering, craving, interference of drinking on work, school, or family, maintaining consumption despite problems resulting from consumption, reducing activities to place more emphasis on consumption, increased risk behavior while consuming or intoxicated, continued consumption despite feelings of depression or anxiety, increased average consumption over the past year, and presence of withdrawal symptoms.

Treatment for AUD can comprise counseling, behavioral modification, and pharmacological intervention. Currently, three drugs, Naltrexone, Acamprosate, and Disulfiram, are approved for treating alcohol use disorder.

Both endogenous opiate and dopamine (DA) signaling regulate many aspects of AUD. Alcohol cues and intravenous alcohol self-administration both increase DA release in animals and human brain imaging suggests the same mechanism in the human ventral striatum (VS). This dopamine release and its effects are blocked by exogenously administered naltrexone in animals and man.

Naltrexone has proven efficacy in the treatment of AUD and has been approved by the FDA for this purpose. However, naltrexone does not work for all individuals with AUD and in fact works well for the minority of individuals. This has led to the speculation that genetic differences might underlie naltrexone's effect. Given that naltrexone specifically binds to a brain mu opiate receptor and that binding is linked to effects on the brain dopamine system (in the ventral striatum and elsewhere) it could be hypothesized that genetic variability (either inherited or acquired) could influence naltrexone's efficacy. As stated previously, it had been reported that a single nucleotide variant (SNP) in the coding region of the mu opiate receptor gene (OPRM1) at the 118 position (A118G) was predictive of naltrexone efficacy. However, this was not universally confirmed. Our past work suggested that this OPRM1 SNP, however, was influenced by and/or interacted with several genetic variants in the dopamine systems, a VNTR in the dopamine transporters (DAT1) gene, and/or a SNP in the catechol-O-methyl transferase (COMT) gene. These functional variants suggest that other mechanisms that affect these dopamine system genes might interact with the OPRM1 gene to also affect naltrexone efficacy. One such mechanism is epigenetic (likely acquired, not inherited) methylation of certain CpG sites in the gene promoter area and elsewhere of the DAT1 and COMT genes.

The DA transporter (DAT) is the primary mechanism for striatal DA clearance. A 40-base-pair variable number tandem repeat (VNTR) polymorphism (rs28363170; ACTG-GAGCGTGTACTACCCCAGGACG-CATGCAGGGCCCCC; SEQ ID NO: 39) in the 3' untranslated region of the DAT1 gene (DAT1/SLC6A3), for which the most common allelic variants are nine (9) and ten (10) repeats, can affect DAT1 function. Relative to the 10-repeat (10R) allele, the 9-repeat (9R) allele has been associated with reduced DAT1 expression and lower striatal DAT1 availability among AUD individuals, potentially leading to relatively increased extrasynaptic DA tone. Consistent with these findings, individuals who carry the 9R allele, relative to 10R homozygotes, display greater VS activation during the anticipation and receipt of monetary reward. Further, nicotine-dependent 9R carriers display greater smoking cue-elicited VS activation and greater VS DA release after smoking.

Thus, in some embodiments the presently disclosed subject matter relates to methods for predicting naltrexone response in subjects with an alcohol use disorder (AUD). In some embodiments, the method comprises, consists essentially of, or consists of performing or having performed one or more methylation assays on a genomic DNA sample isolated from the subject to determine the methylation status of one or more regions of the isolated genomic DNA, wherein the one or more regions of the isolated genomic DNA are subsequences of a gene selected from the group consisting of a mu opioid receptor (OPRM1) gene, a catechol-O-methyltransferase (COMT) gene, and a dopamine transporter (SLC6A3) gene, and further wherein the methylation status of the one or more regions of the isolated genomic DNA determined is predictive of naltrexone response in the subject.

In some embodiments, the one or more regions of the isolated genomic DNA assayed comprise, consist essentially of, or consist of the promoter of the OPRM1 gene, the promoter of the COMT gene, and the 40-base-pair variable number tandem repeat (VNTR) polymorphism in the 3' untranslated region of SLC6A3 gene.

In some embodiments, the one or more regions of the OPRM1 gene include 130 nucleotides upstream and 600 nucleotides downstream of the OPRM1 transcription start site (TSS); optionally comprising one or more of the following subsequences:

| SEQ ID NO: | Sequence |
|---|---|
| 2 | ATGTGTTTGCACAGAAGAGTGCCCAGTGAAGAGACCTACTC CTTGGATCG[1] |
| 3 | TGCACAGAAGAGTGCCCAGTGAAGAGACCTACTCCTTGGAT CG[1]CTTTCG[2] |
| 4 | CTAAGGTGGGAGGGGGCTATACG[3]CAGAGGAGAATGTCAGA TGCTCAGCTC |
| 5 | CGCAGAGGAGAATGTCAGATGCTCAGCTCGGTCCCCTCCG[4] CCTGACG[5]CTC |
| 6 | GTCTCAGCCAGGACTGGTTTCTGTAAGAAACAGCAGGAGCT GTGGCACG[6] |
| 7 | AGGACTGGTTTCTGTAAGAAACAGCAGGAGCTGTGGCACG[6] CG[7]AAAGG |
| 8 | CG[8]TCAGTACC*ATG*GACAGCAGCGCTGCCCCCACGAACGCCA GCAATTGCA |
| 9 | CG[9]TACTCAAGTTGCTCCCCAGCACCCAGCCCCGGTTCCTGG GTCAACTTG |
| 10 | CG[10]ATCATGGCCCTCTACTCCATCGTGTGCGTGGTGGGGCTC TTCGGAAAC |

With reference to the above sequences, nucleotides underlined correspond to exemplary CpG sites for the OPRM1 promoter as identified and numbered in FIGS. 4A and 4B. The initiator codon ATG is indicated in bold italics. In some embodiments, a methylation status for one or more of CG[1-10] in SEQ ID NOs: 2-10 is determined.

In some embodiments, the one or more regions of the SLC6A3 gene comprise one or more of the following subsequences:

| SEQ ID NO: | Sequence |
|---|---|
| 12 | CG[1]TGGGGAGATACAGGGAGAGAACTGTCTGCAACCCCGAAG CGGCCCTCA |
| 13 | CG[2]GCCACTCACCTCGGTGCCTTCTAAGGACCTGGACATCCT GGGCCTTGG |
| 14 | TGGTTTTCTTAGGCGAGTGCGAGGCGGGCCCCTCGGTTCCGA TGCAGGCG[3] |

-continued

| SEQ ID NO: | Sequence |
|---|---|
| 15 | CG[4]GACCCTGTCTACTGGATAAGAGCCCG[5]AGGCCG[6]AGGCT GAGACCG[7]CCCA |
| 16 | TCGGCGGGAGGGCGGGGCGGGCCG[4]GACCCTGTCTACTGGAT AAGAGCCCG[5] |
| 17 | GGAGGGCGGGGCGGGCCG[4]GACCCTGTCTACTGGATAAGAGC CCG[5]AGGCCG[6] |
| 18 | GGGCCG[4]GACCCTGTCTACTGGATAAGAGCCCG[5]AGGCCG[6]AG GCT*GAGA*CCG[7] |
| 19 | CG[5]AGGCCG[6]AGGCTGAGACCG[7]CCCACG[8]CTGCGGAGCGGG AGGGGAGGC |
| 20 | CCGGGCACAGTCTGGGGTCCCCCG[9]TCCCGCAGACCGCGCC GTCTCCAAA |

With reference to the above sequences, nucleotides underlined correspond to exemplary CpG sites for the SLC6A3 promoter as identified and numbered in FIGS. 5A-5C. The transcription start site GAG is indicated in bold italics.

In some embodiments, the SLC6A3 VNTR comprises one or more of the following subsequences:

| SEQ ID NO: | Sequence |
|---|---|
| 22 | CCTATCCCCGGACGCATGCAGGGCCCCCACAGGACCG[10]TGTC CTATCCCCG |
| 23 | CG[10]TGTCCTATCCCCGGACGCATGCAGGGCCCCCACAGGAGC ATGTCCTAT |
| 24 | GCATGCAGGGCCCCCACAGGACCG[11]TGTACTACCCCAGGACG CATGCAGG |
| 25 | CGCATGCAGGGCCCCCACAGGACCG[11]TGTCCTATCCCCGGA CCGGACGCAT |

With reference to the above sequences, nucleotides underlined correspond to exemplary CpG sites for the SLC6A3 VNTR as identified and numbered in FIGS. 5B and 5C. The transcription start site GAG is indicated in bold italics. In some embodiments, a methylation status for one or more of CG[1-11] in SEQ ID NOs: 12-20 and 22-25 is determined.

In some embodiments, the one or more regions of the COMT gene comprise one or more of the following subsequences:

| SEQ ID NO: | Sequence |
|---|---|
| 28 | CG[1]GACTCCTGAGCAAGACTAGACCAAGAGGCCG[2]GTATGTG GACACCCCG[3] |
| 29 | TGTGGCTAGAAGCAGCCCG[1]GACTCCTGAGCAAGACTAGACC AAGAGGCCG[2] |
| 30 | CG[4]CGGACACCTACCGCGGGGACG[5]CCCCGACCCCATCCTAC CTGCTGCGCC |
| 31 | CG[5]CCCCGACCCCATCCTACCTGCTGCGCCCCGCGCCGCGCC CCGCACCCCG[6] |
| 32 | CG[6]CCCGCCACGGCCTGCGTCG[7]CCACCGGAAGCGCCCTCCT AATCCCCGC |

-continued

| SEQ ID NO: | Sequence |
| --- | --- |
| 33 | CG$^{7}$CCACCGGAAGCGCCCTCCTAATCCCCGCACCG$^{8}$CCACCGC CATTGCCGC |
| 34 | CGCCCTCCTAATCCCCGCACCG$^{6}$CCACCGCCATTGCCGCCAT CGTCGTGGG |
| 35 | AAGGCTGGCATTTCTGAACCTTGCCCCTCTGCAAACACAAGG GGGCCG$^{9}$ |
| 36 | CCAAGCAAAGGGGCGTGTGGGTGCTGCAGGAGGAGCACAGAG CACTGCCG$^{10}$ |
| 37 | CG$^{11}$CCCTGCAGATGCCGGAGGCCCCGCCTCTGCTGTTGGCA GCTGTGTTGC |
| 38 | CG$^{12}$AGTTCATCCTGCAGCCCATCCACAACCTGCTCATGGGTG ACACCAAGG |

With reference to the above sequences, nucleotides underlined correspond to exemplary CpG sites for the COMT P2 and P1 promoters as identified and numbered in FIGS. 6A-6C. In some embodiments, a methylation status for one or more of CG$^{1-12}$ in SEQ ID NOs: 12-20 and 22-25 is determined.

In some embodiments, the methylation status of at least one and optionally all four of the promoter of the OPRM1 gene, the promoter of the COMT gene, the promoter of the SCLC6A3, and the 40-base-pair variable number tandem repeat (VNTR) polymorphism in the 3' untranslated region of SLC6A3 gene are determined.

Genomic DNA can be isolated from any biological sample isolated from a subject that includes nucleated cells. Exemplary biological samples include easily obtainable cells including but not limited to blood cells. In some embodiments, genomic DNA is isolated from a cell selected from the group consisting of blood cells, optionally peripheral blood mononuclear cells, and buccal cells, and/or from a biological sample containing cells, optionally, blood, saliva, cerebrospinal fluid, and/or any fraction or component thereof.

As disclosed herein, the presently disclosed methods for predicting naltrexone response comprise, consist essentially of, or consist of performing or having performed one or more methylation assays on a genomic DNA sample isolated from the subject to determine the methylation status of one or more regions of the isolated genomic DNA. Methods for determining methylation statuses of genomic DNA samples are known and include but are not limited to sequencing, methylation-specific PCR (MS-PCR), melting curve methylation-specific PCR (McMS-PCR), MLPA with or without bisulfite treatment, QAMA (Zeschnigk et al., 2004), MSRE-PCR (Melnikov et al., 2005), MethyLight (Eads et al., 2000), ConLight-MSP (Rand et al., 2002), bisulfite conversion-specific methylation-specific PCR (BS-MSP; Sasaki et al., 2003), COBRA (which relies upon use of restriction enzymes to reveal methylation dependent sequence differences in PCR products of sodium bisulfite-treated DNA), methylation-sensitive single-nucleotide primer extension conformation (MS-SNuPE), methylation-sensitive single-strand conformation analysis (MS-SSCA), Melting curve combined bisulfite restriction analysis (McCOBRA; Akey et al., 2002, PyroMethA, HeavyMethyl (Cottrell et al., 2004), MALDI-TOF, MassARRAY, Quantitative analysis of methylated alleles (QAMA), enzymatic regional methylation assay (ERMA), QBSUPT, MethylQuant, Quantitative PCR sequencing and oligonucleotide-based microarray systems, Pyrosequencing, Meth-DOP-PCR, etc. A review of some useful techniques for DNA methylation analysis is provided in Rein et al., 1998; Laird, 2003; and Auerkari, 2006; each of which is incorporated herein in its entirety. See also U.S. Pat. No. 7,425,415.

Techniques for assessing methylation status are based on distinct approaches. Some include use of endonucleases. Such endonucleases may either preferentially cleave methylated recognition sites relative to non-methylated recognition sites or preferentially cleave non-methylated relative to methylated recognition sites. Some examples of the former are Acc III, Ban I, BstN I, Msp I, and Xma I. Examples of the latter are Acc II, Ava I, BssH II, BstU I, Hpa II, and Not I. Differences in cleavage pattern are indicative for the presence or absence of a methylated CpG dinucleotide. Cleavage patterns can be detected directly, or after a further reaction which creates products which are easily distinguishable. Means which detect altered size and/or charge can be used to detect modified products, including but not limited to electrophoresis, chromatography, and mass spectrometry.

Alternatively, the identification of methylated CpG dinucleotides may utilize the ability of the methyl binding domain (MBD) of the MeCP2 protein to selectively bind to methylated DNA sequences (Cross et al., 1994; Shiraishi et al., 1999). The MBD may also be obtained from MBP, MBP2, MBP4, poly-MBD (Jorgensen et al., 2006) or from reagents such as antibodies binding to methylated nucleic acid. The MBD may be immobilized to a solid matrix and used for preparative column chromatography to isolate highly methylated DNA sequences. Variant forms such as expressed His-tagged methyl-CpG binding domain may be used to selectively bind to methylated DNA sequences. Eventually, restriction endonuclease digested genomic DNA is contacted with expressed His-tagged methyl-CpG binding domain. Other methods are well known in the art and include amongst others methylated-CpG island recovery assay (MIRA). Another method, MB-PCR, uses a recombinant, bivalent methyl-CpG-binding polypeptide immobilized on the walls of a PCR vessel to capture methylated DNA and the subsequent detection of bound methylated DNA by PCR.

Further approaches for detecting methylated CpG dinucleotide motifs use chemical reagents that selectively modify either the methylated or non-methylated form of CpG dinucleotide motifs. Suitable chemical reagents include hydrazine and bisulfite ions. The methods of the invention preferably use bisulfite ions. The bisulfite conversion relies on treatment of DNA samples with sodium bisulfite which converts unmethylated cytosine to uracil, while methylated cytosines are maintained (Furuichi et al., (1970). This conversion finally results in a change in the sequence of the original DNA. It is general knowledge that the resulting uracil has the base pairing behavior of thymidine which differs from cytosine base pairing behavior. This makes the discrimination between methylated and non-methylated cytosines possible. Useful conventional techniques of molecular biology and nucleic acid chemistry for assessing sequence differences are well known in the art and explained in the literature. See for example, Sambrook et al., 2001; Gait, 1984; Hames & Higgins, 1985; and the series, Methods in Enzymology, Academic Press, Inc.

Some techniques use primers for assessing the methylation status at CpG dinucleotides. Two approaches to primer design are possible. Firstly, primers may be designed that themselves do not cover any potential sites of DNA methylation. Sequence variations at sites of differential methyl-
ation are located between the two primers and visualization
of the sequence variation requires further assay steps. Such
primers are used in bisulfite genomic sequencing, COBRA,
Ms-SnuPE and several other techniques. Secondly, primers
may be designed that hybridize specifically with either the
methylated or unmethylated version of the initial treated
sequence. After hybridization, an amplification reaction can
be performed and amplification products assayed using any
detection system known in the art. The presence of an
amplification product indicates that a sample hybridized to
the primer. The specificity of the primer indicates whether
the DNA had been modified or not, which in turn indicates
whether the DNA had been methylated or not. If there is a
sufficient region of complementarity, e.g., 12, 15, 18, or 20 nucleotides, to the target, then the primer may also contain
additional nucleotide residues that do not interfere with
hybridization but may be useful for other manipulations.
Examples of such other residues may be sites for restriction
endonuclease cleavage, for ligand binding or for factor
binding or linkers or repeats. The oligonucleotide primers
may or may not be such that they are specific for modified
methylated residues.

A further way to distinguish between modified and
unmodified nucleic acid is to use oligonucleotide probes.
Such probes may hybridize directly to modified nucleic acid
or to further products of modified nucleic acid, such as
products obtained by amplification. Probe-based assays
exploit the oligonucleotide hybridization to specific
sequences and subsequent detection of the hybrid. There
may also be further purification steps before the amplifica-
tion product is detected e.g. a precipitation step. Oligonucle-
otide probes may be labelled using any detection system
known in the art. These include but are not limited to
fluorescent moieties, radioisotope labelled moieties, bioluminescent moieties, luminescent moieties, chemilumines-
cent moieties, enzymes, substrates, receptors, or ligands.

In some embodiments, the methylation status of at least a
subsequence of a genetic locus selected from OPMR1,
DAT1/SLC6A3, and COMT (or portions thereof, in some embodiments the CpG islands) is determined using meth-
ylation specific PCR (MSP), or an equivalent amplification
technique. In the MSP approach, DNA may be amplified
using primer pairs designed to distinguish methylated from
unmethylated DNA by taking advantage of sequence differences as a result of sodium-bisulfate treatment (Herman et
al., 1996; and PCT International Patent Application Publi-
cation No. WO 97/46705). For example, bisulfate ions
modify non-methylated cytosine bases, changing them to
uracil bases. Uracil bases hybridize to adenine bases under
hybridization conditions. Thus an oligonucleotide primer
which comprises adenine bases in place of guanine bases
would hybridize to the bisulfate-modified DNA, whereas an
oligonucleotide primer containing the guanine bases would
hybridize to the non-modified (methylated) cytosine residues in the DNA. Amplification using a DNA polymerase
and a second primer yield amplification products which can
be readily observed, which in turn indicates whether the
DNA had been methylated or not. Whereas PCR is a
preferred amplification method, variants on this basic technique such as nested PCR and multiplex PCR are also
included within the scope of the invention.

Bisulfite sequencing offers another alternative to deter-
mine the methylation status of at least one gene selected
from OPMR1, SLC6A3, and COMT. Primers may be
designed for use in sequencing through the important CpG
islands of the concerned gene. Thus, primers may be designed in both the sense and antisense orientation to direct
sequencing across the region of interest of the selected gene.

As mentioned earlier, an exemplary technique for assess-
ing the methylation status of the relevant gene requires
amplification to yield amplification products. The presence
of amplification products may be assessed directly using
methods well known in the art. They simply may be visu-
alized on a suitable gel, such as an agarose or polyacrylam-
ide gel. Detection may involve the binding of specific dyes,
such as ethidium bromide, which intercalate into double-
stranded DNA and visualization of the DNA bands under a
UV illuminator for example. Another means for detecting
amplification products comprises hybridization with oligo-
nucleotide probes. Alternatively, fluorescence or energy
transfer can be measured to determine the presence of the
methylated DNA.

A specific example of the MSP technique is designated
real-time quantitative MSP (QMSP), and permits reliable
quantification of methylated DNA in real time or at end
point. Real-time methods are generally based on the con-
tinuous optical monitoring of an amplification procedure and
utilize fluorescently labelled reagents whose incorporation
in a product can be quantified and whose quantification is
indicative of copy number of that sequence in the template.
One such reagent is a fluorescent dye, called SYBR Green
I that preferentially binds double-stranded DNA and whose
fluorescence is greatly enhanced by binding of double-
stranded DNA. Alternatively, labeled primers and/or labeled
probes can be used for quantification. They represent a
specific application of the well known and commercially
available real-time amplification techniques such as
TAQMAN®, MOLECULAR BEACONS®, AMPLIF-
LUOR® and SCORPION® DZYNA®, PLEXOR™ etc.

In some embodiments, an Infinium MethylationEPIC
BeadChip (available from Illumina, San Diego, California)
is employed for determining the methylation status of one or
more of the OPMR1, SLC6A3, and COMT genes, or por-
tions thereof, in some embodiments the CpG islands.

III. Methods for Predicting Naltrexone Response and for Treating Subjects with AUD In some embodiments, the presently disclosed subject
matter also relates to methods for treating subjects with
alcohol use disorders. In some embodiments, the methods
comprise, consist essentially of, or consist of performing or
having performed one or more methylation assays on a
genomic DNA sample isolated from the subject to determine
the methylation status of one or more regions of the isolated
genomic DNA, wherein the one or more regions of the
isolated genomic DNA are subsequences of a gene selected
from the group consisting of a mu opioid receptor (OPRM1)
gene, a catechol-O-methyltransferase (COMT) gene, and a
dopamine transporter (SLC6A3) gene, and further wherein
the methylation status of the one or more regions of the
isolated genomic DNA determined is predictive of naltrex-
one response in the subject, followed by a decision with
respect to an appropriate treatment to follow. In some
embodiments, the subject is treated with an effective amount
of naltrexone if the methylation status of one or more
regions of the isolated genomic DNA is predictive of the
subject advantageously responding to the naltrexone. If the
methylation status of one or more regions of the isolated
genomic DNA is not predictive of the subject advanta-
geously responding to the naltrexone an alternative treat-
ment is selected. In some embodiments, such a subject is
treated with an effective amount of an active agent other than naltrexone (referred to herein as a "non-naltrexone agent"). Various non-naltrexone agents can be employed, including but not limited to acamprosate, topiramate, fluoxetine, ondansetron, or any combination thereof.

For the mu opiate gene (OPRM1) the following CpG (cg) sites with a value lower than the mean listed must be present in combination with one of the DAT (SCL6A3) gene CpG (cg) sites with a value lower than the mean listed for naltrexone to be most effective. It would be expected that if the above criteria are met, the patient would have a highly significant chance (p<0.05) of responding to naltrexone compared to the situation where the above criteria are not met. That is, after testing and receiving specific methylation levels/frequencies for these specific CpG sites, a clinician/prescriber could/would choose to recommend/prescribe naltrexone if the above criteria were met.

OPRM1

| Illumina ID | Chromosomal position | Nucleotide Position in SEQ ID NO: 1 | Mean Methylation Values |
|---|---|---|---|
| cg05215925 | 154360587 | 274 | 0.147 |
| cg22719623 | 154360732 | 419 | 0.488 |

DAT1 (SCL6A3)

| Illumina ID | Chromosomal position | Nucleotide Position in SEQ ID NO: 11/21* | Mean Methylation Values |
|---|---|---|---|
| cg16180821 | 1446969 | 576 | 0.651 |
| cg15600751 | 1394054 | 1102 | 0.648 |
| cg12882697 | 1445549 | 46 | 0.089 |

*cg16180821 and cg15600751 are present in SEQ ID NO: 11 and cg12882697 is present in SEQ ID NO: 21.

For the mu opiate gene (OPRM1) the following CpG (cg) sites with a value lower than the mean listed must be present in combination with one of the COMT gene CpG (cg) sites with a value lower than the mean listed for naltrexone to be most effective. It would be expected that if the above criteria are met, the patient would have a highly significant chance (p<0.05) of responding to naltrexone compared to the situation where the above criteria are not met. That is, after testing and receiving specific methylation levels/frequencies for these specific CpG sites the clinician/prescriber could/would choose to recommend/prescribe naltrexone if the above criteria were met.

OPRM1

| Illumina ID | Chromosomal position | Nucleotide Position in SEQ ID NO: 1 | Mean Methylation Values |
|---|---|---|---|
| cg05215925 | 154360587 | 274 | 0.147 |
| cg14348757 | 154360590 | 277 | 0.157 |
| cg12838303 | 154360670 | 357 | 0.126 |
| cg22719623 | 154360732 | 419 | 0.488 |

COMT

| Illumina ID | Chromosomal position | Nucleotide Position in SEQ ID NO: 27 | Mean Methylation Values |
|---|---|---|---|
| cg06346307 | 19949965 | 46 | 0.587 |
| cg22546130 | 19950026 | 107 | 0.546 |

Thus, in some embodiments the presently disclosed subject matter also relates to methods for treating subjects with an alcohol use disorder (AUD). In some embodiments, the presently disclosed methods comprise, consist essentially of, or consist of (a) performing or having performed one or more methylation assays on a genomic DNA sample isolated from the subject to determine the methylation status of one or more regions of the isolated genomic DNA, wherein the one or more regions of the isolated genomic DNA are subsequences of a gene selected from the group consisting of a mu opioid receptor (OPRM1) gene, a catechol-O-methyltransferase (COMT) gene, and a dopamine transporter (SLC6A3) gene, and further wherein the methylation status of the one or more regions of the isolated genomic DNA determined is predictive of naltrexone response in the subject; and either (b1) treating the subject with an effective amount of naltrexone if the methylation status of one or more regions of the isolated genomic DNA is predictive of the subject advantageously responding to the naltrexone; or (b2) treating the subject with an effective amount of a non-naltrexone agent, optionally wherein the non-naltrexone agent is selected from the group consisting of acamprosate, topiramate, fluoxetine, ondansetron, or any combination thereof. In some embodiments, the one or more regions of the isolated genomic DNA assayed comprise, consist essentially of, or consist of the promoter of the OPRM1 gene, the promoter of the COMT gene, the promoter of the CSLC6A3 gene, and the 40-base-pair variable number tandem repeat (VNTR) polymorphism in the 3' untranslated region of SLC6A3 gene. In some embodiments, the one or more regions of the OPRM1 gene include 130 nucleotides upstream and 600 nucleotides downstream of the OPRM1 transcription start site (TSS); optionally comprising one or more of SEQ ID NOs: 2-10. In some embodiments, the one or more regions of the SLC6A3 gene comprise one or more of SEQ ID NOs: 12-20. In some embodiments, the one or more regions of the COMT gene comprise one or more of SEQ ID NOs: 28-38. In some embodiments, the SLC6A3 VNTR comprises one or more of SEQ ID NOs: 22-25. In some embodiments, the methylation status of at least two and optionally all three of the promoter of the OPRM1 gene, the promoter of the COMT gene, and the 40-base-pair variable number tandem repeat (VNTR) polymorphism in the 3' untranslated region of SLC6A3 gene are determined. In some embodiments, the methylation statuses of at least one region of an OPRM1 gene and at least one region of an SLC6A3 gene and/or a COMT gene are determined. In some embodiments, the at least one region of the OPRM1 gene is selected from the group consisting of nucleotide positions 274, 277, 357, and 419 of SEQ ID NO: 1, and further wherein (i) the at least one region of the SLC6A3 is selected from the group consisting of nucleotide position 576 and 1102 of SEQ ID NO: 11, nucleotide position 1102 of SEQ ID NO: 11, and nucleotide position 46 of SEQ ID NO: 21; and/or (ii) the at least one region of the COMT gene is selected from the group consisting of nucleotides 46 and 107 of SEQ ID NO: 27. In some embodiments, a positive response to naltrexone is predicted if the subject has a combination of methylation values that are (a) lower than 0.147 with respect to nucleotide position 27 and/or lower than 0.488 with respect to nucleotide position 419 of SEQ ID NO: 1 in combination with lower than 0.651 with respect to nucleotide position 576 of SEQ ID NO: 11 and/or lower than 0.648 with respect to nucleotide position 1102 of SEQ ID NO: 11 and/or lower than 0.089 with respect to nucleotide position 46 of SEQ ID NO: 21; and/or (b) lower than 0.147 with respect to nucleotide position 27 of SEQ ID NO: 1 and/or lower than 0.157 with respect to nucleotide position 277 of SEQ ID NO: 1 and/or lower than 0.126 with respect to nucleotide position 357 of SEQ ID NO: 1 and/or lower than 0.488 with respect to nucleotide position 419 of SEQ ID NO: 1 in combination with lower than 0.587 with respect to nucleotide position 46 of SEQ ID NO: 27 and/or lower than 0.546 with respect to position 107 of SEQ ID NO: 27. In some embodiments, the genomic DNA is isolated from a cell selected from the group consisting of blood cells, optionally peripheral blood mononuclear cells, and buccal cells, and/or from a biological sample containing cells, optionally, blood, saliva, cerebrospinal fluid, and/or any fraction or component thereof.

In some embodiments, the presently disclosed methods further comprise, consist essentially of, or consist of converting the isolated genomic DNA with bisulfate prior to performing or having performed the one or more methylation assays.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Materials and Methods for the EXAMPLES

Overview. Detailed methods for the parent RCT, including a CONSORT diagram, are described in Anton et al, 2020 and Schacht et al, 2017. The Medical University of South Carolina Institutional Review Board approved all procedures, and all participants provided informed consent before participation. The study consisted of an initial assessment session, a baseline visit, and 9 follow-up visits over the course of a 16-week treatment period. Briefly, participants seeking AUD treatment were recruited from the community with media advertisements, assessed for inclusion/exclusion criteria, and genotyped for rs1799971. One of the aims of the parent RCT was to test the effect of rs1799971 genotype on naltrexone efficacy, so participants who carried the minor (G) allele were over-selected, such that these individuals ultimately comprised ~50% of the 146 participants randomized to medication.

Participants. Participants were required to be ages 18-70; report heavy drinking (at least five/four standard drinks per day for men/women) on at least 50% of the days in the 90 days before assessment; and meet DSM-IV (Diagnostic and Statistical Manual of Mental Disorders, revised 4th edition) diagnostic criteria for Alcohol Dependence, as assessed by the Structured Clinical Interview for DSM-IV (First et al, 2002). Participants were also required to self-identify as Caucasian or Asian, secondary to low rs1799971 G-allele frequency among individuals of African descent; we previously reported that analysis of population allele frequencies for 50 SNPs included on the methylation assay used here indicated a high degree of correspondence between self-reported and SNP-identified ancestry. Participants who reported cocaine or marijuana use in the 90 days before assessment were included, as long as they did not meet DSM-IV criteria for dependence on either substance or any other except nicotine and had a negative urine drug screen upon medication randomization. Exclusion criteria were: current psychotropic medication use other than antidepressants (for which a stable dose for at least one month was required); current DSM-IV Axis I diagnosis or suicidal/homicidal ideation; history of significant medical illness; liver enzyme (ALT or AST) levels>three times normal; and past-month naltrexone, disulfiram, or acamprosate use. Female participants could not be pregnant or nursing. The Table below lists demographic characteristics for the sample. Medication, randomization, and assessment. Participants were required to maintain abstinence for at least four days before medication randomization, and were then urn randomized (Stout et al, 1994) to receive naltrexone (25 mg for two days, then 50 mg thereafter) or placebo for 16 weeks. Randomization was stratified by rs1799971 genotype, with sex, smoking status (non-smoker vs. smoker, defined as ≥10 cigarettes per day), cocaine use, antidepressant use, and AUD family history balanced across medication groups. Study medications were identically over-encapsulated with 100 mg of riboflavin (see (Schacht et al, 2017) for data on adherence, which was high and did not vary between medication groups) and distributed in labeled blister packs. Participants and investigators were blind to genotype and medication assignment. After randomization, participants returned at weeks 1, 2, 3, 4, 6, 8, 10, 12, and 16 for medical management sessions, during which daily drinking since the last visit was assessed with the calendar-based Timeline Follow-back interview (Sobell and Sobell, 1992). Participants who dropped out after randomization were compensated to return at week 16 to provide missing drinking data. Forty participants ultimately dropped out, at similar rates across medication groups, but full drinking data were available on 89% of participants.

Demographic Characteristics and Baseline Alcohol Use

| | Naltrexone (n = 73) | | Placebo (n = 72) | | Test for |
|---|---|---|---|---|---|
| | No. | % | No. | % | difference* |
| Demographics | | | | | |
| Sex, M | 51 | 69.9 | 49 | 68.1 | p = 0.81 |
| Employed | 56 | 76.7 | 57 | 79.2 | p = 0.72 |
| Education ≤12 years | 12 | 16.4 | 11 | 15.3 | p = 0.85 |
| Current nicotine user | 32 | 43.8 | 26 | 36.1 | p = 0.34 |
| Recent cocaine use | 8 | 11.0 | 11 | 15.3 | p = 0.44 |
| Current antidepressant use | 21 | 28.8 | 27 | 37.5 | p = 0.26 |

-continued

| | Mean | SD | Mean | SD | |
|---|---|---|---|---|---|
| Demographics | | | | | |
| | | | | | |
| Age, years | 50.7 | 9.3 | 48.1 | 10.8 | p = 0.13 |
| Alcohol use | | | | | |
| | | | | | |
| Drinks per drinking day | 11.9 | 5.2 | 10.5 | 4.3 | p = 0.11 |
| Drinks per day | 10.3 | 5.3 | 9.0 | 4.5 | p = 0.08 |
| Heavy drinking days (%) | 79.7 | 21.5 | 80.2 | 22.9 | p = 0.89 |
| Days from last drink to randomization | 6.6 | 4.1 | 7.3 | 4.7 | p = 0.33 |

*p values indicate significance of $\chi^2$ and t tests for differences between naltrexone and placebo groups.

DNA collection and genotyping. Genomic DNA was extracted (Gentra Puragene Blood Kit; Qiagen Inc., Valencia, CA) from peripheral blood mononuclear cells collected at the initial assessment session, stored at −80° C., and used to genotype the rs1799971 and rs4680 SNPs and the SLC6A3 VNTR. Details of these assays were previously described (Anton et al, 2020).

Methylation assay. Genomic DNA was quantitated using a Qubit Fluorometer (Thermo Fisher Scientific, Waltham, MA). An Infinium MethylationEPIC BeadChip (Illumina, San Diego, CA), which assays methylation at 866,895 cytosine residues, 99.7% of which are CpG sites, was used to generate a comprehensive genome-wide profile of DNA methylation. For each subject, 500 ng genomic DNA was bisulfate converted, denatured, and amplified, fragmented, resuspended, and hybridized to the BeadChips (eight samples per chip). Each group of eight samples was balanced by medication group, age, and nicotine use, such that each chip included four samples from naltrexone-treated participants and four from placebo-treated participants, with age (median split) and nicotine use (defined as >10 cigarettes per day) evenly distributed within each group of four samples. Age and nicotine use were chosen because these characteristics are known to affect global DNA methylation (Horvath et al, 2012; Joehanes et al, 2016). During hybridization, the amplified and fragmented DNA annealed to fluorophore-linked probes specific to each CpG site (one for methylated and one for unmethylated sites). Processed BeadChips were then scanned on the Illumina iScan System, which used a laser to excite the fluorophores from each probe and record their fluorescence. Summaries of the probe interrogations yielded average signals for the proportion of alleles that were methylated, vs. unmethylated, at each CpG site.

Quality control. The RnBeads R package (Assenov et al, 2014) was used to examine box plots of the quality of the staining, hybridization, extension, target removal, and bisulfate conversion of the genomic DNA. The distributions and medians of negative control box plots were also examined for each sample. Based on these metrics, one participant's data were judged to be of low quality and were excluded from analysis, leaving 145 participants for analysis. Of the initial 866,895 probes, the RnBeads quality control pipeline removed 17,371 probes from the data because they overlapped with SNPs; 6,105 probes using the Greedycut algorithm, which iteratively removes the probes of greatest impurity; and 2,899 probes because they were located in specific contexts (non-CpG positions), leaving 840,520 CpG sites for analysis. Data were normalized using the method from (Pidsley et al, 2013).

To further assess data quality and to examine convergent validity, participants' age and sex were estimated from the methylation data, and methylation differences between smokers (n=57) and non-smokers (n=88) were tested. First, Horvath's DNA Methylation Age Calculator (Horvath, 2013), which estimates age from the methylation of 30,084 CpG sites, was used to predict participants' ages; these predictions correlated highly with participants' self-reported ages (r=0.882, p<0.001). Second, the Horvath algorithm and RnBeads also predict sex based on sex chromosome methylation; both predictions exactly matched participants' self-reported sex. Finally, differences in whole-genome methylation between smokers and non-smokers were tested in RnBeads, and the five CpG sites that were most significantly differentially methylated between these groups were compared with the five CpG sites that most strongly discriminated smokers from non-smokers in a previous paper (Joehanes et al, 2016). Four of the top five sites in our data (Illumina probe IDs cg05575921, cg21161138, cg21566642, and cg01940273, none of which were associated with OPRM1, SLC6A3, or COMT) were among the top five most differentially methylated sites in the Joehanes analysis.

Regions analyzed. FIGS. 4-6 show the CpG sites on the BeadChip located in each gene's promoter. Although 840, 520 CpG sites were available for analysis, not every site in each promoter was represented on the BeadChip. All of the available sites within each promoter were included. For OPRM1, the promoter was defined, consistent with a recent study of OPRM1 methylation effects on naltrexone response (Lin et al, 2020), as the region within 130 nucleotides upstream and 600 nucleotides downstream of the transcription start site (TSS); this comprised 10 CpG sites (Illumina probe IDs cg22370006, cg14262937, cg06649410, cg23143142, cg23706388, cg05215925, cg14348757, cg12838303, cg22719623, cg15085086). For SLC6A3, NCBI AceView lists three possible promoters, one located upstream of the TSS and two in intronic regions. In keeping with prior studies' definitions, the seven CpG sites on the BeadChip in the AceView 5' upstream region (cg16180821, cg13202751, cg14502484, cg05030481, cg27037018, cg04210284, cg12882697) were used. COMT has isoforms that encode both soluble and membrane-bound COMT, each of which has its own promoter (P1 and P2, respectively) (Tenhunen et al, 1994). The four CpG sites in the P1 promoter (cg06346307, cg22546130, cg23601416, cg01335087) and eight in the P2 promoter (cg17810098, cg23268677, cg15834517, cg24899205, cg07019740, cg11032634, cg03205258, cg12175949) on the BeadChip were included. Finally, on an exploratory basis, CpG sites in the SLC6A3 VNTR region were also analyzed. The BeadChip includes three CpG sites in this region (cg15600751, cg1632193, and cg10838500), but one (cg10838500) occurs in the type "E" repeat that is present only in the 10R allele (Fuke et al, 2001). Thus, methylation at the cg15600751 and cg1632193 sites was averaged for this analysis.

Statistical analysis. Interactions between methylation levels (averaged across the proportion of methylated alleles at each site in each region) and medication were tested with linear mixed models (SPSS v. 25 MIXED) in which methylation and medication group (naltrexone vs. placebo) were between-subjects factors and time in study (month 1 to 4) was a repeated within-subjects factor. The dependent variable was percent heavy drinking days (PHDD; i.e., the proportion of study days on which women/men drank 4/5 or more standard drinks), as in our previous analyses (Anton et al, 2020; Schacht et al, 2017). Significant methylation by medication interactions indicated that naltrexone effects on PHDD across all study months differed as a function of methylation; significant methylation by medication by time interactions indicated that these effects differed as a function of both methylation and time in study. For each model, the highest-level significant interaction was interpreted by median-splitting methylation levels for each gene and testing, post hoc, the simple effect of medication within each combination of methylation level (e.g., high vs. low OPRM1, SLC6A3, and COMT methylation). Effect sizes (Cohen's d) were calculated for groups in which this simple effect was significant.

Three primary models were tested: one included OPRM1 promoter methylation, medication, time, and all interactions of these factors, and the second and third added either SLC6A3 promoter methylation or COMT promoter methylation, allowing it to interact with OPRM1 promoter methylation, medication, and time. Alpha for the three primary models was set at a Bonferroni-corrected threshold of p=0.0167 (i.e., 0.05/3). Alpha for post hoc tests was left at p=0.05, as these tests were conducted only to interpret higher-level interactions. A fourth exploratory model included SLC6A3 VNTR (non-promoter) methylation, OPRM1 promoter methylation, medication, time, and all interactions. Each model used an unstructured covariance matrix and, to control for age-related changes in methylation and assay batch effects, also included terms for age and the specific BeadChip on which the sample was run. To test whether methylation effects could be accounted for by the previously reported epistatic interactions (Anton et al, 2020), additional statistical models were performed in which the germ-line single nucleotide, or VNTR polymorphisms, in OPRM1 rs1799971, SLC6A3 VNTR, and COMT rs4680 genotypes (dichotomized as G-allele carriers vs. A-allele homozygotes, 9R-allele carriers vs. 10R-allele homozygotes, and met-allele carriers vs. val-allele homozygotes, respectively) and their interactions with medication and time were to evaluate the novel/independent effects of the methylation levels on naltrexone response.

Example 1

SLC6A3 Promoter and OPRM1 Promoter

The highest-level significant interaction was between SLC6A3 promoter methylation, OPRM1 promoter methylation, medication group, and time. When SLC6A3 and OPRM1 methylation were median-split (FIG. 1; medians were SLC6A3=0.150, OPRM1=0.170), naltrexone, relative to placebo, significantly reduced PHDD at months 2 (F(1, 217.46)=4.87, mean difference between naltrexone and placebo=16.2% HDD (95% CI=1.7-30.7%), d=0.61, p=0.028) and 3 (F(1, 232.53)=4.79, mean difference between naltrexone and placebo=16.5% HDD (95% CI=1.7-31.4%), d=0.62, p=0.030) among individuals with lower methylation of both promoters. The simple effect of medication was not significant at any time point among individuals with any other combination of SLC6A3 and OPRM1 methylation except those with high SLC6A3 and low OPRM1 methylation, among whom this effect was significant at month 3 (F(1, 241.14)=5.35, mean difference between naltrexone and placebo=25.7% HDD (95% CI=3.8-47.7%), d=0.98, p=0.022)), as a function of increased PHDD in the placebo group at that time point. The SLC6A3 by OPRM1 by medication by time interaction remained significant even when rs28363170 (SLC6A3 VNTR variants) genotype, the rs1799971 (OPRM1 A118G SNP) genotype, and their interactions with each other and with medication and time were included in the model, suggesting that the methylation by medication interaction was novel/independent of these other effects.

Example 2

COMT Promoter and OPRM1 Promoter

Figure 2:
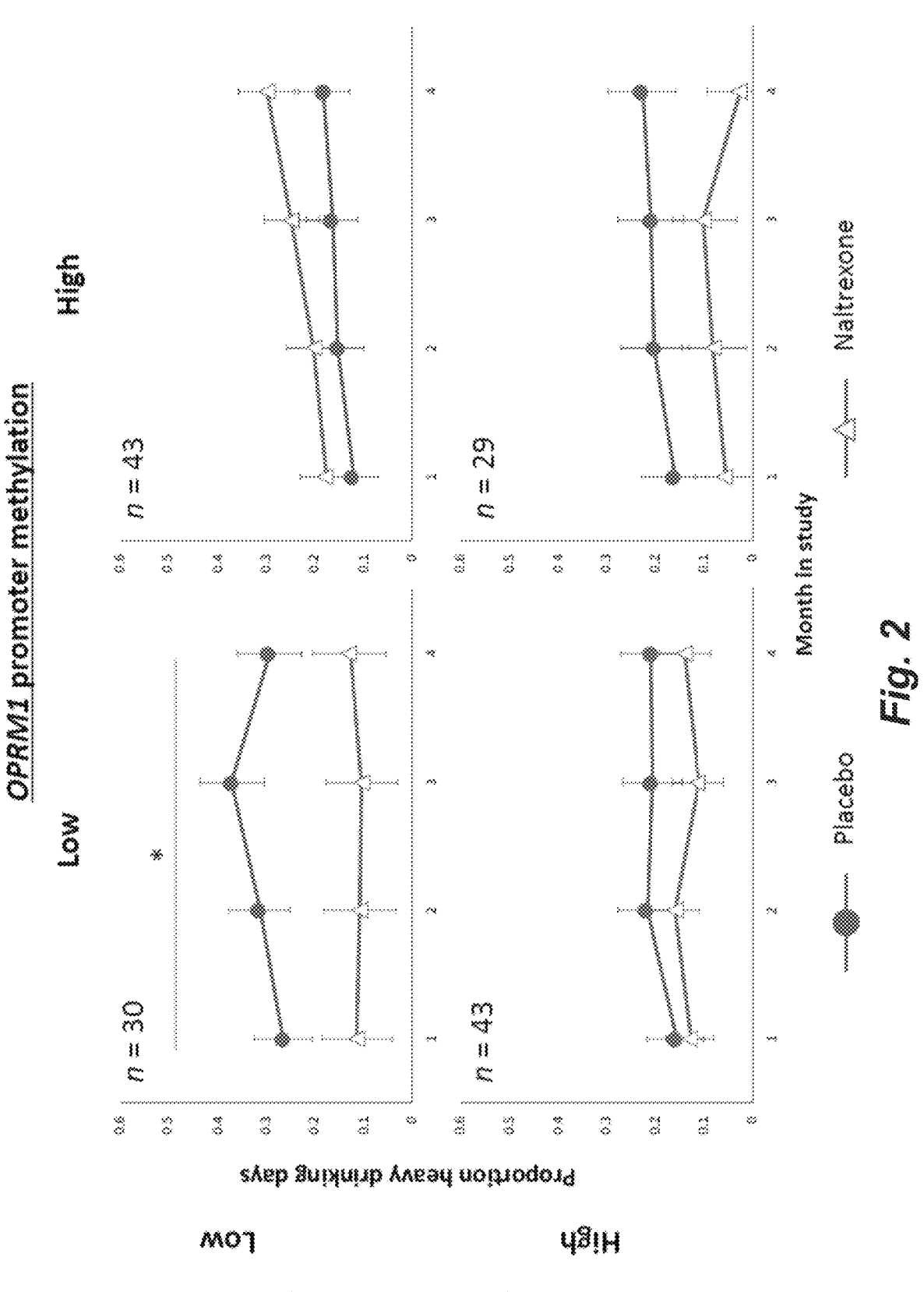
FIG. 2 is a series of graphs showing the effects of naltrexone (open triangles), relative to placebo (closed circles), on percent heavy drinking days (PHDD) during the 16-week trial as a function of COMT promoter and OPRM1 promoter methylation. COMT and OPRM1 methylation are split into low and high groups (below and above the median methylation levels) for display purposes. Naltrexone, relative to placebo, reduced PHDD more among participants with lower COMT promoter and OPRM1 promoter methylation. Figures are estimated marginal means (±standard errors) from the linear mixed model where the independent variables were promoter methylation levels (low or high) and naltrexone or placebo treatment, while the dependent variable was percent heavy drinking days over the treatment period (months).

The highest-level significant interaction was between COMT promoter methylation, OPRM1 promoter methylation, and medication group. Across all study months, naltrexone, relative to placebo, reduced PHDD more among individuals with lower COMT methylation and lower OPRM1 methylation. When COMT and OPRM1 methylation were median-split (FIG. 2; medians were COMT=0.341, OPRM1=0.170), naltrexone, relative to placebo, significantly reduced PHDD across all study months only among individuals with lower methylation of both promoters (F(1, 154.12)=5.41, mean difference between naltrexone and placebo=19.7% HDD (95% CI=3.0-36.5%), d=0.85, p=0.021). This interaction remained significant even when rs4680 (COMT val158met SNP) genotype, rs1799971 (OPRM1 A118G SNP) genotype, and their interactions with each other and with medication and time were included in the statistical model, suggesting that the methylation by medication interaction was novel/independent of these other effects.

Example 3

SLC6A3 VNTR and OPRM1 Promoter

Figure 3:
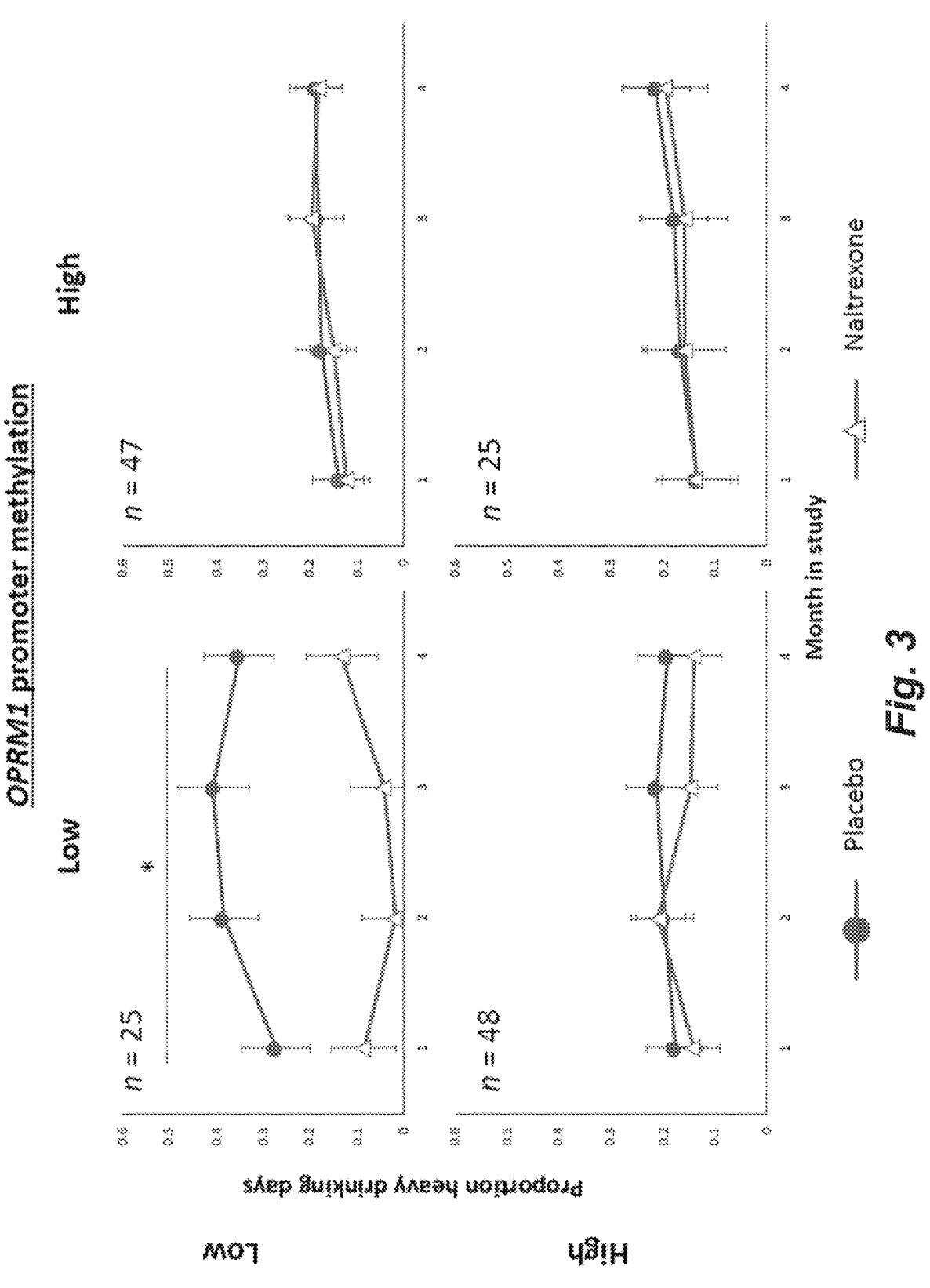
FIG. 3 is a series of graphs showing the effects of naltrexone (open triangles), relative to placebo (closed circles), on percent heavy drinking days (PHDD) during the 16-week trial as a function of SLC6A3 VNTR and OPRM1 promoter methylation. SLC6A3 and OPRM1 methylation are split into low and high groups (below and above the median methylation levels) for display purposes. Naltrexone, relative to placebo, reduced PHDD more among participants with lower SLC6A3 VNTR and OPRM1 promoter methylation. Figures are estimated marginal means (±standard errors) from the linear mixed model. where the independent variables were promoter methylation levels (low or high) and naltrexone or placebo treatment, while the dependent variable was percent heavy drinking days over the treatment period (months).

The highest-level significant interaction was between SLC6A3 VNTR methylation, OPRM1 promoter methylation, and medication group. Across all study months, naltrexone, relative to placebo, reduced PHDD more among individuals with lower SLC6A3 VNTR methylation and lower OPRM1 methylation. When SLC6A3 VNTR and OPRM1 promoter methylation were median-split (FIG. 3; medians were SLC6A3=0.618, OPRM1=0.170), naltrexone, relative to placebo, significantly reduced PHDD across all study months only among individuals with lower methylation of both regions (F(1, 146.43)=9.93, mean difference between naltrexone and placebo=28.5% HDD (95% CI=10.6-46.3%), d=1.25, p=0.002). This interaction remained significant even when rs28363170 genotype, rs1799971 genotype, and their interactions with each other and with medication and time were included in the model, again suggesting that the methylation by medication interaction was independent of these other effects.

Discussion of the Examples

Taken together, these data suggest that methylation differences in genes underlying opioid signaling and dopamine reuptake and inactivation interact to predict naltrexone treatment effects on heavy drinking among AUD outpatients. Specifically, methylation of the promoter regions of SLC6A3 and COMT interacted with OPRM1 promoter methylation to influence naltrexone efficacy, as did, in an exploratory analysis, methylation of the SLC6A3 3' UTR VNTR region. Effect sizes for naltrexone, relative to placebo, on heavy drinking in the subgroups in which it was most effective were in the medium to large range (0.53-1.04), greater than the overall small effect of naltrexone on heavy drinking across all AUD individuals (Maisel et al, 2013). These findings suggested a novel epigenetic predictor of naltrexone response.

The finding that OPRM1 methylation did not independently moderate naltrexone response is consistent with a recent secondary analysis of another AUD naltrexone RCT (Lin et al, 2020), as well as with a recent meta-analysis that concluded that OPRM1 rs1799971 genotype does not consistently moderate naltrexone effects (Hartwell et al, 2020). This meta-analysis included the primary analysis of the data used in the current study (Schacht et al, 2017), which also did not support this OPRM1 alone pharmacogenetic effect. Collectively, these findings suggest that, despite the fact that naltrexone directly antagonizes the MOR, the effects of genetic or epigenetic alteration of OPRM1 alone are likely not sufficiently large to consistently affect naltrexone response.

In contrast, the current data suggest that epigenetic changes in genes that may underlie naltrexone's downstream effects on dopamine signaling interact with OPRM1 methylation to predict its effects on drinking. Alcohol acutely elicits striatal dopamine release (Boileau et al, 2003) and naltrexone blocks this phenomenon (Benjamin et al, 1993; Gonzales et al, 1998). DAT and COMT are the primary methods of dopamine inactivation in the striatum (Ciliax et al, 1999) and PFC (Matsumoto et al, 2003), respectively. SLC6A3 VNTR and OPRM1 rs1799971 variation have previously been reported to interact in their effects on acute response to alcohol, such that individuals carrying the gain-of-function alleles of each polymorphism displayed lower hedonic response (Weerts et al, 2017). Since lower OPRM1, SLC6A3, and COMT promoter methylation has been associated with relatively increased expression of these genes (Andria et al, 1999; Murphy et al, 2005; Wiers et al, 2018), naltrexone might more effectively reduce heavy drinking among individuals with lower methylation of these regions because this pattern of methylation predisposes greater MOR availability and more effective synaptic dopamine clearance after alcohol-induced dopamine release. With respect to methylation of the SLC6A3 3' UTR, CpG methylation outside of gene promoters can also regulate gene expression (Maunakea et al, 2010), and 3' UTRs contain regulatory regions that can influence a variety of posttranscriptional modifications that affect gene expression (Barrett et al, 2012). Thus, greater methylation of this region could modulate posttranscriptional functions that affect SLC6A3 expression. We previously reported epistatic genetic effects on naltrexone efficacy in this sample, but the significance of the methylation effects persisted when these genetic effects were included in the models, suggesting that, even after accounting for variance attributable to epistatic effects, interactions between OPRM1 methylation and SLC6A3 and COMT methylation independently predicted naltrexone effects.

Thus, disclosed herein is the discovery that AUD individuals with less methylation of the OPRM1 and SLC6A3 or COMT promoters, as well as the SLC6A3 3'UTR VNTR, were more likely to benefit from naltrexone, relative to placebo, than individuals with other combinations of methylation in these regions.

While there have been published studies regarding how "inherited" genes and their germ-line mutations might be associated with naltrexone response, these genetic differences cannot/do not pick up genetic modifications that might occur due to "environmental exposure", such as heavy alcohol consumption. Therefore, the use of epigenetic methylation patterns is a fundamentally different, novel, and biologically meaningful way of understanding biological predictors of medication response. And while there has been some discovery that heavy alcohol consumption can modify the epigenetic methylation patterns of many genes overall, there has been few attempts to relate these changes to medication treatment response in Alcohol Use Disorder. It should also be recognized that there are many CpG sites in various genes that may, or may not, be more, or less, methylated due to alcohol exposure, and the discovery of which CpG sites that have relevance to disease and treatment response, is not an obvious or trivial issue. This is partly because methylation of multiple sites (especially in areas of gene transcription promoters) are likely needed for biological variation. As such, it is the pattern of these methylation sites that is important. For instance, several papers have examined the methylation of the OPRM1 gene have found various CpG sites to be hypermethylated in heavy drinkers compared to non-heavy drinkers (Zhang et al., 2012) and that a few CpG site methylation levels were associated with "relapse drinking" (Lin et al., 2020) but specifically NOT associated with naltrexone response. Therefore, the presently disclosed subject matter provides (1) a focus on various combinations of CpG methylation sites; and even more importantly, (2) at the next level, how methylation sites in several other important genes (DAT (SLC6A3 and COMT) might be additive to the methylation pattern of a single gene such as the OPRM1 promoter CpG sites. It is the direction of the methylation amounts/frequencies (lower or higher) at specific CpG sites, as well as the discovery of non-obvious combinations of CpG sites across several genes that predicts naltrexone response that is not obvious and therefore novel. This discovery will allow clinicians/prescribers specific new knowledge to choose which patient with Alcohol Use Disorder to treat with naltrexone, improving clinical care and reducing patient burden.

Summarily, disclosed herein is the identification that several out of many OPRM1 gene CpG methylation sites when combined with several other out of many COMT and DAT gene CpG methylation sites that are associated with naltrexone response for Alcohol Use Disorder individuals. So in essence, it is not the discovery of these sites or even if they are different between heavy drinkers (Alcohol Use Disorder) and non-heavy drinkers that is important for the presently disclosed subject matter, but how to apply these differences for improved treatment outcome to a specific medication.

REFERENCES

All references listed below, as well as all references cited in the instant disclosure, including but not limited to all patents, patent applications and publications thereof, scientific journal articles, and database entries (e.g., GEN-BANK® database entries and all annotations available therein) are incorporated herein by reference in their entireties to the extent that they supplement, explain, provide a background for, or teach methodology, techniques, and/or compositions employed herein.

Akey et al. (2002) Assaying DNA methylation based on high-throughput melting curve approaches. Genomics 80(4): 376-384.

Andria & Simon (1999) Localization of promoter elements in the human mu-opioid receptor gene and regulation by DNA methylation. Brain Res Mol Brain Res 70(1):54-65.

Anton et al. (2020) Opioid and Dopamine Genes Interact to Predict Naltrexone Response in a Randomized Alcohol Use Disorder Clinical Trial. Alcohol Clin Exp Res 44(10): 2084-2096.

Anton et al. (2012) Naltrexone modification of drinking effects in a subacute treatment and bar-lab paradigm: influence of OPRM1 and dopamine transporter (SLC6A3) genes. Alcohol Clin Exp Res 36(11):2000-2007.

Assenov et al. (2014) Comprehensive analysis of DNA methylation data with RnBeads. Nat Methods 11(11): 1138-1140.

Auerkari (2006) Methylation of tumor suppressor genes p16(INK4a), p27(Kip1) and E-cadherin in carcinogenesis. Oral Oncology 42:5-13.

Barrett et al. (2012) Regulation of eukaryotic gene expression by the untranslated gene regions and other non-coding elements. Cell Mol Life Sci 69(21):3613-3634.

Benjamin et al. (1993) Naltrexone reverses ethanol-induced dopamine release in the nucleus accumbens in awake, freely moving rats. Brain Research 621(1):137-140.

Boileau et al. (2003) Alcohol promotes dopamine release in the human nucleus accumbens. Synapse (New York, NY) 49(4):226-231.

Bond et al. (1998) Single-nucleotide polymorphism in the human mu opioid receptor gene alters beta-endorphin binding and activity: possible implications for opiate addiction. Proc Natl Acad Sci USA 95(16):9608-9613.

Chen et al. (2004) Functional analysis of genetic variation in catechol-O-methyltransferase (COMT): effects on mRNA, protein, and enzyme activity in postmortem human brain. Am J Hum Genet 75(5):807-821.

Ciliax et al. (1999) Immunocytochemical localization of the dopamine transporter in human brain. The Journal of Comparative Neurology 409(1):38-56.

Cottrell et al. (2004) A real-time PCR assay for DNA-methylation using methylation-specific blockers. Nucleic Acids Research 32(1):e10.

Cross et al. (1994) Purification of CpG islands using a methylated DNA binding column. Nature Genetics 6:236-244.

Doucette-Stamm et al. (1995) Population genetic study of the human dopamine transporter gene (DAT1). Genet Epidemiol 12(3):303-308.

Eads et al. (2000) MethyLight: a high-throughput assay to measure DNA methylation. Nucleic Acids Research 28 (8):e32.

First et al. (2002) Structured Clinical Interview for DSM-IV-TR Axis I Disorders, Research Version, Non-patient Edition. Biometrics Research, New York State Psychiatric Institute: New York.

Fuke et al. (2001) The VNTR polymorphism of the human dopamine transporter (DAT1) gene affects gene expression. Pharmacogenom J 1(2):152-156.

Furuichi et al. (1970) Chemical modification of tRNA-Tyr-yeast with bisulfate. A new method to modify isopentenyladenosine residue. Biochemical and Biophysical Research Communications 41(5):1185-1191.

Gait (ed.) (1984) Oligonucleotide Synthesis, A Practical Approach, IRL Press, Oxford, England, United Kingdom.

Gonzales & Weiss (1998) Suppression of ethanol-reinforced behavior by naltrexone is associated with attenuation of the ethanol-induced increase in dialysate dopamine levels in the nucleus accumbens. J Neurosci 18(24): 10663-10671.

Hames & Higgins (eds.) (1985) Nucleic Acid Hybridization, A Practical Approach, IRL Press, Washington, DC, United States of America.

Hartwell et al. (2020) Systematic review and meta-analysis of the moderating effect of rs1799971 in OPRM1, the mu-opioid receptor gene, on response to naltrexone treatment of alcohol use disorder. Addiction 115(8):1426-1437.

Heinz et al. (2000) Genotype influences in vivo dopamine transporter availability in human striatum. Neuropsychopharmacology 22(2): 133-139.

Herman et al. (1996) Methylation-specific PCR: a novel PCR assay for methylation status of CpG islands. Proc Natl Acad Sci USA 93:9821-9826.

Hillemacher et al. (2009) Promoter specific methylation of the dopamine transporter gene is altered in alcohol dependence and associated with craving. J Psychiatr Res 43(4): 388-392.

Horvath (2013) DNA methylation age of human tissues and cell types. Genome Biol 14(10):R115.

Horvath et al. (2012) Aging effects on DNA methylation modules in human brain and blood tissue. Genome Biol 13(10):R97.

Illingworth et al. (2008) A novel CpG island set identifies tissue-specific methylation at developmental gene loci. PLoS Biol 6(1):e22.

Jasiewicz et al. (2015) DAT1 methylation changes in alcohol-dependent individuals vs. controls. J Psychiatr Res 64:130-133.

Joehanes et al. (2016) Epigenetic Signatures of Cigarette Smoking. Circ Cardiovasc Genet 9(5):436-447.

Jonas et al. (2014a) Pharmacotherapy for adults with alcohol use disorders in outpatient settings: a systematic review and meta-analysis. JAMA 311(18):1889-1900.

Jonas et al. (2014b) Genetic polymorphisms and response to medications for alcohol use disorders: a systematic review and meta-analysis. Pharmacogenomics 15(13):1687-1700.

Jones (2012) Functions of DNA methylation: islands, start sites, gene bodies and beyond. Nat Rev Genet 13(7):484-492.

Jorgensen et al. (2006) Engineering a high-affinity methyl-CpG-binding protein. Nucleic Acids Research 34:e96.

Lachman et al. (1996) Human catechol-O-methyltransferase pharmacogenetics: description of a functional polymorphism and its potential application to neuropsychiatric disorders. Pharmacogenetics 6(3):243-250.

Laird (2003) The power and the promise of DNA methylation markers. Nature Reviews 3:253-266.

Lin et al. (2020) An analysis of the effect of mu-opioid receptor gene (OPRM1) promoter region DNA methylation on the response of naltrexone treatment of alcohol dependence. Pharmacogenomics J.

Maisel et al. (2013) Meta-analysis of naltrexone and acamprosate for treating alcohol use disorders: when are these medications most helpful? Addiction 108(2):275-293.

Matsumoto et al. (2003) Catechol O-methyltransferase mRNA expression in human and rat brain: evidence for a role in cortical neuronal function. Neuroscience 116(1): 127-137.

Maunakea et al. (2010) Conserved role of intragenic DNA methylation in regulating alternative promoters. Nature 466(7303):253-257.

Melnikov et al. (2005) MSRE-PCR for analysis of gene-specific DNA methylation. Nucleic Acids Research 33(10):e93.

Methods in Enzymology, Academic Press, Inc., Cambridge, Massachusetts, United States of America.

Murphy et al. (2005) Site-specific cytosine methylation in S-COMT promoter in 31 brain regions with implications for studies involving schizophrenia. Am J Med Genet B Neuropsychiatr Genet 133B(1):37-42.

Nieratschker et al. (2014) Epigenetic alteration of the dopamine transporter gene in alcohol-dependent patients is associated with age. Addict Biol 19(2):305-311. PCT International Patent Application Publication No. WO 97/46705.

Pidsley et al. (2013) A data-driven approach to preprocessing Illumina 450K methylation array data. BMC Genomics 14:293.

Rand et al. (2002) Conversion-specific detection of DNA methylation using real-time polymerase chain reaction (ConLight-MSP) to avoid false positives. Methods 27:114-120.

Rein et al. (1998) Identifying 5-methylcytosine and related modifications in DNA genomes. Nucleic Acids Research 26(10):2255-2264.

Sambrook et al. (2001) *Molecular Cloning: A Laboratory Manual, 3rd Edition*, Cold Spring Harbor Laboratory Press, Cold Spring Harbor, New York, United States of America.

Sasaki et al. (2003) Bisulfite conversion-specific and methylation-specific PCR: a sensitive technique for accurate evaluation of CpG methylation. Biochemical and Biophysical Research Communications 309:305-309.

Schacht et al. (2013) Interacting effects of naltrexone and OPRM1 and DAT1 variation on the neural response to alcohol cues. Neuropsychopharmacology 38(3):414-422.

Schacht et al. (2017) Predictors of Naltrexone Response in a Randomized Trial: Reward-Related Brain Activation, OPRM1 Genotype, and Smoking Status. Neuropsychopharmacology 42(13):2640-2653.

Shiraishi et al. (1999) Isolation of DNA fragments associated with methylated CpG islands in human adenocarcinomas of the lung using a methylated DNA binding column and denaturing gradient gel electrophoresis. Proceedings of National Academy of Sciences, USA 96:2913-2918.

Sobell & Sobell (1992) Timeline follow-back: A technique for assessing self-reported alcohol consumption. In: Allen J P, Litten R Z (eds) Measuring alcohol consumption: Psychosocial and biochemical methods. Humana Press: Totowa, NJ, pp 41-72.

Stout et al. (1994) Ensuring balanced distribution of prognostic factors in treatment outcome research. J Stud Alcohol Suppl 12:70-75.

Swift-Scanlan et al. (2014) Comprehensive interrogation of CpG island methylation in the gene encoding COMT, a key estrogen and catecholamine regulator. BMC Med Genomics 7:5.

Tenhunen et al. (1994) Genomic organization of the human catechol O-methyltransferase gene and its expression from two distinct promoters. Eur J Biochem 223(3):1049-1059.

U.S. Patent Application Publication Nos. 2018/0369238, 2018/0371542.

U.S. Pat. No. 7,425,415.

Ursini et al. (2011) Stress-related methylation of the catechol-O-methyltransferase Val 158 allele predicts human prefrontal cognition and activity. J Neurosci 31(18):6692-6698.

Weerts et al. (2013) Influence of OPRM1 Asn40Asp variant (A118G) on [11C]carfentanil binding potential: preliminary findings in human subjects. Int J Neuropsychopharmacol 16(1):47-53.

Weerts et al. (2017) Independent and Interactive Effects of OPRM1 and DAT1 Polymorphisms on Alcohol Consumption and Subjective Responses in Social Drinkers. Alcohol Clin Exp Res 41(6):1093-1104.

Wiers et al. (2018) Methylation of the dopamine transporter gene in blood is associated with striatal dopamine transporter availability in ADHD: A preliminary study. Eur J Neurosci 48(3):1884-1895.

Wiers et al. (2015) Effects of depressive symptoms and peripheral DAT methylation on neural reactivity to alcohol cues in alcoholism. Translational psychiatry 5:e648.

Zeschnigk et al. (2004) A novel real-time PCR assay for quantitative analysis of methylated alleles (QAMA): analysis of the retinoblastoma locus. Nucleic Acids Research 32(16):e125.

Zhang et al. (2012) Hypermethylation of OPRM1 promoter region in European Americans with alcohol dependence. J Hum Genet 57(10):670-675.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for treating an individual with an alcohol use disorder (AUD), the method comprising, consisting essentially of, or consisting of:

(a) performing or having performed:

(i) a first methylation assay on a genomic DNA sample isolated from the individual to determine the methylation status of one or more regions of a mu opioid receptor (OPRM1) gene sequence comprising, consisting essentially of, or consisting of SEQ ID NO: 1 in the isolated genomic DNA; and (ii) at least one additional methylation assay on a genomic DNA sample isolated from the individual to determine the methylation status(es) of a subsequence of a catechol-O-methyltransferase (COMT) gene corresponding to SEQ ID NO: 27, a subsequence of a dopamine transporter (SLC6A3) gene corresponding to SEQ ID NO: 11, and/or a subsequence of an SLC6A3 40-base-pair variable number tandem repeat (VNTR) in the 3' untranslated region of the SLC6A3 gene corresponding to SEQ ID NO: 21; and (b) treating the individual with an effective amount of naltrexone if the methylation status of the one or more regions of the OPRM1 gene sequence corresponding to SEQ ID NO: 1 is low, defined as lower than 0.126 with respect to nucleotide position 357 of the OPRM1 gene sequence corresponding to SEQ ID NO: 1; lower than 0.147 with respect to nucleotide position 274 of the OPRM1 gene sequence corresponding to SEQ ID NO: 1; lower than 0.157 with respect to nucleotide position 277 of the OPRM1 gene sequence corresponding to SEQ ID NO: 1; and/or lower than 0.488 with respect to nucleotide position 419 of the OPRM1 gene sequence corresponding to SEQ ID NO: 1, and in addition:

(1) the methylation status of the subsequence of the COMT gene corresponding to SEQ ID NO: 27 is low, defined as lower than 0.587 with respect to nucleotide position 46 of the COMT gene corresponding to SEQ ID NO: 27 and/or lower than 0.546 with respect to position 107 of the COMT gene corresponding to SEQ ID NO: 27; or (2) the methylation status of the subsequence of the SLC6A3 gene corresponding to SEQ ID NO: 11 is low, defined as lower than 0.651 with respect to nucleotide position 576 of the SLC6A3 gene corresponding to SEQ ID NO: 11 and/or lower than 0.648 with respect to nucleotide position 1102 of the SLC6A3 gene corresponding to SEQ ID NO: 11; or (3) the methylation status of the subsequence of the SLC6A3 40-base-pair VNTR in the 3' untranslated region of the SLC6A3 gene sequence corresponding to SEQ ID NO: 21 is low, defined as lower than 0.089 with respect to nucleotide position 46 of the SLC6A3 40-base-pair VNTR in the 3' untranslated region of SLC6A3 gene corresponding to SEQ ID NO: 21, wherein the individual with a low methylation status with respect to the OPRM1 gene sequence corresponding to SEQ ID NO: 1 in combination with one or more low methylation statuses of the COMT gene corresponding to SEQ ID NO: 27, the SLC6A3 gene corresponding to SEQ ID NO: 11, and/or the SLC6A3 40-base-pair VNTR in the 3' untranslated region of the SLC6A3 gene sequence corresponding to SEQ ID NO: 21 is predicted to respond positively to naltrexone.

2. The method of claim 1, wherein the one or more regions of the OPRM1 gene sequence corresponding to SEQ ID NO: 1 include 130 nucleotides upstream and 600 nucleotides downstream of the OPRM1 transcription start site (TSS); optionally comprising one or more of SEQ ID NOs: 2-10.

3. The method of claim 1, wherein the subsequence of the SLC6A3 gene corresponding to SEQ ID NO: 11 comprises one or more of SEQ ID NOs: 12-20.

4. The method of claim 1, wherein the subsequence of the COMT gene corresponding to SEQ ID NO: 27 comprises one or more of SEQ ID NOs: 28-38.

5. The method of claim 1, wherein the subsequence of the SLC6A3 VNTR corresponding to SEQ ID NO: 21 comprises one or more of SEQ ID NOs: 22-25.

6. The method of claim 1, wherein the methylation statuses of at least one nucleotide position of each of the OPRM1 gene corresponding to SEQ ID NO: 1, the COMT gene corresponding to SEQ ID NO: 27, the dopamine transporter (SLC6A3) gene corresponding to SEQ ID NO: 11, and the 40-base-pair VNTR in the 3' untranslated region of SLC6A3 gene corresponding to SEQ ID NO: 21 are determined.

7. The method of claim 1, wherein the genomic DNA is isolated from a cell selected from the group consisting of blood cells, optionally peripheral blood mononuclear cells, and buccal cells, and/or from a biological sample containing cells, optionally, blood, saliva, cerebrospinal fluid, and/or any fraction or component thereof.

8. The method of claim 1, further comprising converting the isolated genomic DNA with bisulfite prior to performing or having performed the methylation assays.

* * * * *